United States Patent
Phadke et al.

(10) Patent No.: US 11,807,627 B2
(45) Date of Patent: Nov. 7, 2023

(54) MORPHIC FORMS OF COMPLEMENT FACTOR D INHIBITORS

(71) Applicant: Achillion Pharmaceuticals, Inc., Blue Bell, PA (US)

(72) Inventors: Avinash Phadke, Branford, CT (US); Akihiro Hashimoto, Branford, CT (US); Mark Andres, Bend, OR (US)

(73) Assignee: Achillon Pharmaceuticals, Inc., Boston, MA (US)

( * ) Notice: Subject to any disclaimer, the term of this patent is extended or adjusted under 35 U.S.C. 154(b) by 393 days.

(21) Appl. No.: 17/279,767

(22) PCT Filed: Sep. 25, 2019

(86) PCT No.: PCT/US2019/053012
§ 371 (c)(1),
(2) Date: Mar. 25, 2021

(87) PCT Pub. No.: WO2020/069024
PCT Pub. Date: Apr. 2, 2020

(65) Prior Publication Data
US 2021/0332026 A1    Oct. 28, 2021

Related U.S. Application Data

(60) Provisional application No. 62/796,776, filed on Jan. 25, 2019, provisional application No. 62/760,520, filed on Nov. 13, 2018, provisional application No. 62/757,565, filed on Nov. 8, 2018, provisional application No. 62/736,294, filed on Sep. 25, 2018.

(51) Int. Cl.
C07D 401/14    (2006.01)

(52) U.S. Cl.
CPC ........ C07D 401/14 (2013.01); *C07B 2200/13* (2013.01)

(58) Field of Classification Search
CPC ................... C07D 401/14; C07B 2200/13
See application file for complete search history.

(56) References Cited

U.S. PATENT DOCUMENTS

| | | | |
|---|---|---|---|
| 5,628,984 A | 5/1997 | Boucher, Jr. |
| 6,319,897 B1 | 11/2001 | Lambris et al. |
| 6,489,476 B1 | 12/2002 | Dang et al. |
| 6,492,402 B1 | 12/2002 | Lee et al. |
| 6,653,340 B1 | 11/2003 | Babu et al. |
| 7,482,376 B2 | 1/2009 | Subasinghe et al. |
| 7,629,340 B2 | 12/2009 | Schmitz et al. |
| 7,888,323 B2 | 2/2011 | Lambris et al. |
| 7,989,589 B2 | 8/2011 | Lambris |
| 7,999,081 B2 | 8/2011 | Tedesco et al. |
| 8,168,584 B2 | 5/2012 | Deschatelets et al. |
| 8,241,628 B2 | 8/2012 | Diefenbach-Streiber et al. |
| 8,524,716 B2 | 9/2013 | Raboisson et al. |
| 8,580,735 B2 | 11/2013 | Francois et al. |
| 8,883,158 B2 | 11/2014 | Diefenbach-Streiber et al. |
| 8,946,145 B2 | 2/2015 | Lambris et al. |
| 9,056,076 B2 | 6/2015 | Deschatelets et al. |
| 9,085,555 B2 | 7/2015 | Altmann et al. |
| 9,169,307 B2 | 10/2015 | Lambris et al. |
| 9,291,622 B2 | 3/2016 | Zhang et al. |
| 9,371,365 B2 | 6/2016 | Lambris et al. |
| 9,421,240 B2 | 8/2016 | Francois et al. |
| 9,468,661 B2 | 10/2016 | Altmann et al. |
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 9,732,103 B2 | 8/2017 | Wiles et al. |
| 9,732,104 B2 | 8/2017 | Gadhachanda et al. |
| 9,758,537 B2 | 9/2017 | Wiles et al. |
| 9,796,741 B2 | 10/2017 | Gadhachanda et al. |
| 9,828,396 B2 | 11/2017 | Wiles et al. |
| 10,000,516 B2 | 6/2018 | Wiles et al. |
| 10,005,802 B2 | 6/2018 | Wiles et al. |
| 10,011,612 B2 | 7/2018 | Wiles et al. |
| 10,081,645 B2 | 9/2018 | Wiles et al. |
| 10,087,203 B2 | 10/2018 | Wiles et al. |
| 10,092,547 B2 | 10/2018 | Wiles et al. |
| 10,092,584 B2 | 10/2018 | Wiles et al. |
| 10,100,072 B2 | 10/2018 | Wiles et al. |
| 10,106,563 B2 | 10/2018 | Wiles et al. |
| 10,138,225 B2 | 11/2018 | Wiles et al. |
| 10,189,869 B2 | 1/2019 | Gadhachanda et al. |
| 10,253,053 B2 | 4/2019 | Wiles et al. |
| 10,287,301 B2 | 5/2019 | Wiles et al. |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

"Patient Information for TARPEYO (tar-PAY-oh) (budesonide) delayed release capsules," Calliditas Therapeutics AB, Dec. 2021 (2 pages).
Andrighetto et al., "Complement and Complement Targeting Therapies in Glomerular Diseases," Int J Mol Sci. 20(24):6336 (Dec. 2019), available <https://www.ncbi.nlm.nih.gov/pmc/articles/PMC6940904/>, retrieved on May 26, 2022 (21 pages).
Extended European Search Report for European Application No. 19807154.0, dated Feb. 7, 2022 (9 pages).
Extended European Search Report for European Application No. 19857780.1, dated May 13, 2022 (9 pages).
Extended European Search Report for European Application No. 19897806.6, dated Jul. 18, 2022 (12 pages).

(Continued)

*Primary Examiner* — Jeffrey S Lundgren
*Assistant Examiner* — Ellie Park
(74) *Attorney, Agent, or Firm* — Clark & Elbing LLP

(57) ABSTRACT

This invention provides stable, highly crystalline forms of Complement Factor D inhibitor Compound 3 for therapeutic applications.

20 Claims, 49 Drawing Sheets

(56) References Cited

U.S. PATENT DOCUMENTS

| | | |
|---|---|---|
| 10,301,336 B2 | 5/2019 | Wiles et al. |
| 10,370,394 B2 | 8/2019 | Wiles et al. |
| 10,385,097 B2 | 8/2019 | Wiles et al. |
| 10,428,094 B2 | 10/2019 | Wiles et al. |
| 10,428,095 B2 | 10/2019 | Wiles et al. |
| 10,464,956 B2 | 11/2019 | Wiles et al. |
| 10,550,140 B2 | 2/2020 | Wiles et al. |
| 10,660,876 B2 | 5/2020 | Wiles et al. |
| 10,662,175 B2 | 5/2020 | Wiles et al. |
| 10,807,952 B2 | 10/2020 | Wiles et al. |
| 10,822,352 B2 | 11/2020 | Wiles et al. |
| 10,906,887 B2 | 2/2021 | Wiles et al. |
| 10,919,884 B2 | 2/2021 | Wiles et al. |
| 11,001,600 B2 | 5/2021 | Wiles et al. |
| 11,053,253 B2 | 7/2021 | Wiles et al. |
| 11,084,800 B2 | 8/2021 | Wiles et al. |
| 11,407,738 B2 | 8/2022 | Wiles et al. |
| 11,447,465 B2 | 9/2022 | Wiles et al. |
| 2002/0133004 A1 | 9/2002 | Sekiyama et al. |
| 2005/0228000 A1 | 10/2005 | Smallheer et al. |
| 2005/0267108 A1 | 12/2005 | Hsieh et al. |
| 2006/0004000 A1 | 1/2006 | D'Orchymont et al. |
| 2007/0155712 A1 | 7/2007 | Zahn et al. |
| 2008/0075720 A1 | 3/2008 | Holers et al. |
| 2008/0075728 A1 | 3/2008 | Newman |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0237515 A1 | 9/2012 | Bell et al. |
| 2012/0295884 A1 | 11/2012 | Altmann et al. |
| 2013/0029912 A1 | 1/2013 | Holers et al. |
| 2013/0035392 A1 | 2/2013 | McGeer et al. |
| 2013/0296377 A1 | 11/2013 | Adams et al. |
| 2013/0324482 A1 | 12/2013 | Francois et al. |
| 2013/0344073 A1 | 12/2013 | Schwaeble et al. |
| 2014/0050739 A1 | 2/2014 | Francois et al. |
| 2014/0323407 A1 | 10/2014 | Francois et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0158915 A1 | 6/2015 | Lambris et al. |
| 2015/0191462 A1 | 7/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0269868 A1 | 9/2015 | Carney et al. |
| 2015/0322060 A1 | 11/2015 | Flohr et al. |
| 2015/0368271 A1 | 12/2015 | Su et al. |
| 2016/0015810 A1 | 1/2016 | Deschatelets et al. |
| 2016/0024079 A1 | 1/2016 | Adams et al. |
| 2016/0060297 A1 | 3/2016 | Deschatelets et al. |
| 2016/0194359 A1 | 7/2016 | Francois et al. |
| 2016/0215020 A1 | 7/2016 | Francois et al. |
| 2016/0215022 A1 | 7/2016 | Francois et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |
| 2017/0202821 A1 | 7/2017 | Bekker |
| 2017/0202935 A1 | 7/2017 | Lambris et al. |
| 2017/0226142 A1 | 8/2017 | Wiles et al. |
| 2017/0260219 A1 | 9/2017 | Wiles et al. |
| 2017/0298084 A1 | 10/2017 | Wiles et al. |
| 2017/0298085 A1 | 10/2017 | Wiles et al. |
| 2018/0022766 A1 | 1/2018 | Wiles et al. |
| 2018/0022767 A1 | 1/2018 | Wiles et al. |
| 2018/0030075 A1 | 2/2018 | Wiles et al. |
| 2018/0072762 A1 | 3/2018 | Wiles et al. |
| 2018/0177761 A1 | 6/2018 | Wiles et al. |
| 2018/0179185 A1 | 6/2018 | Wiles et al. |
| 2018/0179186 A1 | 6/2018 | Wiles et al. |
| 2018/0179236 A1 | 6/2018 | Wiles et al. |
| 2018/0186782 A1 | 7/2018 | Wiles et al. |
| 2018/0201580 A1 | 7/2018 | Wiles et al. |
| 2018/0305375 A1 | 10/2018 | Wiles et al. |
| 2019/0023729 A1 | 1/2019 | Wiles et al. |
| 2019/0031692 A1 | 1/2019 | Wiles et al. |
| 2019/0038623 A1 | 2/2019 | Huang et al. |
| 2019/0048033 A1 | 2/2019 | Wiles et al. |
| 2019/0085005 A1 | 3/2019 | Wiles et al. |
| 2019/0144473 A1 | 5/2019 | Gadhachanda et al. |
| 2019/0211033 A1 | 7/2019 | Wiles et al. |
| 2019/0359645 A1 | 11/2019 | Birkus et al. |
| 2019/0382376 A1 | 12/2019 | Wiles et al. |
| 2020/0002347 A1 | 1/2020 | Wiles et al. |
| 2020/0062790 A1 | 2/2020 | Wiles et al. |
| 2020/0071301 A1 | 3/2020 | Wiles et al. |
| 2020/0101071 A1 | 4/2020 | Huang et al. |
| 2020/0262818 A1 | 8/2020 | Wiles et al. |
| 2021/0332026 A1 | 10/2021 | Phadke et al. |
| 2022/0079943 A1 | 3/2022 | Huang et al. |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| RU | 2202344 C2 | 4/2003 |
| RU | 2470918 C2 | 12/2012 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/002067 A2 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |

(56) References Cited

FOREIGN PATENT DOCUMENTS

| | | | | |
|---|---|---|---|---|
| WO | WO-2015/130842 A2 | 9/2015 | | |
| WO | WO-2015/130845 A1 | 9/2015 | | |
| WO | WO-2015/130854 A1 | 9/2015 | | |
| WO | WO-2017/035348 A1 | 3/2017 | | |
| WO | WO-2017/035349 A1 | 3/2017 | | |
| WO | WO-2017/035351 A1 | 3/2017 | | |
| WO | WO-2017/035352 A1 | 3/2017 | | |
| WO | WO-2017/035353 A1 | 3/2017 | | |
| WO | WO-2017/035355 A1 | 3/2017 | | |
| WO | WO-2017/035357 A1 | 3/2017 | | |
| WO | WO-2017/035360 A1 | 3/2017 | | |
| WO | WO-2017/035361 A1 | 3/2017 | | |
| WO | WO-2017/035362 A1 | 3/2017 | | |
| WO | WO-2017/035401 A1 | 3/2017 | | |
| WO | WO-2017/035405 A1 | 3/2017 | | |
| WO | WO-2017/035408 A1 | 3/2017 | | |
| WO | WO-2017/035409 A1 | 3/2017 | | |
| WO | WO-2017/035411 A1 | 3/2017 | | |
| WO | WO-2017/035413 A2 | 3/2017 | | |
| WO | WO-2017/035415 A1 | 3/2017 | | |
| WO | WO-2017/035417 A1 | 3/2017 | | |
| WO | WO-2017/035418 A1 | 3/2017 | | |
| WO | WO-2017035353 A1 | * | 3/2017 | ........... A61K 31/416 |
| WO | WO-2017/098328 A2 | 6/2017 | | |
| WO | WO-2017/127761 A1 | 7/2017 | | |
| WO | WO-2017/136395 A1 | 8/2017 | | |
| WO | WO-2018/005552 A1 | 1/2018 | | |
| WO | WO-2018/026722 A1 | 2/2018 | | |
| WO | WO-2018/160889 A1 | 9/2018 | | |
| WO | WO-2018/160891 A1 | 9/2018 | | |
| WO | WO-2018/160892 A1 | 9/2018 | | |
| WO | WO-2018160889 A1 | * | 9/2018 | ........... A61K 31/506 |
| WO | WO-2019/028284 A1 | 2/2019 | | |
| WO | WO-2019/070714 A1 | 4/2019 | | |
| WO | WO-2020/069024 A1 | 4/2020 | | |
| WO | WO-2020/109343 A1 | 6/2020 | | |

OTHER PUBLICATIONS

Gilkeson, "Complement-Targeted Therapies in Lupus," Curr Treat Options in Rheum, 1:10-18 (Jan. 22, 2015).
Harris et al., "Developments in anti-complement therapy; from disease to clinical trial," Mol Immunol. 102:89-119 (Oct. 2018).
Hom et al., "Complement Inhibitors for Treatment of Geographic Atrophy and Advanced Nonexudative AMD," Retinal Physician. 16:28-31 (Mar. 1, 2019) (7 pages).
Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).
International Preliminary Report on Patentability for International Application No. PCT/US2021/018871, dated Sep. 1, 2022 (6 pages).
International Search Report for International Application No. PCT/US20/24017, dated Jun. 26, 2020 (3 pages).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (Abstract only) (May 2018) (1 page).
Mantegazza et al., "Complement Inhibition for the Treatment of Myasthenia Gravis," Immunotargets Ther. 9:317-31 (Dec. 2020), <https://www.ncbi.nlm.nih.gov/pmc/articles/PMC7751298/>, retrieved on May 26, 2022 (24 pages).
Marinozzi et al., "C5 nephritic factors drive the biological phenotype of C3 glomerulopathies," Kidney Int. 92(5):1232-41 (Nov. 2017).
Michels et al., "Long-term follow-up including extensive complement analysis of a pediatric C3 glomerulopathy cohort," Pediatr Nephrol. 37(3):601-12 (Mar. 2022).
Partial Supplementary European Search Report for European Application No. 19857913.8, dated Apr. 13, 2022 (17 pages).
Risitano et al., "Danicopan: an oral complement factor D inhibitor for paroxysmal nocturnal hemoglobinuria," Haematologica. 106(12):3188-97 (Dec. 1, 2021).
Varelas et al., "Complement in Sickle Cell Disease: Are We Ready for Prime Time?," J Blood Med. 12:177-87 (2021), <https://www.ncbi.nlm.nih.gov/pmc/articles/PMC8001680/>, dated Mar. 23, 2021, retrieved on May 26, 2022 (19 pages).
Willows et al., "The role of complement in kidney disease," Clin Med (Lond). 20(2):156-60 (Mar. 2020) (9 pages).
Written Opinion for International Application No. PCT/US20/24017, dated Jun. 26, 2020 (6 pages).
Zhang et al., "Defining the complement biomarker profile of C3 glomerulopathy," Clin J Am Soc Nephrol. 9(11):1876-82 (supplemental materials) (Nov. 7, 2014) (10 pages).
"Are There Any Treatments for ALS?" WebMD, <https://www.webmd.com/brain/understanding-als-treatment#1>, retrieved on May 3, 2019 (8 pages).
"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, last reviewed May 31, 2017 (4 pages).
"What is Dementia?" Alzheimer's Association, <https://www.alz.org/alzheimers-dementia/what-is-dementia>, retrieved on Nov. 17, 2020 (6 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Babiker et al., "Transfer of prostasomal CD59 to CD59-deficient red blood cells results in protection against complement-mediated hemolysis," Am J Reprod Immunol. 47(3): 183-92 (2002) (Abstract Only).
Barraclough et al., "Synthesis of (2S,3R)- and (2S,3S)-[3-$^{2}$H$_{1}$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).
Brodsky, "Eculizumab: another breakthrough," Blood. 129(8):922-3 (2017).

(56) References Cited

OTHER PUBLICATIONS

Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, created Aug. 20, 2012, retrieved Jul. 14, 2020 (9 pages).
Damasio, "Alzheimer's disease and related dementias," Cecil Textbook of Medicine, 20th Edition, vol. 2. Bennet and Plum, Jun. 1992 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C-H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361 /roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) For Treatment of PNH, C3G and Complement-Mediated Diseases: Interim Phase 1 Results In Healthy Volunteers," European Hematology Association, Copenhagen 21st Congress, Jun. 9-12, Abstract ID: EHA-4145 (2016).
Gadhachanda et al., CAplus Database Summary Sheet for Document No. 164:507515, Accession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).

Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood.129(8):970-80 (2017).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).
International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).
International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).

(56) References Cited

OTHER PUBLICATIONS

International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).
International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report for International Application No. PCT/US18/20530, dated Jun. 25, 2018 (3 pages).
International Search Report for International Application No. PCT/US2018/020528, dated Apr. 24, 2018 (3 pages).
International Search Report for International Application No. PCT/US2018/045057, dated Nov. 15, 2018 (5 pages).
International Search Report for International Application No. PCT/US2018/20531, dated May 15, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/050073, dated Nov. 21, 2019 (3 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kinman, "COPD Drugs: A List of Medications to Help Relieve Your Symptoms," Healthline, <https://www.healthline.com/health/copd/drugs>, retrieved on May 3, 2019 (12 pages).
Komiya et al., CAplus Database Summary Sheet for Document No. 162:229476, Accession No. 2015:126147, CAplus on STN. (2015) (2 pages).
Krauss, "Laboratory Diagnosis of Paroxysmal Nocturnal Hemoglobinuria," Annals of Clinical & Laboratory Science. 33(4): 401-406 (2003).

Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition, vol. 2*. J. Claude Bennett and Fred Plum, p. 2050-2057 (1996).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33:479-492 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria" 59th American Society of Hematology Annual Meeting and Exposition, Dec. 9-12, Atlanta, Georgia, Poster Abstract 2198 (2017).
Pearce et al., "Failure modes in anticancer drug discovery and development," Cancer Drug Design and Discovery Edited by Stephen Neidle, Chapter 18, pp. 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann-Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).

(56) References Cited

OTHER PUBLICATIONS

Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure-Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLOS ONE. 9(10):e110053 (2014) (9 pages).
Sica et al., "Eculizumab treatment: stochastic occurrence of C3 binding to individual PNH erythrocytes," J Hematol Oncol. 10(1):126 (2017) (10 pages).
Simone, "Oncology: Introduction," Cecil Textbook of Medicine, 20th Edition, vol. 1, pp. 1004-1010, (1996).
Stanton et al., "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al. "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Written Opinion for International Application No. PCT/US2018/045057, dated Nov. 15, 2018 (7 pages).
Written Opinion for International Application No. PCT/US2019/034210, dated Sep. 13, 2019 (17 pages).
Written Opinion for International Application No. PCT/US2019/050073, dated Nov. 21, 2019 (4 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).

\* cited by examiner

| Index | Angle | d Value | Net Intensity | Gross Intensity | Rel. Intensity |
|---|---|---|---|---|---|
| 0 | 3.730 | 23.66686 | 1589 | 1816 | 100.0 % |
| 1 | 4.142 | 21.31449 | 62.0 | 250 | 3.9 % |
| 2 | 6.715 | 13.15184 | 143 | 259 | 9.0 % |
| 3 | 7.917 | 11.15826 | 151 | 280 | 9.5 % |
| 4 | 8.466 | 10.43556 | 137 | 271 | 8.6 % |
| 5 | 9.349 | 9.45204 | 385 | 527 | 24.2 % |
| 6 | 9.838 | 8.98370 | 151 | 296 | 9.5 % |
| 7 | 10.873 | 8.13027 | 78.2 | 227 | 4.9 % |
| 8 | 11.125 | 7.94668 | 70.0 | 220 | 4.4 % |
| 9 | 11.659 | 7.58414 | 164 | 315 | 10.3 % |
| 10 | 12.066 | 7.32908 | 46.4 | 197 | 2.9 % |
| 11 | 12.802 | 6.90920 | 60.7 | 209 | 3.8 % |
| 12 | 13.295 | 6.65443 | 199 | 343 | 12.5 % |
| 13 | 14.637 | 6.04705 | 164 | 310 | 10.3 % |
| 14 | 15.194 | 5.82843 | 154 | 304 | 9.7 % |
| 15 | 15.520 | 5.70493 | 280 | 432 | 17.6 % |
| 16 | 15.787 | 5.60892 | 243 | 396 | 15.3 % |
| 17 | 16.552 | 5.35135 | 200 | 350 | 12.6 % |
| 18 | 17.527 | 5.05604 | 49.8 | 192 | 3.1 % |
| 19 | 17.660 | 5.01812 | 38.3 | 179 | 2.4 % |
| 20 | 18.497 | 4.79286 | 67.6 | 219 | 4.3 % |
| 21 | 18.611 | 4.76373 | 70.9 | 226 | 4.5 % |
| 22 | 19.021 | 4.66195 | 98.1 | 265 | 6.2 % |
| 23 | 19.380 | 4.57653 | 108 | 284 | 6.8 % |

FIG. 4A

| 24 | 21.375 | 4.15354 | 184 | 392 | 11.6 % |
|---|---|---|---|---|---|
| 25 | 22.049 | 4.02813 | 125 | 336 | 7.9 % |
| 26 | 22.322 | 3.97945 | 146 | 357 | 9.2 % |
| 27 | 23.130 | 3.84230 | 77.6 | 285 | 4.9 % |
| 28 | 23.802 | 3.73538 | 51.6 | 259 | 3.2 % |
| 29 | 24.324 | 3.65625 | 52.9 | 265 | 3.3 % |
| 30 | 24.916 | 3.57083 | 70.8 | 285 | 4.5 % |
| 31 | 25.646 | 3.47078 | 97.8 | 311 | 6.2 % |
| 32 | 26.801 | 3.32376 | 51.0 | 253 | 3.2 % |
| 33 | 27.529 | 3.23746 | 54.0 | 243 | 3.4 % |
| 34 | 27.937 | 3.19111 | 35.6 | 215 | 2.2 % |
| 35 | 43.671 | 2.07101 | 44.1 | 162 | 2.8 % |

FIG. 4B

Compound 1

Compound 2

Compound 3

MORPHIC FORMS OF COMPLEMENT FACTOR D INHIBITORS

CROSS-REFERENCE TO RELATED APPLICATIONS

This application claims the benefit of priority to U.S. Application No. 62/736,294 filed Sep. 25, 2018; U.S. Application No. 62/757,565 filed Nov. 8, 2018; U.S. Application No. 62/760,520 filed Nov. 13, 2018; and U.S. Application No. 62/796,776 filed Jan. 25, 2019. The entirety of each of these applications is incorporated herein by reference.

FIELD OF THE INVENTION

This invention provides advantageous isolated morphic forms of the complement factor D inhibitor (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide.

BACKGROUND

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within the C3 protein to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning of Factor H, the alternative pathway of the complement cascade is overly activated leading to cellular damage.

Paroxysmal nocturnal hemoglobinuria (PNH) is a non-malignant, hematological disorder characterized by the expansion of hematopoietic stem cells and progeny mature blood cells that are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections.

Additional complement-mediated disorders include those classified under component 3 glomerulopathy (C3G). C3G is a recently defined entity comprised of dense deposit disease (DDD) and C3 glomerulonephritis (C3GN) which encompasses a population of chronic kidney diseases wherein elevated activity of the alternative complement pathway and terminal complement pathway results in glomerular deposits made solely of complement C3 and no immunoglobulin (Ig).

Immune-complex membranoproliferative glomerulonephritis (IC-MPGN) is a renal disease which shares many clinical, pathologic, genetic and laboratory features with C3G, and therefore can be considered a sister disease of C3G. In the majority of patients with IC-MPGN, an underlying disease or disorder-most commonly infections, autoimmune diseases, or monoclonal gammopathies—are identified to which the renal disease is secondary. Patients with idiopathic IC-MPGN can have low C3 and normal C4 levels, similar to those observed in C3G, as well as many of the same genetic or acquired factors that are associated with abnormal alternative pathway activity. Although there are current hypotheses suggesting that the majority of IC-MPGN is attributable to over activity of the classical pathway, those patients with a low C3 and a normal C4 are likely to have significant overactivity of the alternative pathway. IC-MPGN patients with a low C3 and a normal C4 may benefit from alternative pathway inhibition.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis optica (NMO), myasthenia gravis (MG), fatty liver, nonalcoholic steatohepatitis (NASH), liver inflammation, cirrhosis, liver failure, dermatomyositis, and amyotrophic lateral sclerosis.

Factor D is an attractive target for inhibition or regulation of the complement cascade due to its early and essential role in the alternative complement pathway, and for its potential role in signal amplification within the classical and lectin complement pathways. Inhibition of Factor D effectively interrupts the pathway and attenuates the formation of the membrane attack complex. Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2012093101, WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, and WO2016088082.

Additional complement factor D inhibitors are described in U.S. Pat. Nos. 9,598,446; 9,643,986; 9,663,543; 9,695,205; 9,732,103; 9,732,104; 9,758,537; 9,796,741; 9,828,396; 10,000,516; 10,005,802; 10,011,612; 10,081,645; 10,087,203; 10,092,584; 10,100,072; 10,138,225; 10,189,869; 10,106,563; 10,301,336; and 10,287,301; International Publication Nos. WO2019/028284; WO2018/160889; WO2018/160891; WO2018/160892; WO2017/035348; WO2017/035349; WO 2017/035351; WO 2017/035352; WO 2017/035353; WO 2017/035355; WO2017/035357; WO2017/035360; WO2017/035361; WO2017//035362; WO2017/035415; WO2017/035401; WO2017/035405; WO2017/035413; WO2017/035409; WO2017/035411; WO2017/035417; WO2017/035408 WO2015/130784; WO2015/130795; WO2015/130806; WO2015/130830; WO2015/130838; WO2015/130842; WO2015/130845; and WO2015/130854; and U.S. Patent Publication Nos. US 2016-0361329; US 2016-0362432; US 2016-0362433; US 2016-0362399; US 2017-0056428; US 2017-0057950; US 2017-0057993; US 2017-0189410; US 2017-0226142; US 2017-0260219; US 2017-0298084; US 2017-0298085; US 2018-0022766; US 2018-0022767; US 2018-0072762; US 2018-0030075; US 2018-0169109; US 2018-0177761; US 2018-0179185; US 2018-0179186; US 2018-0179236; US 2018-0186782; US 2018-0201580; US 2019-0031692; US 2019-0048033; US 2019-0144473; and US 2019-0211033 all owned by Achillion Pharmaceuticals, Inc.

Given the wide variety of medical disorders that are caused by detrimental immune or inflammatory responses, it would be beneficial to provide additional advantageous compounds and forms thereof for advantageous delivery that may increase therapeutic activity and/or stability.

SUMMARY

It has been discovered that Compound 3 ((1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide) can be prepared in only a few highly purified morphic forms that exhibit advantageous properties. Several morphic forms of Compound 3, including Form A, Form B, and Form M, are now found to exist. These morphic forms are beneficial for therapeutic efficacy and for the manufacture of pharmaceutical formulations. Compound 3 is disclosed in PCT Application WO2017035353 assigned to Achillion Pharmaceuticals.

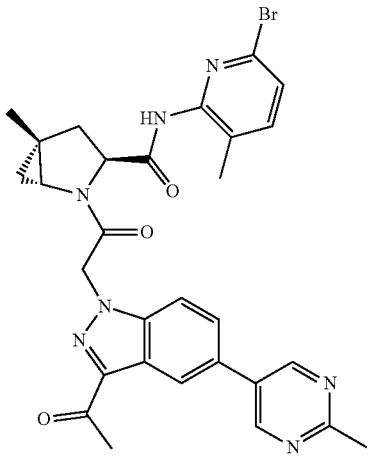

Compound 3

As discussed in Example 2, 27 unique solvents and multiple crystallization techniques, resulted in the discovery of four stable forms: Form A, Form B, Form J, and Form M. In particular, Form A was found to be highly stable at 80° C. with no reduction in purity and was fully characterized (Example 6 and Example 7). Additional studies on Compound 3 Form A involving recrystallization techniques resulted in the formation of Form B, Form M, and Form J. These forms were characterized (see for example, Example 9 and Example 10). Form B is highly stable and no changes by XRPD or HPLC were observed when the material was stored at 40° C./75% RH, 80° C. or at ambient conditions (Example 10).

Thus, the present invention generally provides an isolated morphic form of Compound 3, pharmaceutical compositions containing such morphic form, methods of inhibiting or reducing the activity of the enzyme factor D in a host using said isolated morphic form, as well as treating a host having a paroxysmal nocturnal hemoglobinuria (PNH) or C3 glomerulopathy (C3G) using the morphic form described herein, and methods of preparing such morphic form. In one embodiment, the morphic Form is Form A. In one embodiment, the morphic form is Form B. In one embodiment, the morphic form is Form M.

In one aspect of the present invention the morphic form Compound 3 is characterized by the 2theta values in the following figures ±0.5°, 0.4°, or 0.3° 2theta. In one aspect of the present invention the morphic form of Compound 3 is characterized by the 2theta values in the following figures ±0.2° 2theta. In one aspect of the present invention the morphic form of Compound 3 is characterized by the 2theta values in the following figures ±0.1° 2theta. Therefore, whenever a XRPD peak is discussed or depected as a ±0.2° 2theta, it should be understood that alternative emdiments are ±0.3° 2theta, ±0.4° 2theta and ±0.4° 2theta.

In one aspect of the present invention the morphic form of Compound 3 is characterized by at least three 2theta values from its representative XRPD pattern in the Figures. In one aspect of the present invention the morphic form of Compound 3 is characterized by at least four 2theta values from its representative XRPD pattern in the Figures. In one aspect of the present invention the morphic form of Compound 3 is characterized by at least five, six, seven, or eight 2theta values from its representative XRPD pattern in the Figures.

In this invention, the XRPD pattern is not used to identify the chemical structure of the compound, but instead to distinguish between solid forms of the compound. Therefore, in some cases only a few, or perhaps even one, characterstic peak can distinguish one form from another form of the compound of known chemical structure.

In one embodiment the provided morphic form of Compound 3 is used to produce highly pure material for pharmaceutical grade drug dosage forms. For example, the provided morphic form may be used in a spray dry dispersion technique to produce highly pure amorphous Compound 3.

Improved synthetic methods for the synthesis of Compound 1, Compound 2, and Compound 3 are also provided. Compound 1 is generally disclosed in PCT Application WO2015130795 assigned to Achillion Pharmaceuticals. Compound 2 and Compound 3 are generally disclosed in PCT Application WO2017035353 assigned to Achillion Pharmaceuticals.

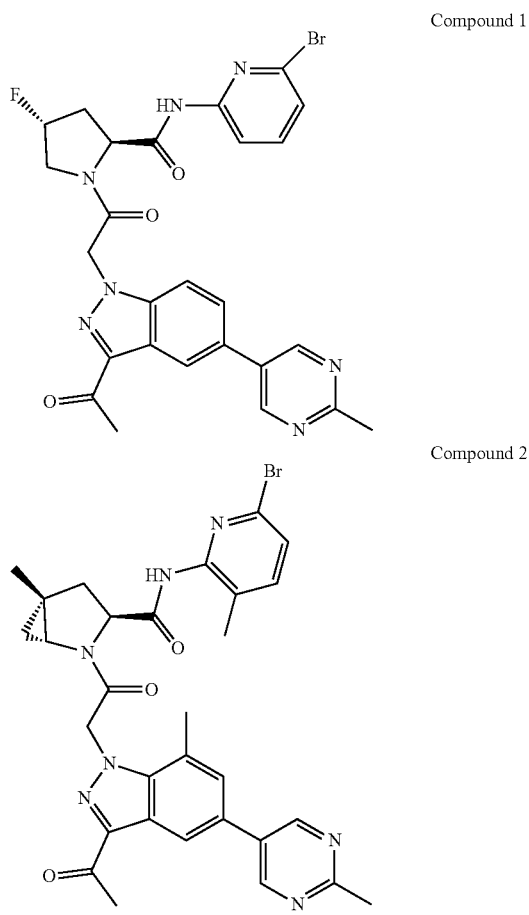

Compound 1

Compound 2

BRIEF DESCRIPTION OF THE DRAWINGS

FIG. 4A and FIG. 4B are peak intensity tables corresponding to the XRPD graph in FIG. 3. In one embodiment Compound 3 Form A is characterized by at least 3, 4, 5, or 6 2theta values ±0.2 2theta with a relative intensity of at least 10%.

DETAILED DESCRIPTION OF THE INVENTION

It cannot be predicted in advance whether a compound exists in more than one solid form or what the various properties of any solid form might be if one or more does exist, or whether the properties are advantageous for a therapeutic dosage form or for manufacturing requirements, meeting pharmaceutical specifications and/or for advantageous formulations. As one example, the drug ritonavir is active in one polymorphic form and inactive in another form, and the inactive form is the more stable.

Solid forms of compounds can be characterized by analytical methods such as X-ray powder diffraction pattern (XRDP or PXRD), thermogravimetric analysis (TGA), TGA with IR off-gas analysis, differential Scanning Calorimetry (DSC), melting point, FT-Raman spectroscopy, dynamic Vapor Sorption (DVS), polarized light microscopy (PLM) or other techniques known in the art.

Compound 3

Polymorph studies of Compound 3 resulted in the discovery of three superior morphic forms (Forms A, B, and M) out of at least thirteen identified forms. Compound 3 Forms are characterized by the XRPD patterns shown in FIGS. 1 to 24 and 51 to 55.

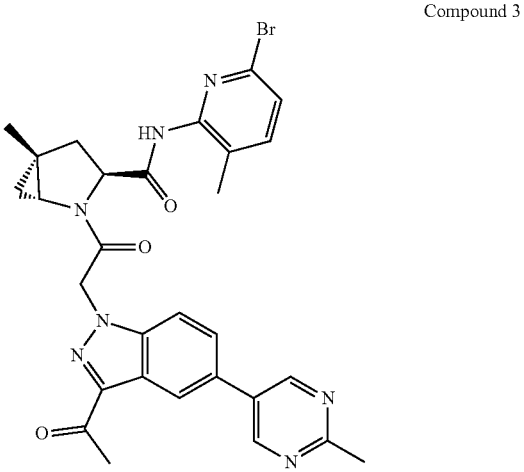

Compound 3

Form A

Figure 3:
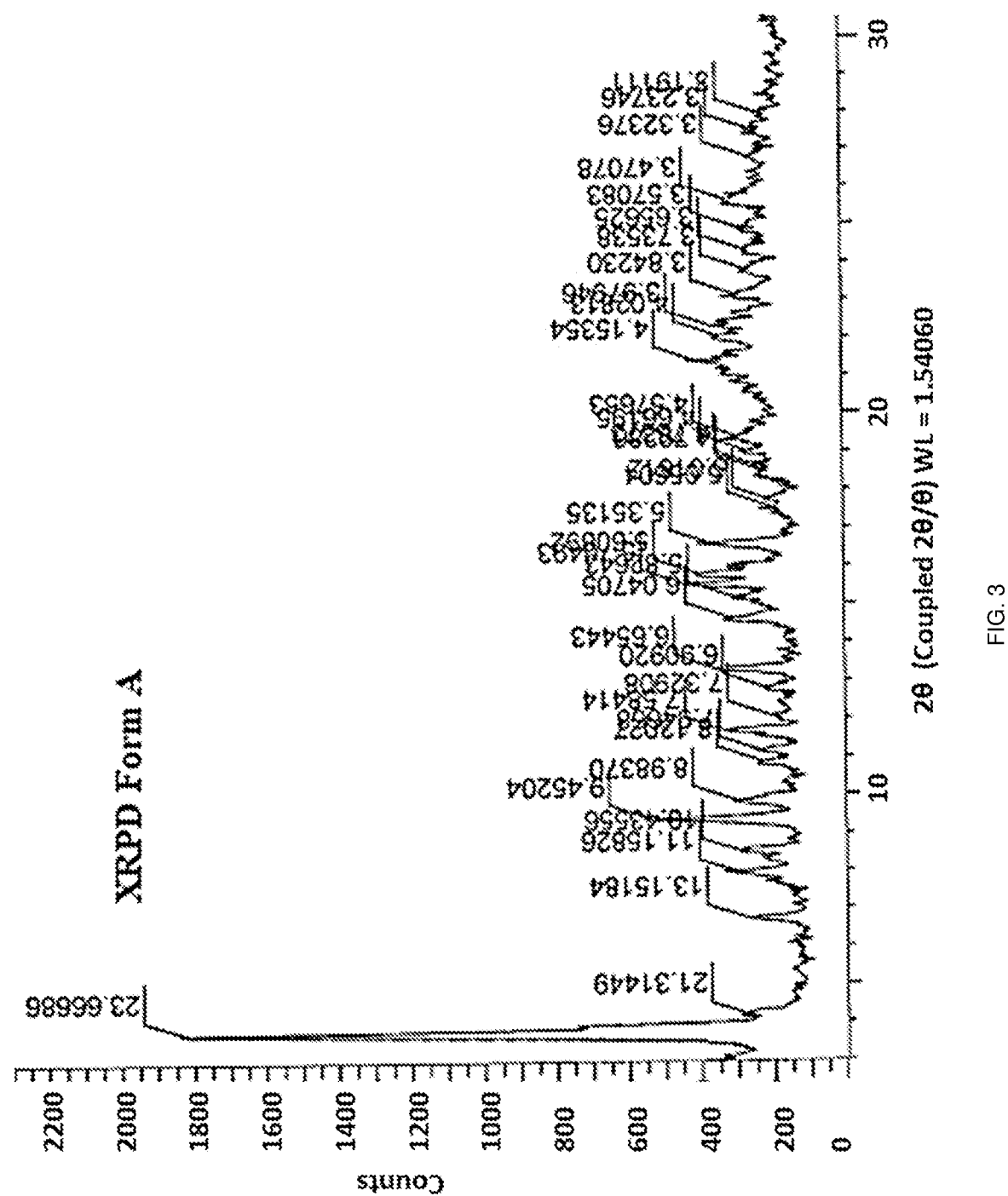
FIG. 3 is an XRPD of Compound 3 Form A as described in Example 2. The x-axis is 2Theta measured in degrees and the y-axis is intensity measured in counts.
Figure 5:
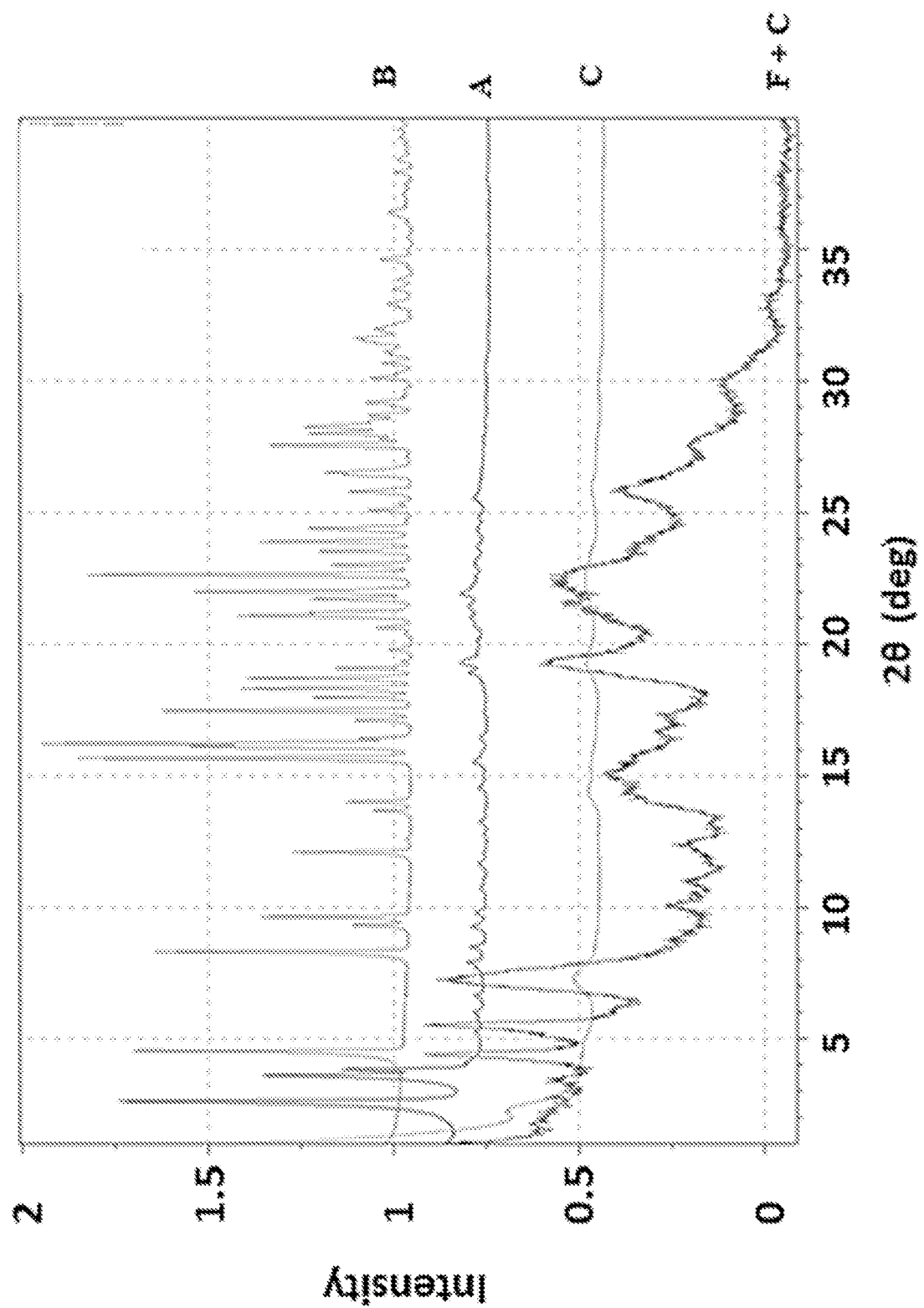
FIG. 5 provides XRPD (X-ray powder diffraction) patterns of several Compound 3 Forms as described in Example 2. The x-axis is 2Theta measured in degrees and the y-axis is intensity measured in counts. Form B, A, C, and a mixture of Form F/Form C are shown.
Figure 6:
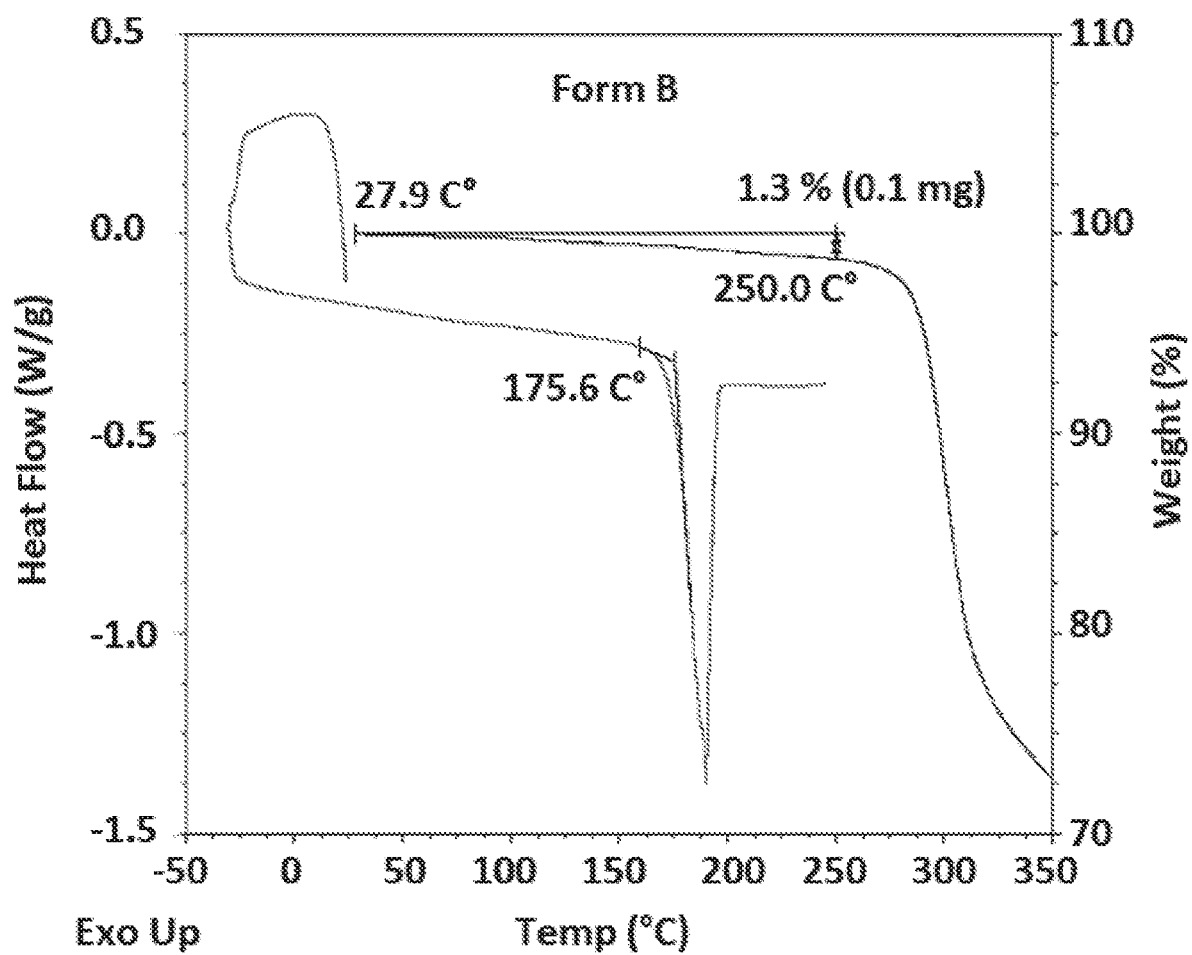
FIG. 6 is a DSC and a TGA graph of Compound 3 Form B as described in Example 2. The x-axis is temperature measured in ° C., the left y-axis is heat flow measured in (W/g), and the right y-axis is weight measured in percent.
Figure 7:
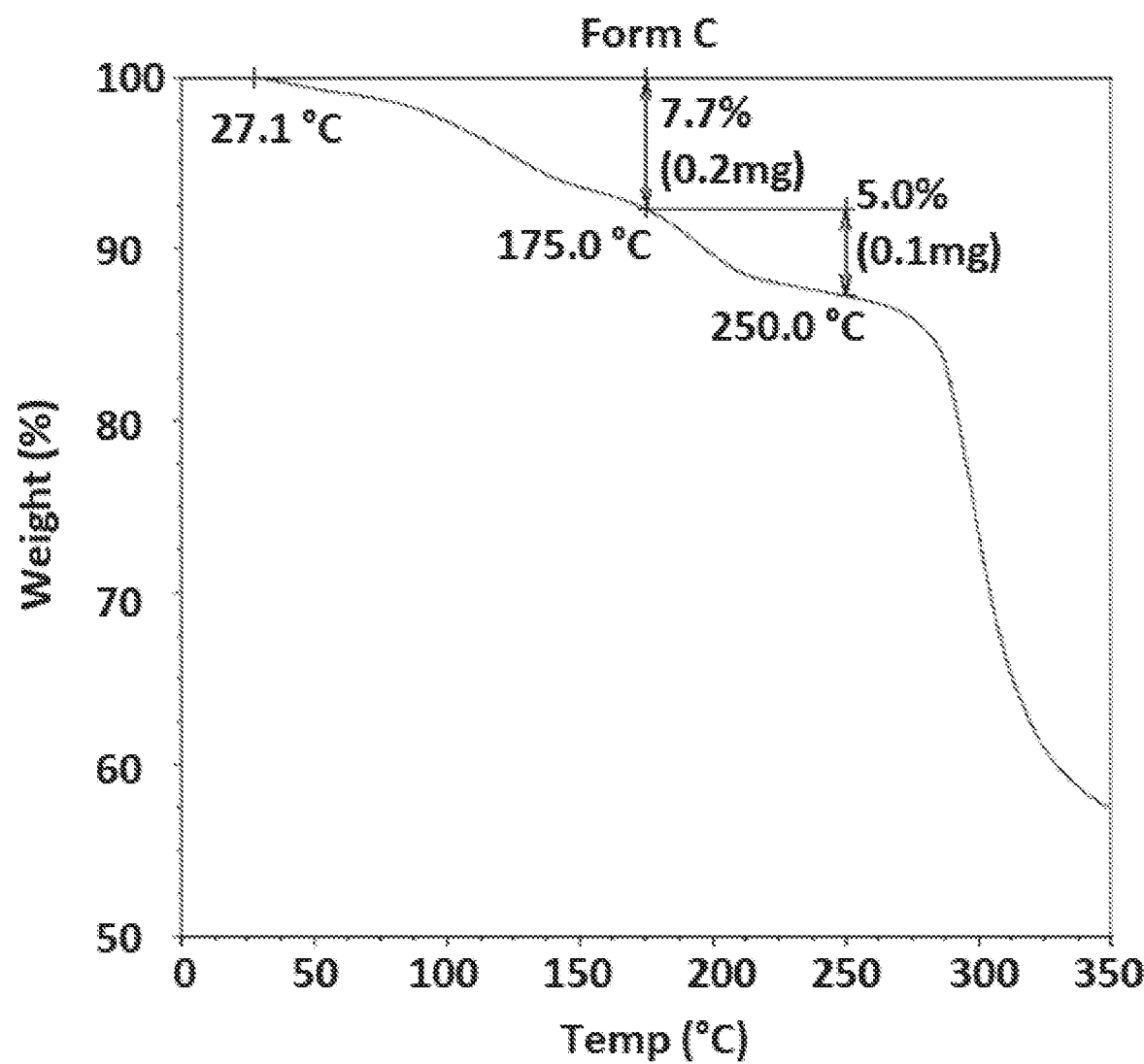
FIG. 7 is a DSC and a TGA graph of Compound 3 Form C as described in Example 2. The x-axis is temperature measured in ° C., the left y-axis is heat flow measured in (W/g), and the right y-axis is weight measured in percent.
Figure 8:
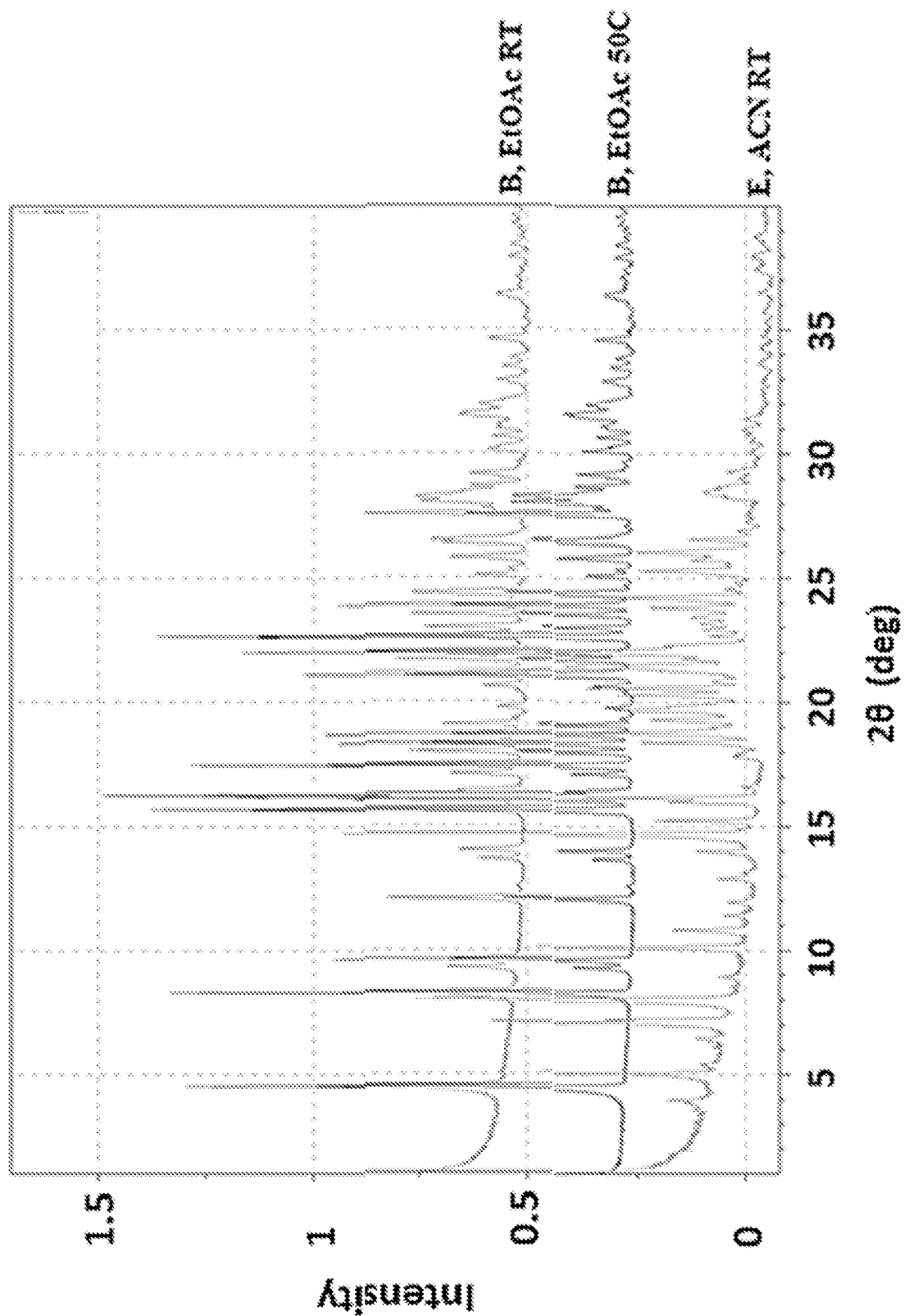
FIG. 8 provides XRPD patterns of Compound 3 Form B before and after 50° C. heat stress in EtOAc slurries and Form E in an acetonitrile slurry at room temperature as described in Example 2.
Figure 9:
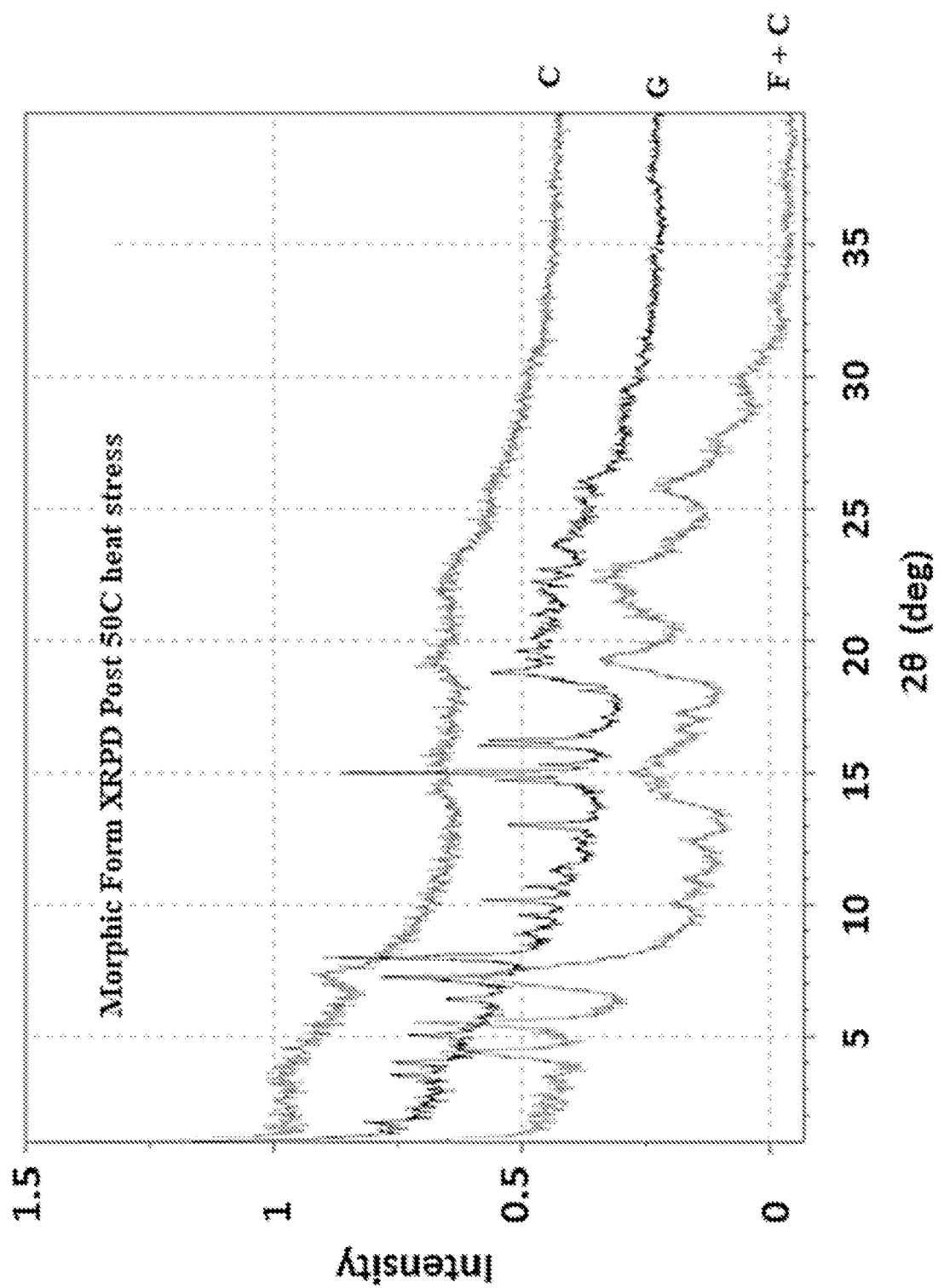
FIG. 9 provides XRPD patterns of Compound 3 Form C, Form G, and a mixture of Form F and C after 50° C. heat stress as described in Example 2.
Figure 51:
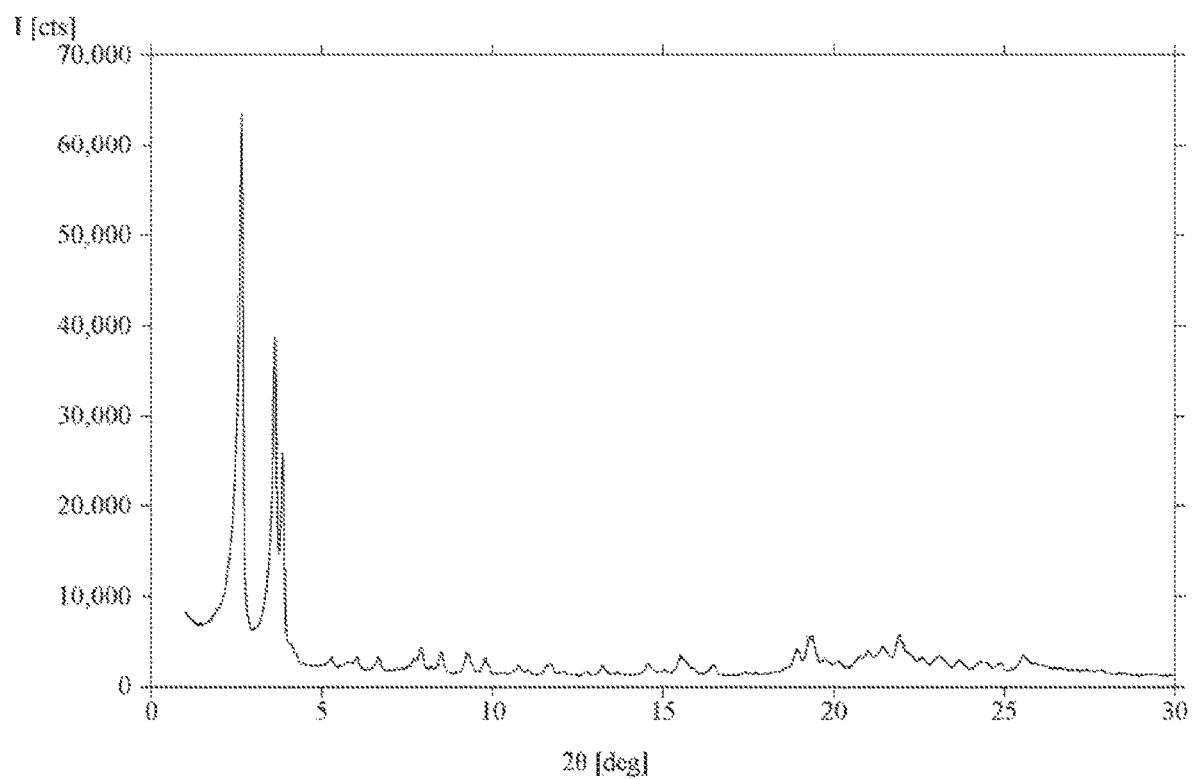
FIG. 51 is an XRPD diffractogram for Compound 3 Form A.

Form A is characterized by a XRPD pattern in or substantially similar to that set forth in FIG. 3 of FIG. 51. In one embodiment, isolated Compound 3 Form A is characterized by the DSC in FIG. 37.

In one embodiment, Compound 3 Form A is characterized by a XRPD pattern comprising
a) 2θ values including or selected from 3.73, 9.3, 11.7, 9.5, 7.6, 6.7, 6.0, 5.7, 5.6, 5.4, and 4.2±0.2°2θ;
b) at least two, three, or four 2θ values selected from 3.73, 9.3, 11.7, 9.5, 7.6, 6.7, 6.0, 5.7, 5.6, 5.4, and 4.2±0.2°2θ;
c) at least five, six, or seven 2θ values selected from 3.73, 9.3, 11.7, 9.5, 7.6, 6.7, 6.0, 5.7, 5.6, 5.4, and 4.2±0.2°2θ;
d) at least eight or nine 2θ values selected from 3.73, 9.3, 11.7, 9.5, 7.6, 6.7, 6.0, 5.7, 5.6, 5.4, and 4.2±0.2°2θ;
e) 2θ values including at least or selected from 3.73, 9.3, 11.7, 9.5, 7.6, 6.7, 6.0, 5.7, 5.6, 5.4, and 4.2±0.2°2θ; or
f) at least one 2θ value selected from 3.73, 9.3, 11.7, 9.5, 7.6, 6.7, 6.0, 5.7, 5.6, 5.4, and 4.2±0.2°2θ.

In one embodiment, isolated Compound 3 Form A is characterized as having a $T_g$ between 110° C. and 120° C. Form A can be prepared using selective crystallization. The method can be carried out by treating a solution comprising a suitable solvent(s) and Compound 3 optionally in the presence of one or more seeds comprising Form A to conditions that provide for the crystallization of Form A as described in more detail below. In one embodiment Form A is highly stabile with a long shelf life and minimal degradation.

The present invention includes at least the following embodiments of Compound 3 Form A:

a) an isolated crystalline Form A of Compound 3 characterized by an XRPD pattern comprising at least three 2theta values selected from 3.7±0.2°, 9.3±0.2°, 11.7±0.2°, 9.5±0.2°, 7.6±0.2°, 6.7±0.2°, 6.0±0.2°, 5.7±0.2°, 5.6±0.2°, 5.4±0.2°, and 4.2±0.2°;
b) the isolated crystalline Form A of Compound 3 of embodiment (a) characterized by an XRPD pattern comprising at least four 2theta values selected from 3.7±0.2°, 9.3±0.2°, 11.7±0.2°, 9.5±0.2°, 7.6±0.2°, 6.7±0.2°, 6.0±0.2°, 5.7±0.2°, 5.6±0.2°, 5.4±0.2°, and 4.2±0.2°;
c) the isolated crystalline Form A of Compound 3 of embodiments (a) or (b) characterized by an XRPD pattern comprising at least the 2theta value of 3.7±0.2°;
d) the isolated crystalline Form A of Compound 3 of embodiments (a), (b), or (c) characterized by an XRPD pattern comprising at least the 2theta value of 9.3±0.2°;
e) the isolated crystalline Form A of Compound 3 of any one of embodiments (a)-(d) wherein the XRPD pattern has the characteristic 2θ values of FIG. 3;
f) a pharmaceutical composition comprising the isolated crystalline Form A of Compound 3 of any one of embodiments (a)-(e) in a pharmaceutically acceptable excipient for solid dosage delivery;
g) a method of the treatment of a Complement Factor D mediated disorder comprising administering to a subject in need thereof a therapeutically effective amount of the isolated crystalline Form A of Compound 3 or a pharmaceutical composition thereof according to any one of embodiments (a)-(e), optionally in a pharmaceutically acceptable excipient for solid dosage delivery;
h) the method of embodiment of (g) wherein the subject is a human;
i) the isolated crystalline Form A of Compound 3 of any one of embodiments (a)-(e), optionally in a pharmaceutically acceptable excipient for solid dosage delivery, for use to treat a Complement Factor D mediated disorder in a subject in need thereof,
j) the isolated crystalline Form A of Compound 3 of embodiment (i), wherein the subject is a human;
k) the use of the isolated crystalline Form A of Compound 3 or a pharmaceutical composition thereof of any of embodiments (a)-(e), optionally in a pharmaceutically acceptable excipient for solid dosage delivery, in the manufacture of a medicament for the treatment of a Complement Factor D mediated disorder in a subject in need thereof;
l) the use of embodiment (k) wherein the subject is a human;
m) any of the above embodiments wherein the peaks are instead within ±0.4°; and
n) any of the above embodiments wherein the peaks are instead within ±0.3°;

In another embodiment the present invention includes at least the following embodiments of Compound 3 Form A:

a) an isolated crystalline Form A of Compound 3 characterized by an XRPD pattern comprising at least one 2theta values selected from 2.6±0.4°, 3.6±0.4°, and 3.8±0.4°;
b) the isolated crystalline Form A of Compound 3 of embodiment (a) characterized by an XRPD pattern comprising at least two 2theta values selected from 2.6±0.4°, 3.6±0.4°, and 3.8±0.4°;
c) the isolated crystalline Form A of Compound 3 of embodiment (a) characterized by an XRPD pattern comprising the 2theta values selected from 2.6±0.4°, 3.6±0.4°, and 3.8±0.4°;
d) the isolated crystalline Form A of Compound 3 of embodiments (a) or (b) characterized by an XRPD pattern comprising at least the 2theta value of 2.6±0.2°;
e) the isolated crystalline Form A of Compound 3 of any one of embodiments (a)-(d) characterized by an XRPD pattern comprising at least the 2theta value of 3.6±0.2°;
f) the isolated crystalline Form A of Compound 3 of any one of embodiments (a)-(e) wherein the XRPD pattern has the characteristic 2θ values of FIG. 51;
g) a pharmaceutical composition comprising the isolated crystalline Form A of Compound 3 of any one of embodiments (a)-(f) in a pharmaceutically acceptable excipient for solid dosage delivery;
h) a method of the treatment of a Complement Factor D mediated disorder comprising administering to a subject in need thereof a therapeutically effective amount of the isolated crystalline Form A of Compound 3 or a pharmaceutical composition thereof according to any one of embodiments (a)-(f), optionally in a pharmaceutically acceptable excipient for solid dosage delivery;
i) the method of embodiment of (h) wherein the subject is a human;
j) the isolated crystalline Form A of Compound 3 of any one of embodiments (a)-(f), optionally in a pharmaceutically acceptable excipient for solid dosage delivery, for use to treat a Complement Factor D mediated disorder in a subject in need thereof,
k) the isolated crystalline Form A of Compound 3 of embodiment (j), wherein the subject is a human;
l) the use of the isolated crystalline Form A of Compound 3 or a pharmaceutical composition thereof of any of embodiments (a)-(f), optionally in a pharmaceutically acceptable excipient for solid dosage delivery, in the manufacture of a medicament for the treatment of a Complement Factor D mediated disorder in a subject in need thereof;
m) the use of embodiment (1) wherein the subject is a human.

Form B

Figure 1:
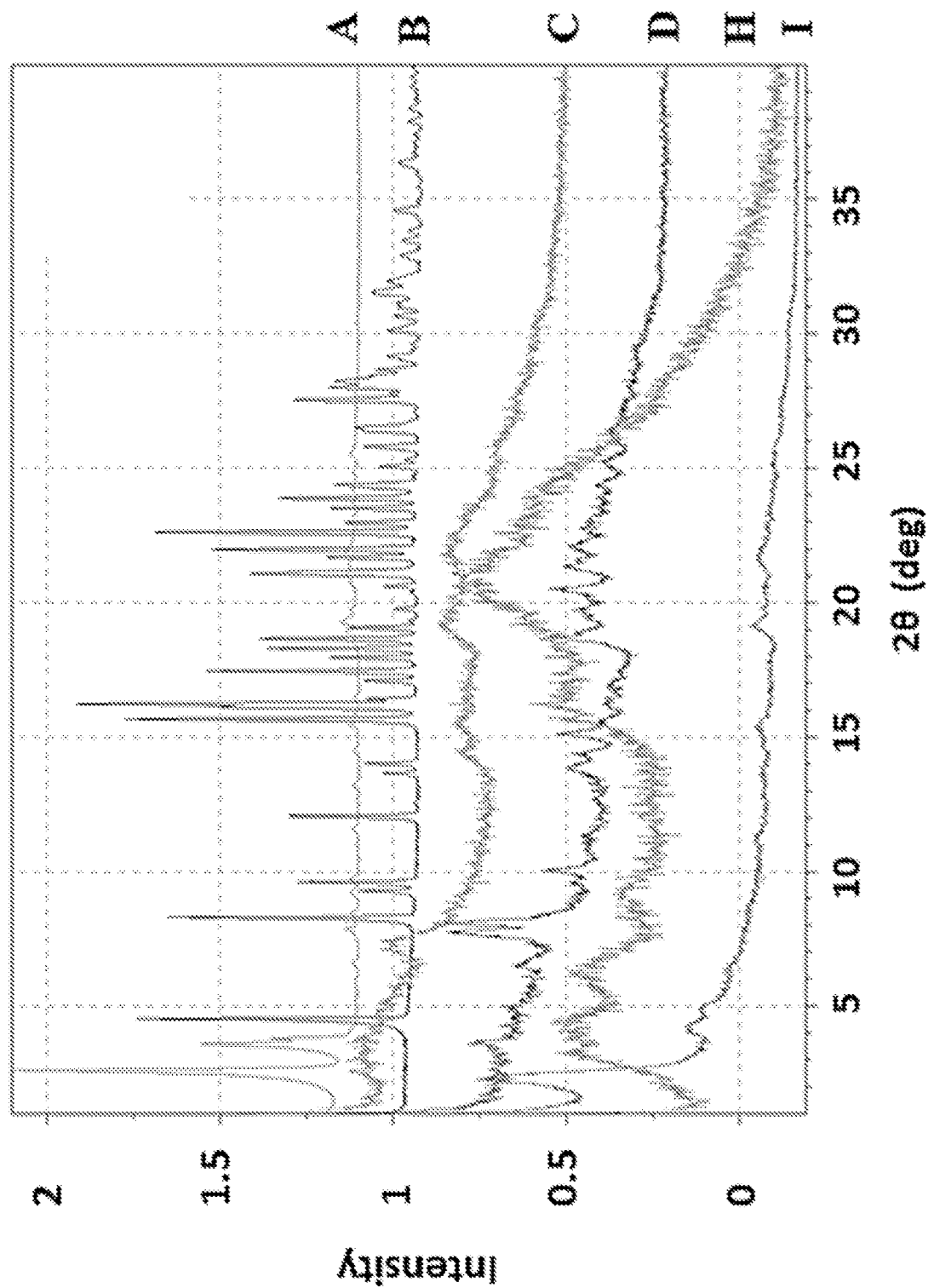
FIG. 1 provides XRPD (X-ray powder diffraction) patterns of several Compound 3 Forms as described in Example 2. The x-axis is 2Theta measured in degrees and the y-axis is intensity measured in counts. Form A, B, C, D, H, and I are shown.
Figure 2:
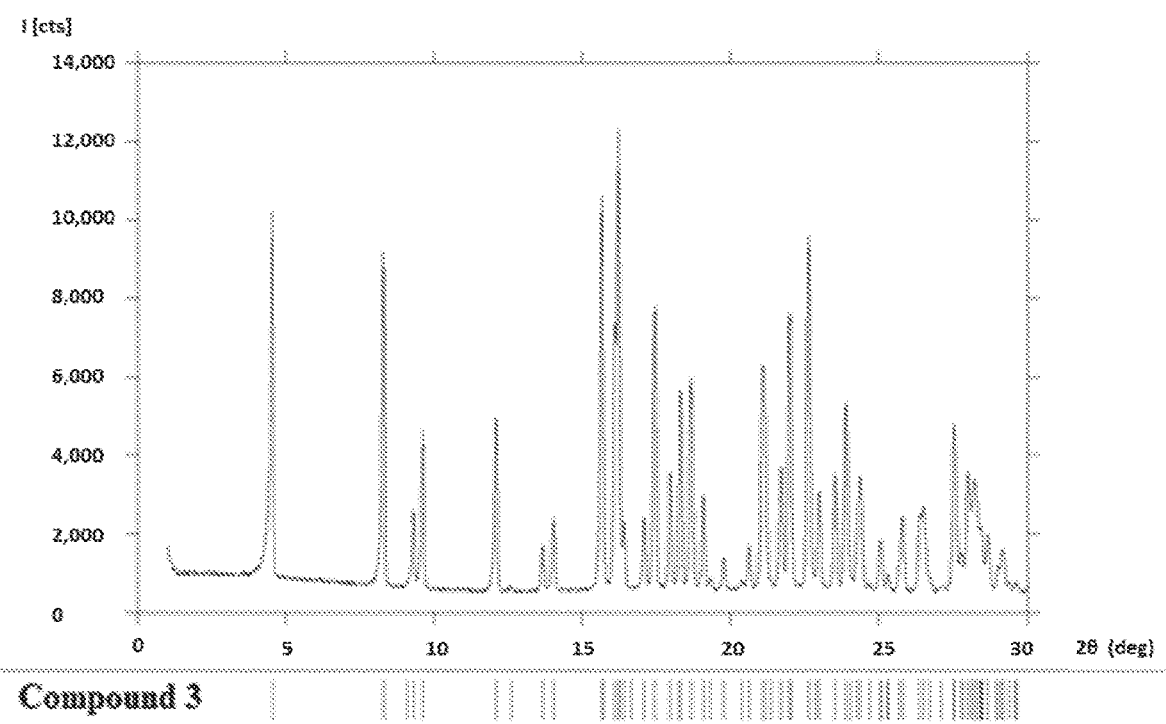
FIG. 2 is an XRPD of Compound 3 Form B collected with Cu-Kα as described in Example 2. The XRPD conditions are as listed: Bravais Type: primitive monoclinic; a [Å]: 10.651; b [Å]: 6.672; c [Å]: 19.447; α [deg]: 90; β [deg]: 93.32; γ [deg]: 90; volume [Å³/cell]: 1,380.9; chiral contents: chiral; extinction symbol: P 1 2₁ 1; and space group(s): P2₁ (4). The x-axis is 2Theta measured in degrees and the y-axis is intensity measured in counts.
Figure 52:
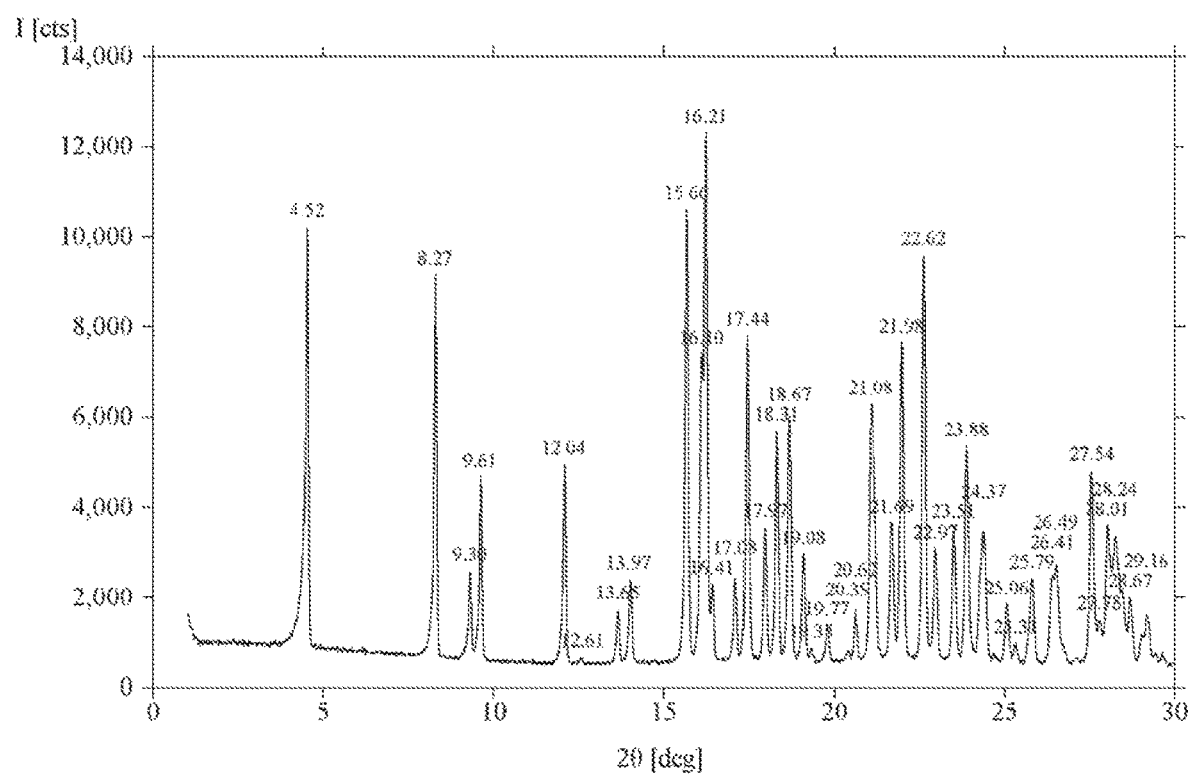
FIG. 52 is an XRPD diffractogram for Compound 3 Form B.

Form B is characterized by a XRPD pattern in or substantially similar to that set forth in FIG. 2 or FIG. 52. In one embodiment, isolated Compound 3 Form B is characterized by the DSC in FIG. 21. In one embodiment, isolated Compound 3 Form B is characterized as having a broad endothermic feature at approximately 176° C. in a differential scanning calorimetry analysis. In one embodiment, isolated Compound 3 Form B is characterized as melting between 150° C. and 250° C. in a VT-XRPD analysis. In one embodiment Form B is highly stabile with a long shelf life and minimal degradation.

The present invention includes at least the following embodiments of Compound 3 Form B:

a) an isolated crystalline Form B of Compound 3 characterized by an XRPD pattern comprising at least three 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
b) the isolated crystalline Form B of Compound 3 of embodiment (a) characterized by an XRPD pattern comprising at least four 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
c) the isolated crystalline Form B of Compound 3 of embodiment (a) characterized by an XRPD pattern comprising at least four 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
d) the isolated crystalline Form B of Compound 3 of embodiment (a) characterized by an XRPD pattern comprising at least five 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
e) the isolated crystalline Form B of Compound 3 of embodiment (a) characterized by an XRPD pattern comprising at least six 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
f) the isolated crystalline Form B of Compound 3 of embodiment (a) characterized by an XRPD pattern comprising all of the 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°;
g) the isolated crystalline Form B of Compound 3 of any one of embodiments (a)-(e) characterized by an XRPD pattern comprising at least the 2theta value of 16.2±0.4°;
h) the isolated crystalline Form B of Compound 3 of any one of embodiments (a)-(e) characterized by an XRPD pattern comprising at least the 2theta value of 15.7±0.4°;
i) the isolated crystalline Form B of Compound 3 of any one of embodiments (a)-(e) wherein the XRPD pattern has the characteristic 2θ values of FIG. 52;
j) the isolated crystalline Form B of Compound 3 of any one of embodiments (a)-(h) wherein each 2theta value is within 0.3°;
k) the isolated crystalline Form B of Compound 3 of any one of embodiments (a)-(h) wherein each 2theta value is within 0.2°;
l) a pharmaceutical composition comprising the isolated crystalline Form B of Compound 3 of any one of embodiments (a)-(k) in a pharmaceutically acceptable excipient for solid dosage delivery;
m) a method of the treatment of a Complement Factor D mediated disorder comprising administering to a subject in need thereof a therapeutically effective amount of the isolated crystalline Form B of Compound 3 or a pharmaceutical composition thereof according to any one of embodiments (a)-(k), optionally in a pharmaceutically acceptable excipient for solid dosage delivery;
n) the method of embodiment of (m) wherein the subject is a human;
o) the isolated crystalline Form B of Compound 3 of any one of embodiments (a)-(k), optionally in a pharmaceutically acceptable excipient for solid dosage delivery, for use to treat a Complement Factor D mediated disorder in a subject in need thereof,
p) the isolated crystalline Form B of Compound 3 of embodiment (o), wherein the subject is a human;
q) the use of the isolated crystalline Form B of Compound 3 or a pharmaceutical composition thereof of any of embodiments (a)-(k), optionally in a pharmaceutically acceptable excipient for solid dosage delivery, in the manufacture of a medicament for the treatment of a Complement Factor D mediated disorder in a subject in need thereof;
r) the use of embodiment (q) wherein the subject is a human.

Form B can be prepared using selective crystallization. The method can be carried out by treating a solution comprising a suitable solvent(s) and Compound 3 optionally in the presence of one or more seeds comprising Form B to conditions that provide for the crystallization of Form B as described in more detail below. In one embodiment, Form B is prepared by temperature cycling amorphous Compound 3 in acetone and 2-propanol/heptane.

Form M

Figure 18:
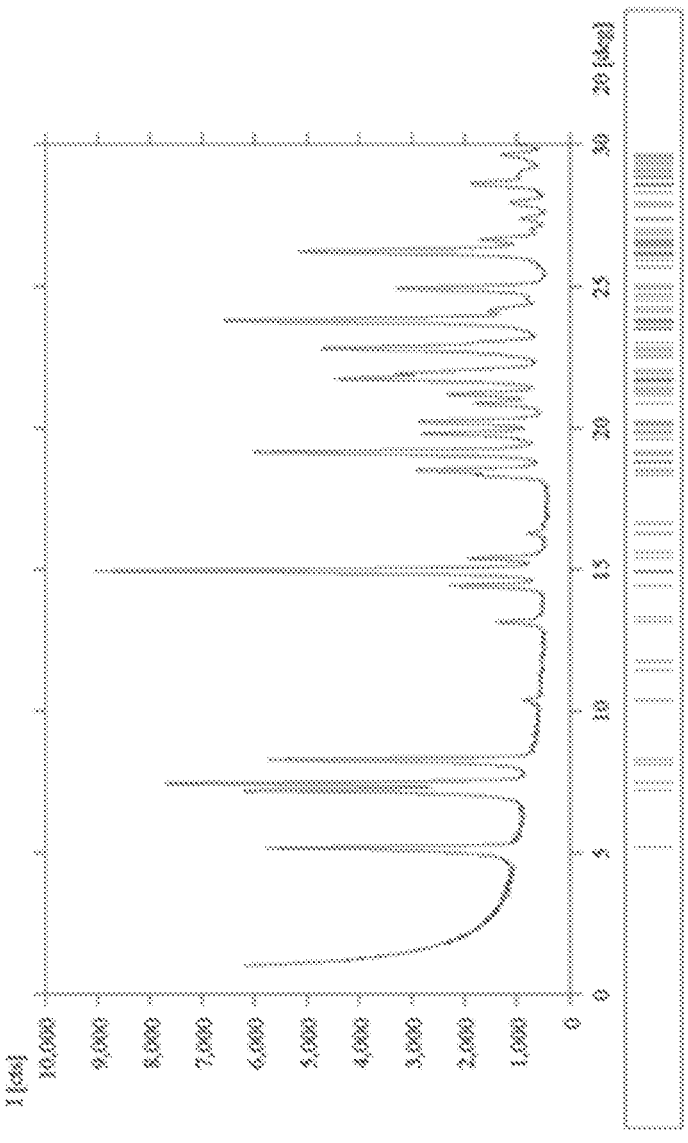
FIG. 18 is an XRPD of Compound 3 Form M as described in Example 2. The XRPD conditions are shown.
Figure 19:
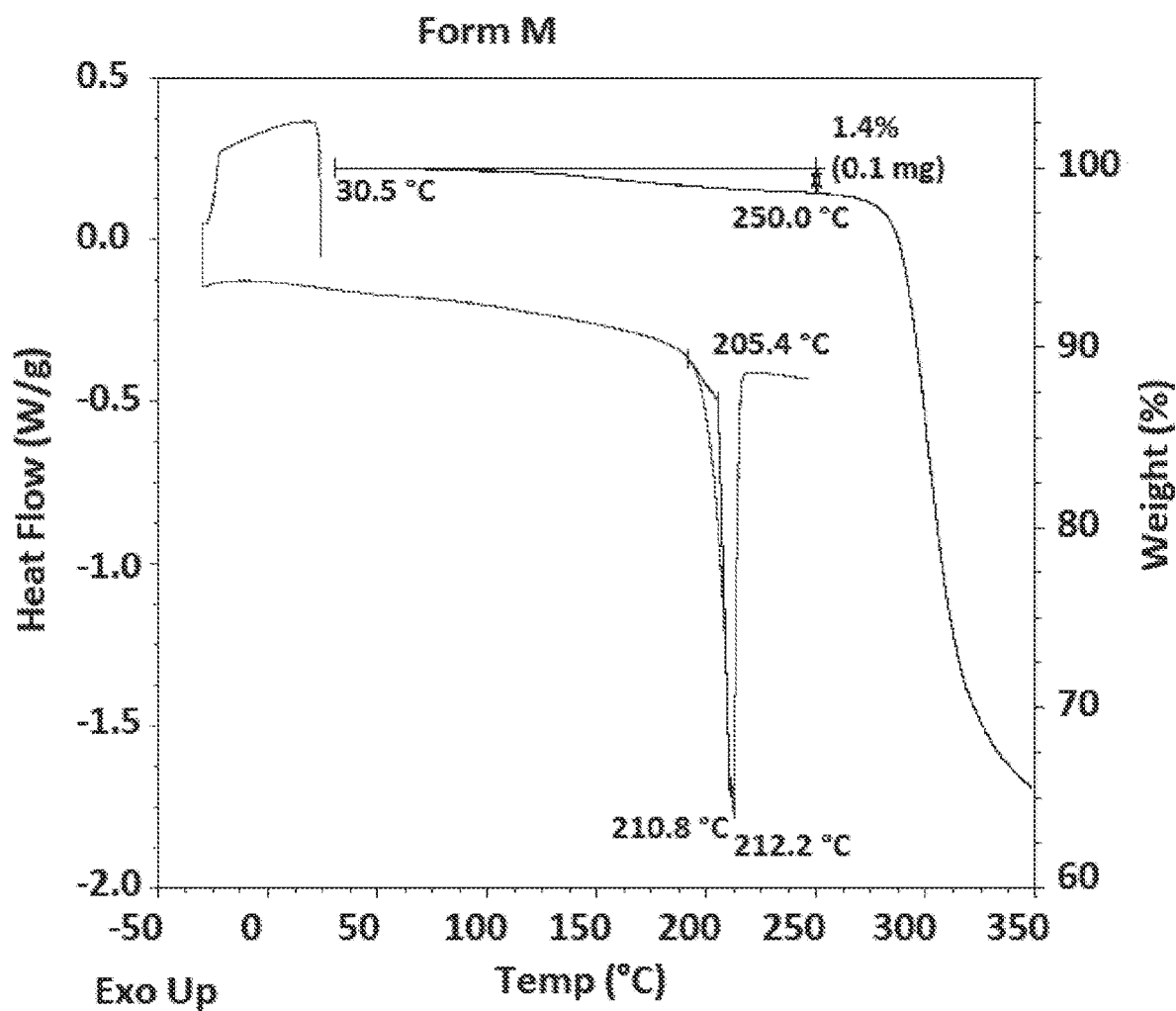
FIG. 19 is a DSC and a TGA graph of Compound 3 Form M as described in Example 2. The x-axis is temperature measured in ° C., the left y-axis is heat flow measured in (W/g), and the right y-axis is weight measured in percent.
Figure 20:
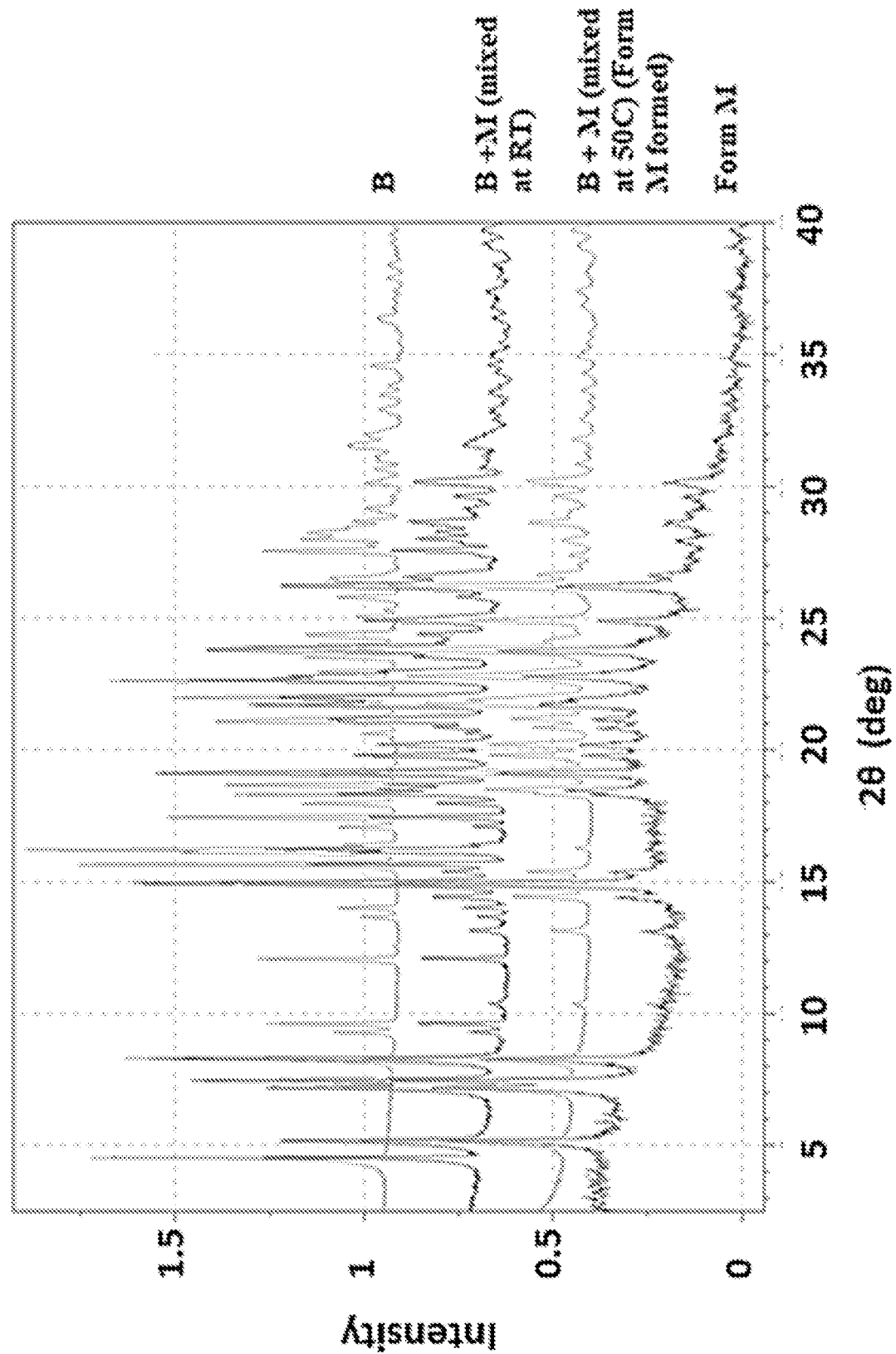
FIG. 20 provides XRPD (X-ray powder diffraction) patterns of several Compound 3 Forms as described in Example 2. The x-axis is 2Theta measured in degrees and the y-axis is intensity measured in counts. When Form B and Form M are mixed at room temperature the two forms remain. When Form B and Form M are mixed at 50° C. Form M is formed.
Figure 21:
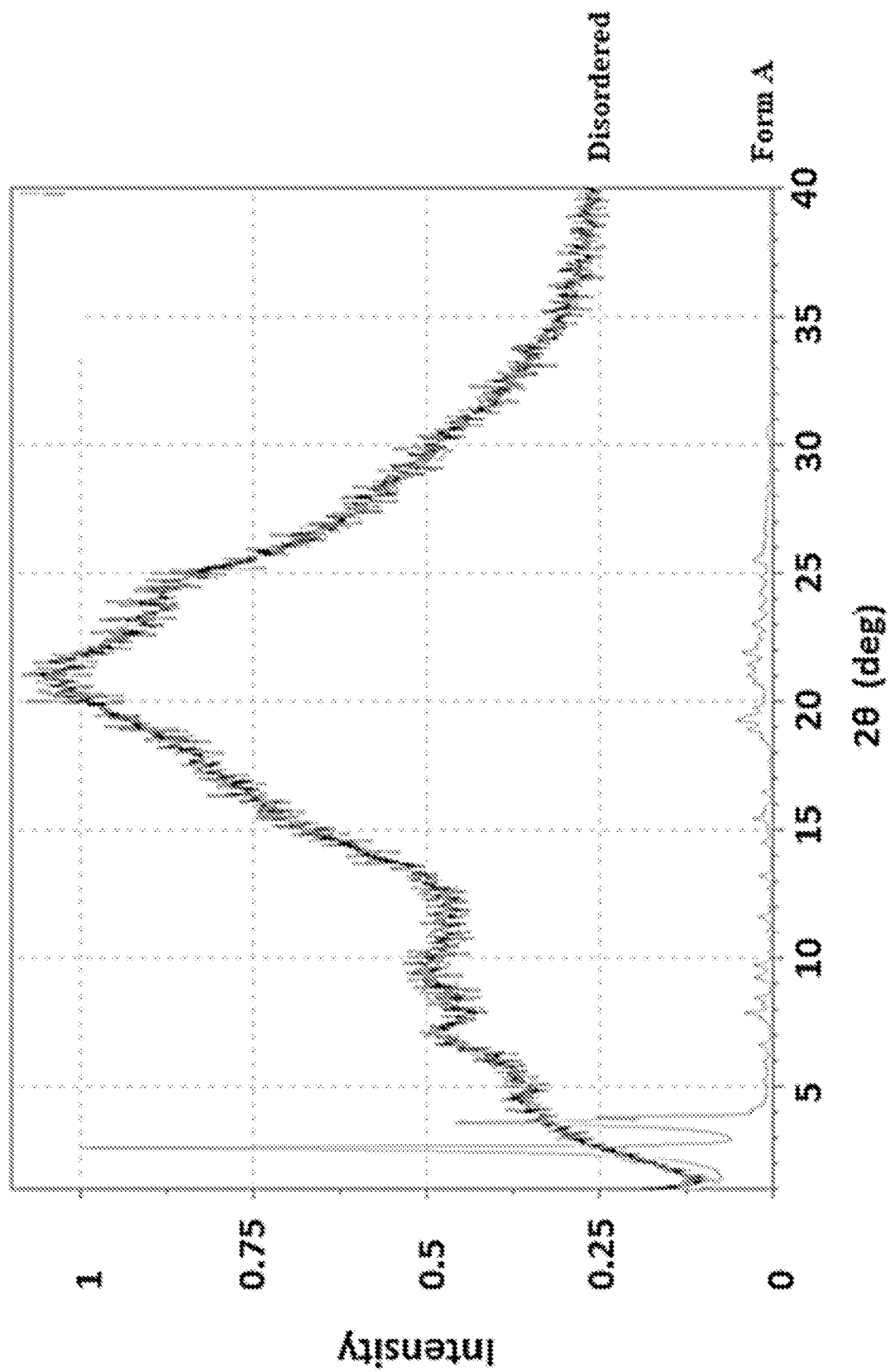
FIG. 21 is a DSC and a TGA graph of Compound 3 Form A as described in Example 2. The x-axis is temperature measured in ° C., the left y-axis is heat flow measured in (W/g), and the right y-axis is weight measured in percent.
Figure 22:
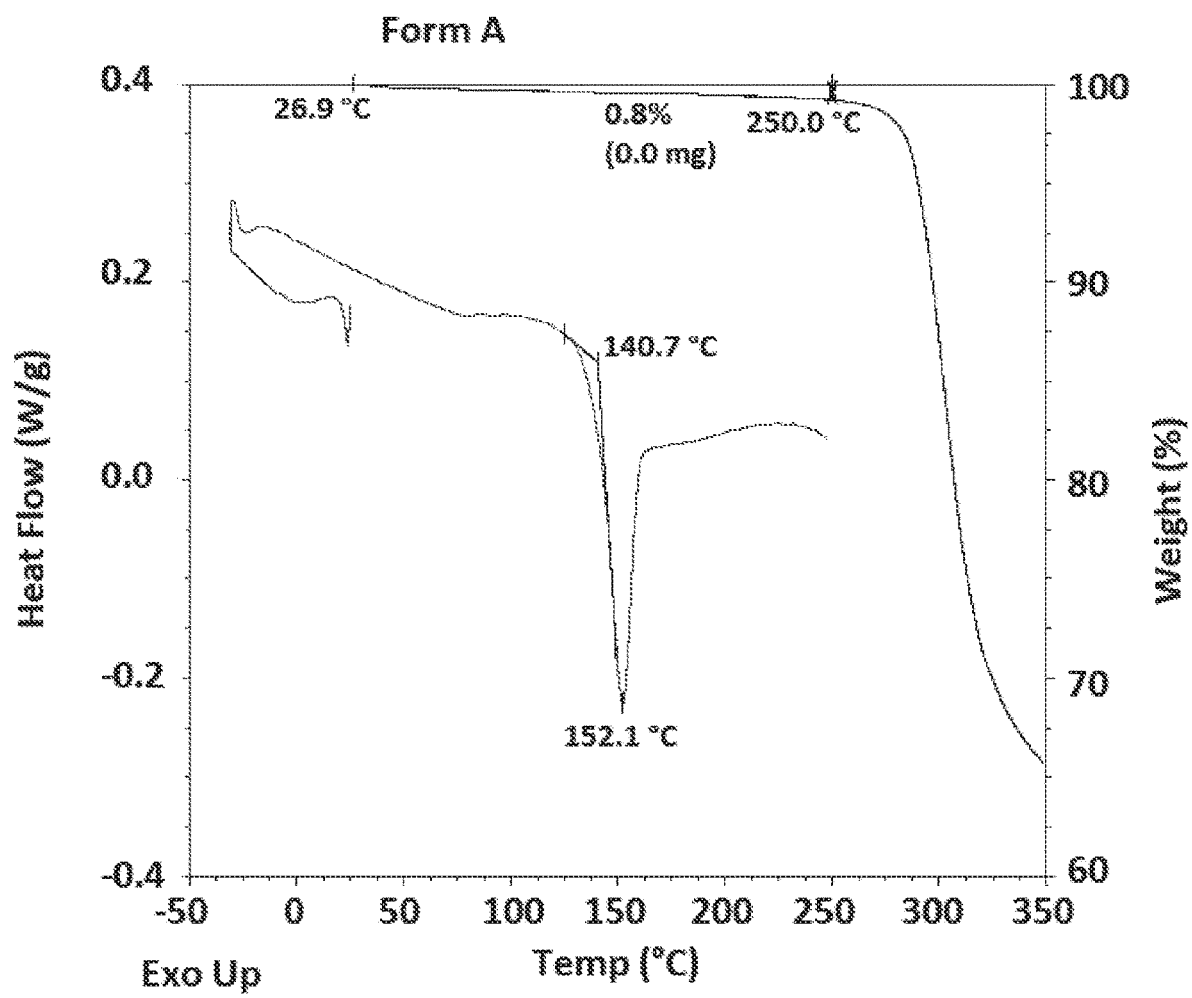
FIG. 22 provides XRPD (X-ray powder diffraction) patterns of Compound 3 Form A and disordered material as described in Example 2. The x-axis is 2Theta measured in degrees and the y-axis is intensity measured in counts.
Figure 23:
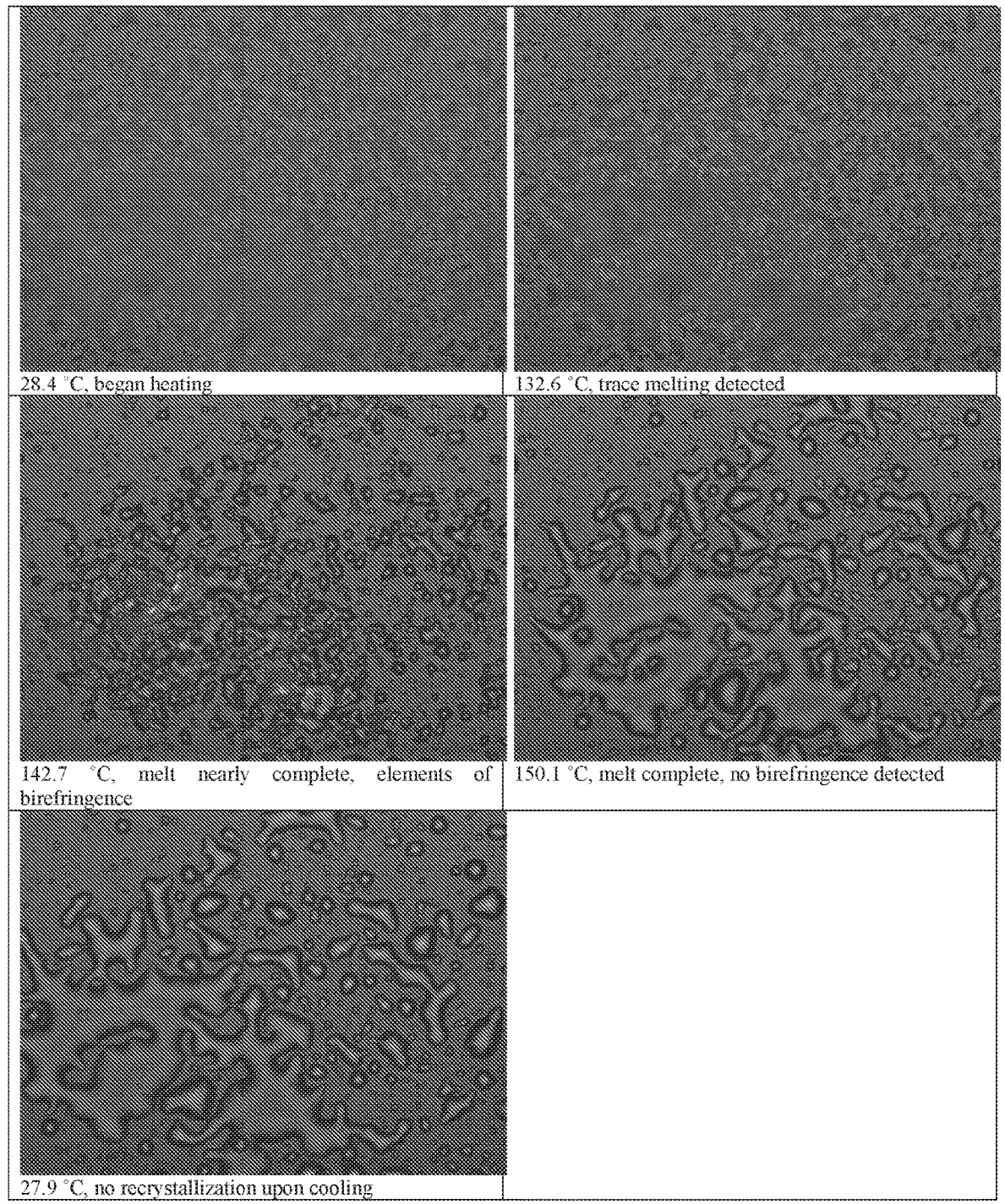
FIG. 23 is melting experiment images for Compound 3 Form A as described in Example 2.
Figure 24:
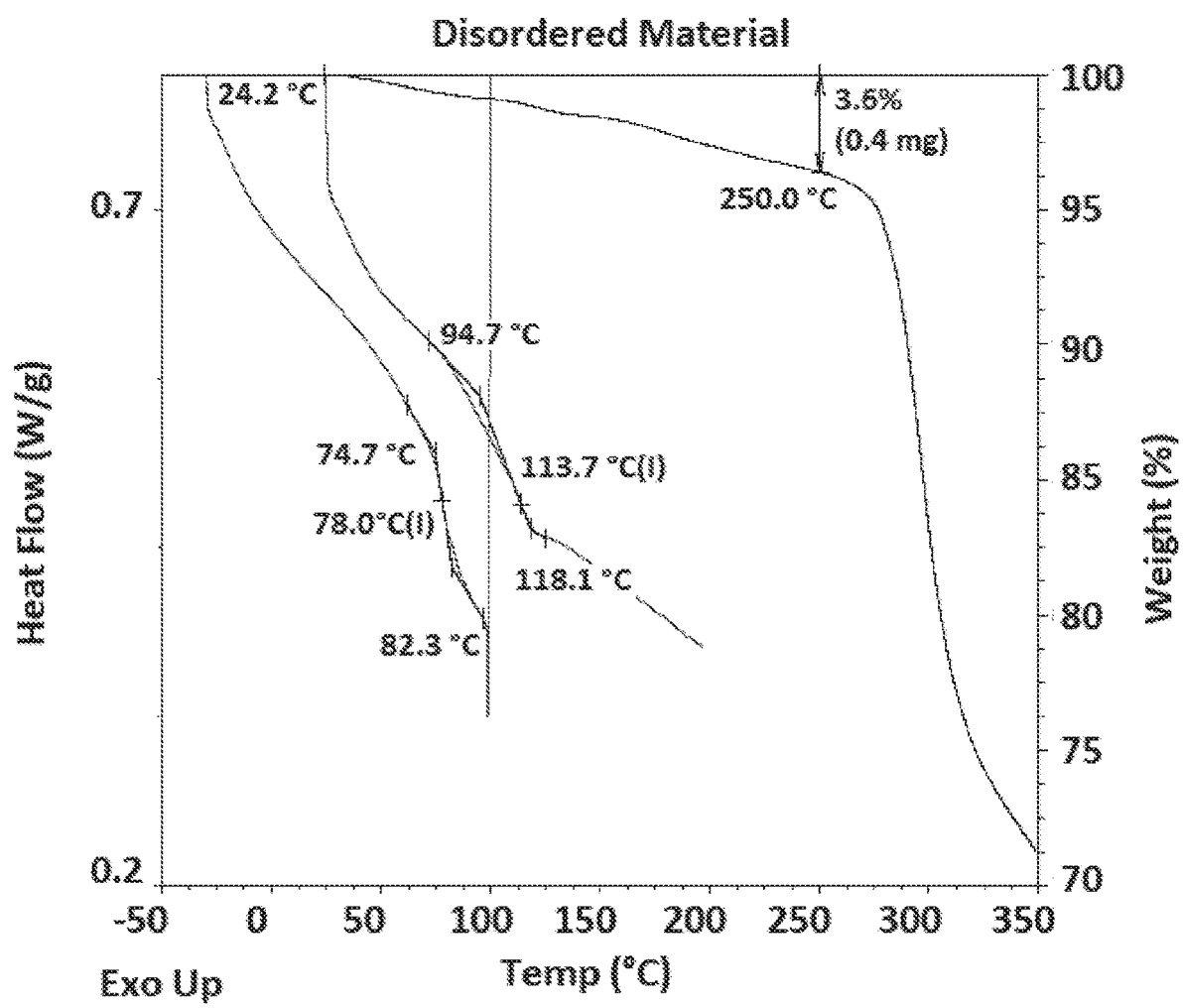
FIG. 24 is a DSC and a TGA graph of Compound 3 disordered material as described in Example 2. The x-axis is temperature measured in ° C., the left y-axis is heat flow measured in (W/g), and the right y-axis is weight measured in percent.
Figure 25:
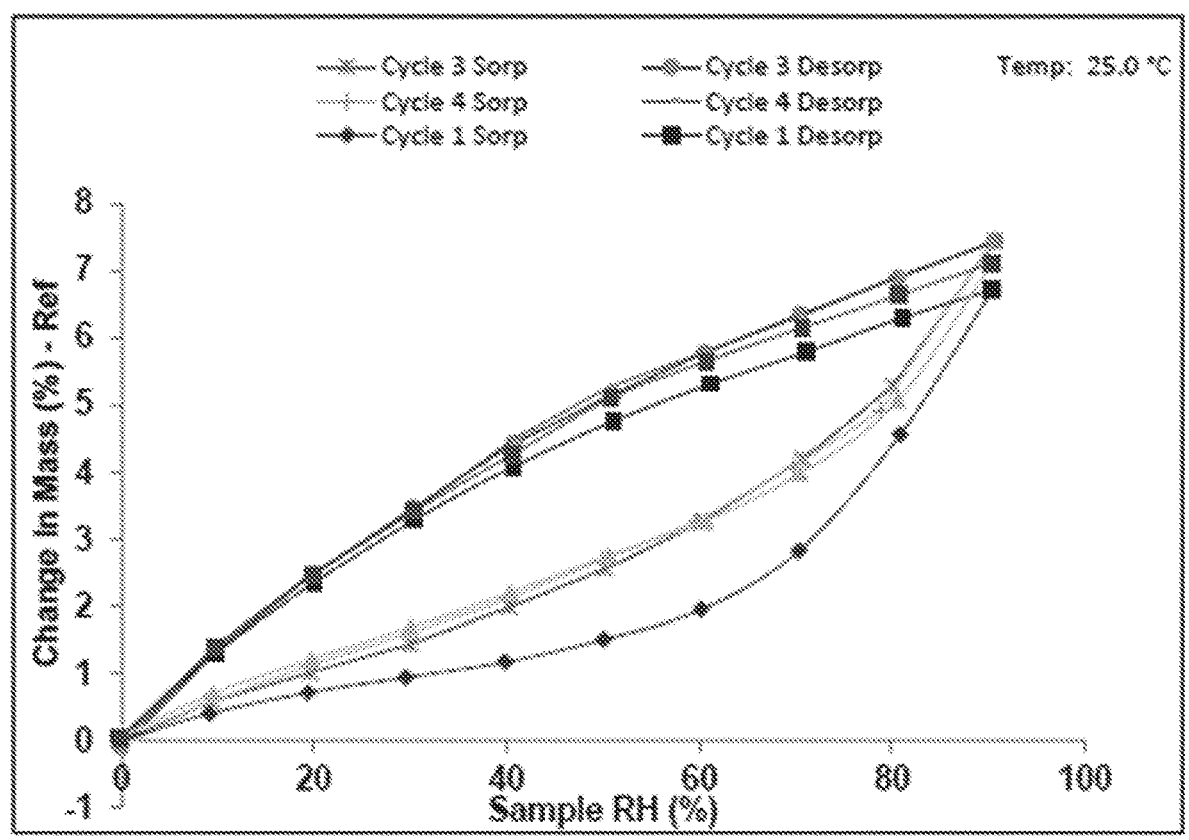
FIG. 25 is a DVS isotherm plot of amorphous Compound 3. The x-axis is RH measured in percent and the y-axis is change in mass measured in percent. The data corresponding to this experiment is presented in Example 3.
Figure 26:
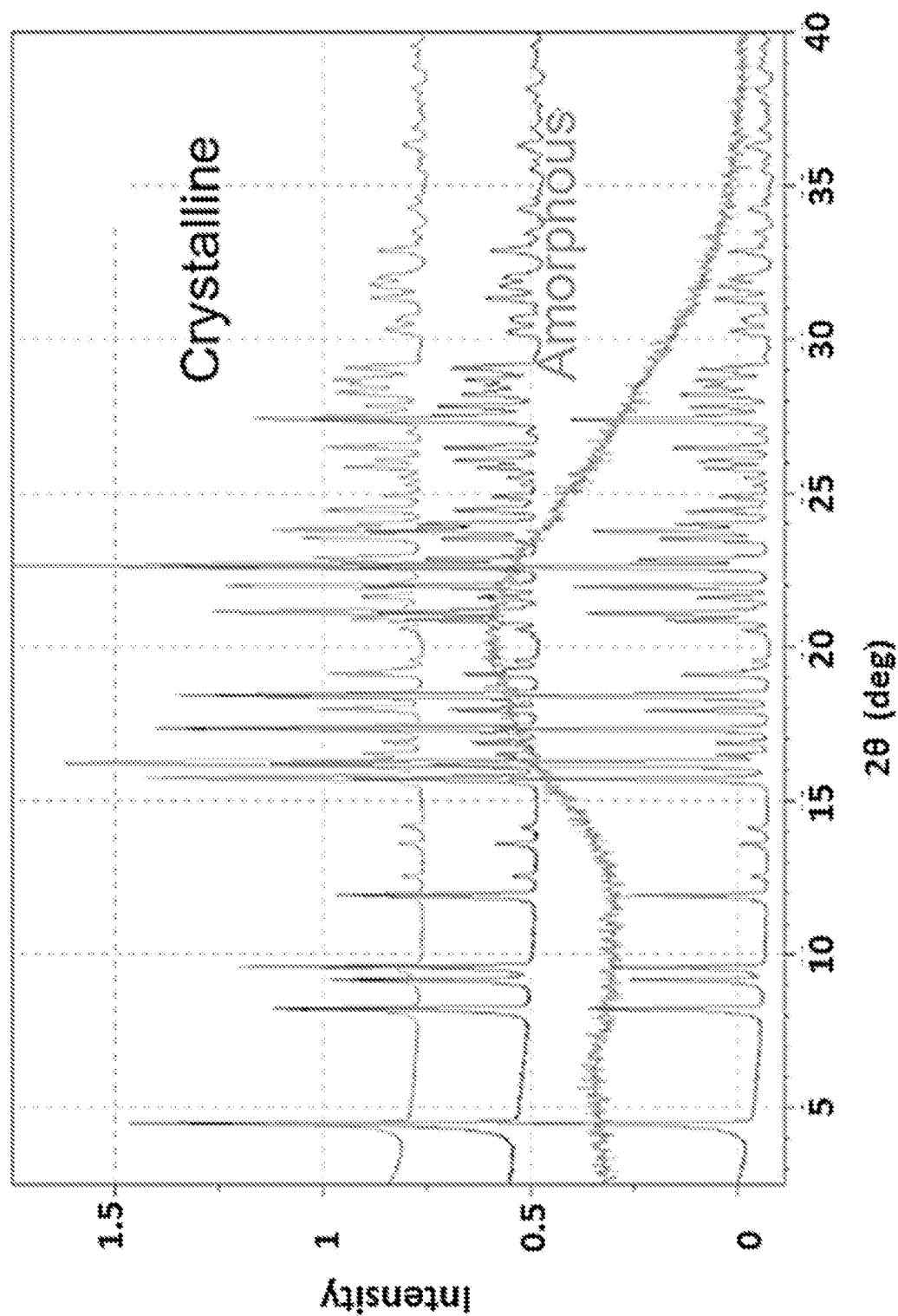
FIG. 26 is a XRPD (X-ray powder diffraction) overlay comparing Compound 2 Form I to amorphous Compound 2.
Figure 27:
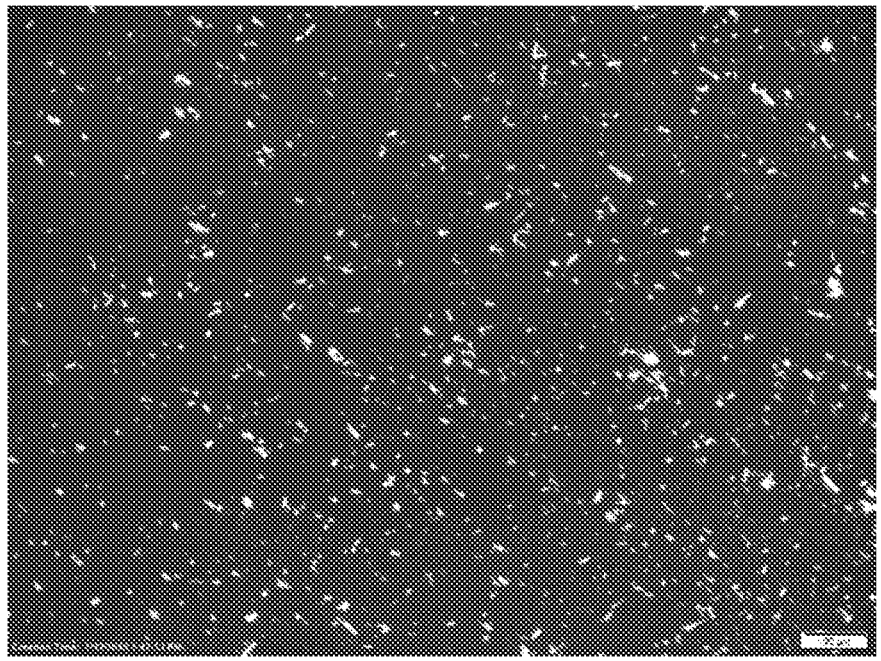
FIG. 27 is an image collected from the hot stage microscopy analysis of Compound 2 Form I. The image shows the birefringence character of the morphic form.
Figure 55:
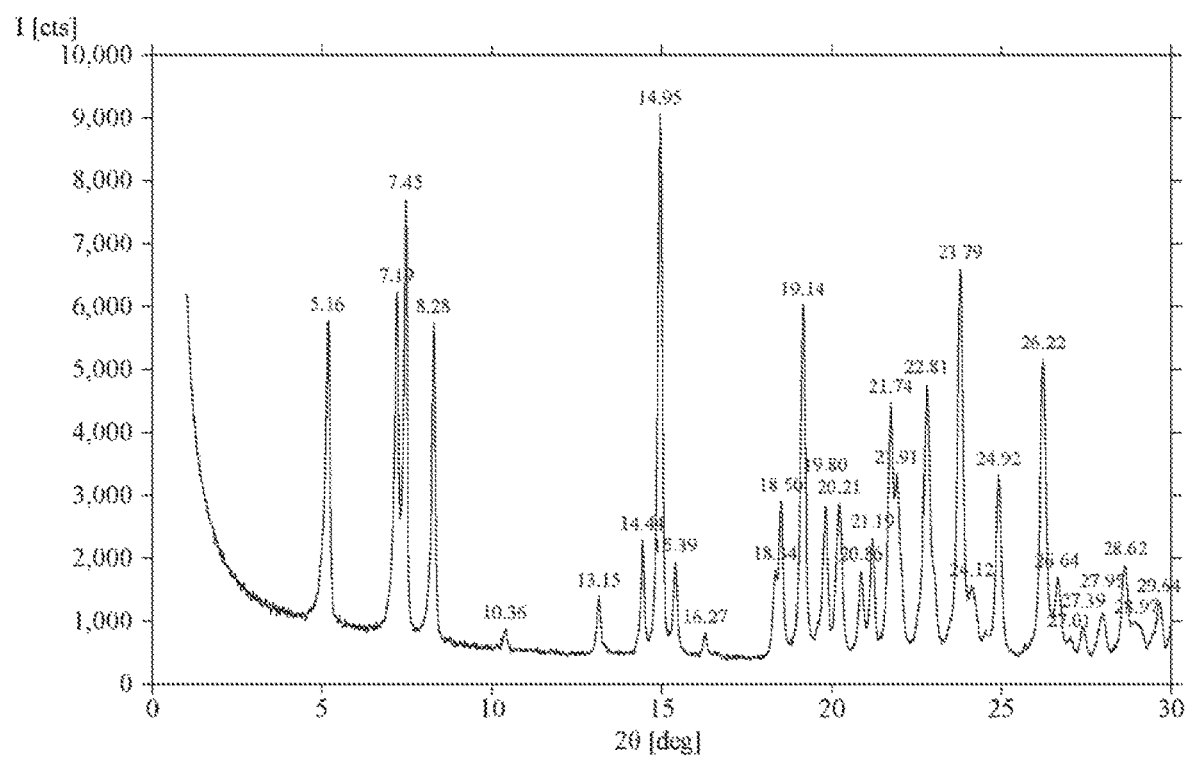
FIG. 55 is an XRPD diffractogram for Compound 3 Form M.

Form M is characterized by a XRPD pattern in or substantially similar to that set forth in FIG. 18 or FIG. 55. In one embodiment, isolated Compound 3 Form M is characterized by the DSC in FIG. 19. In one embodiment, isolated Compound 3 Form M is characterized as having a broad endothermic feature at approximately 205° C. in a differential scanning calorimetry analysis. In one embodiment Form M is highly stabile with a long shelf life and minimal degradation.

The present invention includes at least the following embodiments of Compound 3 Form M:
a) an isolated crystalline Form M of Compound 3 characterized by an XRPD pattern comprising at least three 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
b) the isolated crystalline Form M of Compound 3 of embodiment (a) characterized by an XRPD pattern comprising at least four 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
c) the isolated crystalline Form M of Compound 3 of embodiment (a) characterized by an XRPD pattern comprising at least four 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
d) the isolated crystalline Form M of Compound 3 of embodiment (a) characterized by an XRPD pattern comprising at least five 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
e) the isolated crystalline Form M of Compound 3 of embodiment (a) characterized by an XRPD pattern comprising at least six 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
f) the isolated crystalline Form M of Compound 3 of embodiment (a) characterized by an XRPD pattern comprising all of the 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°;
g) the isolated crystalline Form M of Compound 3 of any one of embodiments (a)-(e) characterized by an XRPD pattern comprising at least the 2theta value of 15.0±0.4°;

h) the isolated crystalline Form M of Compound 3 of any one of embodiments (a)-(e) characterized by an XRPD pattern comprising at least the 2theta value of 7.5±0.4°;

i) the isolated crystalline Form M of Compound 3 of any one of embodiments (a)-(e) wherein the XRPD pattern has the characteristic 2θ values of FIG. 55;

j) the isolated crystalline Form M of Compound 3 of any one of embodiments (a)-(h) wherein each 2theta value is within 0.3°;

k) the isolated crystalline Form M of Compound 3 of any one of embodiments (a)-(h) wherein each 2theta value is within 0.2°;

l) a pharmaceutical composition comprising the isolated crystalline Form M of Compound 3 of any one of embodiments (a)-(k) in a pharmaceutically acceptable excipient for solid dosage delivery;

m) a method of the treatment of a Complement Factor D mediated disorder comprising administering to a subject in need thereof a therapeutically effective amount of the isolated crystalline Form M of Compound 3 or a pharmaceutical composition thereof according to any one of embodiments (a)-(k), optionally in a pharmaceutically acceptable excipient for solid dosage delivery;

n) the method of embodiment of (m) wherein the subject is a human;

o) the isolated crystalline Form M of Compound 3 of any one of embodiments (a)-(k), optionally in a pharmaceutically acceptable excipient for solid dosage delivery, for use to treat a Complement Factor D mediated disorder in a subject in need thereof, p) the isolated crystalline Form M of Compound 3 of embodiment (o), wherein the subject is a human;

q) the use of the isolated crystalline Form M of Compound 3 or a pharmaceutical composition thereof of any of embodiments (a)-(k), optionally in a pharmaceutically acceptable excipient for solid dosage delivery, in the manufacture of a medicament for the treatment of a Complement Factor D mediated disorder in a subject in need thereof;

r) the use of embodiment (q) wherein the subject is a human.

Form M can be prepared using selective crystallization. The method can be carried out by treating a solution comprising a suitable solvent(s) and Compound 3 optionally in the presence of one or more seeds comprising Form M to conditions that provide for the crystallization of Form M as described in more detail below. In one embodiment, Form M is prepared by temperature cycling amorphous Compound 3 in acetone for approximately 2.5 days.

Form G

Figure 10:
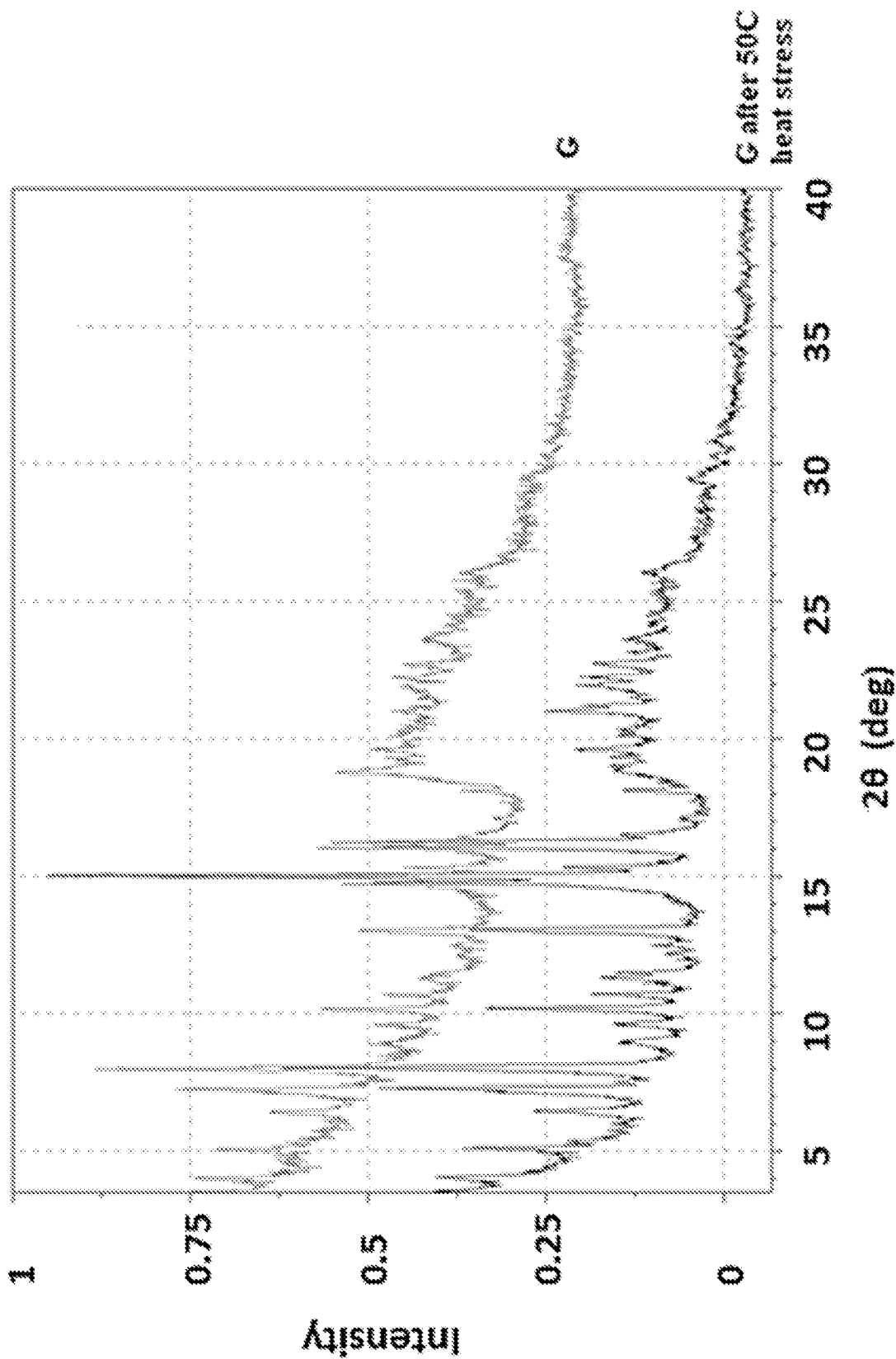
FIG. 10 provides XRPD patterns of Compound 3 Form G before and after 50° C. heat stress as described in Example 2.
Figure 11:
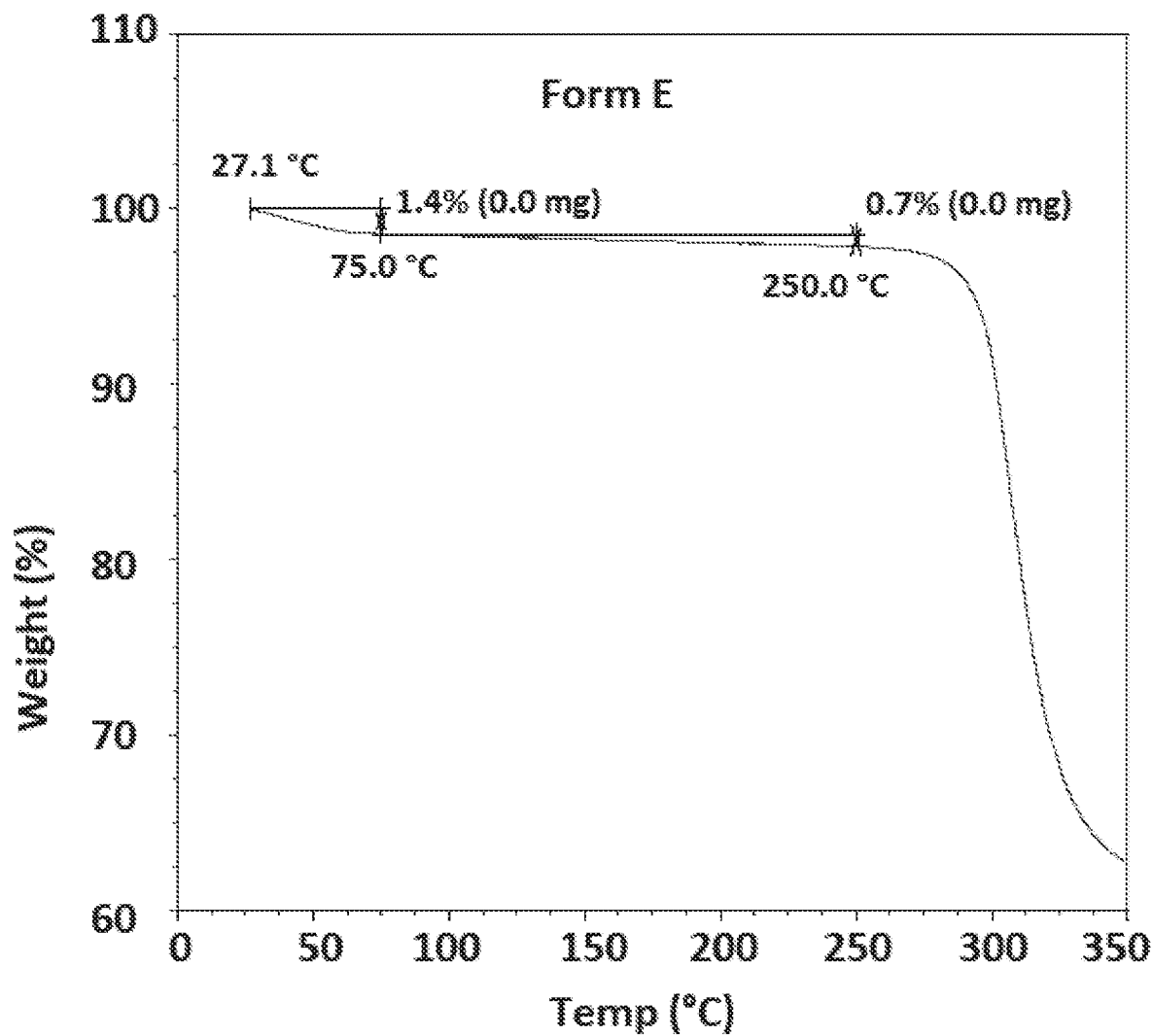
FIG. 11 is a DSC and a TGA graph of Compound 3 Form E as described in Example 2. The x-axis is temperature measured in ° C., the left y-axis is heat flow measured in (W/g), and the right y-axis is weight measured in percent.
Figure 12:
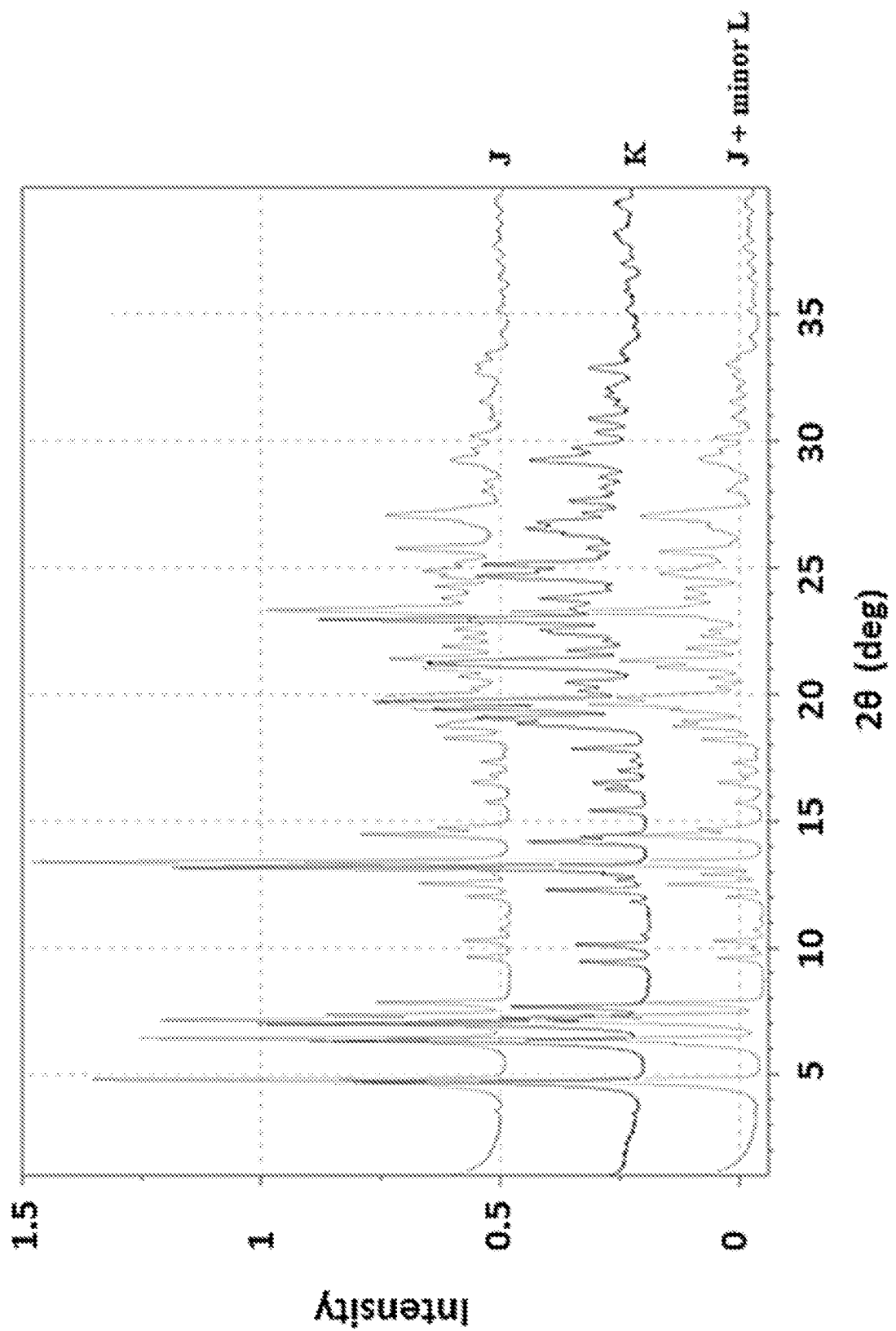
FIG. 12 provides XRPD (X-ray powder diffraction) patterns of several Compound 3 Forms as described in Example 2. The x-axis is 2Theta measured in degrees and the y-axis is intensity measured in counts. Form J, Form K and Form J with a minor Form L impurity are shown
Figure 53:
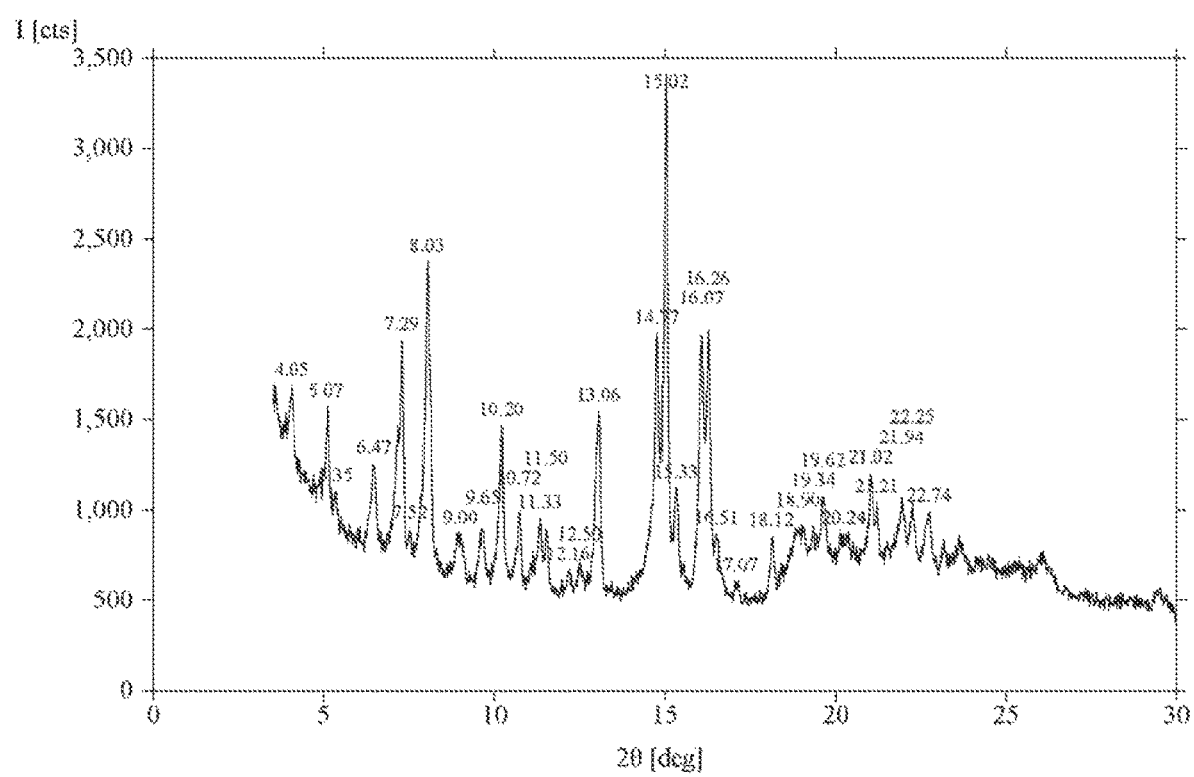
FIG. 53 is an XRPD diffractogram for Compound 3 Form G.

Form G is characterized by a XRPD pattern in or substantially similar to that set forth in FIG. 10 or FIG. 53. In one embodiment, isolated Compound 3 Form G is characterized by the DSC in FIG. 16.

The present invention includes at least the following embodiments of Compound 3 Form G:

a) an isolated crystalline Form G of Compound 3 characterized by an XRPD pattern comprising at least three 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

b) the isolated crystalline Form G of Compound 3 of embodiment (a) characterized by an XRPD pattern comprising at least four 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

c) the isolated crystalline Form G of Compound 3 of embodiment (a) characterized by an XRPD pattern comprising at least four 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

d) the isolated crystalline Form G of Compound 3 of embodiment (a) characterized by an XRPD pattern comprising at least five 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

e) the isolated crystalline Form G of Compound 3 of embodiment (a) characterized by an XRPD pattern comprising at least six 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

f) the isolated crystalline Form G of Compound 3 of embodiment (a) characterized by an XRPD pattern comprising all of the 2theta values selected from 15.0±0.4°, 8.0±0.4°, 16.3±0.4°, 14.8±0.4°, 7.3±0.4°, 16.1±0.4°, 4.1±0.4°, 13.1±0.4°, 10.2±0.4°, and 5.1±0.4°;

g) the isolated crystalline Form G of Compound 3 of any one of embodiments (a)-(e) characterized by an XRPD pattern comprising at least the 2theta value of 15.0±0.4°;

h) the isolated crystalline Form G of Compound 3 of any one of embodiments (a)-(e) characterized by an XRPD pattern comprising at least the 2theta value of 8.0±0.4°;

i) the isolated crystalline Form G of Compound 3 of any one of embodiments (a)-(e) wherein the XRPD pattern has the characteristic 2θ values of FIG. 53;

j) the isolated crystalline Form G of Compound 3 of any one of embodiments (a)-(h) wherein each 2theta value is within 0.3°;

k) the isolated crystalline Form G of Compound 3 of any one of embodiments (a)-(h) wherein each 2theta value is within 0.2°;

l) a pharmaceutical composition comprising the isolated crystalline Form G of Compound 3 of any one of embodiments (a)-(k) in a pharmaceutically acceptable excipient for solid dosage delivery;

m) a method of the treatment of a Complement Factor D mediated disorder comprising administering to a subject in need thereof a therapeutically effective amount of the isolated crystalline Form G of Compound 3 or a pharmaceutical composition thereof according to any one of embodiments (a)-(k), optionally in a pharmaceutically acceptable excipient for solid dosage delivery;

n) the method of embodiment of (m) wherein the subject is a human;

o) the isolated crystalline Form G of Compound 3 of any one of embodiments (a)-(k), optionally in a pharmaceutically acceptable excipient for solid dosage delivery, for use to treat a Complement Factor D mediated disorder in a subject in need thereof, p) the isolated crystalline Form G of Compound 3 of embodiment (o), wherein the subject is a human;

q) the use of the isolated crystalline Form G of Compound 3 or a pharmaceutical composition thereof of any of embodiments (a)-(k), optionally in a pharmaceutically acceptable excipient for solid dosage delivery, in the manufacture of a medicament for the treatment of a Complement Factor D mediated disorder in a subject in need thereof;
r) the use of embodiment (q) wherein the subject is a human.

Form J

Figure 13:
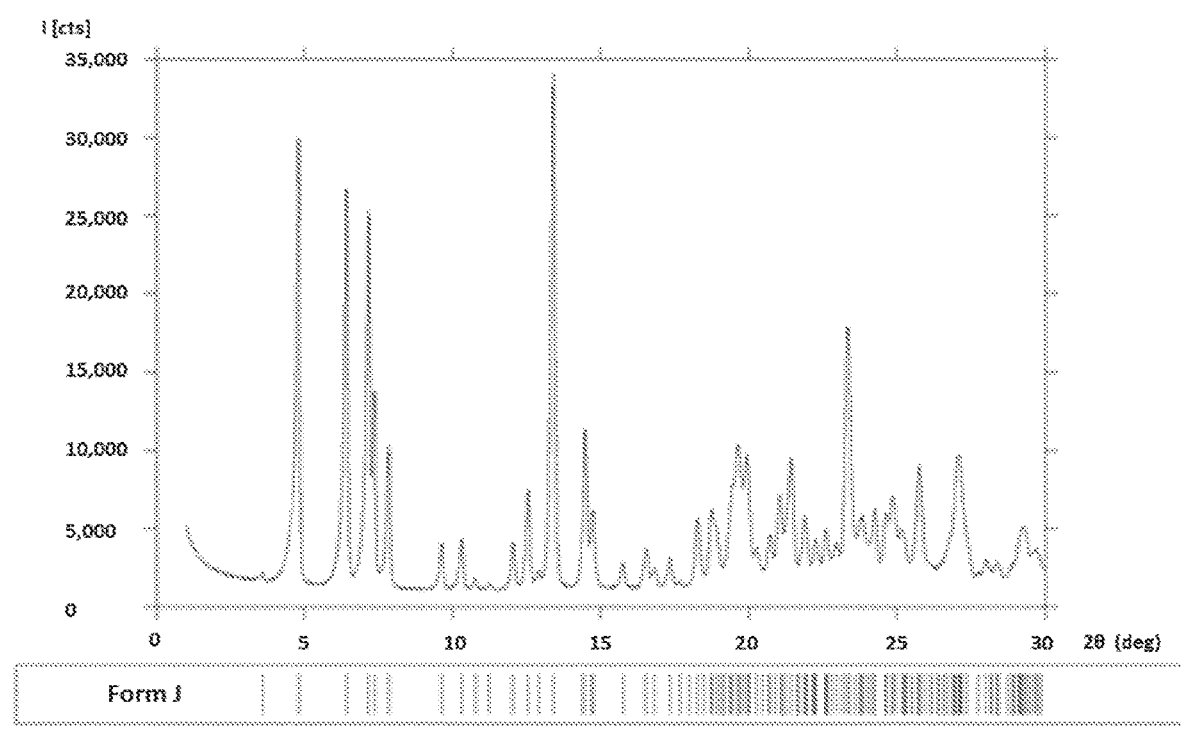
FIG. 13 is an XRPD of Compound 3 Form J as described in Example 2. The XRPD conditions are as listed: Bravais Type: primitive monoclinic; a [Å]: 4.802; b [Å]: 27.440; c [Å]: 24.660; α [deg]: 90; β [deg]: 91.48; γ [deg]: 90; volume [Å³/cell]: 3,248.3; chiral contents: chiral; extinction symbol: P 1 2₁ 1; and space group(s): P2₁ (4). The x-axis is 2Theta measured in degrees and the y-axis is intensity measured in counts.
Figure 14:
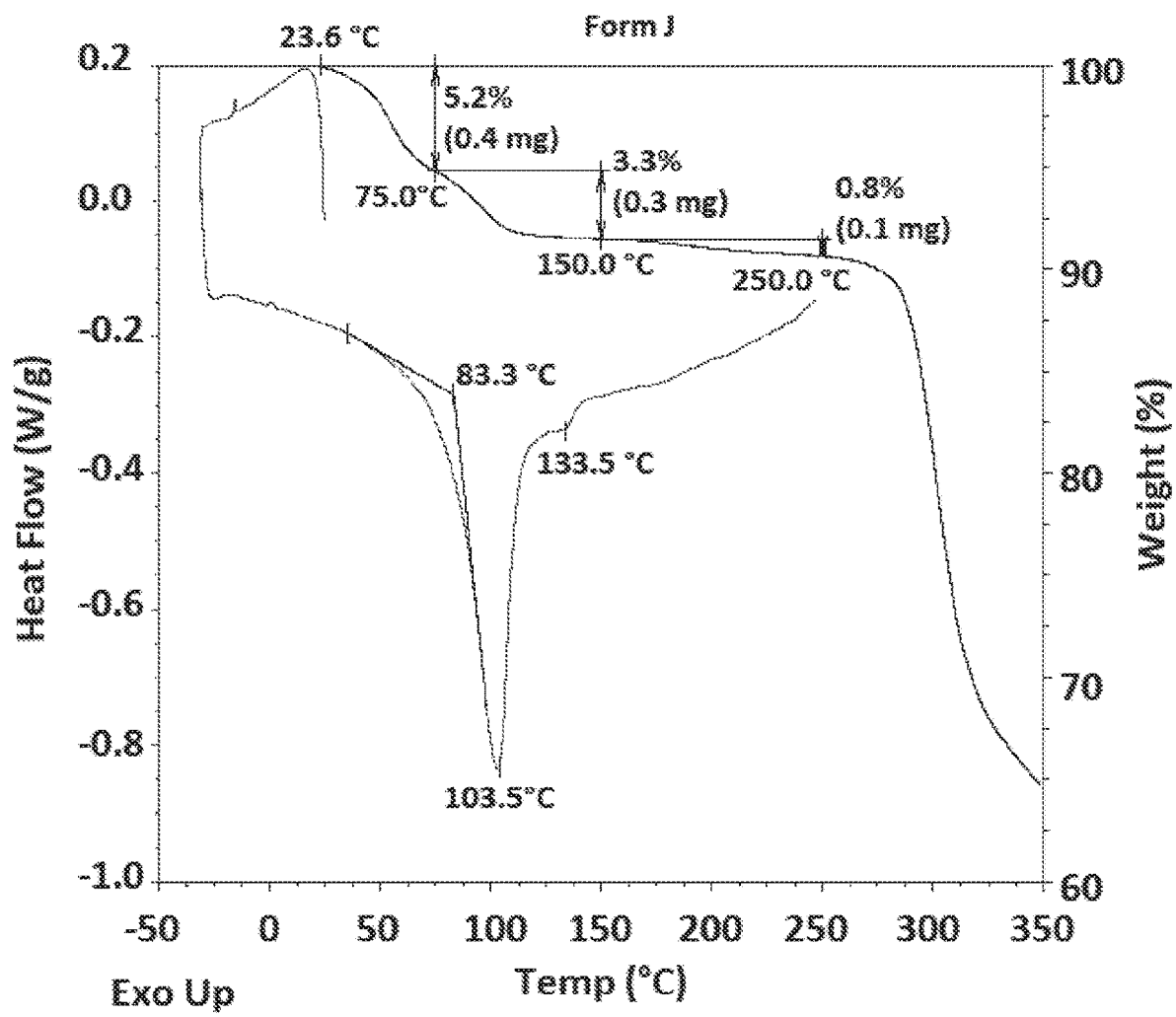
FIG. 14 is a DSC and a TGA graph of Compound 3 Form J. The x-axis is temperature measured in ° C., the left y-axis is heat flow measured in (W/g), and the right y-axis is weight measured in percent as described in Example 2.
Figure 15:
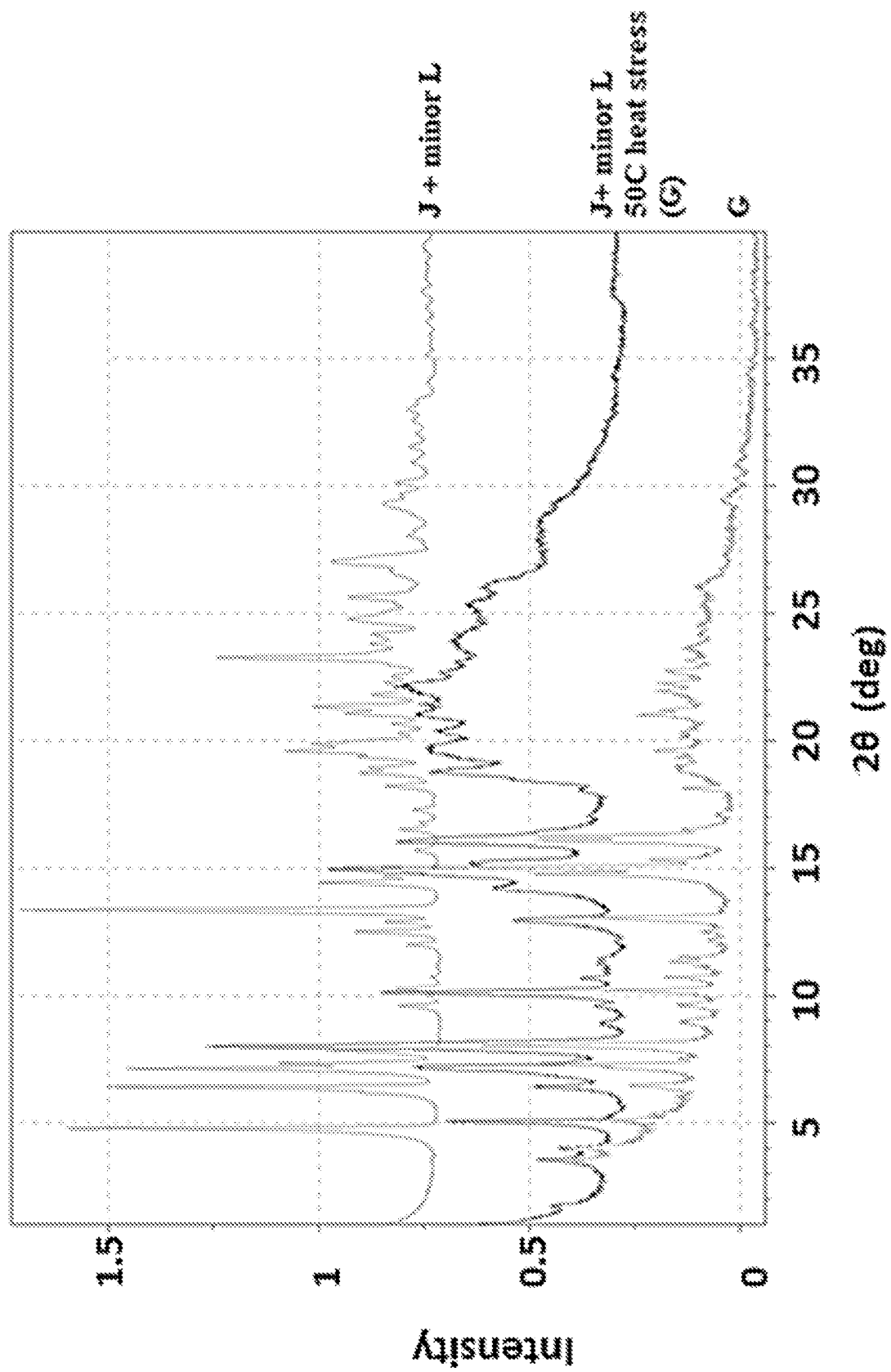
FIG. 15 provides the XRPD pattern of Compound 3 Form J (with minor Form L impurity) compared to the resultant Form G XRPD after Form J (with minor Form L impurity) is subjected to 50° C. heat stress as described in Example 2.
Figure 16:
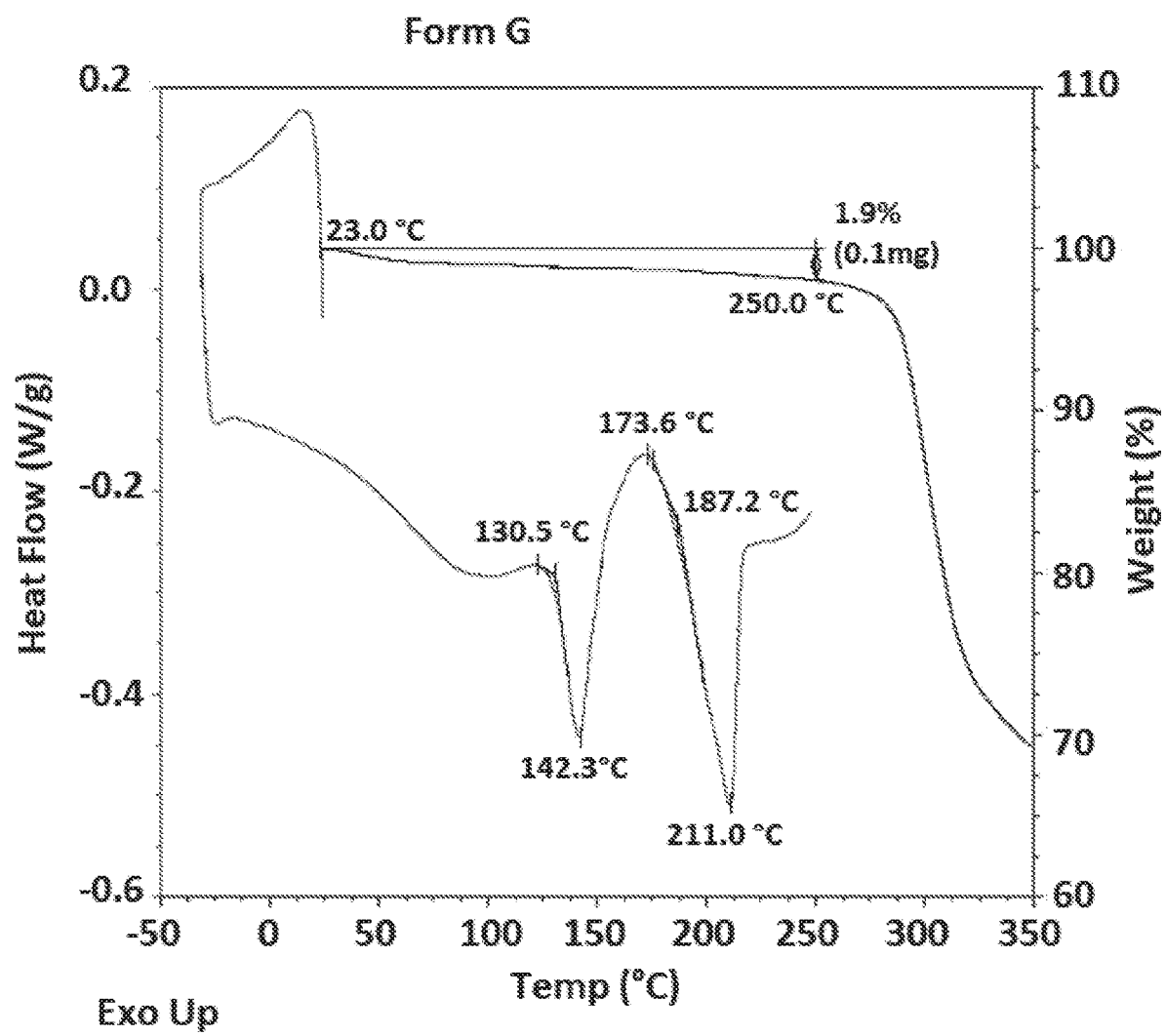
FIG. 16 is a DSC and a TGA graph of Compound 3 Form G as described in Example 2. The x-axis is temperature measured in ° C., the left y-axis is heat flow measured in (W/g), and the right y-axis is weight measured in percent.
Figure 17:
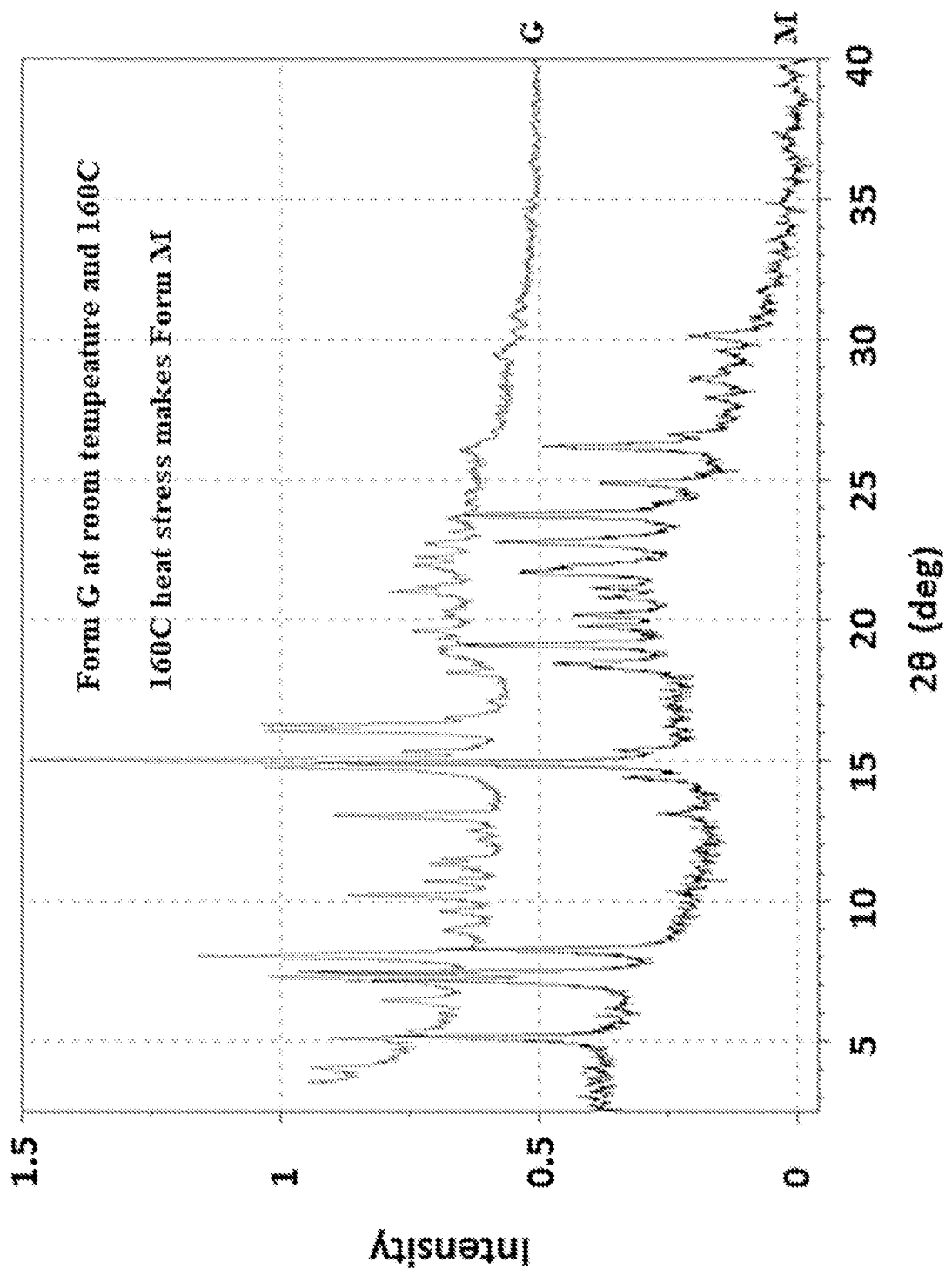
FIG. 17 is an XRPD of Compound 3 Form G compared to the resultant Form M XRPD after Form G is subjected to 160° C. heat stress as described in Example 2.
Figure 54:
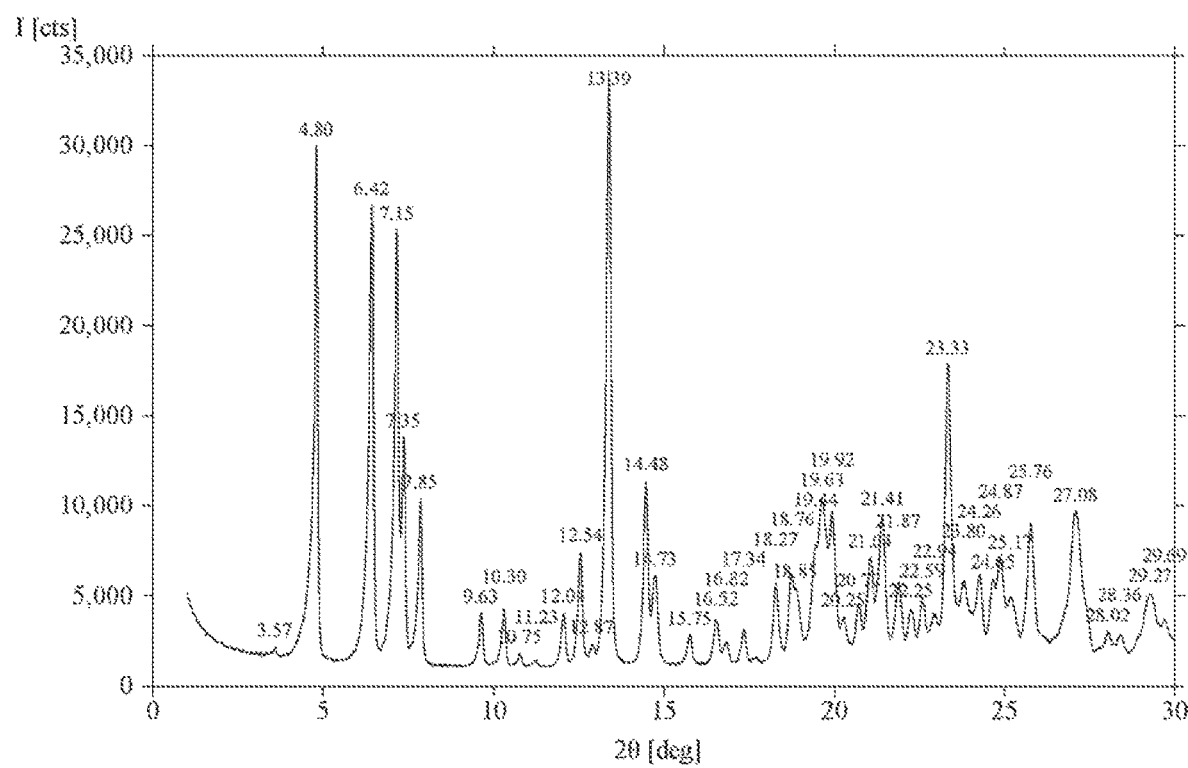
FIG. 54 is an XRPD diffractogram for Compound 3 Form J.

Form J is characterized by a XRPD pattern in or substantially similar to that set forth in FIG. 13 or FIG. 54. In one embodiment, isolated Compound 3 Form J is characterized by the DSC in FIG. 14.

The present invention includes at least the following embodiments of Compound 3 Form J.

a) an isolated crystalline Form J of Compound 3 characterized by an XRPD pattern comprising at least three 2theta values selected from 13.4±0.4°, 4.8±0.4°, 6.4±0.4°, 7.2±0.4°, 23.3±0.4°, and 7.4±0.4°;
b) the isolated crystalline Form J of Compound 3 of embodiment (a) characterized by an XRPD pattern comprising at least four 2theta values selected from 13.4±0.4°, 4.8±0.4°, 6.4±0.4°, 7.2±0.4°, 23.3±0.4°, and 7.4±0.4°;
c) the isolated crystalline Form J of Compound 3 of embodiment (a) characterized by an XRPD pattern comprising at least four 2theta values selected from 13.4±0.4°, 4.8±0.4°, 6.4±0.4°, 7.2±0.4°, 23.3±0.4°, and 7.4±0.4°;
d) the isolated crystalline Form J of Compound 3 of embodiment (a) characterized by an XRPD pattern comprising at least five 2theta values selected from 13.4±0.4°, 4.8±0.4°, 6.4±0.4°, 7.2±0.4°, 23.3±0.4°, and 7.4±0.4°;
e) the isolated crystalline Form J of Compound 3 of embodiment (a) characterized by an XRPD pattern comprising at least six 2theta values selected from 13.4±0.4°, 4.8±0.4°, 6.4±0.4°, 7.2±0.4°, 23.3±0.4°, and 7.4±0.4°;
f) the isolated crystalline Form J of Compound 3 of embodiment (a) characterized by an XRPD pattern comprising all of the 2theta values selected from 13.4±0.4°, 4.8±0.4°, 6.4±0.4°, 7.2±0.4°, 23.3±0.4°, and 7.4±0.4°;
g) the isolated crystalline Form J of Compound 3 of any one of embodiments (a)-(e) characterized by an XRPD pattern comprising at least the 2theta value of 13.4±0.4°;
h) the isolated crystalline Form J of Compound 3 of any one of embodiments (a)-(e) characterized by an XRPD pattern comprising at least the 2theta value of 4.8±0.4°;
i) the isolated crystalline Form J of Compound 3 of any one of embodiments (a)-(e) wherein the XRPD pattern has the characteristic 2θ values of FIG. 54;
j) the isolated crystalline Form J of Compound 3 of any one of embodiments (a)-(h) wherein each 2theta value is within 0.3°;
k) the isolated crystalline Form J of Compound 3 of any one of embodiments (a)-(h) wherein each 2theta value is within 0.2°;
l) a pharmaceutical composition comprising the isolated crystalline Form J of Compound 3 of any one of embodiments (a)-(k) in a pharmaceutically acceptable excipient for solid dosage delivery;
m) a method of the treatment of a Complement Factor D mediated disorder comprising administering to a subject in need thereof a therapeutically effective amount of the isolated crystalline Form J of Compound 3 or a pharmaceutical composition thereof according to any one of embodiments (a)-(k), optionally in a pharmaceutically acceptable excipient for solid dosage delivery;
n) the method of embodiment of (m) wherein the subject is a human;
o) the isolated crystalline Form J of Compound 3 of any one of embodiments (a)-(k), optionally in a pharmaceutically acceptable excipient for solid dosage delivery, for use to treat a Complement Factor D mediated disorder in a subject in need thereof,
p) the isolated crystalline Form J of Compound 3 of embodiment (o), wherein the subject is a human;
q) the use of the isolated crystalline Form J of Compound 3 or a pharmaceutical composition thereof of any of embodiments (a)-(k), optionally in a pharmaceutically acceptable excipient for solid dosage delivery, in the manufacture of a medicament for the treatment of a Complement Factor D mediated disorder in a subject in need thereof;
r) the use of embodiment (q) wherein the subject is a human.

In one embodiment a pharmaceutical composition is provided comprising isolated Compound 3 morphic Form A, Form B, or Form M and a pharmaceutically acceptable excipient.

In one aspect of the present invention, a method for treating a disorder mediated by Complement factor D is provided, for example, paroxysmal nocturnal hemoglobinuria (PNH) or C3 glomerulopathy (C3G) is provided comprising administering to a host in need thereof a therapeutically effective amount of isolated Form of Compound 3. In one embodiment, the Form is selected from Form A, Form B, or Form M.

In one aspect of the present invention, a method for treating a disorder selected from membranoproliferative glomerulonephritis type II (MPGNII), nonalcoholic steatohepatitis (NASH), fatty liver, liver inflammation, cirrhosis, liver failure, dermatomyositis, and amyotrophic lateral sclerosis is provided comprising administering to a host in need thereof a therapeutically effective amount of isolated Form of Compound 3. In one embodiment, the Form is selected from Form A, Form B, or Form M.

In one aspect of the present invention, a method for treating a disorder selected from multiple sclerosis, arthritis, respiratory disease, cardiovascular disease, COPD, rheumatoid arthritis, atypical hemolytic uremic syndrome, and typical hemolytic uremic syndrome is provided comprising administering to a host in need thereof a therapeutically effective amount of isolated Form of Compound 3. In one embodiment, the Form is selected from Form A, Form B, or Form M.

In one aspect of the present invention, a method for treating a disorder selected from membrane glomerulonephritis, age-related macular degeneration (AMD), retinal degeneration, and type I diabetes or complications thereof is provided comprising administering to a host in need thereof a therapeutically effective amount of isolated Form of Compound 3. In one embodiment, the Form is selected from Form A, Form B, or Form M.

In one embodiment a therapeutic method is provided to treat a patient with a complement factor D mediated disorder comprising administering an effective amount of Compound 3 Form A and a C5 inhibitor to the patient in need thereof. In one embodiment Compound 3 Form A and the C5 inhibitor have an overlapping therapeutic effect. In one embodiment a therapeutic method is provided to treat a patient with a complement factor D mediated disorder comprising administering an effective amount of Compound 3 Form A and eculizumab to the patient in need thereof. In one embodiment, Compound 3 Form A and eculizumab have an overlapping therapeutic effect. In one embodiment a therapeutic method is provided to treat a patient with a complement factor D mediated disorder comprising administering Compound 3 Form A and ravulizumab to the patient in need thereof. In one embodiment Compound 3 Form A and ravulizumab have an overlapping therapeutic effect. For example, the therapeutic effect can be combinatorial or synergistic inhibition.

In one embodiment, the AUC for Compound 3 Form A and the C5 inhibitor overlap.

In one embodiment, the C5 inhibitor is eculizumab. In one embodiment, the C5 inhibitor is ravulizumab. In one embodiment the C5 inhibitor is a small molecule. In another embodiment the C5 inhibitor is a polyclonal antibody targeting C5. In yet another embodiment the C5 inhibitor is an aptamer.

In one embodiment a therapeutic method is provided to treat a patient with a complement factor D mediated disorder comprising administering an effective amount of Compound 3 Form B and a C5 inhibitor to the patient in need thereof. In one embodiment Compound 3 Form B and the C5 inhibitor have an overlapping therapeutic effect. In one embodiment a therapeutic method is provided to treat a patient with a complement factor D mediated disorder comprising administering an effective amount of Compound 3 Form B and eculizumab to the patient in need thereof. In one embodiment, Compound 3 Form B and eculizumab have an overlapping therapeutic effect. In one embodiment a therapeutic method is provided to treat a patient with a complement factor D mediated disorder comprising administering Compound 3 Form B and ravulizumab to the patient in need thereof. In one embodiment Compound 3 Form B and ravulizumab have an overlapping therapeutic effect. For example, the therapeutic effect can be combinatorial or synergistic inhibition.

In one embodiment, the AUC for Compound 3 Form B and the C5 inhibitor overlap.

In one embodiment, the C5 inhibitor is eculizumab. In one embodiment, the C5 inhibitor is ravulizumab. In one embodiment the C5 inhibitor is a small molecule. In another embodiment the C5 inhibitor is a polyclonal antibody targeting C5. In yet another embodiment the C5 inhibitor is an aptamer.

In one embodiment a therapeutic method is provided to treat a patient with a complement factor D mediated disorder comprising administering an effective amount of Compound 3 Form M and a C5 inhibitor to the patient in need thereof. In one embodiment Compound 3 Form M and the C5 inhibitor have an overlapping therapeutic effect. In one embodiment a therapeutic method is provided to treat a patient with a complement factor D mediated disorder comprising administering an effective amount of Compound 3 Form M and eculizumab to the patient in need thereof. In one embodiment, Compound 3 Form M and eculizumab have an overlapping therapeutic effect. In one embodiment a therapeutic method is provided to treat a patient with a complement factor D mediated disorder comprising administering Compound 3 Form M and ravulizumab to the patient in need thereof. In one embodiment Compound 3 Form M and ravulizumab have an overlapping therapeutic effect. For example, the therapeutic effect can be combinatorial or synergistic inhibition.

In one embodiment, the AUC for Compound 3 Form M and the C5 inhibitor overlap.

In one embodiment, the C5 inhibitor is eculizumab. In one embodiment, the C5 inhibitor is ravulizumab. In one embodiment the C5 inhibitor is a small molecule. In another embodiment the C5 inhibitor is a polyclonal antibody targeting C5. In yet another embodiment the C5 inhibitor is an aptamer.

Chemical Description and Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed.

"Deuteration" and "deuterated" means that a hydrogen is replaced by a deuterium such that the deuterium exists over natural abundance and is thus "enriched". An enrichment of 50% means that rather than hydrogen at the specified position the deuterium content is 50%. For clarity, it is confirmed that the term "enriched" as used herein does not mean percentage enriched over natural abundance. In other embodiments, there will be at least 80%, at least 90%, or at least 95% deuterium enrichment at the specified deuterated position or positions. In other embodiments there will be at least 96%, at least 97%, at least 98%, or at least 99% deuterium enrichment at the specified deuterated position or positions indicated. In the absence of indication to the contrary, the enrichment of deuterium in the specified position of the compound described herein is at least 90%.

A "dosage form" means a unit of administration of an active agent. Non-limiting examples of dosage forms include tablets, capsules, gel caps, injections, suspensions, liquids, intravenous fluids, emulsions, creams, ointments, suppositories, inhalable forms, transdermal forms, and the like.

"Pharmaceutical compositions" are compositions comprising at least one active agent, such as a compound or salt of one of the active compounds disclosed herein, and at least one other substance, such as a carrier. Pharmaceutical compositions optionally contain more than one active agent. "Pharmaceutical combinations" or "combination therapy" refers to the administration of at least two active agents, and in one embodiment, three or four or more active agents which may be combined in a single dosage form or provided together in separate dosage forms optionally with instructions that the active agents are to be used together to treat a disorder.

The term "carrier" means a diluent, excipient, or vehicle with which a morphic form is provided.

A "pharmaceutically acceptable excipient" means an excipient that is useful in preparing a pharmaceutical composition/combination that is generally safe, is sufficiently non-toxic, and neither biologically nor otherwise undesirable. A "pharmaceutically acceptable excipient" as used in the present application includes both one and more than one such excipient.

A "patient" or "host" is a human or non-human animal, including, but not limited to, simian, avian, feline, canine, bovine, equine or porcine in need of medical treatment. Medical treatment can include treatment of an existing condition, such as a disease or disorder, or a prophylactic or diagnostic treatment. In a particular embodiment, the patient or host is a human patient. In an alternative embodiment, the patient such as a host is treated to prevent a disorder or disease described herein.

The term "isolated" as used herein refers to the material in substantially pure form. An isolated compound does not have another component that materially affects the properties of the compound. In particular embodiments, an isolated form is at least 60, 70, 80, 90, 95, 98 or 99% pure.

Pharmaceutical Preparations

The isolated morphic forms described herein can be administered in an effective amount to a host to treat any of the disorders described herein using any suitable approach which achieves the desired therapeutic result. The amount and timing of the isolated morphic forms administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

An effective amount of a morphic form as described herein, or the morphic form described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder.

Accordingly, an effective amount of the morphic form or composition described herein will provide a sufficient amount of the active agent when administered to a patient to provide a clinical benefit.

The pharmaceutical composition may be formulated as any pharmaceutically useful form, e.g., a pill, a capsule, a tablet, a transdermal patch, a subcutaneous patch, a dry powder, an inhalation formulation, in a medical device, suppository, buccal, or sublingual formulation. Some dosage forms, such as tablets and capsules, are subdivided into suitably sized unit doses containing appropriate quantities of the active components, e.g., an effective amount to achieve the desired purpose.

The therapeutically effective dosage of the morphic forms described herein will be determined by the health care practitioner depending on the condition, size and age of the patient as well as the route of delivery. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The isolated morphic forms disclosed herein or used as described herein may be administered orally, topically, parenterally, by inhalation or spray, sublingually, via implant, including ocular implant, transdermally, via buccal administration, rectally, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers.

In accordance with the presently disclosed methods, an oral dosage form for administration can be in any desired form in which the morphic form is stable as a solid. In certain embodiments, the isolated morphic form is delivered in a solid microparticle or nanoparticle. When administered through inhalation the isolated morphic form may be in the form of a plurality of solid particles or droplets having any desired particle size, and for example, from about 0.01, 0.1 or 0.5 to about 5, 10, 20 or more microns, and optionally from about 1 to about 2 microns. The isolated morphic forms as disclosed in the present invention have good pharmacokinetic and pharmacodynamics properties, for instance when administered by the oral routes.

The pharmaceutical formulations can comprise the isolated morphic forms described herein in any pharmaceutically acceptable carrier.

Particles can be formed from the morphic form as described herein using a phase inversion method. In this method, the morphic form is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In an alternative embodiment, the morphic form is subjected to a milling process, included but not limited to, hand-milling, rotor-milling, ball-milling, and jet-milling to obtain microparticles and nanoparticles.

In one embodiment, the particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Depending on the intended mode of administration, the pharmaceutical compositions can be in the form of solid form or a semi-solid dosage form that the isolated morphic form is stable in, such as, for example, tablets, suppositories, pills, capsules, powders, or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal administration or in a form suitable for administration by inhalation or insufflation. The preferred manner of administration is oral using a convenient daily dosage regimen which can be adjusted according to the degree of affliction. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally form of a tablet, pill, capsule, powder, or the like. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

Pharmaceutical formulations also are provided which provide a controlled release of a compound described herein, including through the use of a degradable polymer, as known in the art.

In one embodiment the additional therapeutic agent described in the Combination Section below is administered as a pharmaceutically acceptable salt, for example, a salt described below.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil, which maintain the stability of the isolated morphic form. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Use of Morphic Form in Spray Dried Dispersion (SDD) to Manufacture the Compound with Increased Purity In one embodiment a morphic form as described herein is used to create a spray dried dispersion (SDD) that is administered to a patient in need thereof. By first converting an amorphic form Compound 3 to the preferred morphic form and then redissolving it and making a SDD higher purity API can be achieved. In this method, a morphic form is dissolved in an organic solvent such as acetone, methylene chloride, methanol, ethanol, or a mixture thereof (as examples 90:10, 80:20, or 50:50 DCM to methanol) or another suitable organic solvent or mixture thereof. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment a morphic form as described herein is administered to a patient in need thereof as a spray dried dispersion (SDD). In another embodiment the present invention provides a spray dried dispersion (SDD) comprising a morphic form of the present invention and one or more pharmaceutically acceptable excipients as defined herein. In another embodiment the SDD comprises a morphic form of the present invention and an additional therapeutic agent. In a further embodiment the SDD comprises a morphic form of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Uses of Active Compounds for Treatment of Selected Disorders

In one aspect, an effective amount of morphic form or composition as described herein is used to treat a medical disorder which is an inflammatory or immune condition, a disorder mediated by the complement cascade (including a dysfunctional cascade) including a complement factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, a method for the treatment of C3 glomerulonephritis (C3G) is provided that includes the administration of an effective amount of a morphic form described herein, optionally in a pharmaceutically acceptable composition.

In one embodiment, a method for the treatment of paroxysmal nocturnal hemoglobinuria (PNH) is provided that includes the administration of an effective amount of a morphic form described herein, optionally in a pharmaceutically acceptable composition.

In another embodiment, a method for the treatment of wet or dry age-related macular degeneration (AMD) in a host is provided that includes the administration of an effective amount of a morphic form described herein, optionally in a pharmaceutically acceptable composition.

In another embodiment, a method for the treatment of rheumatoid arthritis in a host is provided that includes the administration of an effective amount of a morphic form described herein, optionally in a pharmaceutically acceptable composition.

In another embodiment, a method for the treatment of multiple sclerosis or amyotrophic lateral sclerosis in a host is provided that includes the administration of an effective amount of a morphic form described herein, optionally in a pharmaceutically acceptable composition.

In another embodiment, a method for the treatment of membranoproliferative glomerulonephritis type II (MPGN II) in a host is provided that includes the administration of an effective amount of a morphic form described herein, optionally in a pharmaceutically acceptable composition.

In another embodiment, a method for the treatment of nonalcoholic steatophepatitis (NASH) in a host is provided that includes the administration of an effective amount of a morphic form described herein, optionally in a pharmaceutically acceptable composition.

In another embodiment, a method for the treatment of fatty liver, liver inflammation, cirrhosis, or liver failure in a host is provided that includes the administration of an effective amount of a morphic form described herein, optionally in a pharmaceutically acceptable composition.

In another embodiment, a method for the treatment of dermatomyositis in a host is provided that includes the administration of an effective amount of a morphic form described herein, optionally in a pharmaceutically acceptable composition.

In another embodiment, a method for the treatment of arthritis or COPD in a host is provided that includes the administration of an effective amount of a morphic form described herein, optionally in a pharmaceutically acceptable composition.

In another embodiment, a method for the treatment of a respiratory disease or a cardiovascular disease in a host is provided that includes the administration of an effective amount of a morphic form described herein, optionally in a pharmaceutically acceptable composition.

In another embodiment, a method for the treatment of atypical or typical hemolytic uremic syndrome in a host is provided that includes the administration of an effective amount of a morphic form described herein, optionally in a pharmaceutically acceptable composition.

In another embodiment, a method for the treatment of membrane proliferative glomerulonephritis or age-related macular degeneration (AMD) in a host is provided that includes the administration of an effective amount of a morphic form described herein, optionally in a pharmaceutically acceptable composition.

In another embodiment, a method for the treatment of type I diabetes or complications thereof in a host is provided that includes the administration of an effective amount of a morphic form described herein, optionally in a pharmaceutically acceptable composition.

The morphic form, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent.

Another embodiment is provided that includes the administration of an effective amount of a morphic form, optionally in a pharmaceutically acceptable composition to a host to treat an ocular, pulmonary, gastrointestinal, or other disorder that can benefit from topical or local delivery.

In other embodiments of the invention, a morphic form provided herein can be used to treat or prevent a disorder in a host mediated by complement factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of a morphic form or composition as described herein.

In another embodiment, a morphic form or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of a morphic form or composition as described herein.

In one embodiment, the present invention provides a method of treating or preventing amyotrophic lateral sclerosis by administering to a subject in need thereof an effective amount of a morphic form or composition as described herein.

In one embodiment, the present invention provides a method of treating or preventing abdominal aortic aneurysm, hemodialysis complications, hemolytic anemia, or hemodialysis by administering to a subject in need thereof an effective amount of a morphic form or composition as described herein.

In one embodiment, the present invention provides a method of treating or preventing a C3 glomurenopathy by administering to a subject in need thereof an effective amount of a morphic form or composition as described herein. In one embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of a morphic form or composition as described herein.

In one embodiment, the present invention provides a method of treating or preventing a paroxysmal nocturnal hemoglobinuria (PNH) by administering to a subject in need thereof an effective amount of a morphic form or composition as described herein.

In one embodiment, the present invention provides a method of treating or preventing age-related macular degeneration (AMD) by administering to a subject in need thereof an effective amount of a morphic form or composition as described herein.

In one embodiment, the present invention provides a method of treating or preventing rheumatoid arthritis by administering to a subject in need thereof an effective amount of a morphic form or composition as described herein.

In one embodiment, the present invention provides a method of treating or preventing multiple sclerosis by administering to a subject in need thereof an effective amount of a morphic form or composition as described herein.

In one embodiment, the present invention provides a method of treating or preventing myasthenia gravis by administering to a subject in need thereof an effective amount of a morphic form or composition as described herein.

In one embodiment, the present invention provides a method of treating or preventing atypical hemolytic uremic syndrome (aHUS) by administering to a subject in need thereof an effective amount of a morphic form or composition as described herein.

In one embodiment, the present invention provides a method of treating or preventing neuromyelitis optica (NMO) by administering to a subject in need thereof an effective amount of a morphic form or composition as described herein.

In yet another embodiment, the present invention provides a method of treating or preventing a disorder as described below by administering to a subject in need thereof an effective amount of a morphic form or composition as described herein, including: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In another embodiment, the disorder is selected from:wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion, or central retinal vein occulusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by a morphic form or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In an additional alternative embodiment, a morphic form or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of a morphic form or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

In one embodiment, a morphic form or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment a morphic form or composition as described herein is provided at an effective dose to treat a patient with type 1 diabetes. In one embodiment a morphic form or composition as described herein is provided at an effective dose to treat a patient with type 2 diabetes.

Type 1 diabetes is an autoimmune disease. An autoimmune disease results when the body's system for fighting infection (the immune system) attacks a part of the body. In the case of diabetes type 1, the pancreas then produces little or no insulin.

In some embodiments, the present invention provides a method of treating or preventing a IC-MPGN by administering to a subject in need thereof an effective amount of a morphic form or composition as described herein.

In some embodiments, the present invention provides a method of treating or preventing a paroxysmal nocturnal hemoglobinuria (PNH) by administering to a subject in need thereof an effective amount a morphic form or composition as described herein.

In some embodiments, the present invention provides a method of treating or preventing age-related macular degeneration (AMD) by administering to a subject in need thereof an effective amount of a morphic form or composition as described herein.

In some embodiments, the present invention provides a method of treating or preventing macular dystrophy by administering to a subject in need thereof an effective amount of a morphic form or composition as described herein.

In some embodiments, the present invention provides a method of treating or preventing a Crohn's disease by administering to a subject in need thereof an effective amount of a morphic form or composition as described herein.

In some embodiments, the present invention provides a method of treating or preventing asthma (TH2) or asthma (non-TH2) by administering to a subject in need thereof an effective amount of a morphic form or composition as described herein.

In some embodiments, the present invention provides a method of treating or preventing a diabetic retinopathy by administering to a subject in need thereof an effective amount of a morphic form or composition as described herein.

In some embodiments, the present invention provides methods of treating or preventing a nephrology disorder selected from acute kidney injury (AKI), idiopathic membranous nephropathy, IgA nephropathy (IgAN) lupus nephritis (IN), and primary focal segmental glomerulosclerosis by administering to a subject in need thereof an effective amount of a morphic form or composition as described herein.

In some embodiments, the present invention provides methods of treating or preventing preeclampsia by administering to a subject in need thereof an effective amount of a morphic form or composition as described herein.

Combination Therapy

In one embodiment a morphic form or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, a morphic form or composition as described herein may be provided in combination or alternation with at least one additional inhibitor of the complement system or a second active compound with a different biological mechanism of action.

In non-limiting embodiments, a morphic form or composition as described herein may be provided together with a protease inhibitor, a soluble complement regulator, a therapeutic antibody (monoclonal or polyclonal), complement component inhibitor, receptor agonist, or siRNA.

In other embodiments, a morphic form described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, a morphic form as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, a morphic form as described herein can be administered in combination or alternation with an anti-IL6 antibody, including but not limited to tocilizumab (Actemra) and siltuximab (Sylvant).

In an alternative embodiment, a morphic form as described herein can be administered in combination or alternation with an IL17 inhibitor, including but not limited to secukibumab (Cosentyx).

In an alternative embodiment, a morphic form as described herein can be administered in combination or alternation with a p40 (IL12/IL23) inhibitor, including but not limited to ustekinumab (Stelara).

In an alternative embodiment, a morphic form as described herein can be administered in combination or alteration with an IL23 inhibitor, including but not limited to risankizumab.

In an alternative embodiment, a morphic form as described herein can be administered in combination or alteration with an anti-interferon a antibody, for example but not limited to sifalimumab.

In an alternative embodiment, a morphic form as described herein can be administered in combination or alteration with a kinase inhibitor, for example but not limited to a JAK1/JAK3 inhibitor, for example but not limited to tofacitinib (Xelianz). In an alternative embodiment, a morphic form as described herein can be administered in combination or alteration with a JAK1/JAK2 inhibitor, for example but not limited to baracitibib.

In an alternative embodiment, a morphic form as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, a morphic form as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-Li/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived CI-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^v$/TP-20 (Avant Immunotherapeutics); MLN-2222/CAB-2 (Millenium Pharmaceuticals); Mirococept (Inflazyme Pharmaceuticals); Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1, APL-2 (Appelis); CP40/AMY-101, PEG-Cp40 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Additional non-limiting examples that can be used in combination or alternation with a morphic form or composition as described herein include the following.

Non-limiting examples of potential therapeutics for combination therapy

| Name | Target | Company | Class of Molecule |
| --- | --- | --- | --- |
| LFG316 | C5 | Novartis/Morphosys | Monoclonal antibody |
| 4(1MEW)APL-1,APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101,PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOB1002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |

Non-limiting examples of potential therapeutics for combination therapy

| Name | Target | Company | Class of Molecule |
| --- | --- | --- | --- |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| Lampalizumab | fD | Roche | Monoclonal Antibody |
| avacincaptad pegol | C5 | Opthotech | Aptamer |
| regenemab | C6 | Regenesance | Monoclonal Antibody |
| BIVV020 | C1s | Bioverativ | Monoclonal Antibody |
| PRO-02 | C2 | Broteio/Argen-x | Monoclonal Antibody |
| 5C6, compsorbin | fH | Amyndas | Peptide |
| SOBI005 | C5 | Sobi | Protein |
| ISU305 | C5 | ISU ABXIS | Monoclonal Antibody |
| Mubodina | C5 | Adienne | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompé | Small Molecule |
| IPH5401 | C5aR1 | Innate Pharma | Monoclonal Antibody |
| C6-LNA | C6 | Regenesance | Oligonucleotide |
| SKY59 | C5 | Roche | Monoclonal Antibody |
| REGN3918 | C5 | Regeneron | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In one embodiment, a morphic form or composition as described herein may be provided together with a compound that inhibits an enzyme that metabolizes an administered protease inhibitor. In one embodiment, a morphic form or composition may be provided together with ritonavir.

In one embodiment, a morphic form or composition as described herein may be provided in combination with a complement C5 inhibitor or C5 convertase inhibitor. In another embodiment, a morphic form or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, a morphic form or composition as described herein may be provided together with a compound that inhibits Complement Factor D. In one embodiment of the invention, a morphic form or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Biocyst Pharmaceuticals US Patent Application US2019/0142802 describes open chain Factor D inhibitors; Novartis PCT patent publication WO2012/093101 titled "Indole compounds or analogues thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, the present invention provides a method of treating or preventing age-related macular degeneration (AMD) by administering to a subject in need thereof an effective amount of a morphic form or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of a morphic form or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing paroxysmal nocturnal hemoglobinuria (PNH) by administering to a subject in need thereof an effective amount of a morphic form or composition as described herein with an additional inhibitor of the complement system or another active compound with a different biological mechanism of action.

In one embodiment, the present invention provides a method of treating or preventing multiple sclerosis by administering to a subject in need thereof an effective amount of a morphic form or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of a morphic form or composition as described herein in combination or alternation with a corticosteroid. Examples of corticosteroids include, but are not limited to, prednisone, dexamethasone, solumedrol, and methylprednisolone. In one embodiment, a morphic form or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H. P. Acthar Gel (ACTH), or a combination thereof.

In an additional alternative embodiment, a morphic form or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, a morphic form or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a complement component inhibitor, for example but not limited to Compstatin/POT-4 (Potentia Pharmaceuticals); ARC1905 (Archemix); 4(1MEW)APL-1, APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TK1258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera).

In one embodiment, a morphic form or composition as described herein may be provided in combination with a non-steroidal anti-inflammatory drug for the treatment of Lupus.

In one embodiment, a morphic form or composition as described herein may be provided in combination with a corticosteroid for the treatment of Lupus.

In one embodiment, a morphic form or composition as described herein may be provided in combination with a belimumab (Benlysta) for the treatment of Lupus.

In one embodiment, a morphic form or composition as described herein may be provided in combination with hydroxychloroquine (Plaquenil) for the treatment of Lupus.

In one embodiment, a morphic form or composition as described herein may be provided in combination with sifalimumab for the treatment of Lupus.

In one embodiment, a morphic form or composition as described herein may be provided in combination with OMS721 (Omeros) for the treatment of a complement mediated disorder. In one embodiment, a morphic form or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, a morphic form or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, a morphic form or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, a morphic form or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with a morphic form or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-lRA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibiton); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-10 converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, a morphic form or composition as described herein may be provided in combination with a corticosteroid for the treatment or prevention of cytokine or inflammatory reactions in response to the administration of pharmaceuticals or biotherapeutics. In another embodiment, a morphic form or composition as described herein may be provided in combination with etarnercept for the treatment or prevention of cytokine or inflammatory reactions in response to the administration of pharmaceuticals or biotherapeutics. In another embodiment, a morphic form or composition as described herein may be provided in combination with tocilizumab for the treatment or prevention of cytokine or inflammatory reactions in response to the administration of pharmaceuticals or biotherapeutics. In another embodiment, a morphic form or composition as described herein may be provided in combination with etarnercept and tocilizumab for the treatment or prevention of cytokine or inflammatory reactions in response to the administration of pharmaceuticals or biotherapeutics. In another embodiment, a morphic form or composition as described herein may be provided in combination with infliximab for the treatment or prevention of cytokine or inflammatory reactions in response to the administration of pharmaceuticals or biotherapeutics. In another embodiment, a morphic form or composition as described herein may be provided in combination with golimumab for the treatment or prevention of cytokine or inflammatory reactions in response to the administration of pharmaceuticals or biotherapeutics.

C5 Inhibitors

Provided herein are methods for treating factor D mediated disorders in a subject comprising administering to the subject an effective amount of a C5 inhibitor in combination or alternation with an effective amount of a morphic form of Compound 3. In certain embodiments the factor D mediated disorder is PNH.

C5 inhibitors are known in the art. In one embodiment, the C5 inhibitor is a monoclonal antibody targeting C5. In one embodiment, the C5 inhibitor is eculizumab (Soliris™ Alexion Pharmaceuticals, New Haven, CT, see, e.g., U.S. Pat. No. 9,352,035). In one embodiment, the C5 inhibitor is ravulizumab. In one embodiment the C5 inhibitor is a small molecule pharmaceutical. In another embodiment the C5 inhibitor is an antibody. In another embodiment the C5 inhibitor is a polyclonal antibody targeting C5. In yet another embodiment the C5 inhibitor is an aptamer.

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (small animal protein, Volution Immuno-pharmaceuticals, Geneva, Switzerland; see e.g. Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883,158); ARC-1905 (pegylated RNA aptamer, Ophthotech, Princeton, NJ and New York, NY; see Keefe et al., Nature Reviews Drug Discovery, 9, 537-550); RA101348 and RA101495 (macrocyclic peptides, Ra Pharmaceuticals, Cambridge, MA); SOBI002 (affibody, Swedish Orphan Biovitrum, Stockholm, Sweden); ALN-CC5 (Si-RNA, Alnylam Pharmaceuticals, Cambridge, MA); ARC1005 (aptamers, Novo Nordisk, Bagsvaerd, Denmark); SOMAmers (aptamers, SomaLogic, Boulder, Co); SSL7 (bacterial protein toxin, see, e.g. Laursen et al. Proc. Natl. Acad. Sci. U.S.A., 107(8):3681-6); MEDI7814 (monoclonal antibody, MedImmune, Gaithersburg, MD); aurin tricarboxylic acid; aurin tricarboxylic acid derivatives (Aurin Biotech, Vancouver, BC, see U.S. Patent Appl. Pub. 2013/003592); RG6107 (anti-C5 recycling antibody, Roche Pharmaceuticals, Basel, Switzerland); Ravulizumab (ALXN1210) and ALXN5500 (monoclonal antibodies, Alexion Pharmaceuticals, New Haven, CT); TT30 (fusion protein, Alexion Pharmaceuticals, New Haven, CT); REGN3918 (monoclonal antibody, Regeneron, Tarrytown, NY); ABP959 (eculizumab biosimilar, Amgen, Thousand Oaks, CA); or combinations thereof.

In one embodiment, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In one embodiment, the C5 inhibitor is coversin. Coversin is a recombinant protein derived from a protein discovered in the saliva of the *Ornithodoros moubata* tick currently developed as a recombinant protein by *Akari* Therapeutics. Coversin is described in Penabad et al. Lupus 2012, 23(12):1324-6.

In one embodiment, the C5 inhibitor is Tesidolumab/LFG316. Tesidolumab is a monoclonal antibody developed by Novartis and Morphosys. Tesidolumab is described in U.S. Pat. Nos. 8,241,628 and 8,883,158.

In one embodiment, the C5 inhibitor is ARC-1905. ARC-1905 is a pegylated RNA aptamer developed by Ophthotech. ARC-1905 is described in Keefe et al. Nature Reviews Drug Discovery, 9:537-550.

In one embodiment, the C5 inhibitor is RA101348. RA101348 is a macrocyclic peptide developed by Ra Pharmaceuticals.

In one embodiment, the C5 inhibitor is RA101495. RA101495 is a macrocyclic peptide developed by Ra Pharmaceuticals.

In one embodiment, the C5 inhibitor is SOBI002. SOBI002 is an affibody developed by the Swedish Orphan Biovitrum.

In one embodiment, the C5 inhibitor is ARC1005. ARC1005 is an aptamer developed by Novo Nordisk.

In one embodiment, the C5 inhibitor is SOMAmers for C5. SOMAmers are aptamers developed by SomaLogic.

In one embodiment, the C5 inhibitor is SSL7. SSL7 is a bacterial protein toxin described in Laursen et al. Proc. Natl. Acad. Sci. U.S.A., 107(8):3681-6.

In one embodiment, the C5 inhibitor is MEDI7814. MEDI7814 is a monoclonal antibody developed by MedImmune.

In one embodiment, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In one embodiment, the C5 inhibitor is RG6107/SKY59. RG6107/SKY59 is an anti-C5 recycling antibody developed by Roche Pharmaceuticals.

In one embodiment, the C5 inhibitor is Ravulizumab (ALXN1210). In another embodiment, the C5 inhibitor is ALXN5500. ALXN1210 and ALXN5500 are monoclonal antibodies developed by Alexion Pharmaceuticals.

In one embodiment, the C5 inhibitor is TT30. TT30 is a fusion protein developed by Alexion Pharmaceuticals.

In one embodiment, the C5 inhibitor is ABP959. ABP959 is an eculizamab biosimilar monoclonal antibody developed by Amgen.

In one embodiment, the C5 inhibitor is Anti-C5 siRNA. Anti-C5 siRNA was developed by Alnylam Pharmaceuticals.

In one embodiment, the C5 inhibitor is Erdigna®. Erdigna® is an antibody developed by Adienne Pharma.

In one embodiment, the C5 inhibitor is avacincaptad pegol/Zimura®. Avacincaptad pegol is in aptamer developed by Opthotech.

In one embodiment, the C5 inhibitor is SOBI005. SOBI005 is a protein in developed by the Swedish Orphan Biovitrum.

In one embodiment, the C5 inhibitor is ISU305. ISU305 is a monoclonal antibody developed by ISU ABXIS.

In one embodiment, the C5 inhibitor is REGN3918. REGN3918 is a monoclonal antibody developed by Regeneron.

In another embodiment, a morphic form or composition as described herein may be provided in combination with ABP959, a monoclonal antibody directed to the complement factor C5 and manufactured and marketed by Amgen. In another embodiment, a morphic form or composition or composition as described herein may be provided in combination with BOWo8o, a monoclonal antibody directed to the complement factor C5 and manufactured and marketed by Epirus Biopharmaceuticals. In another embodiment, a morphic form or composition or composition as described herein may be provided in combination with SB12, a monoclonal antibody directed to the complement factor C5 and manufactured and marketed by Samsung Bioepis.

C3 Inhibitors

Provided herein are methods for treating factor D mediated disorders in a subject comprising administering to the subject an effective amount of a C3 inhibitor in combination or alternation with an effective amount of a a morphic form of Compound 3. In certain embodiments the factor D mediated disorder is PNH.

In one embodiment the C3 inhibitor is a small molecule. In another embodiment the C3 inhibitor is a polyclonal antibody targeting C3. In another embodiment the C3 inhibitor is a monoclonal antibody targeting C3. In yet another embodiment the C3 inhibitor is an aptamer.

C3 inhibitors are known in the art. In one embodiment, a morphic form or composition of the present invention is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9,371,365; 9,169,307; 8,946,145; 7,989,589; 7,888,323; 6,319,897; and US Patent Appl. Pub. Nos. 2016/0060297; 2016/0015810; 2016/0215022; 2016/0215020; 2016/0194359; 2014/0371133; 2014/0323407; 2014/0050739; 2013/0324482; and 2015/0158915. In one embodiment, the compstatin analog having the amino acid sequence ICVVQDWGHHCRT (SEQ. ID. NO. 1). In another embodiment, the C3 inhibitor is a compstatin analog. In one embodiment, the compstatin analog is 4(1MeW)/APL-1 of the sequence Ac-ICV(1-mW)QDWGAHRCT (SEQ. ID. NO. 2), wherein Ac is acetyl and 1-mW is 1-methyltryptophan. In another embodiment, the compstatin analog is Cp40/AMY-101, which has an amino acid sequence yICV(1 mW)QDW-Sar-AHRC-mI (SEQ. ID. NO. 3), wherein y is D-tyrosine, 1 mW is 1-methyltryptophan, Sar is sarcosine, and mI is N-methylisoleucine. In yet another embodiment, the compstatin analog is PEG-Cp40, having the amino acid sequence PEG-yICV(1 mW)QDW-Sar-AHRC-mI (SEQ. ID. NO. 4), wherein PEG is polyethyleneglycol (40 kDa), y is D-tyrosine, 1 mW is 1-methyltryptophan, Sar is sarcosine, and mI is N-methylisoleucine. In yet another embodiment, the compstatin analog is 4(1MeW)POT-4, 4(1MeW)POT-4 was developed by Potentia. In yet another embodiment, the compstatin analog is AMY-201. AMY-201 was developed by Amyndas Pharmaceuticals.

In one embodiment, the C3 inhibitor is H17. H17 is a humanized monoclonal antibody in development by EluSys Therapeutics. H17 is described in Paixao-Cavalcante et al. J. Immunol. 2014, 192(10):4844-4851.

In one embodiment, the C3 inhibitor is mirococept. Mirococept is a CR1-based protein developed by Inflazyme Pharmaceuticals.

In one embodiment, the C3 inhibitor is sCR1. sCR1 is a soluble form of the CR1 protein developed by Celldex.

In one embodiment, the C3 inhibitor is TT32. TT32 is a CR-1 based protein developed by Alexion Pharmaceuticals.

In one embodiment, the C3 inhibitor is HC-1496. HC-1496 is a recombinant peptide developed by InCode.

In one embodiment, the C3 inhibitor is CB 2782. CB 2782 is novel protease derived from human membrane type serine protease 1 (MTSP-1) that was developed by Catalyst Biosciences.

In one embodiment, the C3 inhibitor is APL-2. APL-2 is a pegylated version of APL-1 developed by Apellis Pharmaceuticals.

Pan-inhibitors of Complement Components

Provided herein are methods for treating PNH comprising administering a pan-inhibitor of complement components in combination or alternation with a compound of the present invention. Pan-inhibitors of complement components are known in the art. In one embodiment, the inhibitor is FUT-175.

Combinations for Prophylactic or Concommitant Anti-Bacterial Therapy

In one aspect of the present invention, a method is provided for treating a host in need thereof that comprises administering an effective amount of a prophylactic anti-bacterial vaccine prior to administration of a morphic form or composition for any of the disorders described herein. In another aspect of the present invention, a method is provided for treating a host in need thereof that comprises administering an effective amount of a prophylactic anti-bacterial drug, such as a pharmaceutical drug, prior to administration of a morphic form or composition for any of the disorders described herein. In one aspect of the present invention, a method is provided for treating a host in need thereof that comprises administering an effective amount of an anti-bacterial vaccine after administration of a morphic form or composition for any of the disorders described herein. In another aspect of the present invention, a method is provided for treating a host in need thereof that comprises administering an effective amount of an anti-bacterial drug, such as a pharmaceutical drug, after administration of a morphic form or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, a morphic form or composition as described herein is administered to a host concomitantly to a subject following the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject and, during the administration period of the morphic form, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered a morphic form or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving a morphic form or composition as described herein, is vaccinated against a bacterial infection caused by the bacterium Neisseria meningitidis. In one embodiment, the subject is vaccinated against a bacterial infection caused by the bacterium Haemophilus influenzae. In one embodiment, the Haemophilus influenzae is Haemophilus influenzae serotype B (Hib). In one embodiment, the subject is vaccinated against a bacterial infection caused by Streptococcus pneumoniae. In one embodiment, the subject is vaccinated against a bacterial infection caused by the bacterium Nisseria meningitidis, Haemophilus influenzae, or Streptococcus pneumoniae, or a combination of one or more of Nisseria meningitidis, Haemophilus influenzae, or Streptococcus pneumoniae. In one embodiment, the subject is vaccinated against a bacterial infection caused by the bacterium Nisseria meningitidis, Haemophilus influenzae, and Streptococcus pneumoniae.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium Nisseria *meningitidis*, *Haemophilus influenzae*, or *Streptococcus pneumoniae*, or a combination of one or more of Nisseria *meningitidis*, *Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the subject is vaccinated with one or more vaccines selected from, but not limited to, typhoid vaccine, live (Vivotif *Berna* Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *haemophilus* b conjugate (prp-t) vaccine (ActHIB, Sanofi; Hibrix, GSK), *haemophilus* b conjugate (hboc) vaccine (HibTITER, Neuron Biotech), *haemophilus* b conjugate (prp-omp) vaccine (PedvaxHIB, Merck), *haemophilus* b conjugate (prp-t) vaccine/meningococcal conjugate vaccine (MenHibrix, GSK), *haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal *Berna*, Hendricks Regional Health), *Bacillus* Calmette and Guerin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/ polio (Kinrix, GSK; Quadracel, Sanofi), diphtheria and tetanus toxois and pertussis tetanus/hepatitis B/polio (Pediarix, GSK), diphtheria and tetanus toxois and pertussis/ polio, *haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Surnamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

EXAMPLES

Example 1

Scheme 1. Synthesis of Compound 3

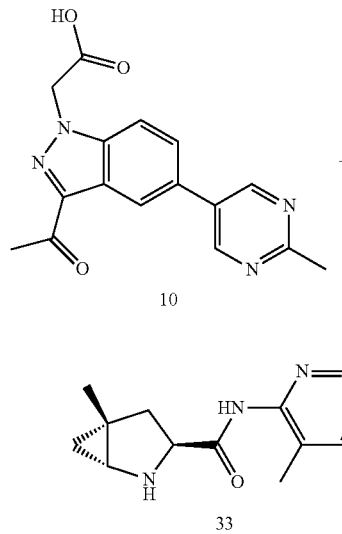

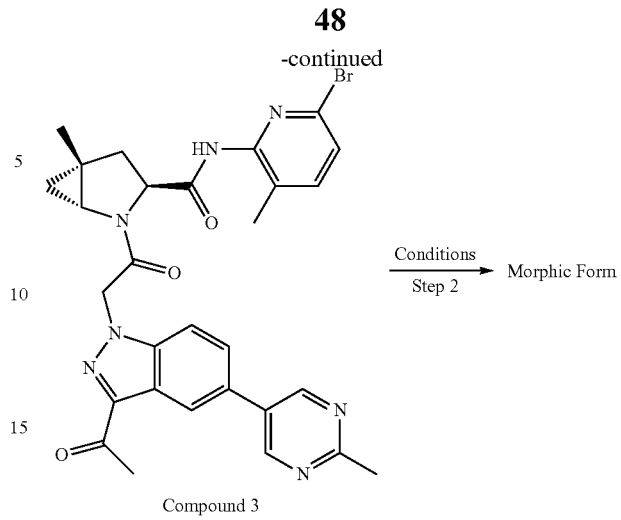

To a solution of intermediate 10 and intermediate 33 in DMF is added N,N-diisopropylethylamine. TBTU is added while maintaining the temperature of the reaction. The reaction is warmed to room temperature and stirred for 4-8 hours. The reaction is diluted with water and the resulting solid formed is collected by centrifugation. The solid is washed with water two times and then dissolved in DCM and treated with siliabondthiol resin and activated charcoal to remove Pd based impurities. The resin and charcoal are removed by filtration and washed with MeOH/IDCM. The filtrates are evaporated to dryness and the residue purified by chromatography over silica gel using methanol/DCM. The pure fractions are combined and evaporated to dryness.

Example 2. Polymorph Experiments of Compound 3

TABLE 1

Polymorph Studies of Compound 3, Starting Material is Disordered Compound 3 unless noted otherwise.

| Solvent | Conditions | Observations | XRPD Result |
|---|---|---|---|
| Acetone | FE | Yellow glass, no B/E | — |
|  | SE | Clear, yellow glass | — |
|  | Δ (~40° C.) | Needles in yellow solution | Form B |
| ACN | FE | Pale yellow glass, no B/E | — |
|  | SE | Needles | Form D |
|  | ET VR/ SC | Solid free solution | — |
|  | Sonication | Solid free solution | — |
| CH$_2$Cl$_2$ | SE | Yellow glass, no B/E | — |
| CH$_2$Cl$_2$ (dry) | SC (~45° C.) | Deep yellow solution, no solids | — |
|  | Sonication | Light yellow film | — |
| CH$_2$Cl$_2$ | Δ (~40° C.) | Yellow glass | — |
|  | Δ (~45° C.) | Yellow glass | — |
|  | ~75% RH/ RT | Yellow glass | — |
|  | Δ (~45° C.) | Yellow glass | — |
| EtOH | SC | Pale yellow solution, no solids | — |
|  | Sample left at RT | Needles in solution | — |
|  | FE | Glassy solids w/ a few, fine needles, s.s. | — |
| EtOH/H$_2$O [40:60] | CP/RT Slurry | Sample immediately turned cloudy with H$_2$O introduction. A few, fine needles + apparent oil present in solution. White needles resulted. | Form B + 2 minor peaks (10.5, 19.5 °2θ) |
| EtOH/Heptane | CP | No solids immediately generated from solution, Yellow, opaque solids (no B/E) resulted | Form A |

TABLE 1-continued

Polymorph Studies of Compound 3, Starting Material is Disordered Compound 3 unless noted otherwise.

| Solvent | Conditions | Observations | XRPD Result |
| --- | --- | --- | --- |
| EtOAc | FE | Pale yellow glass, no B/E | — |
| | RT Slurry | Yellow, opaque solids, no B/E | — |
| | RT Slurry, saturation, ppt | — | Form A |
| | ~50° C. Slurry, saturation, ppt | — | Form A |
| | Solids in contact with EtOAc, ~50° C. | Lot 258-182-4 used as starting material, Yellow, opaque solids (no B/E) + needles | Form A |
| EtOAc (dry) | SC (~50° C.) | Light yellow film in yellow solution | — |
| | Δ (~40 ° C.) | Yellow glass in yellow solution | — |
| | Δ (~45° C.) | Small needles w/ yellow glass | Form B + Form C |
| EtOAc/Heptane | RT, Ppt | No immediate ppt, sample became cloudy | — |
| IPA | SC (~60° C.) | Small quantity of solids persisted in solution (undissolved). Undissolved solids persisted + needles (s.s.) | — |
| | | Needles dissolved. Opaque, white mass and needles generated with time. | — |
| | FE | Mixture of glassy material + needles | Poorly crystalline Form A |
| | RT Slurry | Yellow, opaque solids, no B/E | Form A - add'l peaks present not found in starting material |
| IPA: Ether | CP | Sample remained solids free. Sample capped and left at RT. No solids generated over time. | — |
| | FE | Needles | Form A |
| IPA/H2O | FE | Needles | Form H |
| IPA/Heptane | RT, Ppt | No immediate ppt | — |
| IPA/ H2O [80:20] | RT Slurry | Clear solution resulted | — |
| IPA/ H2O [95:5] | RT Slurry | Yellow solids; no B/E | Form A |
| MeOH | FE | Deep yellow glass, no B/E | — |
| | SE | Clear, yellow glass | — |
| | Δ (~40° C.) | Yellow glass in yellow solution | — |
| | Δ (~45° C.) | Yellow glass | — |
| | ~75% RH/RT | Yellow glass | — |
| | Δ (~45° C.) | Yellow glass | — |
| MEK | FE | Pale yellow glass, no B/E | — |
| MEK (dry) | SC (~50° C.) | Light yellow solution, no solids | — |
| | Sonication | Fine needles in yellow solution | — |
| | FE | Glassy solids; elements of B/E | — |
| | Δ (~40° C.) | Yellow; opaque solids, no BE | Form C |
| MTBE | RT Slurry | Yellow, opaque solids, no B/E | Form I |
| | Solids in contact with MTBE, ~50° C. | Lot 258-182-4 used as startina material. Yellow, opaque solids, no B/E | — |
| MTBE/Heptane | RT, Ppt | No immediate ppt, sample became cloudy | — |
| THF | ET VR/SC | No solids in solution | — |
| | Sonication | Light yellow glass | — |
| THF/Heptane | CP | Sample turned opaque w/ heptane introduction. Oil quickly formed. Yellow, opaque solids (no B/E) formed over time | Form A |
| Toluene | RT Slurry | Yellow, opaque solids, no B/E | — |
| | Solids in contact with toluene, ~50° C. | Lot 258-182-4 used as starting material. Yellow, opaque solids (no BE) + needles | Form A |
| Toluene/Heptane | RT, Ppt | No immediate ppt | — |
| H$_2$O | ET Slurry (~60° C.) | Small tablets | Highly disordered |

TABLE 1-continued

Polymorph Studies of Compound 3, Starting Material is Disordered Compound 3 unless noted otherwise.

| Solvent | Conditions | Observations | XRPD Result |
|---|---|---|---|
| | Solids in contact with H2O, ~50° C. | Lot 258-182-4 used as starting material Layered glass, no B/E | Form B + minor Form A |

*Pattern successfully indexed
FE: Fast evaporation
ET: Elevated temperature fast evaporation
SE: Slow evaporation
VR: Volume reduction
SC: Slow cool
RT ppt: Ambient temperature precipitation.
CP: Crash precipitation
SVD: Solid-vapor diffusion
Roto-vap: Rotary Evaporation The procedures for the conditions in Table 1 are discussed below.

Fast Evaporation (FE)

A solution of Compound 3 and solvent/solvent system of interest was prepared. The sample was filtered and left under ambient conditions until dry.

Slow Evaporation (SE)

A solution of Compound 3 and solvent/solvent system of interest was prepared. The sample was filtered. The sample was covered with aluminum foil perforated with 5 holes. The sample was left under ambient conditions until dry.

Volume Reduction (VR)

A solution of Compound 3 and solvent/solvent system of interest was prepared. The sample was filtered and left under ambient conditions, but not allowed to completely dry. The sample was monitored for the generation of solids within the solution.

Elevated Temperature (ET) Volume Reduction (VR)

A solution of Compound 3 and solvent/solvent system of interest was prepared at elevated temperature. The sample was filtered, at temperature. Evaporation occurred, but the sample was not allowed to completely dry. The sample was monitored for the generation of solids within the solution.

Slurry—Ambient (RT) or Elevated (ET) Temperature

A solution of Compound 3 and solvent/solvent system of interest was prepared. Solids persisted in solution. The samples were placed onto a stir plate at ambient (RT) or elevated (ET) temperatures. The samples were monitored to ensure that solids persisted during the slurry process. The solids were collected via vacuum filtration and dried under ambient conditions.

Slow Cool (SC)

A solution of Compound 3 and solvent/solvent system of interest was prepared. The samples were stirred at elevated temperature. The solutions were monitored to ensure that solids persisted throughout the stirring process. The samples were filtered at temperature in vials equilibrated at the specified temperature. The heat source was shut off and the samples were allowed to slowly cool to ambient temperature.

Ambient Temperature (RT) Precipitation (Ppt)

Saturated solutions of Compound 3 in a solvent of interest were prepared at ambient temperature. The solution was either filtered into an ambient temperature anti-solvent or anti-solvent was added to the Compound 3 solution. The samples were monitored for any sign of solids generation.

Crash Precipitation (CP)

Saturated solutions of Compound 3 in a solvent of interest were prepared at elevated temperature. The solution was filtered into an anti-solvent kept at a lower temperature. The samples were monitored for any sign of solids generation.

Relative Humidity (RH) Stress

Compound 3 was placed into vials which were sealed into chambers containing saturated salt solutions. The samples were kept under these relative humidities for a period of days and then checked for signs of morphology differences.

Solid Vapor Diffusion (SVD)

Compound 3 was placed into vials which were sealed into chambers containing organic solvents. The samples were kept under these conditions for a period of days and then checked for signs of morphology changes.

Heating (A)

Saturated solutions of Compound 3 or solids generated from crystallization attempts were prepared. A small quantity of the sample was placed into an oven set at a specified temperature. The samples were monitored, microscopically, for signs of crystallization.

Sonication

Probe sonication was carried out utilizing a Cole-Parmer Ultrasonic Processor (model CP130) with a 3-mm probe. The settings were: amplitude 40, pulse 2 sec. The solutions were sonicated five times and then sealed and left under ambient conditions.

Instrumental Techniques

The following methods have not been validated for compliance with 21 CFR 211.165(e) for this compound.

X-ray Powder Diffraction (XRPD)

Most XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

A few XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Differential Scanning Calorimetry (DSC)

DSC was performed using a TA Instruments 2920 or Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The method code on the thermogram is an abbreviation for the start and end temperature as well as the heating rate; e.g., -30-250-10 means "from −30° C. to 250° C., at 10° C./min". The following table summarizes the abbreviations used in each image for pan configurations:

| Abbreviation (in comments) | Meaning |
|---|---|
| T0C | Tzero crimped pan |
| HS | Lid hermetically sealed |
| HSLP | Lid hermetically sealed and perforated with a laser pinhole |
| T0BSLP | Tzero pan, lid hermetically sealed and perforated with a laser pinhole |
| C | Lid crimped |
| NC | Lid not crimped |

Thermogravimetric (TG) Analysis

TG analyses were performed using a TA Instruments Q5000 IR thermogravimetric analyzer. Temperature calibration was performed using nickel and Alumel™. Each sample was placed in an aluminum pan. The sample was hermetically sealed, the lid pierced, then inserted into the TG furnace. The furnace was heated under nitrogen. The method code on the thermogram is an abbreviation for the start and end temperature as well as the heating rate; e.g., 00-350-10 means "from 25° C. to 350° C., at 10° C./min".

Hot Stage (HS) Microscopy

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×objective with crossed polarizers and a first order red compensator. Images were captured using SPOT software (v. 4.5.9).

Proton (H) Solution Nuclear Magnetic Resonance (NMR) Spectroscopy

The solution NMR spectra were acquired with an Agilent DD2-400 spectrometer. The samples were prepared by dissolving each sample in DMSO-$d_6$ containing TMS.

An enabling form study was also carried out (Table 2).

TABLE 2

Enabling Form Study for Morphic Forms of Compound 3

| Solvent | Conditions | Observations* | XRPD Result |
|---|---|---|---|
| EtOAc | RT Slurry | ~14.5 mg/mt, solubility | Form B |
| IPA | RT Slurry | ~5.6 mg/mt, solubility | Form A |
| MTBE | RT Slurry | ~1.2 mg/mL solubility | Form C |
| THF | RT Slurry | Solids free solution | — |
| Toluene | RT Slurry | ~13.6 mg/mL solubility | Form C + Form F |

TABLE 3

Characterization of Compound 3 Forms

| Form | Analysis | Result |
|---|---|---|
| A | XRPD | FIG. 3 |
|   | DSC | After heating to ~100° C., apparent $T_g$ ~114° C. |
|   | TG | ~3.6% wt loss to 250° C. |
| B | XRPD | Crystalline - Form B* |
|   | DSC | Broad endo., onset ~176° C. |
|   | TG | 1.3% wt loss to 250° C. |
| C | XRPD | Form C |
|   | TG | 7.7% wt loss to 175° C. |
|   |   | 5.0% wt loss, 175-250° C. |
| E | XRPD | Crystalline - Form E |
|   | TG | 1.4% wt loss to 75° C. |
|   |   | 0.7% wt loss 75-250° C. |
| G | XRPD | Crystalline - Form G |
|   | DSC | Endo. onset ~131° C., max ~142° C. |
|   |   | Exo, max ~174° C. |
|   |   | Endo. onset ~187° C., max ~211° C. |
|   | TG | 1.9% wt loss to 250° C. |
| J | XRPD | Crystalline - Form J* |
|   | DSC | Endo. onset ~83° C., max ~104° C. |
|   |   | Exo. baseline shift ~134° C. |
|   | TG | 5.2% wt loss to 75° C. |
|   |   | 3.3% wt loss, 75-150° C. |
|   |   | 0.8% wt loss, 150-250° C. |
| M | XRPD | Crystalline - Form M* |
|   | DSC | Endo. onset ~205° C., max ~211° C. |
|   | TG | 1.4% wt loss to 250° C. |

TABLE 4

Additional Characterization of Compound 3 Forms

| Form | Thermal | Other Analytical |
|---|---|---|
| A | Melt 133-150° C. 0.8% weight loss to 250° C. | $^1$H NMR spectrum collected |
| B | Apparent melt, onset ~176° C. 1.3% weight loss to 250° C. | $^1$H NMR spectrum collected Possible stable form at or below ambient temperature |

TABLE 4-continued

Additional Characterization of Compound 3 Forms

| Form | Thermal | Other Analytical |
|---|---|---|
| C | 7.7% weight loss to 175° C. 5.0% weight loss 175-250° C. | XRPD results indicated a disordered material was present Resisted solid form change with mild heating |
| D | — | Obtained in acetonitrile |
| E | 1.4% weight loss to 75° C. 0.7% weight loss 75-250° C. | Obtained in acetonitrile |
| F | — | XRPD results indicated a disordered material was present Obtained as a mixed phase through a slurry of material in toluene Resisted solid form change with mild heating |
| G | Apparent melt, onset ~131° C. Possible recrvstallization Possible melt, onset ~187° C. 1.9% wt loss to 250° C. | Obtained through mild heating of Form E Converted to Form B in solution When heated to ~160° C., converted to Form M |
| H | — | XRPD results indicated a disordered material was present Generated in isopropyl alcohol/ water |
| I | — | XRPD results indicated a disordered material was present Obtained through a slurry in MTBE |
| J | Apparent melt, onset ~83° C. Exothermic baseline shifting ~134° C. 5.2% wt loss to 75° C. 3.3% wt loss 75-150° C. 0:8% wt loss 150-250° C. | Generated from a slurry in ACN |
| K | — | Closely Related to Form J Generated from a slurry in ACN/H₂O [1:1] |
| L | — | Only detected as a mixture with Form J Mixture generated from an ACN/H₂O [95:5] slurry |
| M | Apparent melt onset ~205° C. 1.4% wt loss to 250° C. | Generated from heating of Form G at ~160° C. Stable form at ~50° C. |

TABLE 5

Vapor Stress Experiments at Room Temperature

| Solvent | Form | Observations | XRPD Result |
|---|---|---|---|
| EtOAc | A | Mostly yellow, opaque solids (no B/E) w/ fine needles | — |
| MTBE | | Yellow, opaque solids; no B/E | — |
| Toluene | | Mostly yellow, opaque solids (no B/E) w/ fine needles | — |
| H₂O | | Yellow, opaque solids; no B/E | — |
| EtOAc | Dis-ordered | Tacky solids (B/E) | Form B |
| MTBE | | Tacky, yellow, opaque solids | Form C |
| Toluene | | Sample turned glassy; sample left under ambient conditions. Yellow glass resulted | — |
| | | Sample placed in ~50° C. oven | Yellow, opaque solids; no B/E |
| H₂O | | Yellow, opaque solids; no B/E | Highly Disordered |

TABLE 6

Interconversion experiments for Compound 3

| Solvent | Conditions | Observations | XRPD Result |
|---|---|---|---|
| — | Form C, ~50° C. | No melt detected | Form C |
| | Form E, ~50° C. | No melt detected | Form G |
| | Form F + C, ~50° C. | No melt detected | Form F + C |
| | Form G. ~50° C. | No melt detected | Form G |
| | Form G, ~160° C. | Material softened and then solidified without completely melting | Form M |
| | Form J + Form L, ~50° C. | No melt detected | Form G |
| ACN | A vs. B, RT Slurry | — | Form E |
| EtOAc | A vs. B, RT Slurry | — | Form B |
| | A, B, G, RT Slurry | — | Form B |
| | A, B, G, J, and M, RT Slurry | Yellow, opaque solids, no B/E | Form B + Form M |
| | B, G, M. RT Slurry | — | Form B + Form M |
| | A vs. B, ~50° C. Slurry | — | Form B |
| | B, G, M, ~50° C. Slurry | — | Form M* |

*Pattern successfully indexed

TABLE 7

Attempts to generate additional Compound 3 Form E
Starting material: Disordered Compound 3

| Solvent | Conditions | Observations | XRPD Result |
|---|---|---|---|
| ACN | RT Slurry | Sample became a solid plug of solids - no stirring was occurring | Form J* |

TABLE 7-continued

Attempts to generate additional Compound 3 Form E
Starting material: Disordered Compound 3

| Solvent | Conditions | Observations | XRPD Result |
|---|---|---|---|
| ACN/H₂O [1:1] | RT Slurry | Sample became a solid plug of solids - no stirring was occurring | Form K |
| ACN/H₂O [95:5] | RT Slurry | Sample became a solid plug of solids - no stirring was occurring | Form J + minor Form L |

*Pattern successfully indexed

TABLE 8

Attempts to generate additional Compound 3 Form B and M
Starting material: Disordered Compound 3

| Solvent | Conditions | Observations | XRPD Result |
|---|---|---|---|
| EtOAc | Slurry, 2-8° C. | Sample slurried for 7 days | Form B |
|  |  | Sample slurried for 1 day | Forms B + M |
|  | Slurry ~50° C. | Sample slurried for 3 days | Form M |

*Pattern successfully indexed

Thirteen unique XRPD patterns of Compound 3 were generated along with disordered material. XRPD patterns of three forms were indexed (Forms B, J, and M) indicating a single phase had been isolated. In addition, four forms (Forms C, F, H, and I) were poorly crystalline. The XRPD patterns for Forms A and E indicate a 2-dimensional structure.

Thermal analysis of Compound 3 Form E and Form J indicated that these forms were solvated/hydrated. Gentle heating (approximately 50° C.) of Forms E and Form J/Form L produced Form G.

Competitive slurry experiments were carried out on Forms A and G and Form B. Form B appeared to be the more stable form at both ambient and elevated (approximately 50° C.) temperature from ethyl acetate. The same experiments carried out with Forms B and M indicated that Form M was the most stable at elevated (approximately 50° C.) temperature. At ambient temperature, Forms B and M are both present after almost a week of slurrying. This indicates that an enantiotropic system likely exists between these two forms with a transition temperature near ambient.

Compound 3 appears to form solvates and hydrates. The highly solvated/hydrated forms generated during the analyses all dried to a single solid form, Form G. Heating Form G at elevated temperature (approximately 160° C.) generated Form M. Forms B and M were slurried for extended periods of time at ambient temperature and did not convert indicating that an enantiotropic system is likely present with a transition temperature near ambient. Both Forms B and M were successfully scaled up (approximately 250 mgs).

Compound 3 forms highly stable form A.

Morphic forms of Compound 3 are characterized by XRPD and DSC patterns provided in FIGS. 1 to 24.

Example 3: Stress Testing of Compound 3

Compound 3 has the following characteristics related to its stability:

| | |
|---|---|
| Appearance | Off White |
| Flowability | Poor flow (Carr Index: >20-25%) |
| Tmelt | Onset 141° C. and peak at 152° C. |
| Tg | 114° C. |
| Thermal Stability by TGA: | ~0.8% wt loss to 250° C. |
| Hygroscopicity: | Non-hygroscopic (moisture uptake less than 5% at 60% RH) |
| Suggested Storage: | Double PE bags in Al container with desiccant |
| Solid State Stress Testing | |
| Elevated temperature (105° C. - 24 hr) | No degradation |
| Humidity (40° C./75% RH) | No degradation |
| Room Temperature storage | No degradation |
| Photostabillity (exposure to UV visible) | No light senstitivity |
| Solution stress testing | |
| Acid degradation (0.1N HCl) | Degradation observed |
| Base degradation (0.1N NaOH) | Degradation observed |
| Oxidative degradation (H₂O₂) | Not susceptible to oxidation |
| pH Experiments | |
| 1.2 pH | 389.37 µg/mL (degrades) |
| 4.0 pH | 56.68 µg/mL |
| 6.0 pH | 54.60 µg/mL |
| 7.4 pH | 53.41 µg/mL |
| SIF pH = 6.5 | 80.77 µg/mL |
| SGF pH = 1.6 | 96.35 µg/mL |
| Solvent Experiments | |
| DMSO | 104.2 mg/mL |
| Acetone | 34.3 mg/mL |
| Ethanol | 8.38 mg/mL |
| Heptane | 0.865 mg/mL |
| UPLC Water | 1.04 mg/mL |

Additional properties

Caco2: A-B ~17 × $10^{-6}$ cm/s
Efflux ratio (B-A/A-B): 2.2
Fa.SSIF solubility: 75.4 ug/mL
FeSSIF solubility: 153.1 ug/mL
Dose Number for 100 mg dos 3-7
BCS II compound

Example 4: Stress Testing of Compound 2

Compound 2 has the following characteristics related to its stability:

| | |
|---|---|
| Appearance | Off White |
| Flowability | Poor flow Carr Index: >20-25%) |
| Tmelt | Onset 248° C. and peak at 255° C. |
| Tg | 122° C. |
| Thermal Stability by TGA: | ~0.2% wt. loss to 150° C. |
| Solid State Stress Testing | |
| Elevated temperature (10° C. - 7 days) | Amorphous crystallizes out, degradation observed |
| Humidity (70° C./75% RH) | Amorphous crystallizes out |
| Chemical Stability (70° C./75% RH) | No degradation |
| 40° C./75% RH storage in screw cap vials | Maintains x-ray amorphicity & chemical stability |
| Photostability (exposure to UV visible) | No light sensitivity |
| Solution stress testing | |
| Acid degradation (0.1N HCl) | Degradation observed (~8% 7-days at RT) |
| Base degradation (0.1N NaOH) | Degradation observed (~18% 2-days at RT) |
| Oxidative degradation ($H_2O_2$) | Not susceptible to oxidation |
| Additional properties | |

Caco2: A-B ~26 × $10^{-6}$ cm/s
Efflux ratio (B-A/A-B): 1.2
BCS II compound
Solubility in FaSSIF: 2.6 ug/mL
Solubility in FeSSIF: 4.7 ug/mL
Dose Number (for 125 mg): 106-190

Example 5: ICH Stability of Amorphous Compound 2

Compound 2 stored in double LDPE bag with silica gel in aluminum receptacle with lid had the following stability characteristics described in Table 9.

TABLE 9

Stability Characteristics of Compound 2 during ICH Stability Study

| Test | Storage | Time Zero | 2 weeks | 1-month | 3-month |
|---|---|---|---|---|---|
| Water Content | 5° C./NR RH | 1.9% | — | 2.5% | 2.3% |
| | 25° C./60% RH | 1.9% | 2.7%% | 3.0% | 3.1% |
| | 40° C./75% RH | 1.9% | 3.5% | 4.0% | 3.8% |
| Assay | 5° C./NR RH | 97.2% | — | 97.3% | 97.5% |
| | 25° C./60% RH | 97.2% | 99.5% | 97.0% | 97.8% |
| | 40° C./75% RH | 97.2% | 99.8% | 97.5% | 96.4% |
| Total Impurities | 5° C./NR RH | 1.9% | — | 1.9% | 1.7% |
| | 25° C./60% RH | 1.9% | 1.9% | 1.9% | 1.9% |
| | 40° C./75% RH | 1.9% | 1.9% | 1.9% | 1.6% |
| XRPD | 5° C./NR RH | amorphous | — | amorphous | amorphous |

TABLE 9-continued

Stability Characteristics of Compound 2 during ICH Stability Study

| Test | Storage | Time Zero | 2 weeks | 1-month | 3-month |
|---|---|---|---|---|---|
| | 25° C./60% RH | amorphous | amorphous | amorphous | amorphous |
| | 40° C./75% RH | amorphous | amorphous | amorphous | amorphous |

Example 6. Physical Characterization of Compound 3 Form A

Samples of Compound 3 Form A were fully characterized by XRPD, variable-humidity XRPD (VH-XRPD), variable temperature XRPD (VH-XRPD), polarized light microscopy, thermal gravimetric/differential thermal analysis (TG/DTA), differential scanning calorimetry (DSC), and dynamic vapor sorption (DVS). The XRPD, the TG, and the DSC analysis were comparable to the results for Form A discussed in Table 3 and Table 4 of Example 5. The additional methods are discussed below. The material was also characterized by $^1$HNMR, HSQC NMR, HPLC, and HPLC-MS.

Variable Humidity X-ray Powder Diffraction (VH-XRPD)

VT-XRPD analysis was carried out on a Philips X'Pert Pro Multipurpose diffractometer equipped with a humidity chamber. The samples were scanned between 4 and 35.99°2θ using Cu K radiation (α1λ=1.54060 Å; α2=1.54443 Å; β=1.39225 Å; α1: α2 ratio=0.5) running in Bragg-Brentano geometry (step size 0.008°2θ) using 40 kV/40 mA generator settings. Table 10 details the humidity program used. VH-XRPD showed no changes in form between 0 and 90% RH.

TABLE 10

VH-XRPD Humidity Program for Compound 3 Form A

| Target % RH | Scan times |
|---|---|
| 40 | Initial, 30 min |
| 50 | 60 min |
| 60 | Initial, 60, 120, 150 and 180 min |
| 90 | Initial, 60 min |
| 6 (instrument limit) | Initial, 60 min |
| 40 | Initial, 60 min |
| Post-analysis XRPD using PAN alytical instrument | |

Variable Temperature X-Ray Powder Diffraction (VT-XRPD)

VT-XRPD analysis was carried out on a Philips X'Pert Pro Multipurpose diffractometer equipped with a temperature chamber. The samples were scanned between 4 and 35.99°2θ using Cu K radiation (α1λ=1.54060 Å; α2=1.54443 Å; β=1.39225 Å; α1: α2 ratio=0.5) running in Bragg-Brentano geometry (step size 0.008°2θ) using 40 kV/40 mA generator settings. Table 11 details the temperature program used for Form A. Compound 3 Form A was shown to melt between 125-170° C. using VT-XRPD. No recrystallization event was observed upon cooling of the sample.

TABLE 11

VT-XRPD Humidity Program for Compound 3 Form A

| Temperature | Heating Rate | Scan times |
| --- | --- | --- |
| 30 | 0 | Initial Scan |
| 40 | 10 | Initial and after 5 min |
| 50 | 10 | Initial and after 5 min |
| 125 | 10 | Initial and after 5 min |
| 170 | 10 | Initial and after 5 min |
| 30 | −10 | Initial and after 5 min |
| 100 | 10 | Initial and after 5 min |
| 145 | 10 | Initial and after 5 min |
| 30 | −10 | Initial and after 5 min |

Polarized Light Microscopy (PLM)

Figure 28:
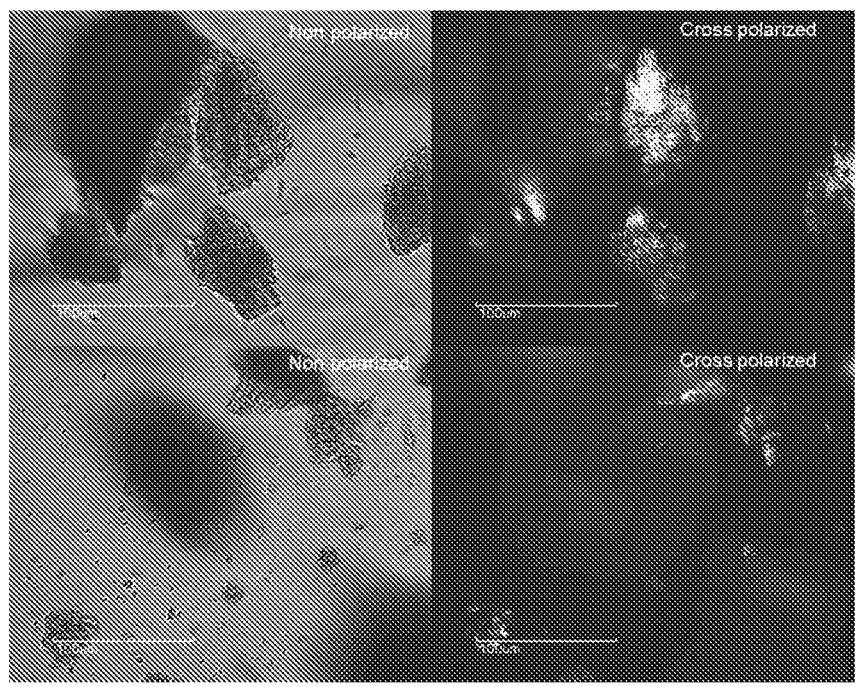
FIG. 28 is a PLM micrograph of Compound 3 Form A as described in Example 6.

The presence of crystallinity (birefringence) was determined using an Olympus BX50 microscope, equipped with cross-polarizing lenses and a Motic camera. Images were captured using Motic Images Plus 2.0. All images were recorded using the 20×objective, unless otherwise stated. All samples were prepared using silicone oil and covered with a cover slip before PLM analysis was completed. PLM analysis showed birefringent agglomerates (FIG. 28).

Thermogravimetric/Differential Thermal Analysis (TG/DTA)

Approximately, 5 mg of material was weighed into an open aluminium pan and loaded into a simultaneous thermogravimetric/differential thermal analyzer (TG/DTA) and held at room temperature. The sample was then heated at a rate of 10° C./min from 20° C. to 400° C. during which time the change in sample weight occurred was recorded along with any differential thermal events (DTA). Nitrogen was used as the purge gas at a flow rate of 300 cm$^3$/min.

Figure 29:
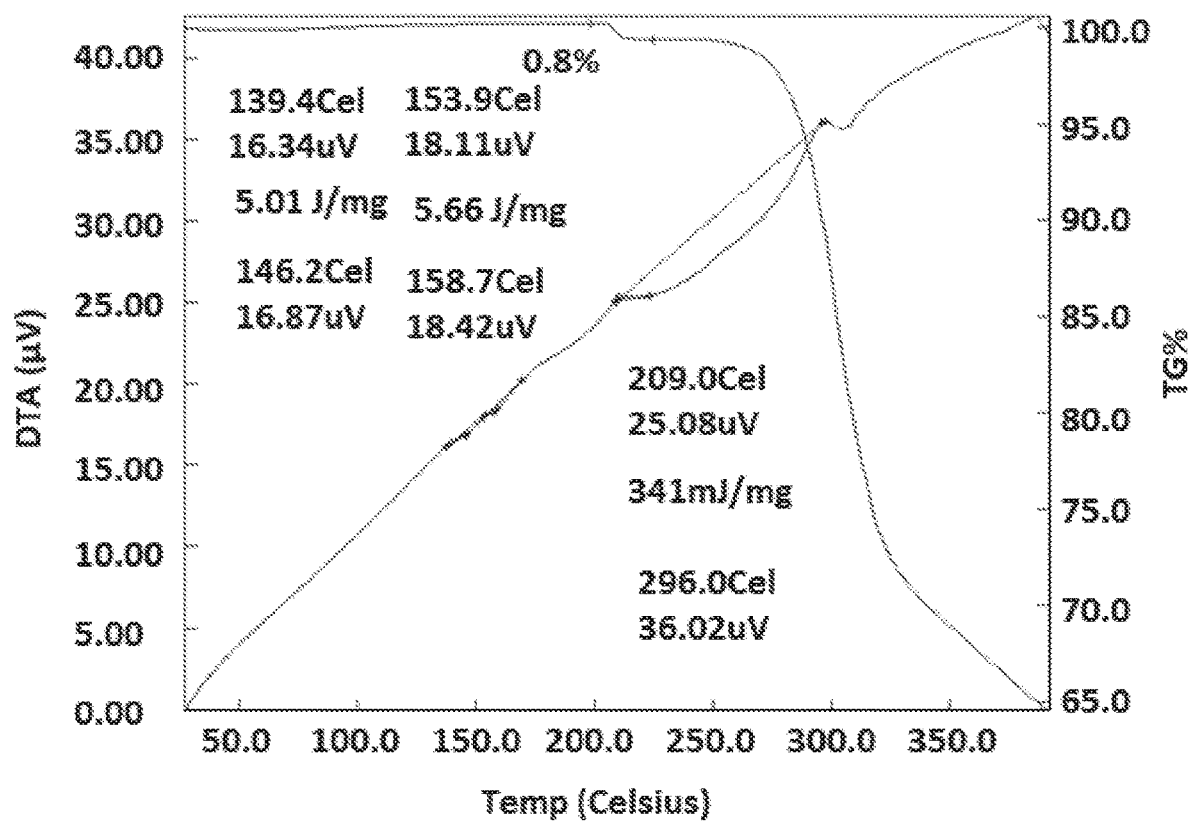
FIG. 29 is a TG/DTA graph of Compound 3 Form A as described in Example 6. The x-axis is temperature measured in Celsius. The right x-axis is weight loss measured in percent and the left x-axis is DTA measured in VN.

The DTA trace showed multiple weak endothermic events with onsets of approximately 139 and 154° C. that were likely related to the melting of the material. A further broad endothermic event from 209 to 296° C. likely associated with sample decomposition was noted. TG trace showed a mass loss of 0.8% at approx. 200° C. relating to the loss of water (0.3 equiv. water) before degradation above 250° C. (FIG. 29).

Dynamic Vapour Sorption (DVS)

Approximately, 10-20 mg of sample were placed into a mesh vapour sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Approximately, 10 mg of sample was placed into a mesh vapour sorption balance pan and loaded into a DVS-1 dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Figure 30:
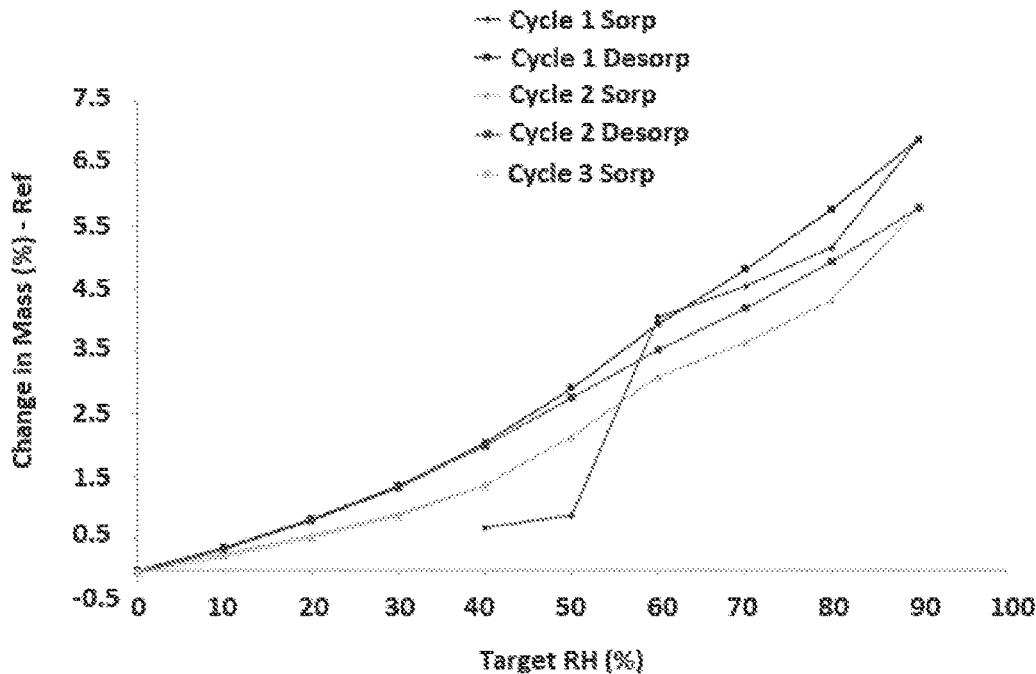
FIG. 30 is a DVS isothermal plot of Compound 3 Form A as described in Example 6. The sample was run at 25° C. The x-axis is target RH measured in percent and the y-axis is change in mass measured in percent.
Figure 31:
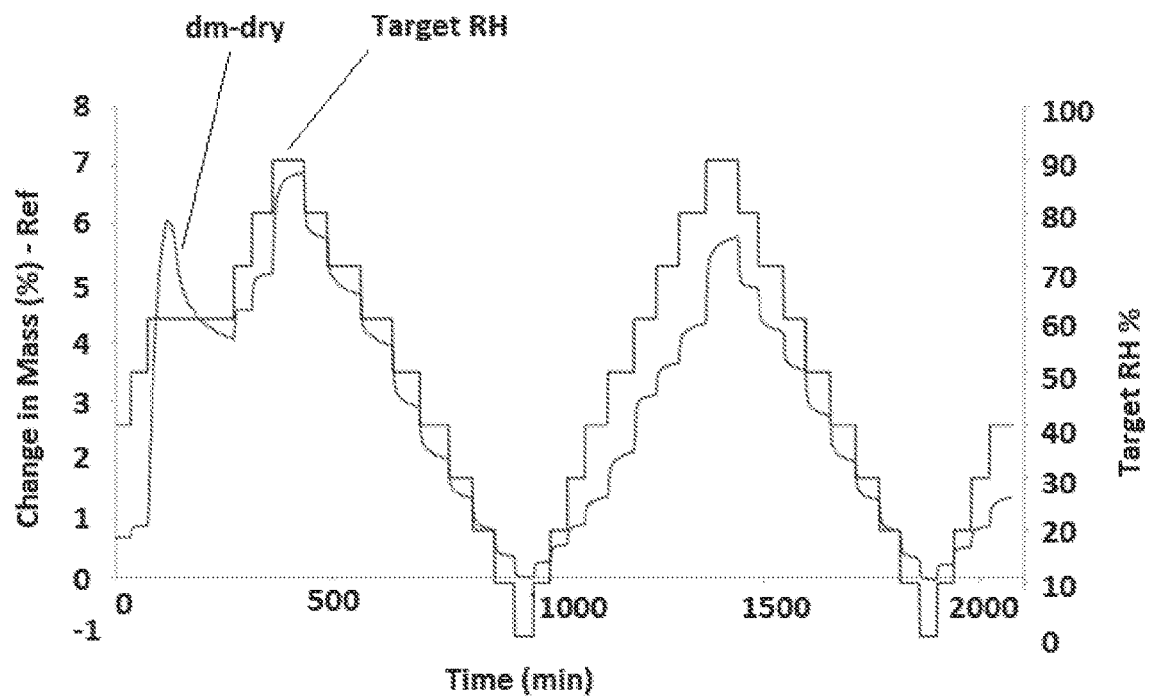
FIG. 31 is a DVS kinetic plot of Compound 3 Form A as described in Example 6. The right y-axis is target RH measured in percent and the left y-axis is change in mass measured in percent. The x-axis time measured in minutes.

DVS analysis found the material to be hygroscopic with a total uptake of 6.9% (2.5 equiv. water) at 90% RH. Between 50-60% RH, a sharp uptake of 3.0% (1.0 equiv. water) was observed. From both desorption cycles, it was noted that the material lost all moisture that was adsorbed at higher humidity (FIG. 30). The DVS kinetic plot (FIG. 31) showed a sharp mass increase between 50-60% RH, where one equivalent of water was absorbed by the material. This could indicate the formation of a hydrated form. However, VH-XRPD confirmed that there was no form change upon the uptake of 1.0 equiv. water and no hydrated form of Compound 3 was observed. This sharp mass increase was noted in the second sorption cycle.

KF analysis returned an average (over 3 injections) of 0.5% water. This value agrees with the data generated from DVS analysis at ambient RH.

Example 7. Stability Studies of Compound 3 Form A

Initial stability of Compound 3 Form A showed the material to be stable at 80° C. with no reduction in purity by HPLC (relative area). Material that was stored at 40° C./75% RH (uncapped) resulted in predominantly Form A. There was no purity change observed from this sample. A repeat of 40° C./75% RH stability study resulted in weakly crystalline (WC) Form A material from capped and uncapped vials. Storage of Form A at 25° C./60% RH returned weakly crystalline Form A from an uncapped vial and Form A material from a capped vial. Lyophilized Compound 3 showed no recrystallization upon storage at 40° C./75% RH or 25° C./60% RH in a capped or uncapped vial.

Figure 32:
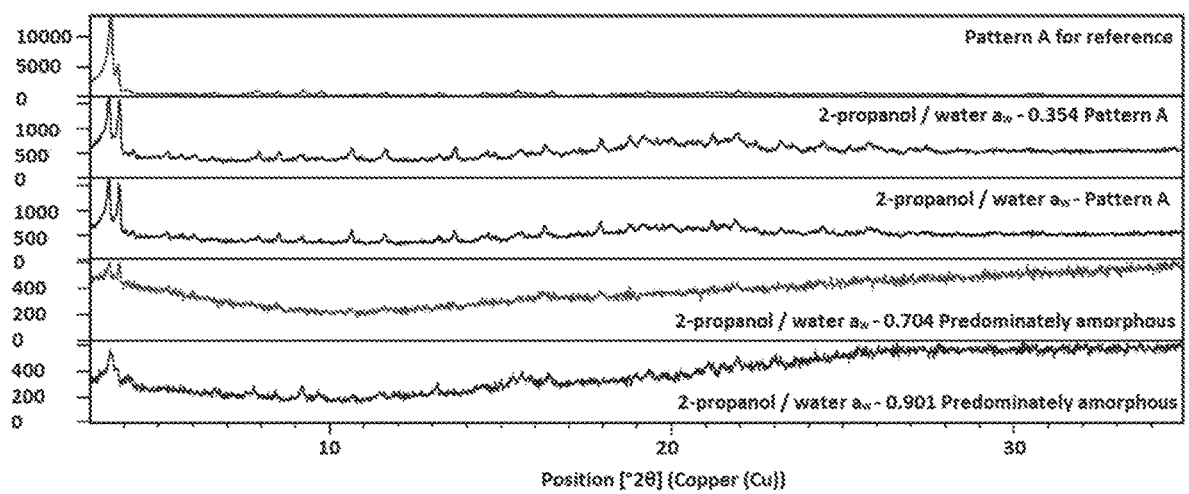
FIG. 32 provides an XRPD analysis post-hydration study of Compound 3 Form A as described in Example 7. The x-axis is 2Theta measured in degrees and the y-axis is intensity.

A hydration study of Compound 3 Form A was conducted using 4 different $a_w$ 2-propanol/water solvent systems. Approximately 20 mg of Compound 3 Form A was weighed into four 2 mL glass vials. An appropriate volume of solvent system was added to the solids and samples were agitated for about 48 hours under ambient conditions. After 48 hours, solids were isolated using centrifuge filtration and analyzed by XRPD. The hydration study of Compound 3 Form A slurried in selected 2-propanol/water systems showed there was a loss in crystallinity as the water activity increased. (FIG. 32)

TABLE 12

Hydration of Compound 3 Form A

| Water activity ($a_w$) | XRPD results |
| --- | --- |
| 0.354 | Form A |
| 0.526 | Form A |
| 0.704 | Predominantly amorphous |
| 0.910 | Predominantly amorphous |

Compound 3 Form A material was milled using a Precellys® Evolution SUPER Homogenizer. Approximately 50 mg of Compound 3 Form A was weighed into 2×plastic 2 mL bead mill vials and 5×2.4 min metal beads were placed into each vial. Sample 1 was milled using the following: RPM=5000; Cycles=2×60 seconds; Pause=10 seconds (between cycles). Sample 2 was milled using the above method but 5×60 seconds cycles instead of 2×60 seconds. After milling, a sub-sample was taken from each and analyzed by XRPD and PLM. The above procedure was repeated and the resulting samples were analyzed by XRPD and DSC analysis.

Figure 33:
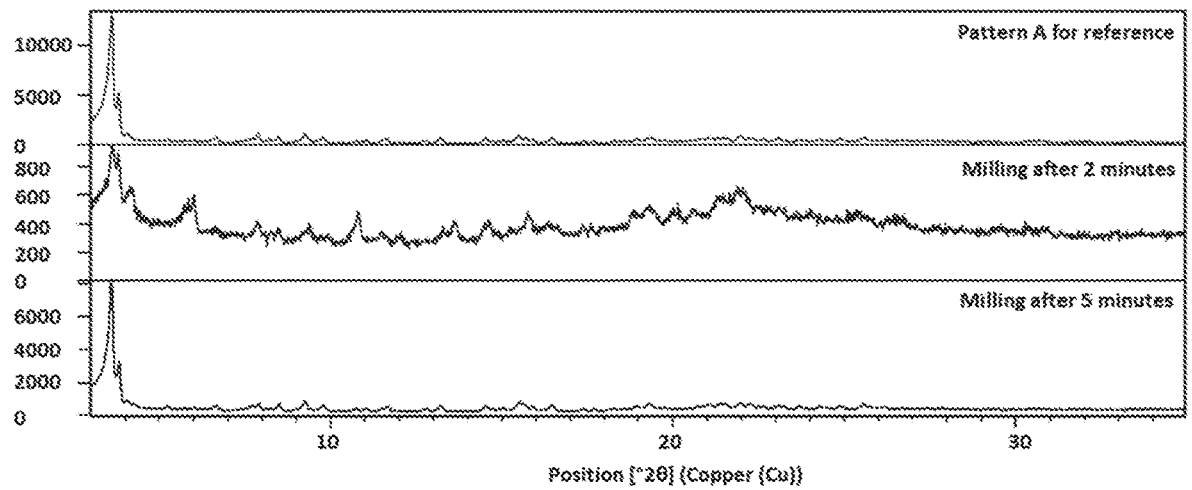
FIG. 33 provides an XRPD analysis of Compound 3 Form A following 2 and 5 minutes of milling as described in Example 7. The x-axis is 2Theta measured in degrees and the y-axis is intensity.
Figure 34A:
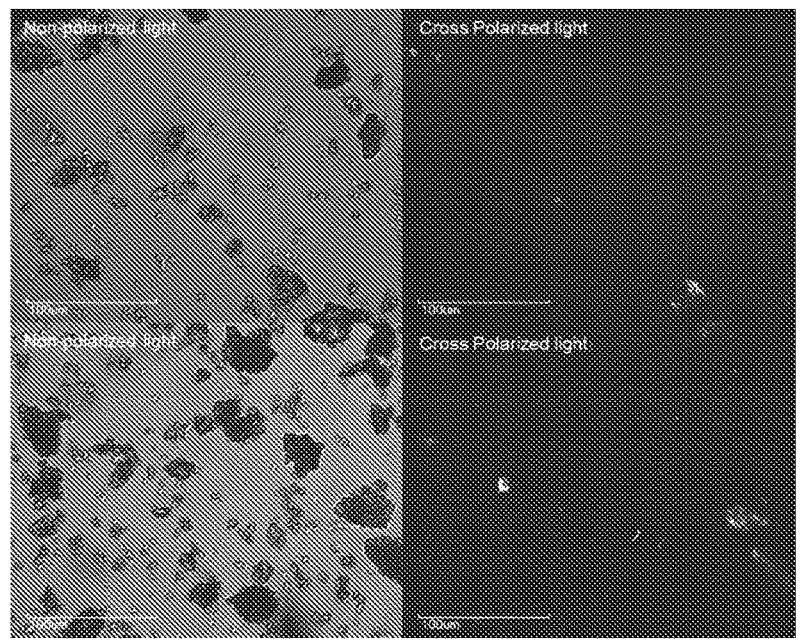
FIG. 34A is a PLM micrograph of Compound 3 Form A following 2 minutes of milling as described in Example 7.
Figure 34B:
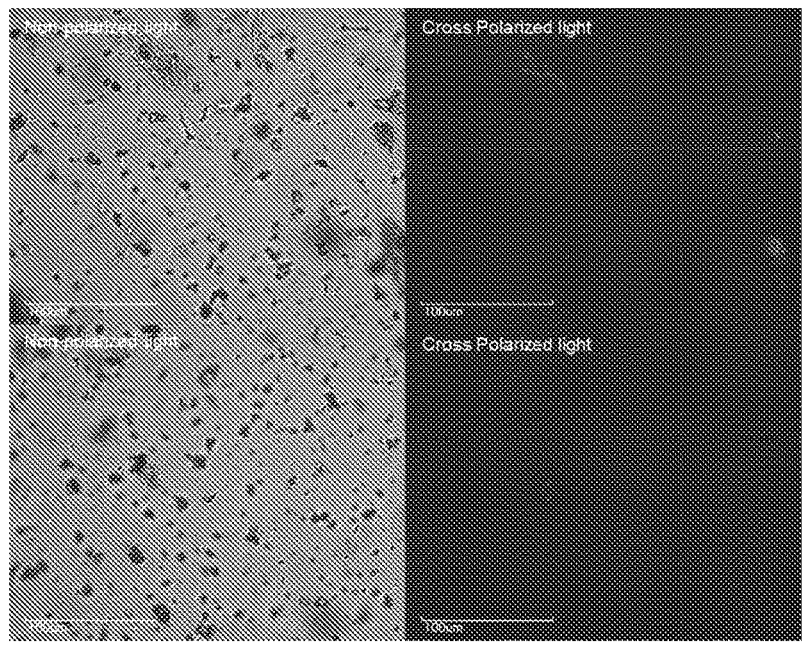
FIG. 34B is a PLM micrograph of Compound 3 Form A following 5 minutes of milling as described in Example 7.

Table 13 below details the results from milling experiments conducted on Compound 3 Form A. Milling of Form A returned predominantly amorphous material by XRPD analysis, but birefringence was observed within PLM analysis indicating that the material likely consisted of small crystalline particles (FIG. 33 and FIG. 34A-FIG. 34B are XRPD and PLM results from the initial milling process).

TABLE 13

Compound 3 Form A Milling Results

| Milling | | XRPD | PLM | DSC |
|---|---|---|---|---|
| Initial | 2 min | Predominantly amorphous with peaks of Form A | Small birefringent agglomerates | N/A |
| | 5 min | Form A | Small, poorly birefringent agglomerates | N/A |
| Repeat 1 | 2 min | Amorphous | Small non-birefringent agglomerates | N/A |
| | 5 min | Amorphous | Small non-birefringent agglomerates | N/A |
| Repeat 2 | 2 min | Predominantly amorphous with signs of Form A | N/A | No recrystallisation of amorphous material was observed |
| | 5 min | Predominantly amorphous with signs of Form A | N/A | No recrystallisation of amorphous material was observed |

Figure 35A:
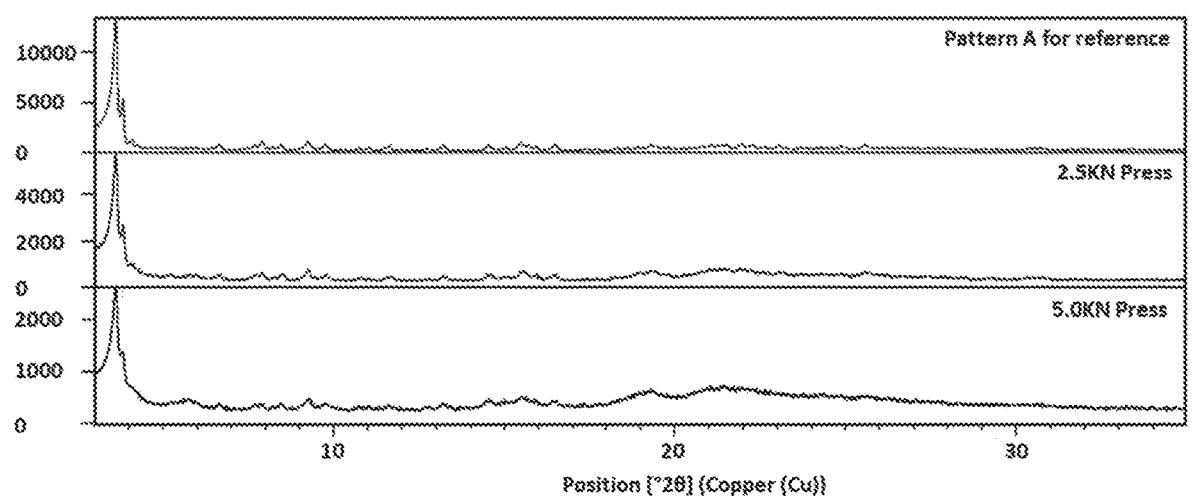
FIG. 35A provides an XRPD analysis of Compound 3 Form A following 2.5 KN and 5.0 KN compression as described in Example 7. The x-axis is 2Theta measured in degrees and the y-axis is intensity.
Figure 35B:
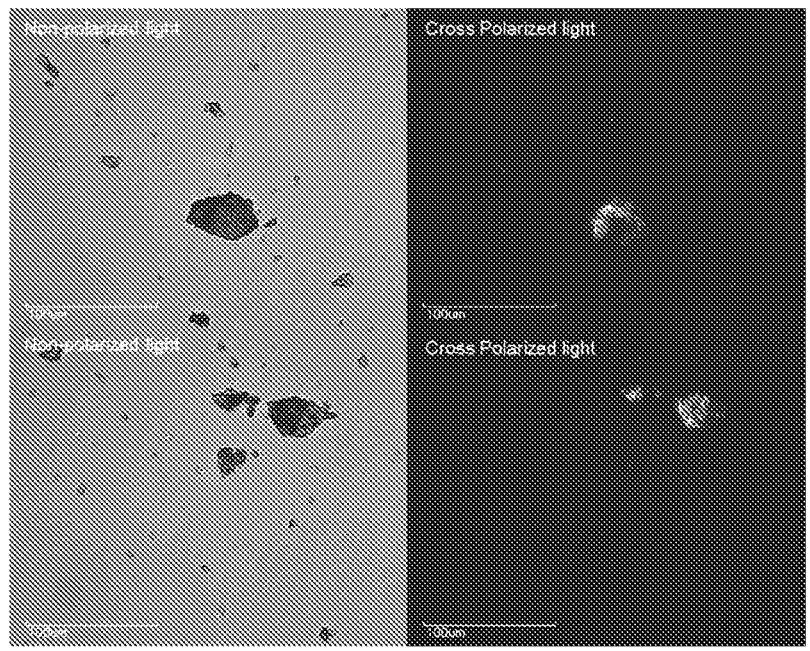
FIG. 35B is a PLM micrograph of Compound 3 Form A following 2.5 KN compression as described in Example 7.
Figure 35C:
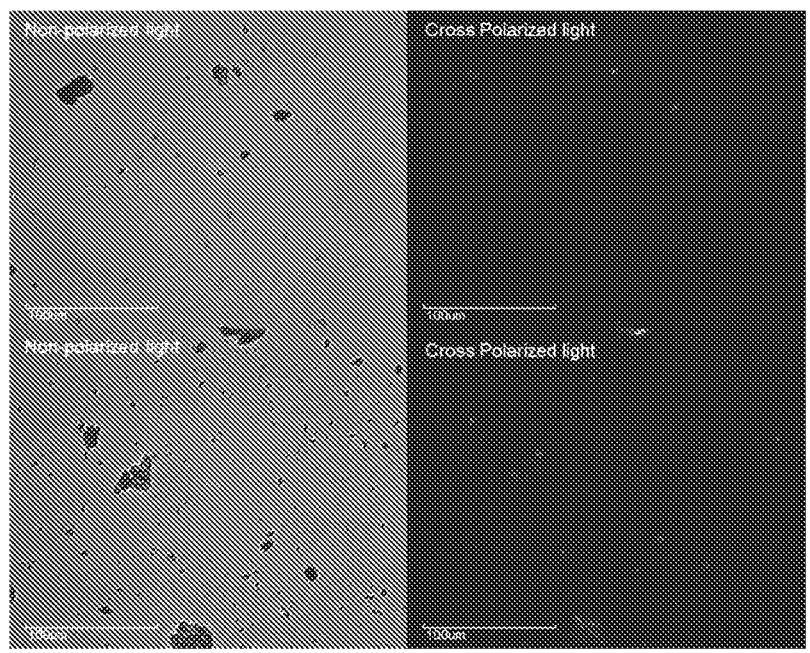
FIG. 35C is a PLM micrograph of Compound 3 Form A following 5.0 KN compression as described in Example 7.

Compound 3 Form A material was compressed using a specac press. Approximately 125 mg of Compound 3 Form A was weighed into a 20 mL glass vial. The material was then transferred into an IR die and pressed to 2.5 KN for approx. 5 seconds. The resulting material was (ground lightly to break the disk that was returned and) analyzed by XRPD and PLM. The material was then placed back into the die and pressed to 5.0 KN (for approx. 5 seconds). The resulting material was ground lightly to break the disk that was returned and analyzed by XRPD and PLM. The procedure detail was repeated, using separate batches of solid for 2.5 KN and 5.0 KN experiments. XRPD analysis and PLM analysis was completed on the material returned after pressing. Table 14 lists the results of the compression studies of Compound 3 Form. All samples returned Form A material by XRPD and consisted of small birefringent particles with no clear morphology by PLM (FIG. 35A-FIG. 35C).

TABLE 14

Compound 3 Form A Compression results

| Compression | | Characterization | |
|---|---|---|---|
| | | XRPD | PLM |
| Initial | 2.5 KN | Form A | Small birefringent particles with no clear morphology |
| | 5.0 KN | Form A | Small birefringent particles with no clear morphology |
| Repeat | 2.5 KN | Form A | Small birefringent particles with no clear morphology |
| | 5.0 KN | Form A | Small birefringent particles with no clear morphology |

Figure 36:
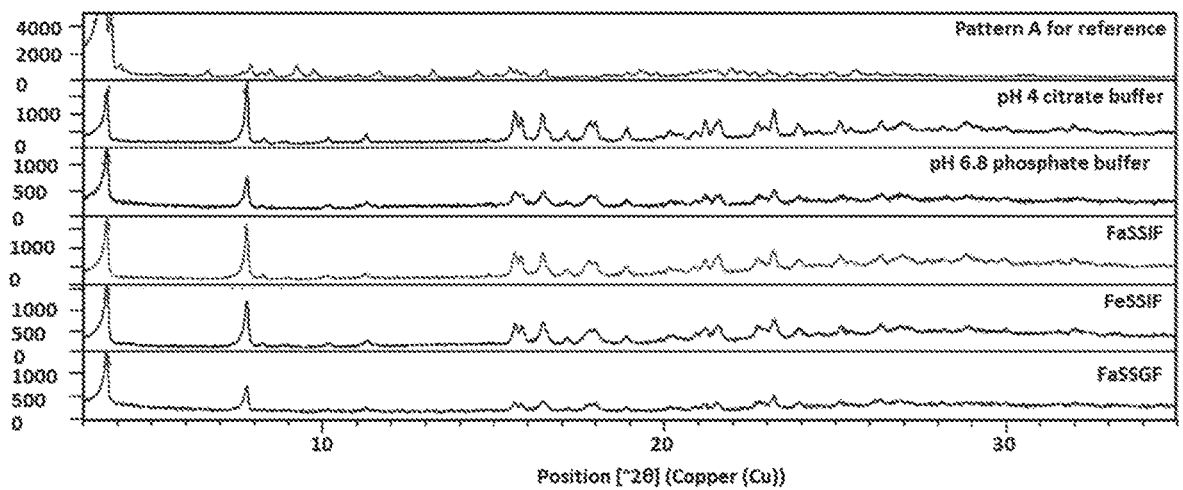
FIG. 36 is an XRPD overlay of Compound 3 Form A after stirring in selected media (FaSSIF, FeSSIF, FaSSGF, pH 4 citrate and pH 6.8 phosphate) as described in Example 7. The x-axis is 2Theta measured in degrees and the y-axis is intensity.

The solubility of Compound 3 Form A in select media was also tested and the results are shown in Table 15. Solubility within selected media (FaSSIF, FeSSIF, FaSSGF, pH 4 citrate and pH 6.8 phosphate) was measured to be <0.01 mg/mL. The XRPD results from the study are shown in FIG. 36.

TABLE 15

Compound 3 Form A Solubility Results

| Media | XRPD Results | HPLC Result (mg/mL) |
|---|---|---|
| FaSSIF | Form A | <0.01 |
| FeSSIF | Form A | <0.01 |
| FaSSGF | Form A | <0.01 |
| pH 4 citrate buffer | Form A | Not detected |
| pH 6.8 phosphate buffer | Form A | <0.01 |

The pH 4 citrate buffer was prepared by dissolving sodium citrate (987 mg) and citric acid (1.28 g) in 100 mL $H_2O$. The pH was adjusted to 4. The pH 6.8 phosphate buffer was prepared by dissolving dibasic sodium phosphate dihydrate (873 mg) and monobasic sodium phosphate monohydrate (708 mg) in 100 mL $H_2O$. The pH was adjusted to 6.8. The FaSSIF media was prepared with sodium hydroxide (108 mg), sodium chloride (1.55 g) and monobasic sodium phosphate dihydrate (1.12 g) in $H_2O$ (0.25 L) and the pH adjusted to 6.5. FaSSIF/FeSSIF/FaSSGF (0.56 g) was dissolved in the buffer and mixed until opalescent. The FeSSIF media was prepared by dissolving sodium hydroxide (1.01 g), sodium chloride (2.96 g) and glacial acetic acid (2.97 g) in $H_2O$ (0.25 L) and the pH adjusted to pH 5. FaSSIF/FeSSIF/FaSSGF (2.81 g) was dissolved in the buffer and thoroughly mixed. The FaSSGF media was prepared by dissolving FaSSIF/FeSSIF/FaSSGF (0.06 g) in a solution of sodium chloride (2.00 g) dissolved in $H_2O$ (1 L) and mixing thoroughly.

Example 8. Solvent Solubility of Compound 3 Form A

A solvent solubility screen was conducted using 32 solvent systems. Approximately 360 mg of Compound 3 Form A was weighed into a 20 mL glass vial and dissolved using 18 mL of 1,4-dioxane. 0.5 mL of the solution was then dispensed into thirty-four 2 mL glass vials (approx. 10 mg per vial). The Compound 3 Form A solutions were then frozen (at −50° C.) and dried by lyophilization using a Lablyo mini freeze drier. Post-lyophilization, a sub-sample was taken and analyzed by XRPD. Material was successfully rendered amorphous by lyophilization.

The material produced from lyophilization was used for the solubility assessment. Solubility was estimated by a solvent addition technique. The solubility study was completed as follows:

Each solvent system was added to the appropriate vial in 5 volume aliquots until 100 volumes had been added or until the API dissolved;

Between each addition, samples were heated to 40° C. to check dissolution at elevated temperatures;

If 100 volumes of solvent were added without dissolution, solubility was calculated to be below this point.

Samples where dissolution was not observed were isolated using centrifuge filtration and solids analyzed by XRPD. Samples where dissolution was observed were evaporated under ambient conditions to return solids. Where applicable, solids were analyzed by XRPD. Table 16 details observations and XRPD results from evaporation experiments post-solubility assessment. Solids recovered upon solvent evaporation were exclusively Form A.

Lyophilized Compound 3 Form A showed high solubility (≥200 mg/mL) in the majority of solvent systems investigated: 1,4-dioxane, 1-butanol, 2-methyl tetrahydrofuran, 95% 2-propanol/5% water ((% v/v) calc. $a_w$=0.5); acetone, acetonitrile, 95% acetonitrile/5% water ((% v/v) calc. $a_w$=0.4), chloroform, dichloromethane, dimethylsulfoxide, ethyl acetate (dry), ethanol, isopropyl acetate, methanol, methylethyl ketone, methylisobutyl ketone, N,N'-dimethylformamide, N,N'-dimethylacetamide, tetrahydrofuran, and 95% methanol/5% water ((% v/v) calc. $a_m$=0.2). In certain solvents (2-propanol, 95% 2-propanol/5% heptane (% v/v), 70% 2-propanol/30% heptane (% v/v), and toluene), dissolution (>200 mg/mL) was observed at elevated temperatures.

Solvent system mixtures containing heptane (50% 2-propanol/50% heptane (% v/v) and 50% ethanol/50% heptane (% v/v)) showed a slightly lower solubility of >100 mg/mL. Common anti-solvents such as n-heptane and tert-butylmethyl ether, ethyl ether, water, and solvent/water mixtures (50% 2-propanol/50% water ((% v/v) $a_w$=0.7) and 40% ethanol/60% water ((% v/v) calc. $a_w$=0.7)) showed low solubility of <10 mg/mL.

TABLE 16

Observations and XRPD results from evaporation post-solubility assessment

| Solvent system | Observations after 120 hours evaporation | XRPD results |
|---|---|---|
| 1,4-Dioxane | Oil | N/A |
| 1-Butanol | White solid | Form A |
| 2-Methyl tetrahydrofuran | White solid | Insufficient material for XRPD analysis |
| 2-Propanol | White solid | Form A |
| 95% 2-Propanol / 5% heptane (% v/v) | White solid | Form A |
| 70% 2-Propanol / 30% heptane (% v/v) | White solid | Form A |
| 50% 2-Propanol / 50% heptane (% v/v) | White solid | Amorphous |
| 95% 2-Propanol / 5% water (% v/v) calc. $a_w$ = 0.5 | White solid | Form A |
| 50% 2-Propanol / 50% water (% v/v) $a_w$ = 0.7 | Gum (not evaporated) | N/A |

TABLE 16-continued

Observations and XRPD results from evaporation post-solubility assessment

| Solvent system | Observations after 120 hours evaporation | XRPD results |
|---|---|---|
| Acetone | White solid | Insufficient material for XRPD analysis |
| Acetonitrile | White solid | Amorphous |
| 95% Acetonitrile / 5% water (% v/v) calc. $a_w$ = 0.4 | Gum | N/A |
| tert-Butylmethyl Ether | Emulsion | Amorphous |
| Chloroform | Gum | N/A |
| Dichloromethane | Oil | N/A |
| Dimethylsulfoxide | Gum | N/A |
| Ethyl Acetate (dry) | Gum | N/A |
| Ethanol | White solid | Some peaks of Form A |
| 40% Ethanol / 60% Water (% v/v) calc. $a_w$ = 0.7 | Gum | N/A |
| 50% Ethanol / 50% Heptane (% v/v) | White solid | Form A |
| Ethyl Ether | Gum | N/A |
| n-Heptane | White slurry | Amorphous |
| Isopropyl Acetate | Gum | Weakly crystalline form A |
| Methanol | Oil | Amorphous after drying |
| Methylethyl Ketone | Needle-like crystals present within a gum | N/A |
| Methylisobutyl Ketone | White solid | Predominantly amorphous with possible peaks of Form M |
| N,N'-Dimethylformamide | Evaporation stopped after 7 days | N/A |
| N,N'-Dimethylacetamide | Evaporation stopped after 7 days | N/A |
| Tetrahydrofuran | Glassy solid | N/A |
| Toluene | Gum | N/A |
| Water | White slurry | Amorphous |
| 95% Methanol / 5% Water (% v/v) calc. $a_w$ = 0.2 | Oil | N/A |

Example 9. Polymorph Studies of Compound 3 Form A

Approximately 960 mg of Compound 3 Form A was weighed into a 20 mL glass vial and dissolved using 12 mL 1,4-dioxane. 0.5 mL of the solution was then dispensed into twenty-four 1.5 mL HPLC glass vials (approx. 40 mg per vial). The Compound 3 Form A solutions were then frozen (at −50° C.) and dried by lyophilization using a Lablyo mini freeze drier. Post-lyophilization, a sub-sample was taken and analyzed by XRPD. Material was successfully rendered amorphous by lyophilization.

A polymorph study was completed using 24 different solvent systems and four different crystallization techniques: temperature cycling, crash-cooling anti-solvent addition, and solvent evaporation. Each of these is described below.

Temperature Cycling

An appropriate volume of solvent (solvent systems are detailed in Table 17) was added to lyophilized solids. The samples were temperature cycled between ambient and 40° C. (4 hour cycles) for around 72 hours. Observations were made after 72 hours temperature cycling. Further solvent was added to the samples to produce a mobile slurry and slurries were agitated at 40° C. for approximately 18 additional hours. A sub-sample of solid (where applicable) was analyzed by XRPD. Samples were heated using a heat gun to aid dissolution to ensure saturated solutions were produced. Saturated solutions were syringe filtered to remove any potential seed material (as a precaution) and divided between three different crystallization conditions: cooling, evaporation, and anti-solvent addition (volumes of saturated solutions per condition can be found in Table 17).

TABLE 17

Solvent Volumes used for Conditions in Temperature Cycling Experiment

| | Volume of solvent per condition (μL) | | | | |
|---|---|---|---|---|---|
| | Temperature cycling (total) | | Anti- | | |
| Solvent System | Initial volume | Additional volume | solvent addition | Cooling | Evaporation |
| 1,4-Dioxane | 150 | 0 | 25 | 25 | 0 |
| 1-Butanol | 100 | 400 | 100 | 100 | 100 |
| 2-Methyl Tetrahydrofuran | 100 | 400 | 100 | 100 | 100 |
| 2-Propanol | 200 | 400 | 100 | 100 | 100 |
| 95% 2-Propanol / 5% heptane (% v/v) | 200 | 400 | 100 | 100 | 100 |
| 70% 2-Propanol / 30% Heptane (% v/v) | 1000 | 400 | 100 | 100 | 100 |
| 70% 2-Propanol / 30% Heptane (% v/v) re-prepared sample | 500 | 0 | 100 | 100 | 100 |
| 50% 2-Propanol / 50% Heptane (% v/v) | 200 | 400 | 50 | 50 | 25 |
| 95% Heptane / 5% 2-Propanol (% v/v) | 1000 | 400 | 200 | 200 | 200 |
| 70% 2-Propanol / 30% Water (% v/v) $a_w = 0.8$ | 200 | 400 | 100 | 100 | 100 |
| Acetone | 100 | 400 | 100 | 100 | 100 |
| Acetonitrile | 100 | 400 | 50 | 50 | 50 |
| 50% Acetonitrile / 50% Water (% v/v) calc. $a_w = 0.9$ | 100 | 200 | 50 | 50 | 50 |
| tert-Butylmethyl Ether | 1000 | 0 | 100 | 100 | 100 |
| Ethyl Acetate (dry) | 100 | 400 | 100 | 100 | 100 |
| 40% Ethanol:60% Water (% v/v) calc. $a_w = 0.7$ | 300 | 400 | 100 | 100 | 100 |
| 50% Ethanol:50% Heptane (% v/v) | 200 | 400 | 100 | 100 | 100 |
| Ethanol | 100 | 400 | 100 | 100 | 100 |
| 95% Methanol:5% Water (% v/v) calc. $a_w = 0.2$ | 100 | 400 | 100 | 100 | 100 |
| Methanol | 100 | 400 | 100 | 100 | 100 |
| Methylethyl Ketone | 100 | 400 | 100 | 100 | 100 |
| Methylisobutyl Ketone | 100 | 400 | 100 | 100 | 100 |
| n-Heptane | 1000 | 0 | 100 | 100 | 100 |
| Toluene | 200 | 400 | 100 | 100 | 100 |
| Tetrahydrofuran | 100 | 300 | 100 | 100 | 100 |

Figure 37:
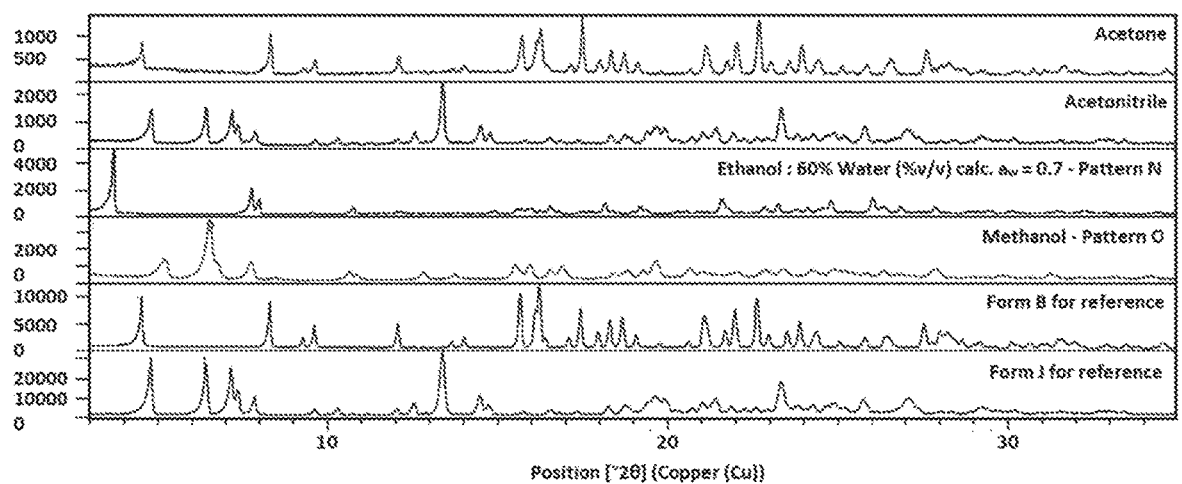
FIG. 37 provides an XRPD overlay of Form N and Form O along with isolated Form B and Form J following the temperature cycling experiments as described in Example 9. The x-axis is 2Theta measured in degrees and the y-axis is intensity.

Form A was returned from the majority of solvent systems post-temperature cycling. Two new patterns were discovered, pattern N isolated from 40% ethanol/60% water (% v/v) and pattern O isolated from methanol. Two previously seen forms were also isolated, Form B from acetone and Form J from acetonitrile. FIG. 37 shows the XRPD diffractograms of the isolated patterns N and O along with isolated Form B and Form J. The characterization of Form B and Form J corresponded to the characterizations described in Table 3 and Table 4 of Example 5. Specifically, for Form B, the DT trace showed an endothermic event with an onset of approx. 180° C. related to the melting of the material (SSCI report onset=~176° C.). The TG trace showed the material to degrade above approx. 270° C. For Form J, the TG trace showed a mass loss of 3.5 wt % (0.5 equiv. acetonitrile) when heated to approx. 120° C. and the material degraded above 250° C.

Figure 38:
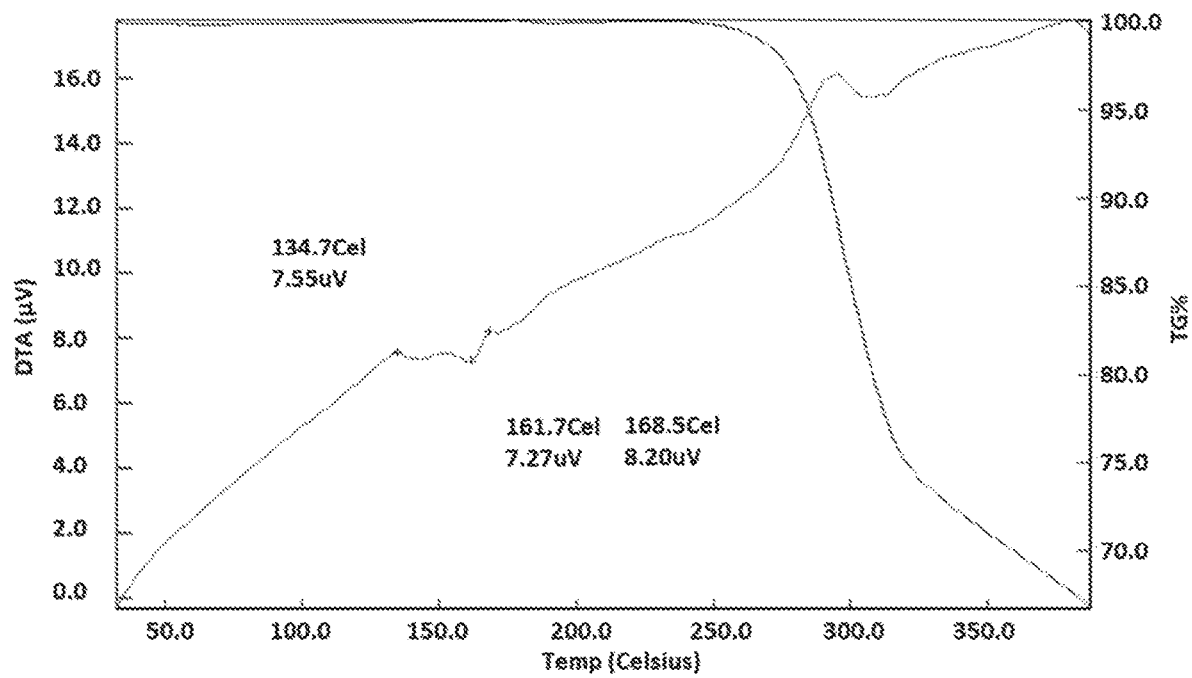
FIG. 38 is a TG/DTA thermogram of isolated pattern N as described in Example 9. The x-axis is temperature measured in Celsius. The right x-axis is weight loss measured in percent and the left x-axis is DTA measured in V.
Figure 39:
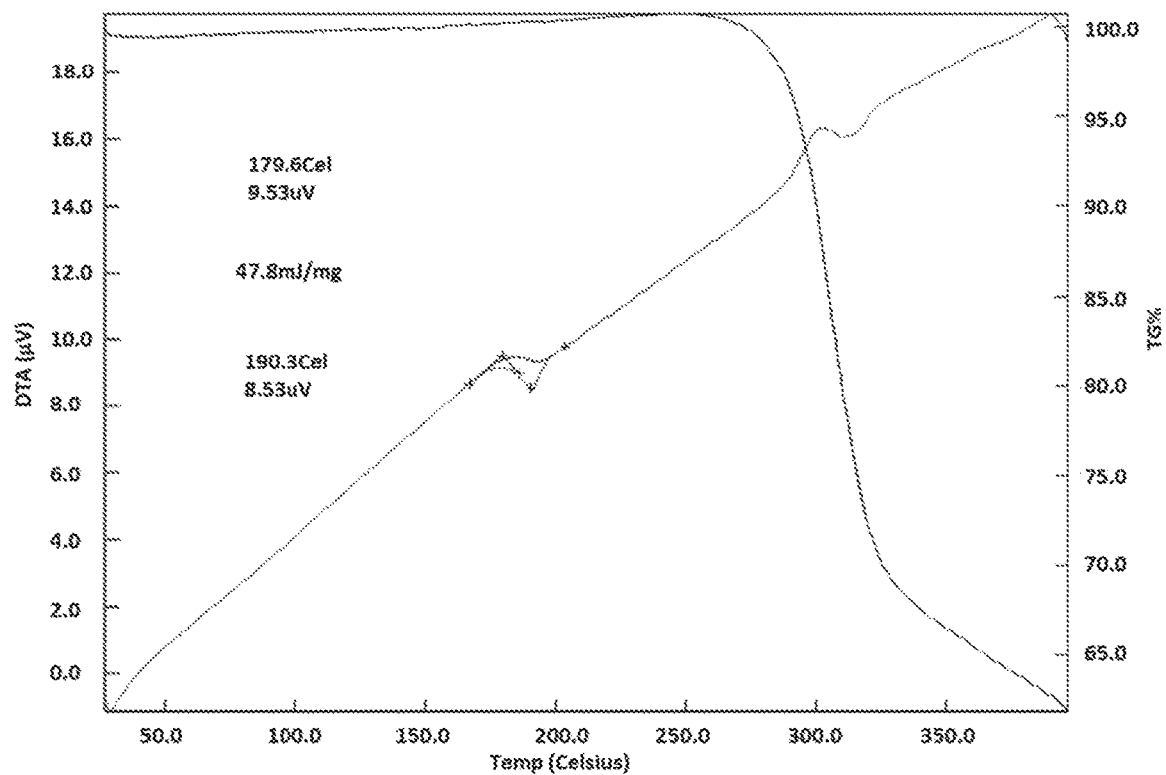
FIG. 39 is a TG/DTA thermogram of isolated pattern 0 as described in Example 9. The x-axis is temperature measured in Celsius. The right x-axis is weight loss measured in percent and the left x-axis is DTA measured in V.

Pattern N was characterized with TG/DTA. The DT trace (FIG. 38) showed complex weak thermal events with an onset of approximately 135° C. possibly related to the melting of the material. From the TG trace, no mass loss was observed prior to degradation (approximately 270° C.), implying the material was anhydrous. Pattern O was characterized by an endothermic event with an onset of approximately 180° C. (peak 190° C.) related to the melting of the material was seen within the DT trace (FIG. 39). From the TG trace, no mass loss was observed prior to degradation (approximately 270° C.), implying the material was anhydrous.

Table 18 details the observations and XRPD results after 72 hours temperature cycling.

TABLE 18

Observations and XRPD results produced from 72 hours temperature cycling

| Solvent System | Observations after solvent addition | Observations after approx. 72 hours temperature cycling | XRPD analysis results after temperature cycling |
|---|---|---|---|
| 1,4-Dioxane | Clear solution | Clear solution | N/A |
| 1-Butanol | Clear solution | White solid, no mother liquor | Form A |
| 2-Methyl Tetrahydrofuran | Clear solution | White solid, no mother liquor | Form A |
| 2-Propanol | Gum | White solid, no mother liquor | Form A |
| 95% 2-Propanol / 5% heptane (% v/v) | Gum | White solid, no mother liquor | Form A |
| 70% 2-Propanol / 30% Heptane (% v/v) | Gum | White solid, no mother liquor | Predominantly amorphous, traces of Form B |
| 70% 2-Propanol / 30% Heptane (% v/v) re-prepared sample | Gum | White slurry | Form A |
| 50% 2-Propanol / 50% Heptane (% v/v) | Gum | White solid, no mother liquor | Predominantly amorphous, traces of Form A |
| 95% Heptane / 5% 2-Propanol (% v/v) | Gum | White solid, no mother liquor | Predominantly amorphous, traces of Form A |
| 70% 2-Propanol / 30% Water (% v/v) $a_w = 0.8$ | Gum | White slurry | Form A |
| Acetone | Clear solution | Off white solid, no mother liquor | Form B |
| Acetonitrile | Clear solution | White solid, no mother liquor | Form J |
| 50% Acetonitrile / 50% Water (% v/v) calc. $a_w = 0.9$ | Clear solution | Clear solution | N/A |
| tert-Butylmethyl Ether | Slurry | White slurry | Amorphous |
| Ethyl Acetate (dry) | Clear solution | White solid, no mother liquor | Amorphous |
| 40% Ethanol:60% Water (% v/v) calc. $a_w = 0.7$ | Gum | White slurry + white stuck to bottom of vial | New Pattern - Pattern N |
| 50% Ethanol:50% Heptane (% v/v) | Gum | White solid, no mother liquor | Amorphous |
| Ethanol | Clear solution | White solid, no mother liquor | Amorphous |
| 95% Methanol:5% Water (% v/v) calc. $a_w = 0.2$ | Clear solution | Gum | Amorphous |

TABLE 18-continued

Observations and XRPD results produced from 72 hours temperature cycling

| Solvent System | Observations after solvent addition | Observations after approx. 72 hours temperature cycling | XRPD analysis results after temperature cycling |
|---|---|---|---|
| Methanol | Clear solution | White solid, no mother liquor | New Pattern - Pattern O |
| Methylethyl Ketone | Clear solution | White solid, no mother liquor | Form A |
| Methylisobutyl Ketone | Clear solution | Off white solid | Predominantly amorphous, traces of Form A |
| n-Heptane | Gum | Gum | Amorphous |
| Toluene | Clear solution | Gum | Amorphous |
| Tetrahydrofuran | Clear solution | Clear solution | N/A |

Crash Cooling

Saturated solutions of Compound 3 produced from temperature cycling experiments were placed into a fridge to crash cool to 4° C. After about 4 days, observations were made and solids produced were isolated using centrifuge filtration and analyzed by XRPD. Where no solids were recovered, solutions were placed into a freezer (−20° C.) for 14 days. Any solids produced were isolated by centrifuge filtration and analyzed by XRPD (Table 19).

Table 19 detail observations and XRPD results returned from crash cooling experiments. Where crystalline material was precipitated, Form A material was seen by XRPD analysis. No new forms were observed from the crash cooling experiments. The material was also subjected to XRPD after 14 days storage at −20° C., but no new forms were observated after 14 days.

TABLE 19

Observations and XRPD results after approximately 96 hours storage at 4° C.

| Solvent System | Observations after ~96 hours storage at 4° C. | XRPD analysis |
|---|---|---|
| 1,4-Dioxane | Clear solution | N/A |
| 1-Butanol | Solid | Form A |
| 2-Methyl Tetrahydrofuran | Clear solution | N/A |
| 2-Propanol | Solid | Form A |
| 95% 2-Propanol / 5% heptane (% v/v) | Solid | Form A |
| 70% 2-Propanol / 30% Heptane (% v/v) | Clear solution | N/A |
| 70% 2-Propanol / 30% Heptane (% v/v) re-prepared sample | Solid | Amorphous |
| 50% 2-Propanol / 50% Heptane (% v/v) | Clear solution | N/A |
| 95% Heptane / 5% 2-Propanol (% v/v) | Clear solution | N/A |
| 70% 2-Propanol / 30% Water (% v/v) $a_w$ = 0.8 | Solid | Form A |
| Acetone | Clear solution | N/A |
| Acetonitrile | Clear solution | N/A |
| 50% Acetonitrile / 50% Water (% v/v) calc. $a_w$ = 0.9 | Clear solution | N/A |
| tert-Butylmethyl Ether | Solid | Form A |
| Ethyl Acetate (dry) | Solid | Amorphous |
| 40% Ethanol/60% Water (% v/v) calc. aw = 0.7 | Solid | Form A |
| 50% Ethanol:50% Heptane (% v/v) | Solid | Predominantly Amorphous |
| Ethanol | Clear solution | N/A |
| 95% Methanol:5% Water (% v/v) calc. aw = 0.2 | Clear solution | N/A |
| Methanol | Clear solution | N/A |
| Methylethyl Ketone | Clear solution | N/A |
| Methylisobutyl Ketone | Clear solution | N/A |
| n-Heptane | Solid | Amorphous |
| Toluene | Clear solution | N/A |
| Tetrahydrofuran | Clear solution | N/A |

Anti-Solvent Addition

Anti-solvent additions were completed on saturated solutions of Compound 3 produced from temperature cycling experiments. Precipitation of solids was observed (before anti-solvent additions were completed) from selected solvent systems when storage under ambient conditions. Precipitated solids were analyzed by XRPD and re-dissolved using gentle heating and addition of minimal solvent. An appropriate anti-solvent was added to each saturated solution in 50μL aliquots until precipitation was observed or a total of 1 mL anti-solvent had been added. Samples where solids were precipitated were isolated using centrifuge filtration and analyzed by XRPD. Samples where a clear solution remained were placed into a fridge (4° C.) to induce precipitation for approximately 48 hours. Samples where solids had precipitated were isolated using centrifuge filtration and analyzed by XRPD (Table 20A and Table 20B).

Table 20A and Table 20B lists observations and XRPD results returned from anti-solvent addition to saturated solutions of Compound 3. Form A material was returned from the majority of samples where crystalline material was returned. A mixture of Patterns L and M was returned from 70% 2-propanol/30% heptane (0% v/v) and 40% ethanol/6% water (% v/v). No new forms were observed from the anti-solvent addition experiments.

TABLE 20A

Anti-Solvent Observations and XRPD Results

| Solvent System | Anti-solvent used | Observations anti-solvent addition | XRPD analysis |
|---|---|---|---|
| 1,4-Dioxane | Heptane | Cloudy solution | Insufficient solid for analysis |
| 1-Butanol | Heptane | Solid present before additions* | Predominantly amorphous signs of form A * |
| 2-Methyl Tetrahydrofuran | Heptane | Cloudy solution | Insufficient solid for analysis |
| 2-Propanol | Heptane | Solid present before additions* | Form A * |
| 95% 2-Propanol / 5% heptane (% v/v) | Heptane | Solid present before additions* | Form A * |
| 70% 2-Propanol / 30% Heptane (% v/v) | Heptane | Solid present before additions | Mixture L & M* |
| 70% 2-Propanol / 30% Heptane | Heptane | Clear solutions | |

TABLE 20A-continued

Anti-Solvent Observations and XRPD Results

| Solvent System | Anti-solvent used | Observations anti-solvent addition | XRPD analysis |
|---|---|---|---|
| (% v/v) re-prepared sample 50% 2-Propanol / 50% Heptane (% v/v) | Heptane | Solid present before additions* | WC Form A* |
| 95% Heptane / 5% 2-Propanol (% v/v) | Heptane | Clear solution | |
| 70% 2-Propanol / 30% Water (% v/v) aw = 0.8 | Heptane | Clear solution | |
| Acetone | Heptane | Solid present before additions* | Form A * |
| Acetonitrile | tert-Butylmethyl Ether | Clear solution | |
| 50% Acetonitrile / 50% Water (% v/v) calc. $a_w = 0.9$ | tert-Butylmethyl Ether | Precipitation | Insufficient solid for analysis |
| tert-Butylmethyl Ether | Heptane | N/A | Heptane |
| Ethyl Acetate (dry) | Heptane | Solid present before additions* | Heptane |
| 40% Ethanol:60% Water (% v/v) calc. $a_w = 0.7$ | Heptane | Solid present before additions* | Heptane |
| 50% Ethanol:50% Heptane (% v/v) | Heptane | Solid present before additions* | Heptane |
| Ethanol | Heptane | Solid present before additions* | Heptane |
| 95% Methanol:5% Water (% v/v) calc. aw = 0.2 | tert-Butylmethyl Ether | Clear solution | tert-Butylmethyl Ether |
| Methanol | tert-Butylmethyl Ether | Clear solution | tert-Butylmethyl Ether |
| Methylethyl Ketone | Heptane | Slurry | Heptane |
| Methylisobutyl Ketone | Heptane | Slurry | Heptane |
| n-Heptane | tert-Butylmethyl Ether | N/A | tert-Butylmethyl Ether |
| Toluene | Heptane | Slurry | Heptane |
| Tetrahydrofuran | Heptane | Slurry | Heptane |

*= solids that precipitated under ambient conditions after 8 days

TABLE 20B

Additional Anti-Solvent Observations and XRPD Results for Select Solvents

| Solvent System | Observation after re-dissolution and anti-solvent addition | Observations after storage in the fridge for ca. 48 hours | XRPD analysis after re-dissolution and storage at 4° C. for ca. 48 hours |
|---|---|---|---|
| 1-Butanol | Clear colourless solution | Precipitation of white solid | WC Form A |
| 2-Propanol | Clear colourless solution | Precipitation of white solid | Form A |
| 95% 2-Propanol / 5% heptane (% v/v) | Cloudy white solution | Cloudy white solution | Form A |
| 70% 2-Propanol / 30% Heptane (% v/v) | Clear solution | Clear solution | |
| 70% 2-Propanol / 30% Heptane (% v/v) re-prepared sample | | Clear solution | |
| 50% 2-Propanol / 50% Heptane (% v/v) | Clear solution | Clear solution | |
| 95% Heptane / 5% 2-Propanol (% v/v) | | Clear solution | |
| 70% 2-Propanol / 30% Water (% v/v) aw = 0.8 | | Clear solution | |
| Acetone | Cloudy white solution | Precipitation of white solid | Form A |
| Acetonitrile | | Clear solution | |
| Ethyl Acetate (dry) | Precipitation of white solid | White solid | Amorphous |
| 40% Ethanol:60% Water (% v/v) calc. $a_w = 0.7$ | Cloudy white solution | Precipitation of white solid | Mixture L & M |
| 50% Ethanol:50% Heptane (% v/v) | Cloudy white solution | Precipitation of white solid | Form A |
| Ethanol | Cloudy white solution | Precipitation of white solid | Form A |
| 95% Methanol:5% Water (% v/v) calc. $a_w = 0.2$ | | Clear solution | |
| Methanol | | Clear solution | |

Evaporation

Saturated solutions of Compound 3 produced from temperature cycling experiments were evaporated under ambient conditions. After approximately 4 days, observations were made, and solids recovered were analyzed by XRPD (Table 21).

Observations and XRPD results of solids returned from evaporation experiments under ambient conditions can be found in Table 21 below. Crystalline material returned from evaporation experiments was found to be Form A only, but the majority of solids recovered were amorphous.

TABLE 21

Evaporation Observations and XRPD results

| Solvent System | Observations after ~96 hours evaporation under ambient conditions | XRPD analysis |
|---|---|---|
| 1,4-Dioxane | N/A | N/A |
| 1-Butanol | Solid | Poorly Crystalline Form A |
| 2-Methyl Tetrahydrofuran | Solid | Poorly Crystalline Form A |
| 2-Propanol | Solid | Form A |
| 95% 2-Propanol / 5% heptane (% v/v) | Solid | Form A |
| 70% 2-Propanol / 30% Heptane (% v/v) | N/A | N/A |

TABLE 21-continued

Evaporation Observations and XRPD results

| Solvent System | Observations after ~96 hours evaporation under ambient conditions | XRPD analysis |
|---|---|---|
| 70% 2-Propanol / 30% Heptane (% v/v) re-prepared sample | Solid | Insufficient material for analysis |
| 50% 2-Propanol / 50% Heptane (% v/v) | Solid | Amorphous |
| 95% Heptane / 5% 2-Propanol (% v/v) | Solid | Amorphous |
| 70% 2-Propanol / 30% Water (% v/v) $a_w$ = 0.8 | Solid | Amorphous |
| Acetone | Solid | Poorly Crystalline Form A |
| Acetonitrile | Solid | Amorphous |
| 50% Acetonitrile / 50% Water (% v/v) calc. $a_w$ = 0.9 | Solid | Amorphous |
| tert-Butylmethyl Ether | No solid | N/A |
| Ethyl Acetate (dry) | Solid | Amorphous |
| 40% Ethanol:60% Water (% v/v) calc. $a_w$ = 0.7 | Solid | Amorphous |
| 50% Ethanol:50% Heptane (% v/v) | Solid | Amorphous |
| Ethanol | Solid | Poorly Crystalline Form A |
| 95% Methanol:5% Water (% v/v) calc. $a_w$ = 0.2 | Solid | Amorphous |
| Methanol | Solid | Amorphous |
| Methylethyl Ketone | Solid | Amorphous |
| Methylisobutyl Ketone | Solid | Amorphous |
| n-Heptane | No solid | Amorphous |
| Toluene | Solid | Amorphous |
| Tetrahydrofuran | No solid | N/A - no solid returned |

Samples produced from thermal cycling, cooling and evaporation experiments were dried at 50° C. for approximately 24 hours to assess any de-solvation/dehydration. From temperature cycling experiments, 3 samples converted upon drying:

Acetonitrile sample converted from Form J to amorphous;

40% Ethanol/60% Water (% v/v) converted from Form N to Form P; and

Methanol sample converted from Form O to amorphous.

Figure 40:
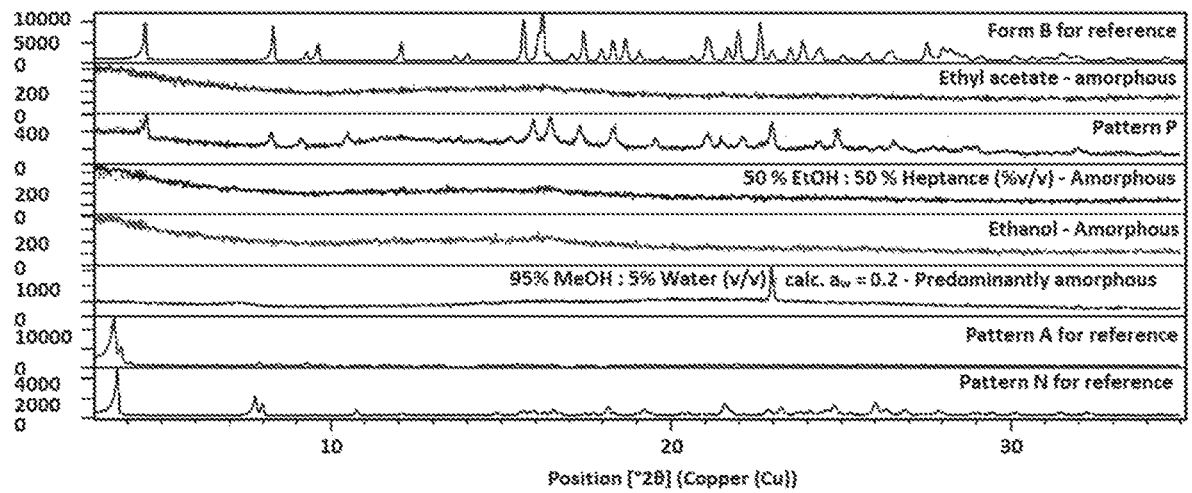
FIG. 40 provides an XRPD overlay of selected solids, including pattern P, resulting from the temperature cycling as described in Example 9. The x-axis is 2Theta measured in degrees and the y-axis is intensity.

The XRPD pattern of pattern P is shown in FIG. 40.

No significant changes were seen upon drying the cooling and evaporation isolated samples at 50° C. for approximately 24 hours.

From the four techniques, Form A was the predominant form produced. Form B and J were observed after temperature cycling experiments from acetone and acetonitrile solvent systems, respectively. Three new patterns were observed (pattern N, O and P) from 40% ethanol. 60% water (% v/v) and methanol solvent systems. Patterns N, O and P's solid-state properties were poor and were not observed from any other crystallization experiments. A mixture of pattern L and M was observed via precipitation from a saturated solution under ambient conditions of 70% 2-propanol/30% heptane (% v/v) and 40% ethanol. 60% water (% v/v). Weakly crystalline pattern E was returned from evaporation from tert-butylmethyl ether. Table 22A is a summary of the results from the four techniques used in the polymorph study and Table 22B is a comparison of the properties of the observed Forms.

TABLE 22A

Summary of Results from Crystallization Techniques

| Solvent System | Crystallization technique | | | |
|---|---|---|---|---|
| | Maturation | Anti-solvent Additions | Cooling | Evaporations |
| 1,4-Dioxane | Clear solution | Insufficient solid for XRPD | Insufficient solid for XRPD | Insufficient solid for XRPD |
| 1-Butanol | Form A | Form A (WC) * | Form A | Amorphous |
| 2-Methyl Tetrahydrofuran | Form A | Insufficient solid for XRPD | Clear solution | Form A (WC) |
| 2-Propanol | Form A | Form A* | Form A | Amorphous |
| 95% 2-Propanol / 5% Heptane (% v/v) | Form A | Form A* | Form A | Form A (WC) |
| 70% 2-Propanol / 30% Heptane (% v/v) | Form B (WC) | Mixture L + M* | Clear solution | Insufficient solid for XRPD |
| 50% 2-Propanol / 50% Heptane (% v/v) | Form A (WC) | Form A (WC) * | Form A (WC) | Amorphous |
| 95% Heptane / 5% 2-Propanol (% v/v) | Form A (WC) | Insufficient solid for XRPD | Clear solution | Amorphous |
| 70% 2-Propanol / 30% Water (% v/v) aw = 0.8 | Form A | Clear solution | Clear solution | Amorphous |
| Acetone | Form B | Form A* | Form A | Form A (WC) |
| Acetonitrile | Form J | Insufficient solid for XRPD | Clear solution | Amorphous |

TABLE 22A-continued

Summary of Results from Crystallization Techniques

| Solvent System | Crystallization technique | | | |
|---|---|---|---|---|
| | Maturation | Anti-solvent Additions | Cooling | Evaporations |
| 50% Acetonitrile / 50% Water (% v/v) calc. aw = 0.9 | Clear solution | Insufficient solid for XRPD | Clear solution | Amorphous |
| tert-Butylmethyl Ether | Amorphous | N/A | Clear solution | WC (Pattern E) |
| Ethyl Acetate (dry) | Amorphous | Form A* | Amorphous | Amorphous |
| 40% Ethanol / 60% Water (% v/v) calc. aw = 0.7 | Pattern N | Mixture L + M* | Amorphous | Amorphous |
| 50% Ethanol / 50% Heptane (% v/v) | Amorphous | Form A* | Form A | Amorphous |
| Ethanol | Amorphous | Form A* | Amorphous | Form A (WC) |
| 95% Methanol / 5% Water (% v/v) calc. aw = 0.2 | Amorphous | Clear solution | Clear solution | Amorphous |
| Methanol | Pattern O | Clear solution | Clear solution | Amorphous |
| Methylethyl Ketone | Form A | Form A | Clear solution | Amorphous |
| Methylisobutyl Ketone | Form A (WC) | Form B | Clear solution | Amorphous |
| n-Heptane | Amorphous | Clear solution | Clear solution | Amorphous |
| Toluene | Amorphous | Amorphous | Amorphous | Amorphous |
| Tetrahydrofuran | Clear solution | Form A | Clear solution | Insufficient solid for XRPD |

WC = weakly crystalline;
*solids that precipitated under ambient conditions

TABLE 22B

Comparison of Isolated Forms and Patterns

| Material | Onset Temp (° C.) | Mass loss within the TG trace | $^1$H NMR Residual Solvent Content | Thermal events from SSCI report |
|---|---|---|---|---|
| Form A | Melting 139.4, melting 153.9, decomposition 209.0 | 0.8% mass loss up to 250° C. | Grease | Melt 133-150° C. 0.8% mass loss up to 250° C. |
| Form B | Melting 179.8 | N/A | 0.22 wt. % acetone + grease | ~176° C. 1.3% weight loss up to 250° C. |
| Form J | Solvent loss 129.3, melting transition 200.0 | 2.2 wt % loss up to 150° C. | Grease, acetonitrile residual solvent peak under API peak | Exothermic base line shifts ~134° C., apparent melt onset 83° C. Total mass loss of 9.3 wt % prior to degradation |
| Pattern N | Weak thermal events with an onset of 134.7 | N/A | Grease | N/A |
| Pattern O | Melting 179.6 | N/A | Traces of methanol + grease | N/A |

Example 10. Polymorph Study of Form B and Form J Form B

A polymorph study was completed for Form B. The production of Form B was completed by temperature cycling amorphous Compound 3 in 125μL of acetone (Form B) with drying the material under ambient conditions for about 24 hours.

Form B was characterized by XRPD, TG/DTA, DSC, DVS, VT-XRPD, and PLM. The XRPD, the TG, and the DSC analysis were comparable to the results for Form B discussed in Table 23 and Table 24 of Example 8. The material was also characterized by $^1$HNMR, HPLC, and FT-IR.

Figure 41A:
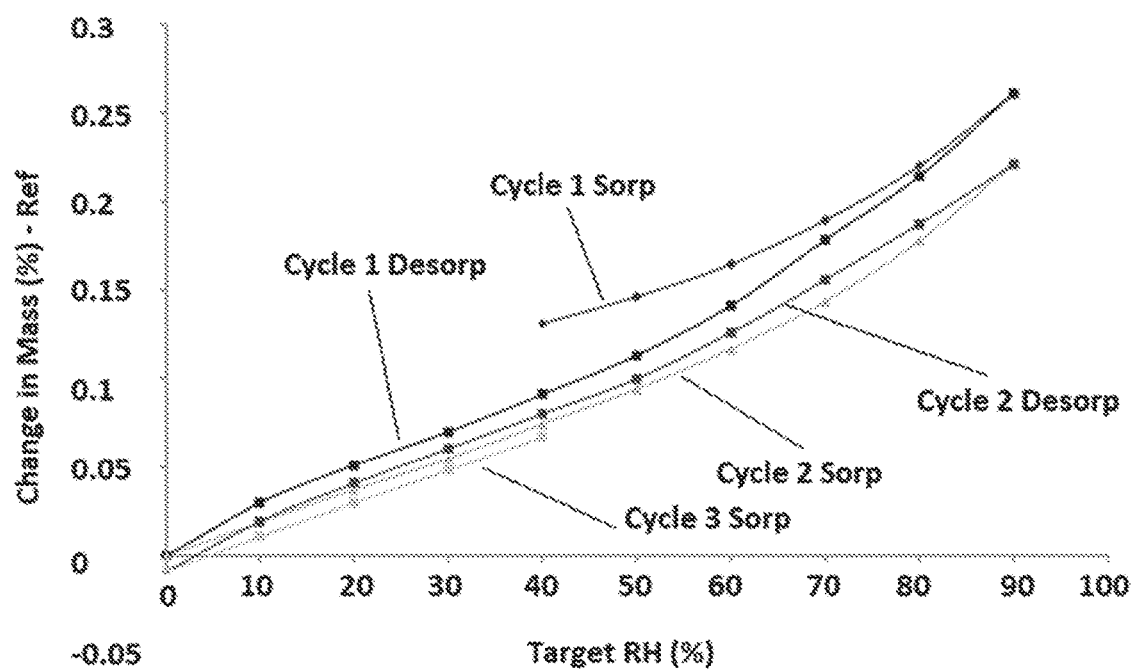
FIG. 41A is a DVS isothermal plot of Compound 3 Form B as described in Example 10. The x-axis is target RH measured in percent and the y-axis is change in mass measured in percent.
Figure 41B:
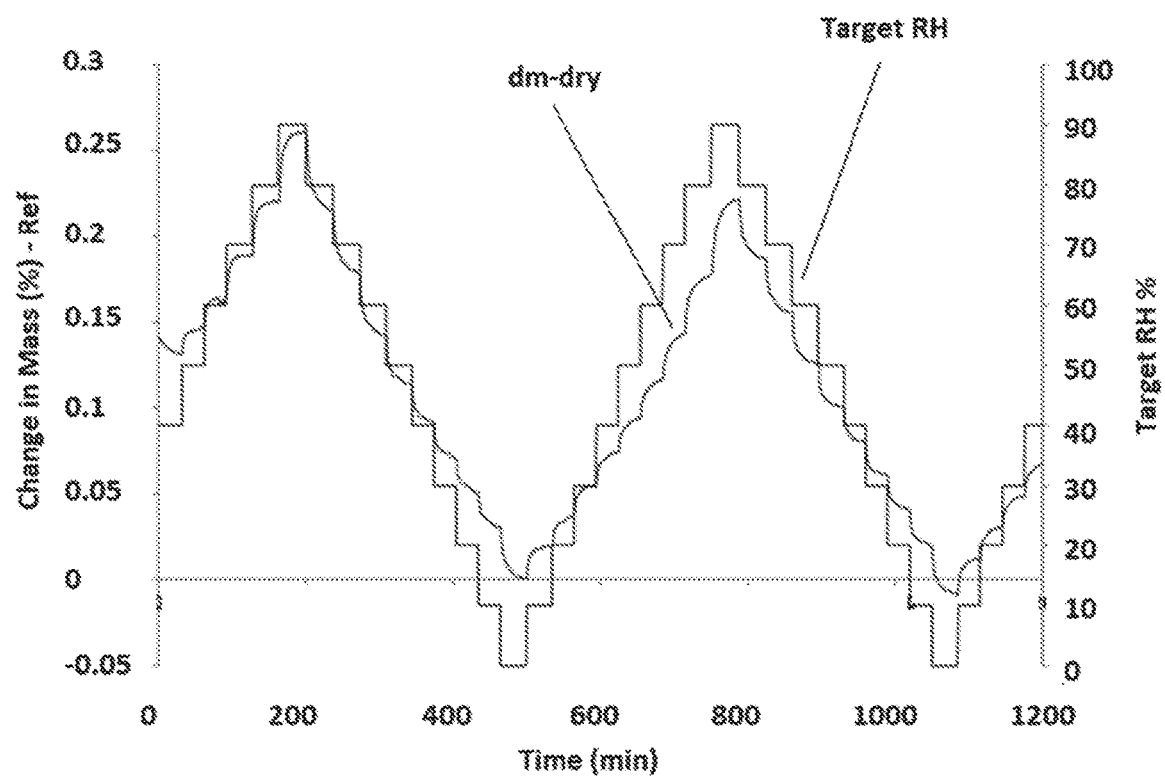
FIG. 41B is a DVS kinetic plot of Compound 3 Form B as described in Example 10. The right y-axis is target RH measured in percent and the left y-axis is change in mass measured in percent. The x-axis time measured in minutes.
Figure 42:
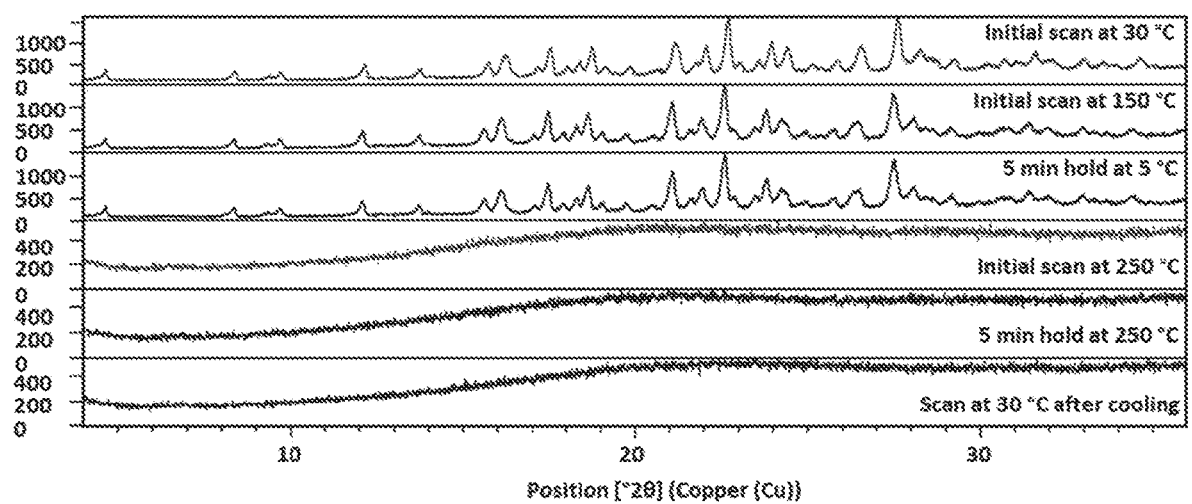
FIG. 42 provides VT-XRPD diffractograms as the sample of Compound 3 Form B was heated to 250° C. as described in Example 10. The x-axis is 2Theta measured in degrees and the y-axis is intensity.
Figure 43:
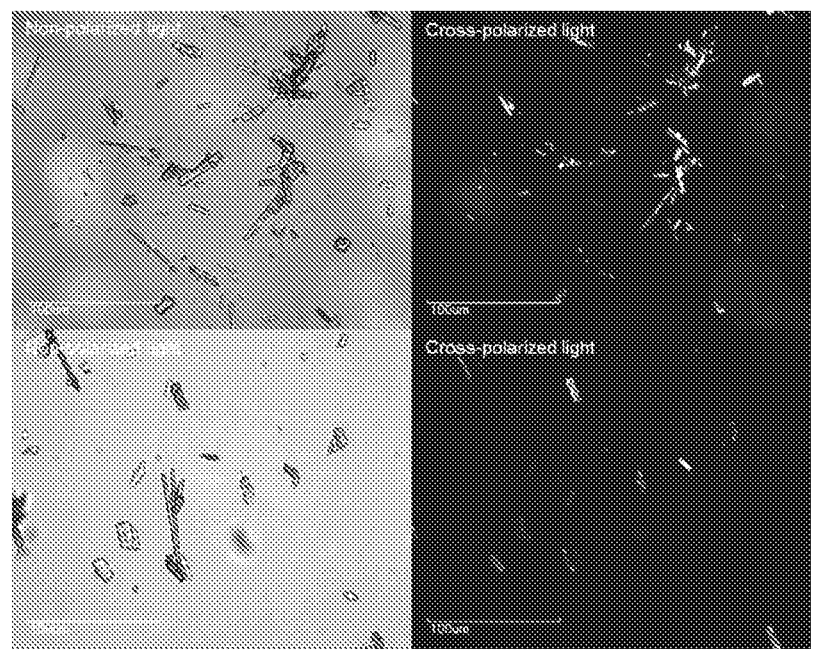
FIG. 43 is a PLM micrograph of Compound 3 Form B as described in Example 10.

Form B material was found to be slightly hygroscopic by DVS analysis, with an uptake of 0.26 wt % (0.1 equiv. water) up to 90% RH. From the isothermal plot (FIG. 41A), the isotherms were type 1, indicating reversible adsorption onto the particle surface. From the kinetic plot (FIG. 41B), no significant mass increase or decrease was observed, suggesting that no re-crystallization events had occurred. VT-XRPD showed the material to melt between 150° C. and 250° C. No recrystallisation was observed upon cooling the sample (FIG. 42) and PLM analysis showed that Form B was consistent of a birefringent rod-like morphology (FIG. 43).

No changes by XRPD or HPLC purity were observed when the material was stored at 40° C./75% RH, 80° C. or under ambient conditions. Form B was poorly soluble in the selected pH 4, pH 6.8, FaSSIF, FeSSIF and FaSSGF media.

Form J

A polymorph study was completed for Form J. The production of Form J was completed by temperature cycling amorphous Compound 3 in acetonitrile (Form B) with drying the material under ambient conditions for about 24 hours. The exact procedure with observations and XRPD results for each step is given in Table 22.

TABLE 22

Process for the Formation of Form J

| Step No. | Procedure | Observation | XRPD result |
|---|---|---|---|
| 1 | Lyophilization | White solid post lyophilization | Amorphous |
| 2 | Temperature cycling 96 hours | Clear pale-yellow solution | N/A |
| 3 | Crash cooling (4° C.) | Clear pale-yellow solution | N/A |
| 4 | Evaporation under ambient conditions | Crust formation after ca. 18 hours | Crust = Form J |
| 5 | Re-slurry in 5 mL acetonitrile | Clear pale-yellow solution | Form J |
| 6 | Drying 40° C. under vacuum 18 hours | White solid | Weakly crystalline pattern G |
| 7 | Re-slurry in 1 mL acetonitrile 18 hours | Immobile slurry | Poorly crystalline Form J |
| 8 | Re-slurry in 1.5 mL acetonitrile 18 hours | Immobile slurry | Form J |
| 9 | Drying ambient under vacuum 1 hour | White solid | Form J decrease in crystallinity |
| 10 | Drying ambient under vacuum 2 hours | White solid | Predominantly amorphous |
| 11 | Re-slurry 4 ml acetonitrile 18 hours | Immobile slurry | Form J |
| 12 | Air drying 2, 5 and 24 hours | White solid | Form J |
| 13 | After 5 days storage under ambient conditions | White solid | Amorphous |
| 14 | Re-slurry 4 ml acetonitrile 18 hours | Immobile slurry | Form J |
| 15 | Isolation using Buchner funnel (10-15 seconds on filter bed) | White solid | Amorphous |
| 16 | Re-slurry 4 ml acetonitrile 4 hours | Immobile slurry | Form J |
| 17 | Isolation using centrifuge filtration | White solid | Form J |
| 18 | Ambient drying 18 hours | White solid | Form J |

Form J was characterized via XRPD, TG, DCS, DVS, 1HNMR, HPLC, PLM, and FT-IR. The XRPD, TG, and DSC results were comparable with the results in Table 3 and Table 4 of Example 8. The 1HNMR, FT-IR, and HPLC were characteristic of Form J.

Figure 44A:
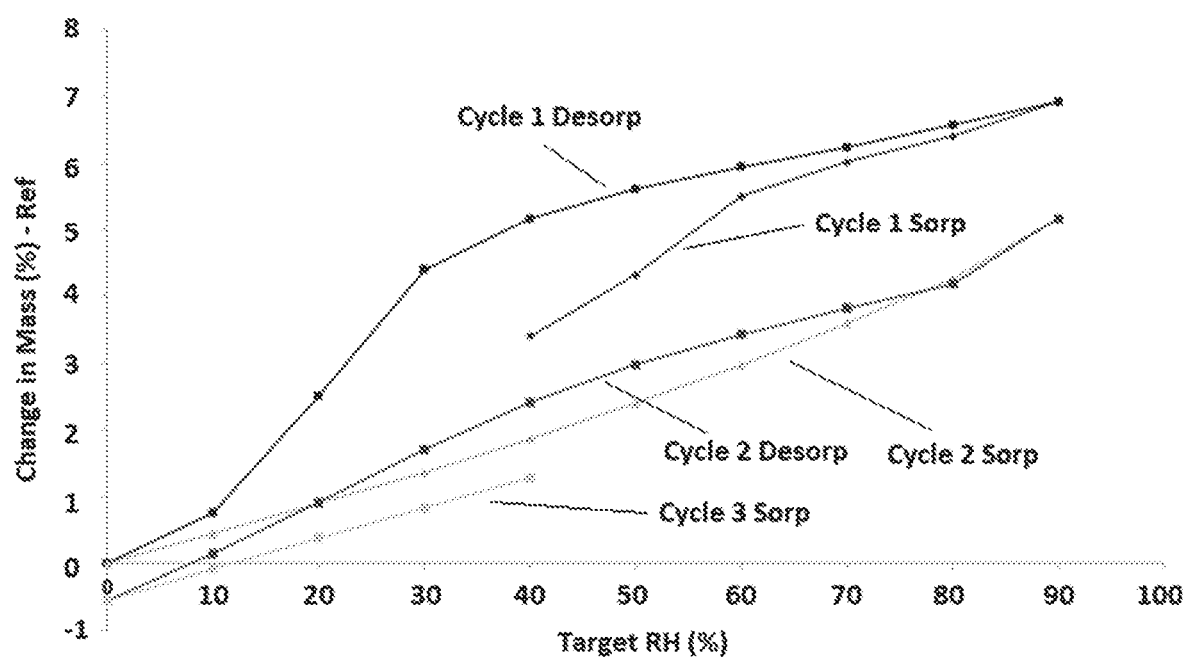
FIG. 44A is a DVS isothermal plot of Compound 3 Form J as described in Example 10. The x-axis is target RH measured in percent and the y-axis is change in mass measured in percent.
Figure 44B:
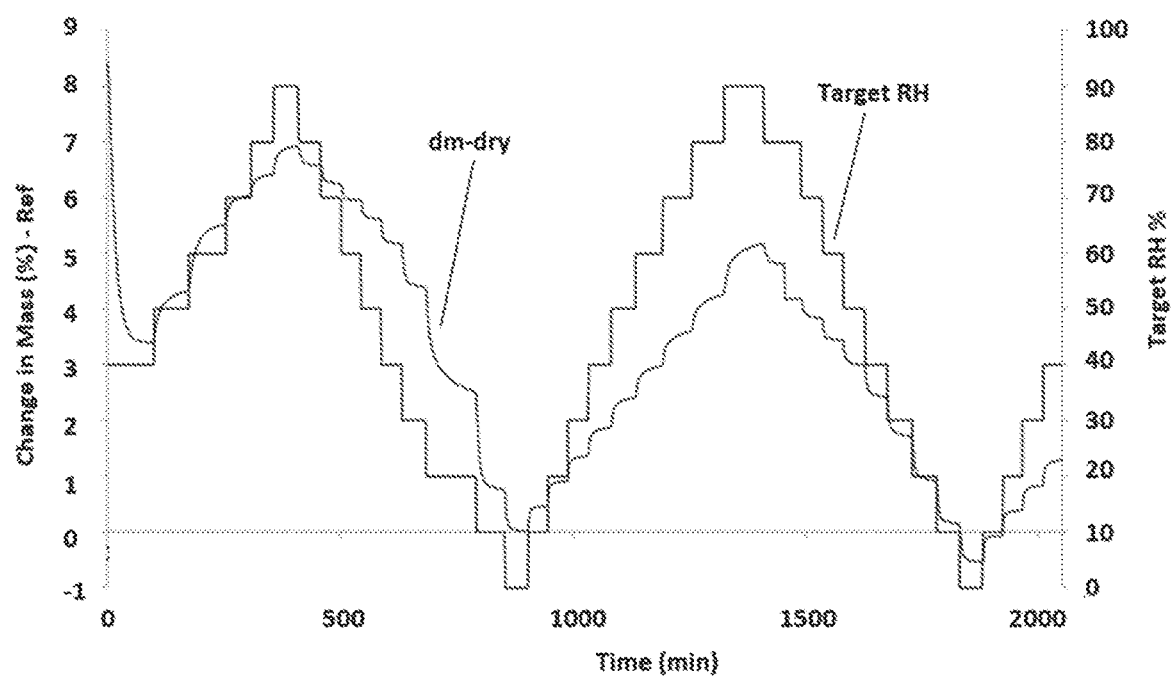
FIG. 44B is a DVS kinetic plot of Compound 3 Form J as described in Example 10. The right y-axis is target RH measured in percent and the left y-axis is change in mass measured in percent. The x-axis time measured in minutes.
Figure 44C:
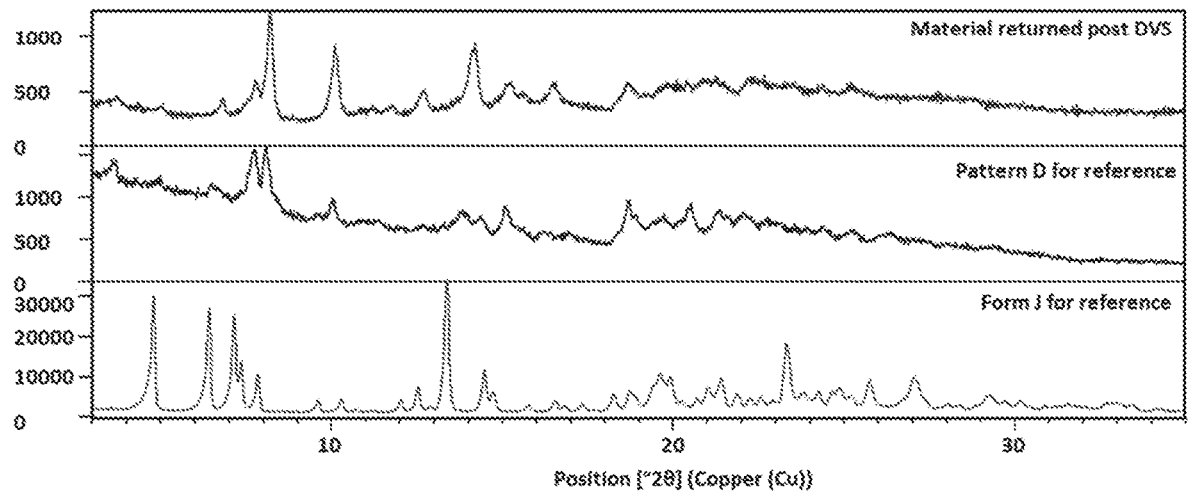
FIG. 44C provides an XRPD analysis post-DVS of Compound 3 Form J as described in Example 10. The x-axis is 2Theta measured in degrees and the y-axis is intensity.

DVS analysis showed the material to be hygroscopic form with an uptake of 6.9 wt % (2.5 equiv. water) in the first sorption cycle and an uptake of 5.2 wt % (1.8 equiv. water) in the second sorption cycle. There was a difference of 2.2 wt % (loss of 0.3 wt % acetonitrile) between the start and end of analysis which is likely due to the acetonitrile within the sample. A Type 1 isotherm was observed which indicated reversible adsorption onto the particle surface. From the kinetic plot, the initial mass loss of 5 wt % (0.8 equiv. acetonitrile) indicated the drying/removal of excess acetonitrile from the sample. Post-DVS XRPD analysis returned pattern D (FIG. 44A-FIG. 44C).

Figure 44D:
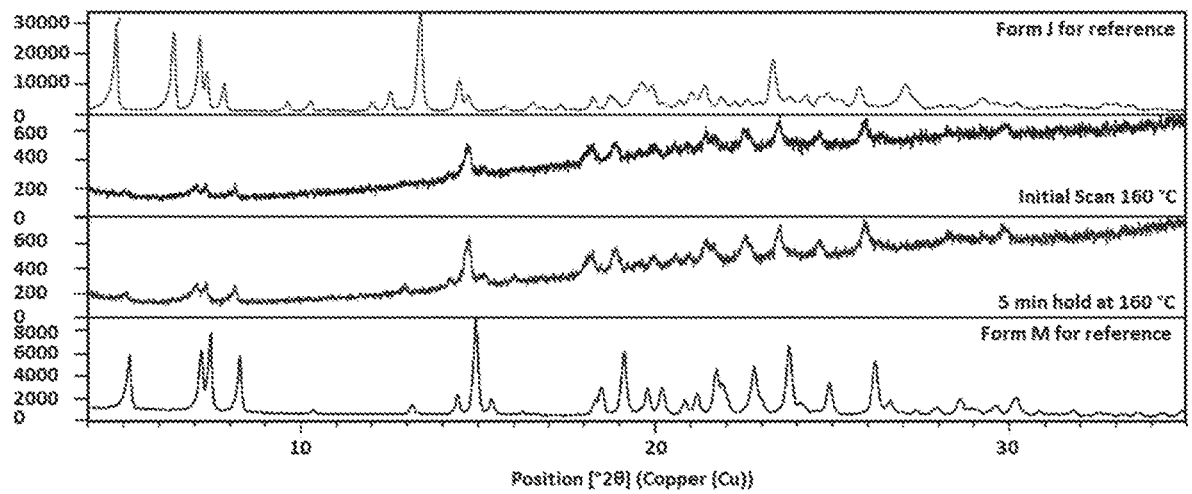
FIG. 44D provides an overlay of VT-XRPD diffractograms as the sample of Compound 3 Form J was heated to 170° C. as described in Example 10. The x-axis is 2Theta measured in degrees and the y-axis is intensity.

Although the XRPD pattern was indicative of Form J, the VT-XRPD results indicated that Form J is an acetonitirile hemi-solvate that desolvated via Form G to Form M upon heating to 170° C. (FIG. 44D).

Figure 44E:
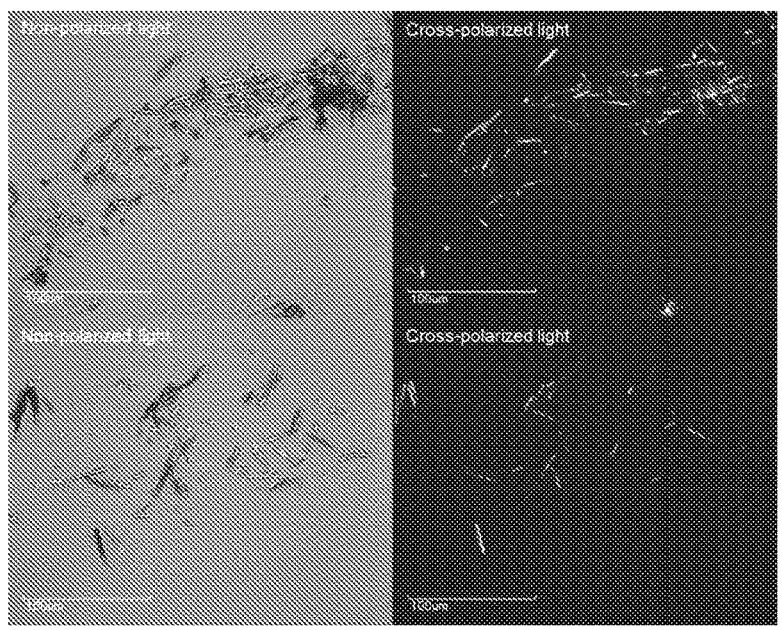
FIG. 44E is a PLM micrograph of Compound 3 Form J as described in Example 10.

PLM analysis showed that Form J consisted of a birefringent rod-like morphology (FIG. 44E).

Figure 45:
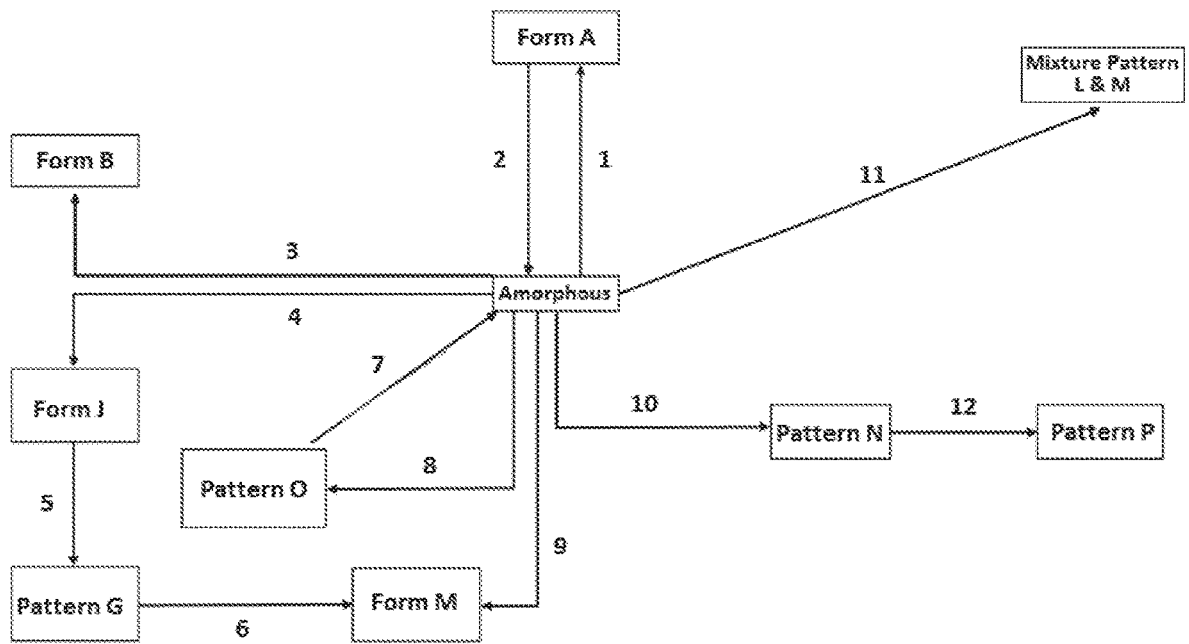
FIG. 45 is a flow diagram of the polymorph studies as described in Example 9 and Example 10. Each number represents a crystallization technique that affords the form, pattern, or amorphous material indicated by the arrow. The numbered crystallization techniques are as follows: 1) temperature cycling in 2-propanol, methyl ethyl ketone, 2-methyl THF, 1-butanol, 2-propanol/heptane (95:5% v/v), and 2-propanol/water (70:30% v/v); 2) drying at 50° C. for 24 hours, drying 2-propanol/water (70:30% v/v) or lyophilization (1,4-dioxane); 3) temperature cycling in acetone and 2-propanol/heptane (70:30% v/v) or anti-solvent (heptane) addition to a saturated MBK solution; 4) temperature cycling in acetonitrile; 5) heat to 120° C.; 6) heat to 160° C.; 7) 24 hours drying at 50° C.; 8) temperature cycling in methanol; 9) temperature cycling in acetone for 2.5 days; 10) temperature cycling in ethanol/water (40:60% v/v); 11) anti-solvent (water) addition to a saturated ethanol:water (40:60% v/v) solution or anti-solvent (heptane) addition to a saturated 2-propanol/heptane (70:30% v/v) solution; and 12) drying at 50° C. for about 24 hours.

FIG. 45 is a diagram of the polymorph studies described in Example 9 and Example 10.

Example 11. Competitive Slurries

About 10 mg of Form A, Form B and Form J were weighed separately and the solids were combined into one vial. An appropriate volume of selected solvent was then added to form a slurry. Slurries were then agitated under ambient or elevated temperatures for about 48 hours. Post agitation, solids were isolated using centrifuge filtration and XRPD analysis was collected. Table 23 below details selected solvent systems and volumes used.

Solvent was re-introduced (volumes as per Table 24) to the samples and the samples were agitated for a further 72 hours as no single polymorphic form was returned from the experiments after 48 hours agitation. Solids were isolated using centrifuge filtration and XRPD analysis was collected.

Samples were repeated in 2-propanol and 2-propanol/heptane (70/30% v/v) at 60° C. using the above procedure. Samples were agitated for 24 hours and solvent volumes can be found in Table 24 below. No clear polymorphic form was identified as the most stable form. Isolation of single forms via competitive slurrying appeared to be solvent dependent, as Forms B and J were produced from acetone and acetonitirile, respsectively. Prolonged slurrying in these solvent systems resulted in conversion of both forms to Form A. Conversion of Form B (observed in acetone initially) to Form A over 72 hours indicated that Form A may be the most stable form. Both Forms A and B could be isolated from competitive slurrying experiments from different solvent systems but neither was exclusively predominant at a specific temperature.

TABLE 24

Input solvents, temperatures and volumes used for initial competitive slurry experiments

| Solvent System | Material Used | Temperature (° C.) | Volume of solvent added (µL) |
|---|---|---|---|
| Acetone | Form A, Form B and Form J | Ambient | 150 |
| | | 40 | 100 |
| Acetonitrile | | Ambient | 150 |
| | | 60 | 100 |
| 2-Propanol | | Ambient | 200 |
| | | 60 | 100 |
| 70% 2-propanol/ 30% heptane (% v/v) | | Ambient | 200 |
| | | 60 | 100 |
| Water | Form A and Form B | Ambient | 400 |
| | | 60 | 400 |
| Heptane | | Ambient | 400 |
| | | 60 | 400 |
| 70% 2-propanol/ 30% heptane (% v/v) repeat | Form A, Form B and Form J | 60 | 100 |
| 2-propanol | | 60 | 100 |

Figure 46:
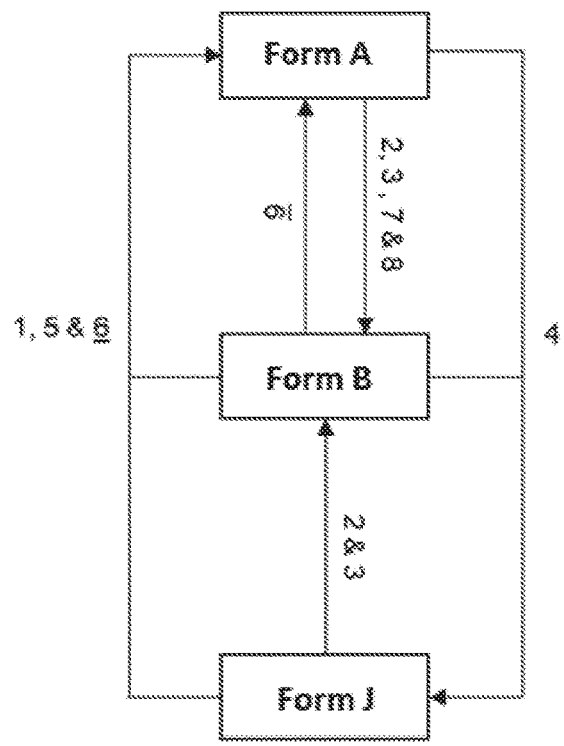
FIG. 46 is a flow diagram of the competitive slurry experiment as described in Example 11. The conditions are as described. Condition 1: 70% 2-propanol/30% heptane (% v/v) ambient 2 days agitation. Condition 2: heptane 60° C. 5 and 12 days agitation. Condition 3: acetone ambient and 40° C. 2 days agitation. Condition 4: acetronitrile ambient and 60° C. 2 days agitation. Condition 5: acetonitrile ambient 5 days agitation. Condition 6: acetone ambient 5 days agitation. Condition 7: acetone ambient and 40° C. 1 week and 12 days (using saturated solution of Compound 3). Condition 8: Water 60° C. 5 days and 12 days agitation (using saturated solution of Compound 3). Condition 9: 50% 2-propanol/50% heptane (% v/v) 60° C. 12 days (predominately amorphous with signs of A (using saturated solution of Compound 3).

An additional competitive slurry experiment was conducted. Approximately 20 mg of Form A and Form B were weighed into separate vials. Solids were combined and 0.5 mL of filtered saturated Compound 3 solution (using the selected solvent) was added to form a slurry. Table 25 details solvent systems and temperatures selected for competitive slurry experiments. Slurries were agitated (within an incubator shaker) at ambient and elevated temperature for about 2 weeks. Sub samples were isolated using centrifuge filtration and XR-PD analysis collected for all solids returned after 1 week and 12 days. Table 25 details the solvents and temperatures of the additional competitive slurry experiment and Table 26 details the XR-PD results. Form B was recovered from slurries of Form A and Form B in acetone, water and heptane. Form A was not recovered as a single phase from any of the solvent systems tested, with the exception of a small number of peaks corresponding to Form A in amorphous samples. This indicates that Form B is likely the most thermodynamically stable form. A mixture of Form A and B was returned from all other solvent systems after 2 weeks agitation at a specific temperature. FIG. 46 is a diagram of the competitive slurry experiment.

TABLE 25

Input solvents, temperatures and volumes used for additional competitive slurry experiments

| Solvent System | Temperature | Input Material |
|---|---|---|
| Acetone | Ambient | A + B |
| 2-Propanol | Ambient | A + B |
| Water | Ambient | A + B |
| Heptane | Ambient | A + B |
| 70% 2-Propanol/ 30% Heptane (% v/v) | Ambient | A + B |
| 30% 2-Propanol/ 70% Heptane (% v/v) | Ambient | A + B |
| 50% 2-Propanol/ 50% Heptane (% v/v) | Ambient | A + B |
| Acetone | 40° C. | A + B |
| 2-Propanol | 60° C. | A + B |
| Water | 60° C. | A + B |
| Heptane | 60° C. | A + B |
| 70% 2-Propanol/ 30% Heptane (% v/v) | 60° C. | A + B |
| 30% 2-Propanol/ 70% Heptane (% v/v) | 60° C. | A + B |
| 50% 2-Propanol/ 50% Heptane (% v/v) | 60° C. | A + B |

TABLE 26

Results from Additional Competitive Slurry Experiment

| Solvent System | Temperature | XRPD Results 1 Week | XRPD Results 2 Weeks |
|---|---|---|---|
| Acetone | Ambient | Form B | N/A |
| 2-Propanol | Ambient | Mixture A + B | Mixture |
| Water | Ambient | Mixture A + B | Mixture A + B |
| Heptane | Ambient | Mixture A + B | Mixture A + B |
| 70% 2-Propanol/ 30% Heptane (% v/v) | Ambient | Mixture A + B | Mixture A + B |
| 30% 2-Propanol/ 70% Heptane (% v/v) | Ambient | Mixture A + B | Predominantly amorphous with signs of A + B |
| 50% 2-Propanol/ 50% Heptane (% v/v) | Ambient | Mixture A + B | Mixture A + B |
| Acetone | 40° C. | Form B | Form B * |
| 2-Propanol | 60° C. | Predominantly A with some peaks of B | Predominantly A with some peaks of B |
| Water | 60° C. | Form B | Predominantly amorphous with signs of from B * |
| Heptane | 60° C. | Form B | Predominantly amorphous with signs of from B * |
| 70% 2-Propanol/ 30% Heptane (% v/v) | 60° C. | Predominantly A with some peaks of B | Predominantly A with some peaks of B |
| 30% 2-Propanol/ 70% Heptane (% v/v) | 60° C. | Predominantly A with some peaks of B | Predominantly A with some peaks of B |
| 50% 2-Propanol/ 50% Heptane (% v/v) | 60° C. | Predominantly A with some peaks of B | Predominantly amorphous with signs of A and B |

* = XRPD results alter 12 days

Table 27A is a summary of the properties of Form A, Form B, and Form J and Table 27B is a summary of the stability and solubility of Form A, Form B, and Form J.

TABLE 27A

Properties of Form A, Form B, and Form J from Polymorph Studies of Example 9 and Example 10

| Characterization Technique | Material | | |
|---|---|---|---|
| | Form A | Form B | Form J |
| XRPD | Form A | Form B | Form J with an additional peak |
| VT-XRPD | Melt between 125-170° C. | Melt between 150-250° C. | Form J de-solvated to Pattern G (120° C.) Pattern G converted to Form M and then melted (190° C.-230° C.). |
| PLM | Birefringent agglomerates | Birefringent rods | Birefringent rods |
| TG/DTA | Melting 139.4° C. melting 153.9° C., decomposition 209° C. | Melting 178.4° C. | Solvent loss 138.5° C., melting 206.7° C. |
| DSC | Melting 138° C. (peak 151.4° C.) | Melting 178.4° C. (peak 186.3° C.) | Solvent loss 138.5° C. (peak 152.4° C.) melting 202.9° C. (peak 213.3° C.) |
| DVS | Hygroscopic 6.9 wt % (2.5 eq. H$_2$O) | Slightly hygroscopic 0.26 wt % (0.1 eq. H$_2$O) | Hygroscopic first sorption cycle 6.9 wt % (2.5 eq. H$_2$O) and 5.2 wt % (1.8 eq. H$_2$O) uptake at 90% RH |

TABLE 27A-continued

Properties of Form A, Form B, and Form J from Polymorph Studies of Example 9 and Example 10

| Characterization Technique | Material | | |
|---|---|---|---|
| | Form A | Form B | Form J |
| XRPD post DVS | Weakly crystalline form A | | Form B |
| $^1$HNMR | Consistent with structure | Consistent with structure | Consistent with structure |
| HPLC Purity (relative area) | 99.7% | 99.7 | 99.9% |

TABLE 27B

Solubility and Stability of Form A, Form B, and Form J from Polymorph Studies of Example 9 and Example 10

| | | Material | | |
|---|---|---|---|---|
| | | Form A | Form B | Form J |
| 1 week stability | 40° C./75% RH XRPD (uncapped) | WC Form A | Form B | Form A + Form J |
| | 80° C. XRPD (capped) | Form A | Form B | Pattern D |
| | 25° C./60% RH XRPD (uncapped) | WC Form A | N/A | N/A |
| | Ambient conditions XRPD (capped) | N/A | Form B | Form A + Form J |
| | 40° C./75% RH HPLC (uncapped) | 99.7% (by relative area) | 99.8% (by relative area) | 99.8% relative area |
| | 80° C. HPLC (capped) | 99.7% (by relative area) | 99.9% (by relative area) | 99.9% relative area |
| | Ambient conditions HPLC (capped) | N/A | 99.8% (by relative area) | 99.9% relative area |
| Solubility (mg/mL) | FaSSIF | <0.01 | <0.01 | <0.01 |
| | FeSSIF | <0.01 | <0.01 | <0.01 |
| | FaSSGF | <0.01 | <0.01 | <0.01 |
| | pH 4 | Not detected | Not detected | Not detected |
| | pH 6.8 | <0.01 | Not detected | Not detected |

Figure 47:
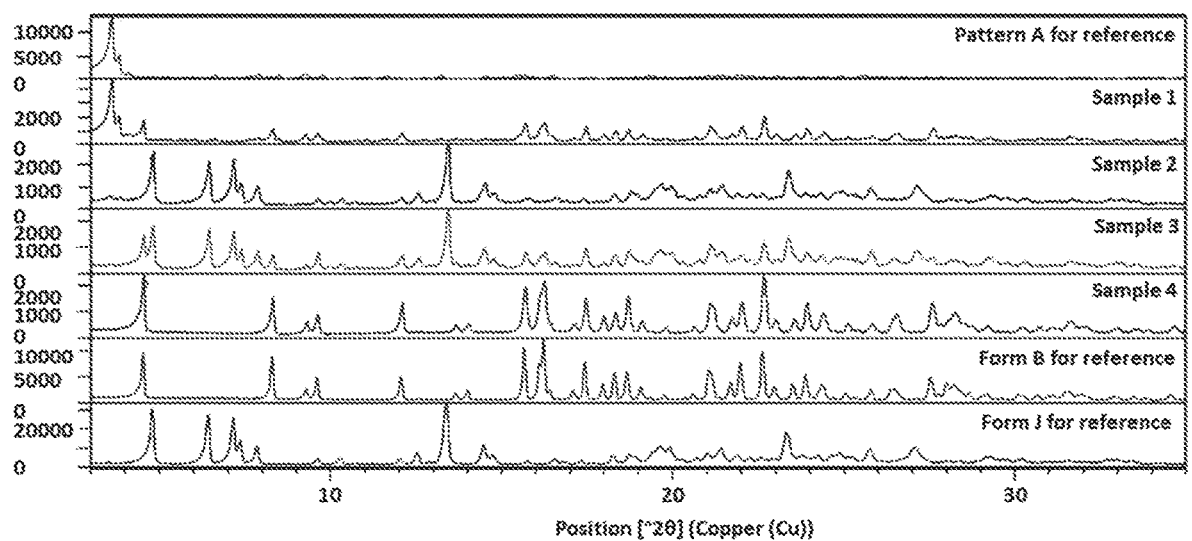
FIG. 47 provides an overlay of XRPD diffractograms following the grinding experiments as described in Example 12. The x-axis is 2Theta measured in degrees and the y-axis is intensity.

Example 12. Grinding Study 10 mg of the appropriate Compound 3 material (detailed in Table 28) was weighed into separate HPLC vials. The solids were then ground using a pestle and mortar. Resulting materials were analyzed by XRPD (FIG. 47). The results are shown in Table 28. From samples where mixtures of forms were used, mixtures of forms were recovered. Where all 3 forms were used, Form A was not returned, although it is possible that the already small particle size of Form A was reduced further by grinding and therefore not detected by XRPD analysis. Form B upon grinding did not change form.

TABLE 28

Composition of Materials in Grinding Study

| Sample Number | Forms | XRPD Results |
|---|---|---|
| 1 | A + B | Mixture A + B |
| 2 | A + J | Mixture A + J |
| 3 | A + B + J | Mixture B + J |
| 4 | B | B |

Example 13. Compression Study

Figure 48A:
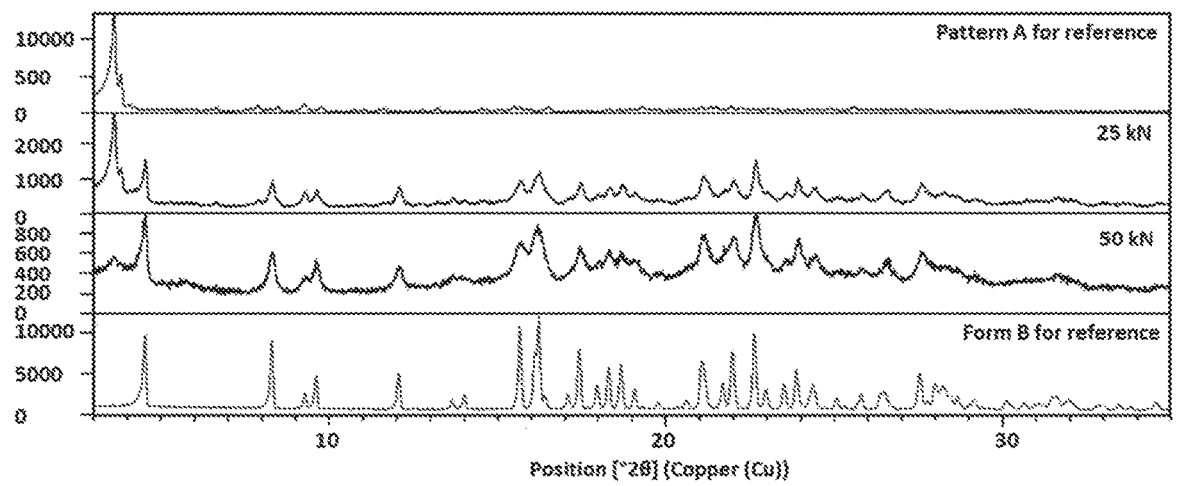
FIG. 48A provides an overlay of XRPD diffractograms following the compression of a mixture of Compound 3 Form A and Form B as described in Example 13. The x-axis is 2Theta measured in degrees and the y-axis is intensity.
Figure 48B:
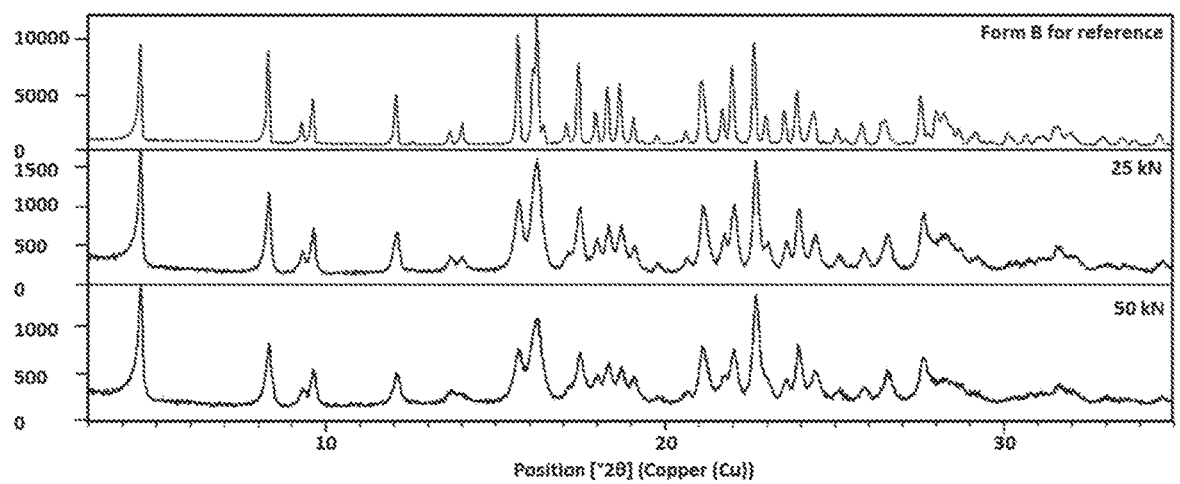
FIG. 48B provides an overlay of XRPD diffractograms following the compression of Compound 3 Form B as described in Example 13. The x-axis is 2Theta measured in degrees and the y-axis is intensity.

A mixture of Form A ±Form B and Form B were compressed using a specac IR die press. A total of approximately 100 mg (50 mg A ±50 mg B and 100 mg B) were weighed into separate 2 mL glass vials. The solids were then placed into the IR dies and pressed under 25 kN and 50 kN for about 10-15 seconds. After pressing to 25 kN, material was removed from the dies and ground slightly. A sub-sample was taken and XRPD analysis was collected. Material was then placed back into the dies and pressed to 50 kN. After pressing to 50 kN, material was removed from the dies and ground slightly before collecting XRPD analysis. The results from the compression study are shown in Table 29 and the XRPD results are shown in FIG. 48A and FIG. 48B. Both samples observed a small color change from white to off-white after being pressed to 25 kN. Form B did not change under pressure. No single form was observed when compressing a mixture of Forms A and form B material, but a decrease in crystallinity was observed when exerting 50 kN on the mixture.

TABLE 29

Compression Study Results

| Input material | Pressure Exerted (kN) | XRPD Results |
|---|---|---|
| Form A + Form B | 25 | Mixture A + B |
| | 50 | Poorly crystalline mixture A + B |
| Form B | 25 | Form B |
| | 50 | Form B |

Example 14. DSC Analysis of Form A ±Form B Mixture

Figure 49:
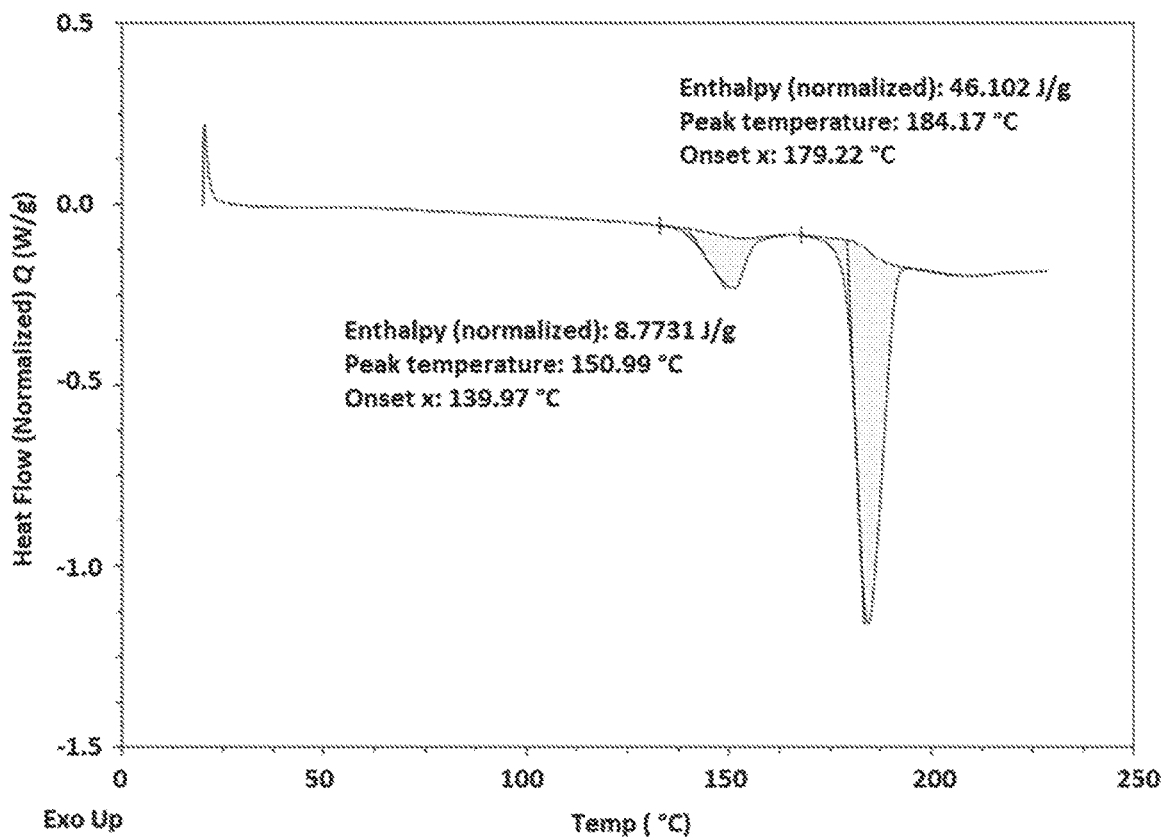
FIG. 49 is the DSC thermogram of a mixture of Compound 3 Form A and Form B as described in Example 14. The x-axis is temperature measured in Celuius and the y-axis is normalized heat flow measured in (W/g).
Figure 50:
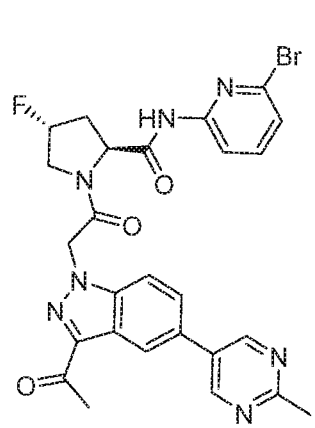
FIG. 50 is factor D inhibitors Compound 1, Compound 2, and Compound 3.
Figure 50:
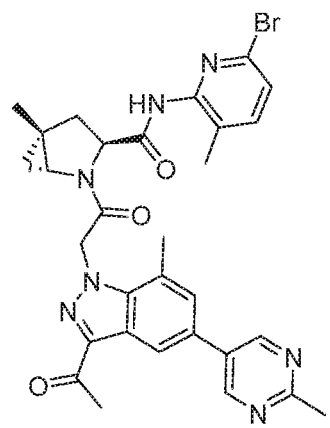
Figure 50:
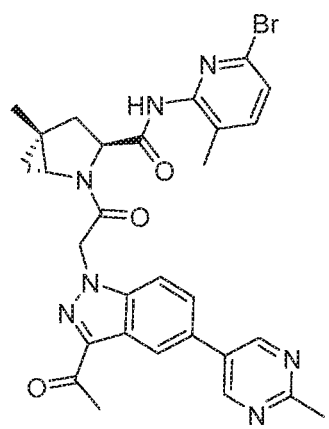

Approximately, 5 mg of a mixture of Form A and Form B was weighed into an aluminium DSC pan and sealed non-hermetically with a pierced aluminium lid. The sample pan was then loaded into a Seiko DSC6200 (equipped with a cooler). Once a stable heat-flow response was obtained, the sample and reference were heated to 250° C. at scan rate of 10° C./min and the resulting heat flow response monitored. Nitrogen was used as the purge gas, at a flow rate of 50 cm3/min. Two endothermic events were observed within the heating cycle of the DSC. The first endothermic event had an onset of approximately 140° C. (Form A melting transition) and the second had an onset of about 180° C. (Form B melting transition). The DSC is shown in FIG. 49.

Example 15. Process Description for the Manufacture of Intermediate 3

In Scheme 2 below, boc-trans-4-fluoroproline (intermediate 1) was reacted with 2-amino-6-bromo pyridine (intermediate 2) in the presence of methyl imidazole (NMI) and methane sulfonyl chloride (MsCl). The reaction completion was monitored by HPLC and the product was extracted with dichloromethane and precipitated with dichloromethane/n-heptane. The product was dried under vacuum in a vacuum tray dryer.

Scheme 2. Synthesis of Intermediate 3

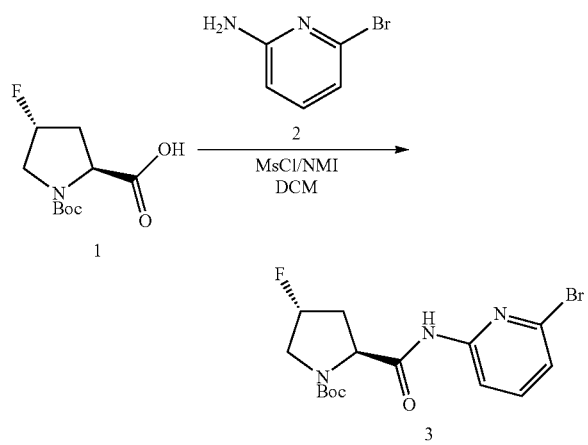

The process description is as follows: The reactor was charged with DCM (dry) (20.0 vol.) and boc-trans-4-fluoroproline (1.0 w/w) at 25±5° C. under $N_2$ atmosphere. The reaction mass was cooled to 0±5° C. and stirred for 15 minutes. The reactor was slowly charged with 1-methyl imidazole (0.88 w/w) at 0±5° C. and stirred for 15 minutes (a change in temperature was observed from 0.8° C. to 3.8° C.). Methane sulfonyl chloride (0.59 w/w) was slowly added into the reactor at 0±5° C. and stirred for 60 minutes. 2-Amino-6-bromo pyridine was added (0.74 w/w) at 0±5° C. and the mass temperature was maintained between 0° C. to 25±5° C. and stirred until reaction was complete. After completion of reaction, the reactor was charged with purified water (10.0 vol.), stirred for 20 minutes, and the layers were separated. The aqueous layer was extracted with DCM (20 vol.) and then with an additional (10 vol.) of DCM. The organic layers were combined and washed with 10% HCl solution (purified water 9.0 w/w, HCl 1.0 w/w), sodium bicarbonate solution (purified water 9.5 w/w, $NaHCO_3$ 0.5 w/w) and brine (purified water 9.0 w/w, NaCl 1.0 w/w). The organic layer was concentrated under vacuum below 40° C. until no distillate was observed. The reactor was charged with DCM (2 vol.) and n-heptane (6 vol.) and stirred for 30 minutes. The reaction mass was cooled to 25±5° C. and stirred for 1 hour. The mass was filtered through A Nutsche filter and the cake was washed with n-heptane (2 vol.). The cake was vacuumed-dried on the filter for 40-50 minutes while keeping the Nutsche filter under suction. The material was dried in a vacuum tray drier at 25±5° C. for 2 hours and then at 30±5° C. for 6 hours or until water content was achieved (acceptance criteria: water content: NMT 1.0%). The product was stored at the controlled temperature.

Table 29 contains examples of quantities of reagents and yield of product for the most recent two batches.

TABLE 29

Scale and Yields of Two Batches of Intermediate 3

| Batch No. of Intermediate 3 | Intermediate 1 | 1-methyl imidazole | MsCl | Intermediate 2 | HPLC | Yield | % Yield |
|---|---|---|---|---|---|---|---|
| Batch 1 | 66.24 Kg | 58.29 Kg | 39.08 Kg | 49.01 Kg | 99.57% | 98.28 Kg | 89.13 |
| Batch 2 | 49.5 Kg | 43.56 Kg | 29.2 Kg | 36.63 Kg | 99.83% | 72.3 Kg | 87.75 |

Example 16. Process Description for the Manufacture of Intermediate 4

In Scheme 3 below, intermediate 3 was hydrolyzed with hydrochloric acid in dioxane. The reaction was monitored by HPLC for the consumption of intermediate 3. The reaction mixture was treated with $NaHCO_3$ and the product was extracted with dichloromethane. Dichloromethane was removed by distillation and replaced with dichloromethane and heptane to precipitate the product. After isolation by filtration, the wet cake was washed with heptane and then vacuum dried in a vacuum tray drier.

Scheme 3. Synthesis of Intermediate 4

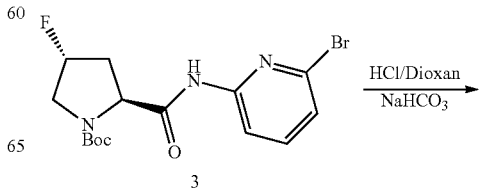

-continued

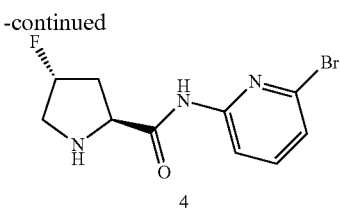
4

The process description is as follows: HCl (4M) in dioxane (6 vol.) and intermediate 3 (1.0 w/w) were charged into a reactor at 20±5° C. under nitrogen atmosphere and the mass was stirred at 20±5° C. for 4 hours. After completion of reaction, the reactor was charged with DCM (20.0 vol.) and stirred for 15 minutes. NaHCO₃ solution (purified water 22.5 w/w, NaHCO₃ 2.5 w/w) was slowly added to the reaction mass and the pH was adjusted to 7-8 and stirred for 20 minutes. The layers were separated and the aqueous layer was extracted with DCM (20.0 vol. ×2 times). The organic layer was concentrated below 40° C. and co-evaporated with n-heptane (5 vol.) below 50° C. The reactor was charged with DCM (2 vol.) and n-heptane (6 vol.) and stirred for 40-60 minutes. The resulting mass was filtered and the cake was washed with n-heptane (2 vol.). The cake was vacuumed and dried for 2 hours. The material was dried at 25±5° C. for 2 hours in a vacuum tray-drier and then at 45±5° C. for 12 hours or until water content was achieved.

Table 30 contains examples of quantities of reagents and yield of product for the most recent two batches.

TABLE 30

Scale and Yields of Two Batches of Intermediate 4

| Batch No. of Intermediate 4 | Intermediate 3 | 4M HCl in dioxane | HPLC | Yield | % Yield |
|---|---|---|---|---|---|
| Batch 1 | 70.0 Kg | 294.0 Kg | 99.58% | 46.23 Kg | 88.66% |
| Batch 2 | 99.5 Kg | 471.0 Kg | 99.48% | 63.54 Kg | 86.05% |

Example 17. Process Description for the Manufacture of Intermediate 10

In Scheme 4 below, intermediate 10 was manufactured in three steps starting from 3-acetyl-5-bromoindazole (intermediate 5). Intermediate 5 was alkylated with tert-butylbromoacetate and then coupled with in situ generated 2-methylpyrimidine-5-boronate ester (intermediate 8) to produce intermediate 9. The tert-butyl ester was then hydrolyzed to give 2-(3-acetyl-5-bromo-1H-indazol-1-yl)acetic acid (10) which was then vacuum dried. This route is composed of Steps 3-5 in the scheme shown below.

Scheme 4. Synthesis of Intermediate 10

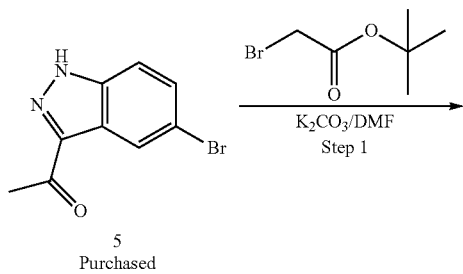
5
Purchased

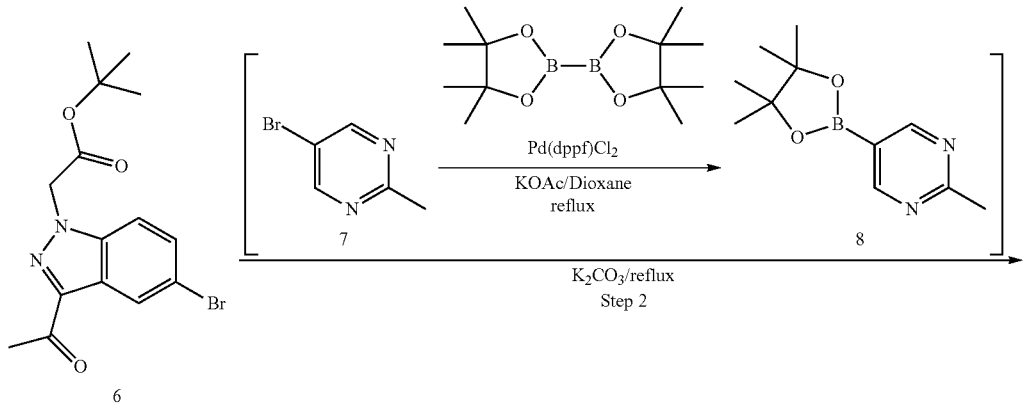
6

-continued

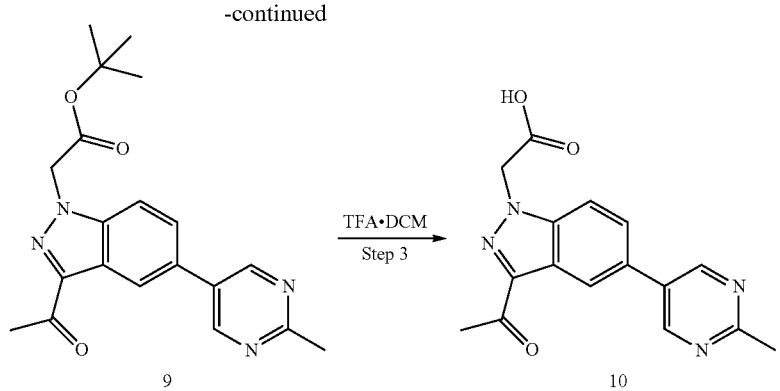

Synthesis of Intermediate 6

In Scheme 4, Step 1, 3-acetyl-5-bromoindazole (intermediate 5) was alkylated with tert-butylbromoacetate in DMF in the presence of potassium carbonate. The reaction was monitored for the conversion of starting materials by HPLC. The product was precipitated with purified water and isolated by filtration. After washing with purified water, ethyl acetate and heptane, the product was vacuum dried in a vacuum tray dryer.

The process description is as follows: The vessel was charged with 1-(5-bromo-1H-indazol-3-yl) ethan-1-one (1.0 w/w) and DMF (7.0 vol.) at 25±5° C. under nitrogen atmosphere and stirred for 15 minutes. The vessel was then charged with potassium carbonate (1.15 w/w) and stirred for 15 minutes. tert-Butylbromoacetate was added (0.97 w/w) slowly to the reaction mass at 30±10° C. The reaction mass temperature was raised to 50±5° C. and stirred for 1 hour at 50±5° C. The reaction mass was cooled to 25±5° C. and purified water (21 vol.) was added slowly. The obtained solid was stirred for 1 hour. The reaction mass was filtered, and the bed was washed with purified water (3 vol.). The wet cake was stirred with purified water (10 vol.) for 15 minutes. The cake was filtered and washed with water (3 vol.). If the sample failed, the wet cake was charged to a mixture of ethyl acetate (10 vol.) and n-heptane (10 vol.). The mass was stirred at 25±5° C. for 1 hour. The mass was filtered, and the cake was washed with a mixture of ethyl acetate (0.1 vol.) and n-heptane (0.9 vol.). The cake was dried at 25±5° C. for 2 hours and then at 50±5° C. for 12 hours in a vacuum tray drier.

Table 31 contains the quantities of reagents and the yield of product for the most recent two batch campaign.

TABLE 31

Scale and Yields of Two Batches of Intermediate 6

| Batch No. of Intermediate 6 | Intermediate 5 | $K_2CO_3$ | t-butyl bromo acetate | HPLC | Yield | % Yield |
|---|---|---|---|---|---|---|
| Batch 1 | 69.5 Kg | 79.93 Kg | 67.42 Kg | 99.46% | 87.15 Kg | 84.9 |
| Batch 2 | 95.74 Kg | 110.1 Kg | 92.87 Kg | 97.26% | 140.96 Kg | 99.6 |

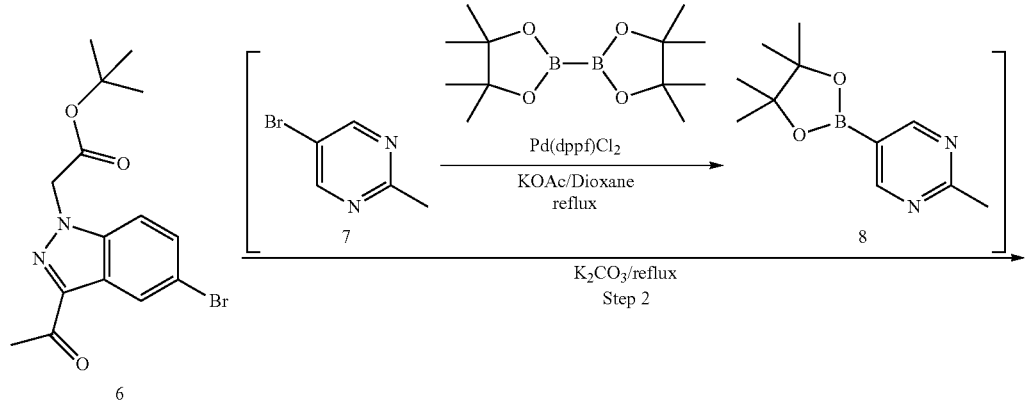

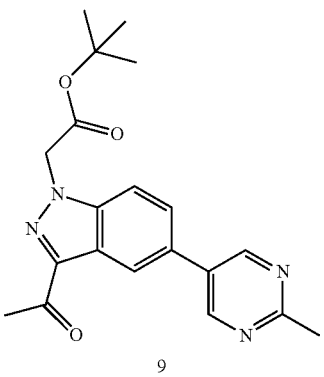

9

Synthesis of Intermediate 9

In Scheme 4, Step 2, 5-bromo-2-methylpyrimidine is reacted with bis-pinacolatodiborane in 1,4-dioxane in the presence of a palladium catalyst (Pd(dppf)Cl$_2$). The reaction is monitored for the conversion of starting materials by HPLC. Intermediate 6 is added and the coupling reaction is monitored by HPLC for the consumption of intermediate 6. After extraction and carbon treatment, L-cysteine is added to scavenge palladium. A thiol resin may also be used for scavenging palladium. Once acceptable levels of Pd are achieved, the product mixture is treated with charcoal and the product is precipitated with MTBE and heptane. After isolated by filtration, the wet cake is washed with MTBE and heptane, and then vacuum dried in a vacuum tray dryer.

The process description is as follows: The reactor was charged with 1,4-dioxane (20 Vol) and 5-bromo-2-methyl pyrimidine (1.0 w/w) at 25±5° C. under nitrogen atmosphere. The reactor was charged with bis-pinacolatodiborane (1.47 w/w) and potassium acetate (1.7 w/w), and the mass was stirred at 25±5° C. for 15 minutes. The reaction mass was degassed using nitrogen for 30 minutes. The reactor was charged with Pd(dppf)Cl$_2$.DCM (0.093 w/w). The mass temperature was raised to 85° C.-90±5° C., and the mass was stirred until the starting pyrimidine content was achieved. After completion of the reaction, the mass was cooled to 25±5° C. The vessel was charged with intermediate 6 (1.63 w/w) and K$_2$CO$_3$ (2.39 w/w). The vessel was charged with purified water (1.0 w/w). The reaction mass was stirred at 25±5° C. for 15 minutes. The reaction mass was degassed using nitrogen for 30 minutes. The mass temperature was raised to 85° C.-90±5° C., and the mass was stirred until the Starting Material content is achieved. After completion of the reaction, the mass was cooled to 25±5° C. The vessel was charged with ethyl acetate (30.0 vol.) and cooled to 15±5° C. Purified water was slowly added (20.0 w/w) at 15±5° C. The vessel was charged with activated charcoal (0.15 w/w). The mass temperature was raised to 25±5° C. and stirred for 30 minutes. The mass was filtered through celite bed, and the bed was washed with ethyl acetate (4.5 vol.). The layers were separated, and the aqueous layer was extracted with ethyl acetate (10.0 vol.). The organic layers were charged back to the reactor. The reactor was charged with a sodium chloride solution (purified water 20.0 w/w & NaCl 1.0 w/w), and the layers were separated. The organic layer was charged with a 5% L-cysteine solution (purified water 20.0 w/w & L-cysteine 1.0 w/w) and stirred for 15 minutes. The layers were separated. A sample of organic layer after concentration was submitted to QC for Pd content. The organic layer was charged with 5% L-cysteine solution (purified water 20.0 w/w & L-cysteine 0.6 w/w) and stirred for 15 minutes. The layers were separated. The organic layer was charged with purified water (20.0 w/w) and stirred for 30 minutes. The layers were separated. The organic layer was charged with purified water (20.0 w/w) and stirred for 30 minutes. The layers were separated. The organic layer was charged with activated charcoal (0.1 w/w) and stir for 60 minutes. The mass was filtered through celite bed, and the bed was washed with ethyl acetate (3.0 vol.). The filtrate was concentrated under vacuum below 55° C. until no distillate was observed. The filtrate was co-evaporated with n-heptane (2.0 vol.) under vacuum below 55° C. until no distillate was observed. The vessel was charged with MTBE (7.0 vol.), the temperature was raised to 45±5° C., and stirred for 60 minutes. n-Heptane was slowly added (3.0 vol.) and stirred at 45±5° C. for 60 minutes. The mass was cooled to 10±5° C. and stirred for 60 minutes. The mass was filtered through a Nutsche filter, and the cake was washed with a mixture of MTBE (1.0 vol.) and n-heptane (3.0 vol.). If the sample did not pass acceptance criteria the purification steps were repeated. The wet cake was charged to an n-heptane (5.0 vol.) and MTBE (5.0 vol.) mixture and stirred for 40 minutes at 25±5° C. The mass was filtered, and the cake was washed with a n-heptane (3.0 vol.) and MTBE (1.0 vol.) mixture. The material was dried in a vacuum tray drier at 25±5° C. for 2 hours and 50±5° C. for 8 hours or until the desired water content is achieved (Acceptance criteria: water content: NM4T 5.00%).

Table 32 contains the quantities of reagents and the yield of product for the most recent five batch campaign.

TABLE 32

Scale and Yields of Five Batches of Intermediate 9

| Batch No. of Interm. 9 | Interm. 7 | Potassium Acetate | Interm. 6 | Pd(dppf) Cl$_2$•DCM | Bis-pinacol- atodiborane | HPLC | Yield % (kg) | Yield* |
|---|---|---|---|---|---|---|---|---|
| Batch 1 | 40.0 Kg | 68.0 Kg | 73.2 Kg | 8.0 Kg | 56.0 Kg | 98.58% | 48.85 | 57.7 |
| Batch 2 | 10.0 Kg | 17.0 Kg | 16.3 Kg | 0.9 Kg | 14.67 Kg | 96.91% | 14.41 | 68 |

TABLE 32-continued

Scale and Yields of Five Batches of Intermediate 9

| Batch No. of Interm. 9 | Interm. 7 | Potassium Acetate | Interm. 6 | Pd(dppf) Cl$_2$•DCM | Bis-pinacolatodiborane | HPLC | Yield (kg) | % Yield* |
|---|---|---|---|---|---|---|---|---|
| Batch 3 | 10.0 Kg | 17.0 Kg | 16.33 Kg | 0.94 Kg | 14.67 Kg | 96.85% | 11.78 | 55.6 |
| Batch 4 | 37.0 Kg | 62.97 Kg | 60.31 Kg | 3.44 Kg | 54.39 Kg | 95.78% | 46.54 | 59.4 |
| Batch 5 | 36.0 Kg | 61.2 Kg | 58.68 Kg | 3.35 Kg | 52.92 Kg | 97.26% | 51.05 | 66.96 |

*yield calculated based on amount of Pyrimidine used. The yield is ~80% based on the limiting reactant, 0.8 equivalents of intermediate 6

Intermediate 9 can be used in the synthesis of Compound 1 or Compound 3. For example, in the synthesis of Compound 1 or Compound 3, intermediate 9 was synthesized from intermediate 6 via a one-pot palladium-catalyzed Miyaura borylation/Suzuki cross-coupling reaction. 4-Bromo-2-methylpyrimidine (7) was reacted with bis(pinacolato)diboron to afford boronate ester 8. In the presence of catalyst Pd(ddpf)Cl$_2$, intermediate 6 underwent a Suzuki reaction with boronate ester 8 to generate the coupled product, intermediate 9.

This one-pot Miyaura borylation/Suzuki coupling can be conducted between bromine-containing reagents, chloride-containing reagents, iodide-containing reagents, organotriflate-containing reagents, or any combination thereof. As described in Molander et al. (*Journal of Organic Chemistry*, 2012, 72, 8678-8688), the reaction can also be conducted with alternative Suzuki catalysts including, but not limited to, XPhos-Pd-G1, XPhos-Pd-G2, XPhos, or CataCXium A as defined in Molander et al. In one embodiment, the reaction is conducted with Suzuki catalysts XPhos-Pd-G1 and XPhos or XPhos-Pd-G2 and XPhos. In addition to bis(pinacolato)diboron, the borylation reagent can also be selected from, but not limited to, pinacolborane or bisboronic acid.

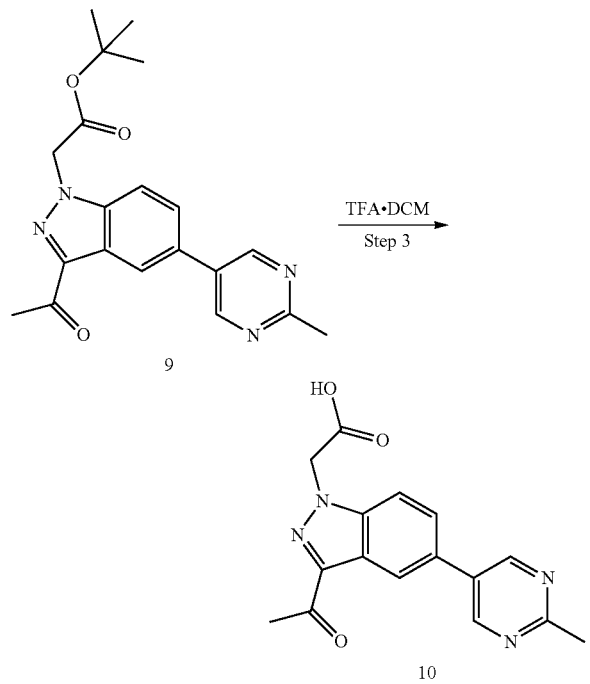

Synthesis of Intermediate 10

In Scheme 4, Step 3, intermediate 9 was hydrolyzed with trifluoroacetic acid in dichloromethane. The reaction was monitored by HPLC for the consumption of intermediate 9. The reaction mixture was treated with NaHCO$_3$ to reduce impurity at RRT 0.86 which was monitored by HPLC. The product was isolated by filtration, the wet cake was washed with water and MTBE and then vacuum dried in a vacuum tray dryer.

The process description is as follows: The vessel was charged with intermediate 9 (1.0 w/w) and DCM (7.0 vol.) at 25±5° C. under nitrogen atmosphere, and the mass was stirred for 15 minutes. The reaction mass was cooled to 15±5° C. Trifluroacetic acid (7.49 w/w) was slowly added at 15±5° C. to the reaction mass and stirred for 10-15 minutes at 15±5° C. The mass temperature was raised to 35±5° C. and stirred for 2 hours at 35±5° C. The reaction mass was concentrated to remove DCM and trifluroacetic acid below 55° C. The vessel was charged with DCM (10.0 vol.) and stirred to obtain a clear solution. The above mass was charged to a NaHCO$_3$ solution (purified water 15.0 w/w, NaHCO$_3$ 1.5 w/w) at 20±5° C. The mass was stirred for 15 minutes at 25±5° C. The pH of the mass was checked, and more NaHCO$_3$ solution was added if needed (Acceptance criteria: pH 7-8). To the NaHCO$_3$ solution was slowly added (purified water 10.0 w/w, NaHCO$_3$ 1.0 w/w), and stirred for 40 min or until the impurity at RRT 0.86 content was achieved. To the above mass was added HCl (0.8-2.0 w/w) at 25±5° C. to adjust the pH to 2-3. The pH of the mass was checked. The reaction mass was stirred for 15 minutes. The mass was centrifuged, and the cake was washed with purified water (5.0 vol.). The mass was spin dried for 3-4 hours. If the sample did not meet the acceptance criteria, the wet cake was charged to MTBE (15.0 vol.) and stirred at 25±5° C. for 20-30 minutes. The mass was centrifuged, and the cake was washed with MTBE (3.0 vol.). The material was dried at 25±5° C. for 2 hours and then at 55±5° C. for 8 hours in a vacuum tray drier.

Table 33 contains the quantities of reagents and the yield of product for the most recent four batch campaign.

TABLE 33

Scale and Yields of Four Batches of intermediate 10

| Batch No. of Intermediate 10 | Intermediate 9 | TEA | HPLC | Yield | % Yield |
|---|---|---|---|---|---|
| Batch 1 | 48.7 Kg | 364.76 Kg | 98.41% | 41.05 Kg | 99.54% |
| Batch 2 | 46.0 Kg | 344.54 Kg | 98.5% | 40.56 Kg | 104.11% |
| Batch 3 | 25.8 Kg | 193.24 Kg | 97.89% | 21.8 Kg | 99.77% |
| Batch 4 | 50.0 Kg | 374.5 Kg | 98.2% | 42.4 Kg | 100.14% |

Example 18. Process Description for the Manufacture of Compound 1, Compound 2, and Compound 3

In Scheme 5 below, intermediate 4 was coupled with intermediate 10 in the presence of TBTU/DIPEA in DMF to generate Compound 1 drug substance. The coupling reaction was monitored by HPLC for the consumption of intermediate 10. After extraction into ethyl acetate the solution was treated with silica gel, charcoal and if needed, aqueous potassium carbonate and SiliaMetS® Thiol resin until acceptable levels of fluorine and Pd were achieved. Ethyl acetate was removed by distillation and replaced with IPA to produce crystalline Compound 1. Heptane was added to aid the isolation of the product. After isolation by filtration, the wet cake was washed with a mixture of IPA and heptane and then vacuum dried in a VTD.

Scheme 5. Large Scale Synthesis of Compound 1

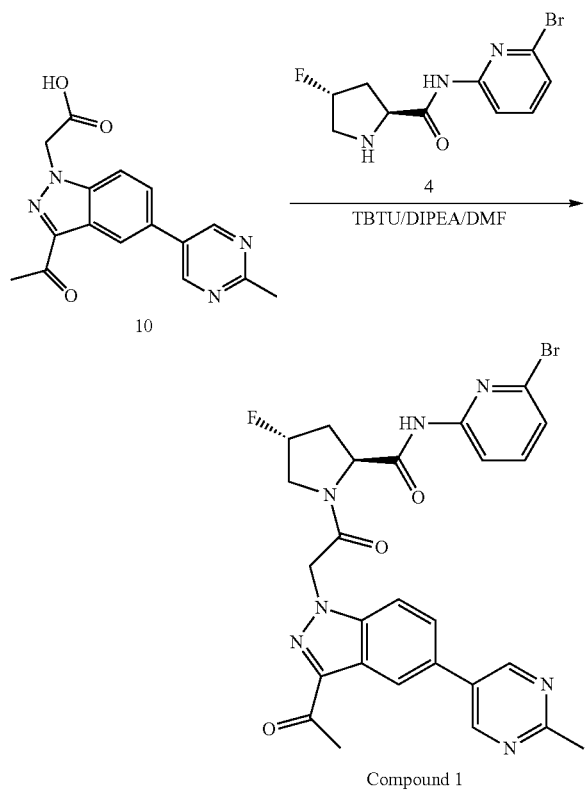

Compound 1

The process description is as follows: A reactor was charged with intermediate 10 (1.0 w/w) and DMF (7.0 vol.) at 25±5° C. under nitrogen atmosphere. The reactor was then charged with intermediate 4 (0.922 w/w), stirred for 10 minutes, and the resulting mass was cooled to 10±5° C. The reactor was next charged with TBTU (1.35 w/w) and N,N-diisopropylethylamine (LR) (2.06 w/w) was slowly added to the reaction mass at 10±5° C. and stirred for 20 minutes. The temperature was a raised to 25±5° C. and stirred for 6 hours. The reactor was charged with ethyl acetate (35 vol.) and stirred for 15 minutes. Purified water (25 vol.) was slowly added and stirred for 15 minutes. The layers were separated and the aqueous layer was extracted with ethyl acetate (15 w/w). The organic layers were combined and washed with purified water (20.0 vol. ×2 times).

The solvent from a small sample (100 mL) was evaporated and the sample was submitted to QC for $^{19}$F peak by $^{19}$F NMR (acceptance criteria: Fluorine peak at −145 to −150 ppm absent by $^{19}$F NMR). The pH of the aqueous layer was checked (acceptance criteria: pH 7-8) and the aqueous layer was continually washed if the sample did not meet acceptance criteria. The organic layer was charged with sodium sulphate (0.25 w/w) and silica gel (60-120)(0.5 w/w) and the resulting mass was stirred for 30 minutes at 25±5° C. (In some batches, the slurry with silica gel was omitted). The reaction mass was passed through a glass chromatography column with silica gel (40 kg relative to 20 kg intermediate 10 used) and the column was washed with EtOAc. The fractions containing API were charged with activated charcoal (0.05 w/w) and the mass temperature was raised to 35±5° C. for 60-70 minutes. The mass was then cooled to 25±5° C. and filtered through celite. The cake was washed with ethyl acetate (2.0 w/w).

If the Pd content was not appropriate, the filtrate was charged with SiliaMetS® Thiol (0.25 w/w) and silica gel (60-120)(0.25 w/w) and stirred for 8 hours or until the Pd content was achieved.

The mass was then filtered and washed with ethyl acetate (2.0 w/w). The filtrate/solution was passed through a 5.0μ cartridge filter followed by 0.2μ cartridge. The line was rinsed with ethyl acetate (1.0 w/w) and the filtrate was concentrated below 45° C. until no distillate was observed. The filtrated was co-evaporated with IPA (2.5 w/w) below 55° C. until no distillate was observed. IPA (7 vol.) was charged to the vessel through a 5.0μ cartridge filter followed by 0.2μ cartridge and the mass temperature was raised to 60±5° C. and stirred for 6 hours (API crystallizes at this step). n-Heptane (3 vol.) was slowly added to the vessel through a 5.0 cartridge filter followed by 0.2μ cartridge at 60±5° C. and stirred for 2 hours. The mass temperature was cooled to 25±5° C. and stirred for 2-3 hours. The mass was centrifuged and the cake was washed with cartridge-filtered (5.0 cartridge filter followed by 0.2μ cartridge) IPA (2.35 vol.) and n-heptane (2.5 vol.) mixture.

If the material did not pass acceptance criteria, the material was dissolved in DCM, evaporated, and the vessel was again charged with IPA through a 5.0μ cartridge filter followed by 0.2μ cartridge, the mass temperature was raised to 60±5° C. and stirred for 6 hours. n-Heptane (3 vol.) was slowly added to the vessel through a 5.0μ cartridge filter followed by 0.2μ cartridge at 60±5° C. and stirred for 2 hours. The mass temperature was cooled to 25±5° C. and stirred for 2-3 hours. The mass was centrifuged and the cake was washed with cartridge-filtered (5.0 cartridge filter followed by 0.2μ cartridge) IPA (2.35 vol.) and n-heptane (2.5 vol.) mixture.

The material was dried at 25±5° C. for 2 hours and then at 55±5° C. for 16 hours in a vacuum tray drier. The tray-drier was cooled to 25±5° C., the material was milled, and sieved using a No. 10 mesh.

Table 34 contains examples of quantities of reagents and yield of product for the most recent three batches.

The above-described process can be applied to Compound 2 and Compound 3 by substituting intermediate 10 and 4 with the appropriately substituted heteroaryl group and pyrrolidine respectively.

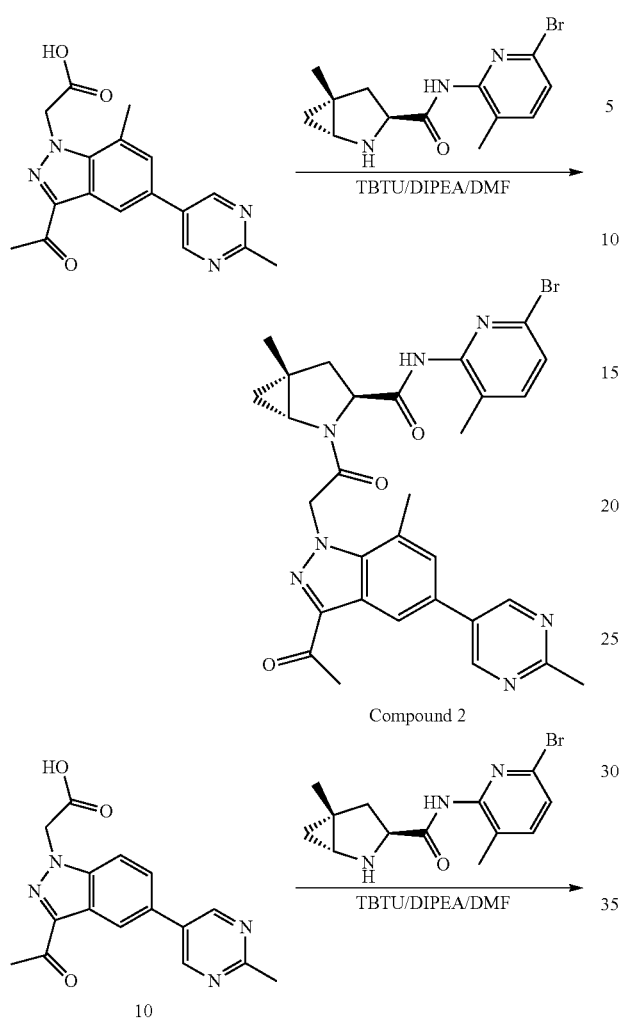

Compound 2

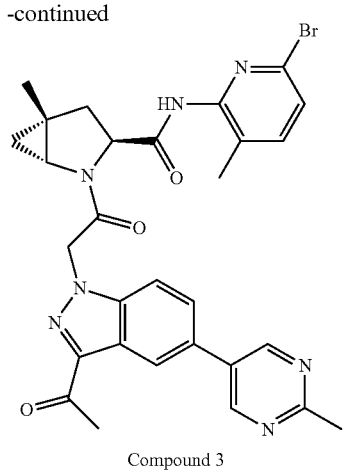

Compound 3

Once formed, Compound 3 can be prepared as morphic form A, B, or M using the methods described above. This morphic form can then be dissolved in acetone, DCM, or ethanol or a mixture thereof for use in a spray dry dispersions. The resultant material from the spray dry dispersion will be amorphous but of higher purity than the originally synthesized Compound 3. This advantageous procedure can be conducted with any volatile solvent or mixture of volatile solvents that achieves the desired effect. For example, Compound 3 can be dissolved in a 90:10, 80:20, or 50:50 mixture of acetone and DCM. In another embodiment, Compound 3 is dissolved in a 90:10, 80:20, or 50:50 mixture of acetone and ethanol. In another embodiment, Compound 3 is dissolved in a 90:10, 80:20, or 50:50 mixture of DCM and ethanol.

TABLE 34 Scale and Yields of Three Batches of Compound 1

| Batch No. of Compound 1 | Interm. 10 | Interm. 4 | TBTU | DIPEA | HPLC | Yield | % Yield |
|---|---|---|---|---|---|---|---|
| Batch 1 | 40.5 Kg | 37.34 Kg | 54.68 Kg | 83.43 Kg | 99.32% | 55.69 Kg | 73.51% |
| Batch 2 | 40.0 Kg | 36.88 Kg | 54.0 Kg | 82.4 Kg | 99.48% | 52.25 Kg | 69.83% |
| Batch 3 | 42.0 Kg | 38.72 Kg | 56.7 Kg | 86.52 Kg | 99.54% | 60.01 Kg | 76.39% |

In one embodiment the amide coupling reagent used to connect the pyrrolidine with the indazole fragment (for example intermediate 4 with intermediate 10) is a diimide, for example: dicyclohexylcarbodiimide (DCC), diisopropylcarbodiimide (DIC), N-cyclohexyl, N'-isopropylcarbodiimide (CIC), N-tert-butyl, N'-methylcarbodiimide (BMC), N-tertbutyl, N'-ethylcarbodiimide (BEC), N,N'-dicyclopentylcarbodiimide (CPC), bis[[4-(2,2-dimethyl-1,3-dioxolyl)] methyl]carbodiimide (BDDC), N-ethyl, N-phenylcarbodiimide (PEC), N-phenyl, N-isopropylcarbodiimide (PIC), N-(3-dimethylaminopropyl)-N'-ethylcarbodiimide * HCl, or N-(3-dimethylaminopropyl)-N'-ethylcarbodiimide.

In one embodiment the diimide is used in conjunction with an additive, for example: 1-Hydroxybenzotriazole (HOBt), 1-Hydroxybenzotriazole-6-sulfonamidomethyl resin HCl (HOBt-6-sulfonamidomethyl resin HCl), 1-hydroxy-6-nitrobenzotriazole (6-nitro-HOBt), 6-trifluoromethyl-1-hydroxy benzotriazole (6-CF$_3$—HOBt), 6-chloro-1-hydroxy benzotriazole (6-Cl-HOBt), Hydroxy-3,4-dihydro-4-oxo-1,2,3-benzotriazine (HOOBt), N-Hydroxysuccinimide (HOSu), 1-Hydroxy-7-aza-1H-benzotriazole (HOAt), 4-aza-1-hydroxybenzotriazole (4-HOAt), 5-aza-1-hydroxybenzotriazole (5-HOAt), 6-aza-1-hydroxybenzotriazole (6-HOAt), 3,4-dihydro-3-hydroxy-4-oxo-1,2,3-benzotriazine (HODhbt), 3-hydroxy-4-oxo-3,4-dihydro-5-azabenzo-1,2,3-triazene (HODhat), 3-hydroxy-4-oxo-3,4-dihydro-5-azabenzo-1,3-diazene (HODhad), N-hydroxy-5-norborene-endo-2,3-dicarboxyimide (HONB), 1-hydroxy-1H-1,2,3-triaozle, 5-chloro-1-hydroxy-1H-1,2,3-triazole, 5-acetyl-1-hydroxy-1H-1,2,3-triazole, 1-(1-hydroxy-1H-1,2,3-trizol-5-yl)propan-2-one, ethy-1-hydroxy-1H-1,2,3-triazole-4-carboxylate (HOCt), 1-hydroxy-1H-1,2,3,5-tetrazole, 1-hydroxxyy-2 pyridinone (HOPy), N-hydroxy-2-phenybenzimidzole (HOBI), N-hydroxyindolin-2-one (HOI), 6-chloro-N-hydroxy-2-phenylbenzimidazole (6-CL-HOBI), Ethyl 2-cyano-2-(hydroximino)acetate (Oxyma), or 4-(N,N-Dimethylamino)pyridine (DMAP).

In another embodiment the amide coupling reagent used to connect the pyrrolidine with the indazole fragment (for example intermediate 4 with intermediate 10) is an active ester, for example: p-nitrophenyl active ester, 2,4,5-trichlorophenyl active ester, pentafluoro active ester, o-phthalimido active ester, N-succinimide active ester, N-hydroxy-5-norborene-endo-2,3-dicarboximide active ester, or 4-oxo-3,4-dihydrobenzotriazinyl active ester.

In another embodiment the amide coupling reagent used to connect the pyrrolidine with the indazole fragment (for example intermediate 4 with intermediate 10) is a chlorinating agent, for example: pivaloyl chloride, phthaloyl chloride, thionyl chloride, oxalyl chloride, phosgene, CC, DMCT, TPP, tetramethyl-a-chloroenamine, or BTC.

In another embodiment the amide coupling reagent used to connect the pyrrolidine with the indazole fragment (for example intermediate 4 with intermediate 10) is a flourinating agent, for example: cyanuric fluoride (CF), 2-fluoro-1-ethyl pyridinium tetrafluoroborate (FEP), 2-fluoro-1-ethyl pyridinium hexachloroantimonate (FEPH), TFFH, BTFFH, 2-fluoro-1,3-dimethylimidazolidinium hexafluoro-phosphate (FIP), HEFFH, DMFH, 1,2-diethyl-3,3-tetramethylene fluoroformami-dinium hexafluorophosphate (DEFFH), 1,2-dimethyl-3,3-tetramethylene fluoroforma-midinium hexafluorophosphate (DMFFH), or PTF.

In another embodiment the amide coupling reagent used to connect the pyrrolidine with the indazole fragment (for example intermediate 4 with intermediate 10) is a phosphonium reagent, for example: Benzotriazol-1-yloxy-tris(dimethylamino)- phosphonium hexafluorophosphate (BOP), Benzotriazol-1-yloxy-tripyrrolidino-phosphonium hexafluorophosphate (PyBOP), Bromo-tripyrrolidino-phosphonium hexafluorophosphate (PyBrOP), 7-Aza-benzotriazol-1-yloxy-tripyrrolidinophosphonium hexafluorophosphate (PyAOP), Ethyl cyano(hydroxyimino)acetato-O2)-tri-(1-pyrrolidinyl)-phosphonium hexafluorophosphate (PyOxim), 3-(Diethoxy-phosphoryloxy)-1,2,3-benzo[d]triazin-4(3H)-one (DEPBT), BrOP, PyCloP, PyBroP, CloP, AOP, [(7-azabenzotriazol-1-yl)oxy]tris(pyrrolidino) phosphonium hexafluorophosphate (PyAOP), PyNOP, [[6-(trifluoromethyl)benzotriazol-1-yl]oxy]-tris(pyrrolidino) phosphonium hexafluoropho-sphate (PyFOP), [4-nitro-6-(trifluoromethyl)benzotriazol-1-yl)-oxy]tris(pyrrolidino) phosphonium hexafluor-ophosphate (PyFNBOP), (6-chloro-benzotriazol-1-yloxy)tris(pyrrolidino) phosphonium hexafluorophosphate (PyCloK), (pentafluorophenyloxy)tris (pyrrolidino) phos-phonium hexafluorophosphate (PyPOP), (pyridyl-2-thio)tris(pyrrolidino) phosphonium hexafluorophosphate (PyTOP), (pentafluorophenyloxy)tris(pyrrolidino) phos-phonium hexafluorophosphate (PyDOP), or [(3, 4-dihydro-4-oxo-5-azabenzo-1,2,3-triazin-3-yl]tris (pyrrolidino) phosphonium hexa-fluorophosphate (PyDAOP).

In another embodiment the amide coupling reagent used to connect the pyrrolidine with the indazole fragment (for example intermediate 4 with intermediate 10) is a aminium or uranium-imonium reagent, for example: 2-(1H-Benzotriazol-1-yl)-N,N,N',N'- tetramethylaminium tetrafluoroborate/hexafluorophosphate (TBTU/HBTU), (2-(6-Chloro-1H-benzotriazol-1-yl)-N,N,N',N'-tetramethylaminium hexafluorophosphate (HCTU), N-[(5-Chloro-1H-benzotriazol-1-yl)- dimethylamino-morpholino]-uronium hexafluorophosphate N-oxide (HDMC), 2-(7-Aza-1H-benzotriazol-1-yl)-N,N,N',N'- tetramethylaminium tetrafluoroborate/hexafluorophosphate (TATU/HATU), 1-[1-(Cyano-2-ethoxy-2-oxoethylideneaminooxy)-dimethylamino-morpholino]- uronium hexafluorophosphat (COMU), 2-(1-Oxy-pyridin-2-yl)-1,1,3,3-tetramethylisothiouronium tetrafluoroborate (TOTT), tetramethylfluoroformamidinium hexafluorophosphate (TFFH), TDTU, HDTU, TDATU, HDATU, TPTU, HPTU, TSTU, HSTU, TPFTU, HPFTU, N-CF3-TBTU, N-CF3-HBTU, N-HATU, N-TATU, N-HATTU, HOTT, TOTU, HOTU, HTODC, HTODeC, HTOPC, TNTU, TPhTU BTCFH, HBPyU, HAPyU, HDPyU, HPyOPfp, HPySPfp, HAPyTU, HPyONP, HPyOTCp, HBPipU, HAPipU, TOPPipU, CIP, HBMDU, HAMDU, CPP, HBMTU, HAMTU, HBPTU, HAPTU, HBM$_2$PyU, HAM$_2$PyU, HBM$_2$PipU, HAM$_2$PipU, HBE$_2$PyU, HAE$_2$PyU, HBE$_2$PipU, HAE$_2$PipU, HBTeU, HATeU, DMCH, HDMB, HDMA, HDMC, 4-HDMA, 6-HDMFB, HDMPfp, HDMP, HDTMA, HDTMB, HDMODC, HDMODcC, HDMOPC, HDmPyODC, HMPyODC, HDmPyODeC, HDmPyOC, HMPyOC, BOMI, BDMP, AOMP, BPMP, FOMP, SOMP, or DOMP.

In another embodiment the amide coupling reagent used to connect the pyrrolidine with the indazole fragment (for example intermediate 4 with intermediate 10) is an organophosphorous reagent, for example: DECP, DEPB, DEPC, DPPA, MPTA, MPTO, 2-5-dioxopyrrolidin-1-yl diphenyl phosphate, NDPP, FNDPP, Cpt-Cl, BMP-Cl, DEBP, BDP, bis(2-nitrophenyl)phenylphosphonate, (5-nitro-pyridyl)diphenyl phosphinate, DPOOP, BIODPP, ADP, BDOP, ADOP, BDTP, ADTP, DPPCl, FDPP, DEBPO, DOBPO, DOPBT, DEPBT, BOP-Cl, T3P, DEPAT, DPPAT, diphenyl 4-oxobenzo[d][1,2,3]triazin-3(4H)-ylphosphonate, DOEPBI, DOPPBI, DPPBI, tris(4-nitrophenyl)phosphonate, ethyl-bis(2-nitrophonely)phosphonate, tripyrimidin-2-yl phosphate, CDPOP, CDPP, dipyrimidin-2-yl phenylphosphonate, bis(4-nitrophenyl) phenylphosphonate, bis(4-cyanophenyl)phenylphosphonate, 4-nitrophenyl phenyl phenylphosphonate, 3-nitrophoneyl phenyl phenylphosphonate, 4-nitrophenyl methyl(phenyl)phosphinate, 4-nitrophenyl methoxymethyl(phenyl)phosphinate, 4-nitrophenyl-dimethylphosphinate, 4-nitrophenyl diethylphosphinate, FDMP, PyDPP, or TFMS-DEP.

In another embodiment the amide coupling reagent used to connect the pyrrolidine with the indazole fragment (for example intermediate 4 with intermediate 10) is an organophosphorous reagent, for example: 1-((naphthalen-2-ylsulfonyl)methyl)-1H-benzo-[d][1,2,3]triazole (NBs), 3-((naphthalen-2-ylsulfonyl)methyl)-3H-[1,2,3]-triazolo[4, 5-b]pyridine (NAs), 1H-benzo[d][1,2,3]triazol-1-yl 4-nitrobenzene-sulfonate (4-NBs), 3H-[1,2,3]triazolo[4,5-b]

pyridin-3-yl 4-nitro-benzenesulfonate (4-NAs), 1H-benzo[d][1,2,3]triazol-1-yl 4-methylbenzene-sulfonate (TBs), 3H-[1,2,3]triazolo[4,5-b]pyridin-3-yl 4-methyl-benzenesulfonate (TAs), 1H-benzo[d][1,2,3]triazol-1-yl 2-nitrobenzene-sulfonate (2-NBs), 3H-[1,2,3]triazolo[4,5-b]pyridin-3-yl 2-nitrobenzenesulfonate (2-NAs), DNBs, DNAs, HCSP, HCSCP, PFNB, SMDOP, SPDOP, and MSOxm.

In another embodiment the amide coupling reagent used to connect the pyrrolidine with the indazole fragment (for example intermediate 4 with intermediate 10) is a triazine reagent, for example: DMCT, DMTMM, 4-(4,6-dimethoxy-1,3,5-triazin-2-yl)-4-methyl-morpholinium tetrafluoroborate (TBCRi), 1-(4,6-dimethoxy-1,3,5-triazin-2-yl)-1-methyl-piperydinium tetrafluoroborate (TBCR$_2$), 1-(4,6-dimethoxy-1,3,5-triazin-2-yl)quinu-clidinium tetrafluoroborate (TBCR$_3$), or TBCR$_4$.

In another embodiment the amide coupling reagent used to connect the pyrrolidine with the indazole fragment (for example intermediate 4 with intermediate 10) is a pyrindinium reagent, for example: PS-EDC, PS-DCC, PS-TBTU, PS-DCT, PS-HOBt, PS—SO$_2$HOBt, PS-HOSu, PS-IIDQ, or PS-EEDQ.

In another embodiment the amide coupling reagent used to connect the pyrrolidine with the indazole fragment (for example intermediate 4 with intermediate 10) is a polymer-supported reagent, for example: mukaiyama's reagent, 2-bromo-3-ethyl-4-methyl thiazolium tetra-fluoroborate (BEMT), 2-bromo-1-ethyl pyridinium tetrafluoroborate (BEP), FEP, 2-bromo-1-ethyl pyridinium hexachloroantimonate (BEPH), or 2-fluoro-1-ethyl pyridinium hexachloroantimonate (FEPH).

In another embodiment the amide coupling reagent is selected from: N-Ethoxycarbonyl-2-ethoxy-1,2-dihydroquinoline (EEDQ), 2-Propanephosphonic acid anhydride (T3P), 4-(4,6-Dimethoxy-1,3,5-triazin-2-yl)- 4-methylmorpholinium salts (DMTMM), bis-Trichloromethylcarbonate or "Triphosgene (BTC), or 1,1'-Carbonyldiimidazole (CDI).

Methods of using and preparing these reagents are well known in the art, for example *Peptide Coupling Reagents, More than a Letter Soup by E*1-*Faham*, et. al., Chem. Rev. 2011, 111, 6557-602 provides several experimental schemes. This paper is incorporated by referenced.

The above reagents can be used for the synthesis of Compound 1, Compound 2, or Compound 3.

Non-limiting examples of these coupling reagent substitutions are shown below for the final step in the synthesis of Compound 1.

Scheme 6. Synthesis of Compound 1 with Alternative Coupling Reagents

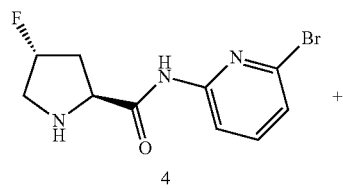

4

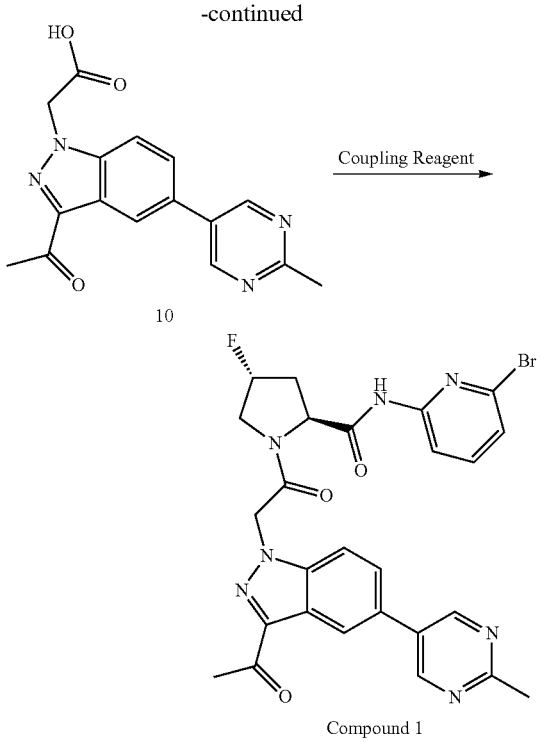

Compound 1

Intermediate 10 (10.8 g, 34.7 mmol) and Intermediate 4 (10.0 g, 34.7 mmol) was dissolved in DMF (70 mL). DIPEA (5 eq) was added at 10±5° C. and stirred for 5 min at 10±5° C. T3P (50% in DMF, 1.3 eq) was added slowly by maintaining temperature 5-10° C. and stirred for 2 hrs at 25±5° C. Purification by silicagel chromatography to afforded 18.5 g of Compound 1 (92%).
TBTU
Intermediate 10 (10.8 g, 34.7 mmol) and Intermediate 4 (10.0 g, 34.7 mmol) was dissolved in DMF (70 mL). DIPEA (5 eq) was added at 10±5° C. and stirred for 5 min at 10±5° C. TBTU (1.3 eq) was added slowly by maintaining temperature 5-10° C. and stirred for 2 hrs at 25±5° C. Purification by silicagel chromatography to afforded 17.9 g of Compound 1 (89%).
HATU
Intermediate 10 (10.8 g, 34.7 mmol) and Intermediate 4 (10.0 g, 34.7 mmol) was dissolved in DMF (70 mL). DIPEA (5 eq) was added at 10±5° C. and stirred for 5 min at 10±5° C. HATU (1.3 eq) was added slowly by maintaining temperature 5-10° C. and stirred for 2 hrs at 25±5° C. Purification by silicagel chromatography to afforded 18.3 g of Compound 1 (91%).
MsCl
Intermediate 10 (10.8 g, 34.7 mmol) and Intermediate 4 (10.0 g, 34.7 mmol) was dissolved in DCM (200 mL). Imidazole (5 eq) was added at 10±5° C. and stirred for 5 min at 10±5° C. MsCl (1.3 eq) was added slowly by maintaining temperature 5-10° C. and stirred for 2 hrs at 25±5° C. Purification by silicagel chromatography afforded 15.7 g of Compound 1 (78%).
HOBt, EDC
Intermediate 10 (10.8 g, 34.7 mmol) and Intermediate 4 (10.0 g, 34.7 mmol) was dissolved in DMF (70 mL). DIPEA (5 eq) was added at 10±5° C. and stirred for 5 min at 10±5° C. HOBt (1.3 eq) and EDC (1.3 eq) were added slowly by maintaining temperature 5-10° C. and stirred for 2 hrs at 25±5° C. Purification by silicagel chromatography afforded 15.1 g of Compound 1 (75%).

EEDQ

Intermediate 10 (10.8 g, 34.7 mmol) and Intermediate 4 (10.0 g, 34.7 mmol) was dissolved in toluene (80 mL). EEDQ (1.2 eq) was added at 10±5° C. and stirred for 16 hr maintaining temperature at 60~65° C. Purification by silicagel chromatography afforded 17.1 g of Compound 1 (85%).

IBCF

Intermediate 10 (10.8 g, 34.7 mmol) and TEA (6 eq) was dissolved in THF (250 mL) and IBCF (Isobutyl chloroformate, 1.3 eq) were added at −25±5° C. and stirred for 1 hrs at −25±5° C. Intermediate 4 (10.0 g, 34.7 mmol) was added at −25±5° C., followed by TEA at −25±5° C. The reaction was stirred for 3-4 hrs at 25±5° C. Purification by silicagel chromatography afforded 5.44 g of Compound 1 (27%).

Ethyl Cyanoglyoxylae Oxime

Intermediate 10 (10.8 g, 34.7 mmol) and Intermediate 4 (10.0 g, 34.7 mmol) was dissolved in DMF (70 mL) and ethyl cyanoglyoxylae oxime (1.3 eq) and EDC.HCl (1.3 eq) were added at 25±5° C. The reaction was stirred at 25±5° C. for 12 hrs. Purification by silicagel chromatography afforded 14.7 g of Compound 1 (73%).

Cyanuric Chloride

Intermediate 10 (10.8 g, 34.7 mmol) and cyanuric chloride (1.3 eq) was dissolved in DCM (100 ml) and TEA (25 eq) were added at 15±5° C. and stirred for 3 hrs at 25±5° C. Intermediate 4 was added and stirred for 3 hrs at 25±5° C. Purification by silicagel chromatography afforded 8.1 g of Compound 1 (40%).

Example 19: Representative Example of Use of Morphic Form A in Spary Dry Dispersion Compound 3 morphic Form A is dissolved in acetone with stirring. The mixture is stirred until dissolved. The mixture is then spray dried with this spray solution using a suitable spray dryer and collecting the resulting spray dry product in a suitable container. The spray dried product is then dried in a suitable dryer. A similar method can be employed for Form B or Form M and the solvent can be substituted for other volatile solvents such as DCM or ethanol, or a mixture thereof.

Example 20. XRPD Peak Tables Corresponding to FIGS. 51-55

The identified peaks from FIG. 51 are displayed in Table 35 below.

TABLE 35

Compound 3 Form A XRPD Peaks

| 2 Theta (°) | d-spacing (Å) | Intensity (%) |
|---|---|---|
| 2.62 ± 0.20 | 33.694 ± 2.572 | 100 |
| 3.61 ± 0.20 | 24.455 ± 1.354 | 62 |
| 3.81 ± 0.20 | 23.172 ± 1.216 | 38 |
| 4.05 ± 0.20 | 21.799 ± 1.076 | 8 |
| 5.26 ± 0.20 | 16.787 ± 0.638 | 5 |
| 5.79 ± 0.20 | 15.252 ± 0.526 | 4 |
| 6.01 ± 0.20 | 14.694 ± 0.489 | 5 |
| 6.65 ± 0.20 | 13.281 ± 0.399 | 5 |
| 7.69 ± 0.20 | 11.487 ± 0.298 | 5 |
| 7.90 ± 0.20 | 11.182 ± 0.283 | 7 |
| 8.20 ± 0.20 | 10.774 ± 0.262 | 4 |
| 8.49 ± 0.20 | 10.406 ± 0.245 | 6 |
| 9.26 ± 0.20 | 9.543 ± 0.206 | 6 |
| 9.78 ± 0.20 | 9.036 ± 0.184 | 5 |
| 10.28 ± 0.20 | 8.598 ± 0.167 | 2 |
| 10.73 ± 0.20 | 8.238 ± 0.153 | 4 |
| 11.05 ± 0.20 | 8.001 ± 0.144 | 3 |
| 11.64 ± 0.20 | 7.596 ± 0.130 | 4 |
| 12.05 ± 0.20 | 7.339 ± 0.121 | 3 |
| 12.76 ± 0.20 | 6.932 ± 0.108 | 3 |
| 13.23 ± 0.20 | 6.687 ± 0.101 | 4 |
| 13.65 ± 0.20 | 6.482 ± 0.095 | 3 |
| 14.54 ± 0.20 | 6.087 ± 0.083 | 4 |
| 15.01 ± 0.20 | 5.898 ± 0.078 | 3 |
| 15.51 ± 0.20 | 5.709 ± 0.073 | 6 |
| 15.86 ± 0.20 | 5.583 ± 0.070 | 3 |
| 16.44 ± 0.20 | 5.388 ± 0.065 | 4 |
| 17.37 ± 0.20 | 5.101 ± 0.058 | 3 |
| 18.92 ± 0.20 | 4.687 ± 0.049 | 7 |
| 19.30 ± 0.20 | 4.595 ± 0.047 | 9 |
| 19.73 ± 0.20 | 4.496 ± 0.045 | 5 |
| 20.11 ± 0.20 | 4.412 ± 0.043 | 5 |
| 20.75 ± 0.20 | 4.277 ± 0.041 | 6 |
| 21.01 ± 0.20 | 4.225 ± 0.040 | 6 |
| 21.44 ± 0.20 | 4.141 ± 0.038 | 7 |
| 21.92 ± 0.20 | 4.052 ± 0.037 | 9 |
| 22.57 ± 0.20 | 3.936 ± 0.034 | 5 |
| 23.07 ± 0.20 | 3.852 ± 0.033 | 5 |
| 23.68 ± 0.20 | 3.754 ± 0.031 | 5 |
| 24.30 ± 0.20 | 3.660 ± 0.030 | 5 |
| 24.85 ± 0.20 | 3.580 ± 0.028 | 4 |
| 25.54 ± 0.20 | 3.485 ± 0.027 | 6 |

The identified peaks from FIG. 52 are displayed in Table 36 below.

TABLE 36

Compound 3 Form B XRPD Peaks

| 2 Theta (°) | d-spacing (Å) | Intensity (%) |
|---|---|---|
| 4.52 ± 0.20 | 19.518 ± 0.862 | 79 |
| 8.27 ± 0.20 | 10.682 ± 0.258 | 60 |
| 9.30 ± 0.20 | 9.504 ± 0.204 | 21 |
| 9.61 ± 0.20 | 9.200 ± 0.191 | 35 |
| 12.04 ± 0.20 | 7.345 ± 0.122 | 31 |
| 12.61 ± 0.20 | 7.012 ± 0.111 | 5 |
| 13.65 ± 0.20 | 6.480 ± 0.094 | 14 |
| 13.97 ± 0.20 | 6.333 ± 0.090 | 14 |
| 15.66 ± 0.20 | 5.655 ± 0.072 | 87 |
| 16.10 ± 0.20 | 5.500 ± 0.068 | 60 |
| 16.21 ± 0.20 | 5.462 ± 0.067 | 100 |
| 16.41 ± 0.20 | 5.399 ± 0.065 | 19 |
| 17.08 ± 0.20 | 5.186 ± 0.060 | 20 |
| 17.44 ± 0.20 | 5.080 ± 0.058 | 64 |
| 17.97 ± 0.20 | 4.933 ± 0.054 | 29 |
| 18.31 ± 0.20 | 4.842 ± 0.052 | 46 |
| 18.67 ± 0.20 | 4.748 ± 0.050 | 49 |
| 19.08 ± 0.20 | 4.648 ± 0.048 | 24 |
| 19.33 ± 0.20 | 4.589 ± 0.047 | 7 |
| 19.77 ± 0.20 | 4.487 ± 0.045 | 11 |
| 20.39 ± 0.20 | 4.353 ± 0.042 | 7 |
| 20.62 ± 0.20 | 4.304 ± 0.041 | 14 |
| 21.08 ± 0.20 | 4.211 ± 0.039 | 52 |
| 21.69 ± 0.20 | 4.094 ± 0.037 | 30 |
| 21.98 ± 0.20 | 4.040 ± 0.036 | 62 |
| 22.62 ± 0.20 | 3.928 ± 0.034 | 79 |
| 22.97 ± 0.20 | 3.868 ± 0.033 | 25 |
| 23.51 ± 0.20 | 3.781 ± 0.032 | 29 |
| 23.88 ± 0.20 | 3.723 ± 0.031 | 44 |
| 24.37 ± 0.20 | 3.649 ± 0.029 | 28 |
| 25.06 ± 0.20 | 3.550 ± 0.028 | 15 |
| 25.31 ± 0.20 | 3.516 ± 0.027 | 8 |
| 25.79 ± 0.20 | 3.451 ± 0.026 | 20 |
| 26.41 ± 0.20 | 3.372 ± 0.025 | 20 |

TABLE 36-continued Compound 3 Form B XRPD Peaks

| 2 Theta (°) | d-spacing (Å) | Intensity (%) |
|---|---|---|
| 26.49 ± 0.20 | 3.362 ± 0.025 | 21 |
| 27.54 ± 0.20 | 3.236 ± 0.023 | 40 |
| 27.78 ± 0.20 | 3.209 ± 0.023 | 12 |
| 28.01 ± 0.20 | 3.183 ± 0.022 | 30 |
| 28.24 ± 0.20 | 3.158 ± 0.022 | 28 |
| 28.67 ± 0.20 | 3.111 ± 0.021 | 16 |
| 29.16 ± 0.20 | 3.060 ± 0.021 | 13 |

The identified peaks from FIG. 53 are displayed in Table 37 below.

TABLE 37

Compound 3 Form G XRPD Peaks

| 2 Theta (°) | d-spacing (Å) | Intensity (%) |
|---|---|---|
| 4.05 ± 0.20 | 21.799 ± 1.076 | 48 |
| 5.07 ± 0.20 | 17.416 ± 0.687 | 41 |
| 5.35 ± 0.20 | 16.505 ± 0.617 | 31 |
| 6.47 ± 0.20 | 13.650 ± 0.422 | 36 |
| 7.29 ± 0.20 | 12.116 ± 0.332 | 57 |
| 7.52 ± 0.20 | 11.746 ± 0.312 | 26 |
| 8.03 ± 0.20 | 11.001 ± 0.274 | 69 |
| 9.00 ± 0.20 | 9.818 ± 0.218 | 25 |
| 9.65 ± 0.20 | 9.158 ± 0.189 | 26 |
| 10.20 ± 0.20 | 8.665 ± 0.169 | 43 |
| 10.72 ± 0.20 | 8.246 ± 0.153 | 29 |
| 11.33 ± 0.20 | 7.803 ± 0.137 | 28 |
| 11.50 ± 0.20 | 7.689 ± 0.133 | 26 |
| 12.16 ± 0.20 | 7.273 ± 0.119 | 19 |
| 12.50 ± 0.20 | 7.076 ± 0.113 | 71 |
| 13.06 ± 0.20 | 6.773 ± 0.103 | 45 |
| 14.77 ± 0.20 | 5.993 ± 0.081 | 58 |
| 15.02 ± 0.20 | 5.894 ± 0.078 | 100 |
| 15.33 ± 0.20 | 5.775 ± 0.075 | 33 |
| 16.07 ± 0.20 | 5.511 ± 0.068 | 57 |
| 16.26 ± 0.20 | 5.447 ± 0.067 | 59 |
| 16.51 ± 0.20 | 5.365 ± 0.065 | 25 |
| 17.07 ± 0.20 | 5.190 ± 0.060 | 17 |
| 18.12 ± 0.20 | 4.892 ± 0.054 | 24 |
| 18.90 ± 0.20 | 4.692 ± 0.049 | 26 |
| 19.34 ± 0.20 | 4.586 ± 0.047 | 27 |
| 19.62 ± 0.20 | 4.521 ± 0.046 | 32 |
| 20.24 ± 0.20 | 4.384 ± 0.043 | 24 |
| 21.02 ± 0.20 | 4.223 ± 0.040 | 34 |
| 21.21 ± 0.20 | 4.186 ± 0.039 | 30 |
| 21.94 ± 0.20 | 4.048 ± 0.036 | 31 |
| 22.25 ± 0.20 | 3.992 ± 0.035 | 29 |
| 22.74 ± 0.20 | 3.907 ± 0.034 | 29 |

The identified peaks from FIG. 54 are displayed in Table 38 below.

TABLE 38

Compound 3 Form J XRPD Peaks

| 2 Theta (°) | d-spacing (Å) | Intensity (%) |
|---|---|---|
| 3.57 ± 0.20 | 24.762 ± 1.389 | 6 |
| 4.80 ± 0.20 | 18.407 ± 0.767 | 88 |
| 6.42 ± 0.20 | 13.759 ± 0.428 | 79 |
| 7.15 ± 0.20 | 12.345 ± 0.345 | 75 |
| 7.35 ± 0.20 | 12.011 ± 0.326 | 41 |
| 7.85 ± 0.20 | 11.260 ± 0.287 | 30 |
| 9.63 ± 0.20 | 9.178 ± 0.190 | 12 |
| 10.30 ± 0.20 | 8.583 ± 0.166 | 13 |
| 10.75 ± 0.20 | 8.223 ± 0.153 | 5 |
| 11.23 ± 0.20 | 7.870 ± 0.140 | 4 |
| 12.04 ± 0.20 | 7.347 ± 0.122 | 12 |
| 12.54 ± 0.20 | 7.052 ± 0.112 | 22 |
| 12.87 ± 0.20 | 6.870 ± 0.106 | 7 |
| 13.39 ± 0.20 | 6.610 ± 0.098 | 100 |
| 14.48 ± 0.20 | 6.112 ± 0.084 | 33 |
| 14.73 ± 0.20 | 6.007 ± 0.081 | 18 |
| 15.75 ± 0.20 | 5.621 ± 0.071 | 8 |
| 16.52 ± 0.20 | 5.361 ± 0.064 | 11 |
| 16.82 ± 0.20 | 5.267 ± 0.062 | 7 |
| 17.34 ± 0.20 | 5.109 ± 0.058 | 9 |
| 18.27 ± 0.20 | 4.851 ± 0.053 | 17 |
| 18.76 ± 0.20 | 4.726 ± 0.050 | 18 |
| 18.85 ± 0.20 | 4.703 ± 0.049 | 16 |
| 19.44 ± 0.20 | 4.562 ± 0.046 | 37 |
| 19.63 ± 0.20 | 4.518 ± 0.046 | 30 |
| 19.92 ± 0.20 | 4.453 ± 0.044 | 29 |
| 20.25 ± 0.20 | 4.382 ± 0.043 | 11 |
| 20.72 ± 0.20 | 4.284 ± 0.041 | 13 |
| 21.04 ± 0.20 | 4.220 ± 0.040 | 21 |
| 21.41 ± 0.20 | 4.147 ± 0.038 | 28 |
| 21.87 ± 0.20 | 4.060 ± 0.037 | 16 |
| 22.25 ± 0.20 | 3.993 ± 0.035 | 13 |
| 22.59 ± 0.20 | 3.934 ± 0.034 | 14 |
| 22.94 ± 0.20 | 3.873 ± 0.033 | 11 |
| 23.33 ± 0.20 | 3.809 ± 0.032 | 53 |
| 23.80 ± 0.20 | 3.735 ± 0.031 | 17 |
| 24.26 ± 0.20 | 3.666 ± 0.030 | 18 |
| 24.65 ± 0.20 | 3.608 ± 0.029 | 18 |
| 24.87 ± 0.20 | 3.577 ± 0.028 | 21 |
| 25.17 ± 0.20 | 3.535 ± 0.028 | 15 |
| 25.76 ± 0.20 | 3.456 ± 0.026 | 27 |
| 27.08 ± 0.20 | 3.291 ± 0.024 | 28 |
| 28.02 ± 0.20 | 3.181 ± 0.022 | 9 |
| 28.36 ± 0.20 | 3.144 ± 0.022 | 8 |
| 29.27 ± 0.20 | 3.049 ± 0.020 | 15 |
| 29.69 ± 0.20 | 3.007 ± 0.020 | 11 |

The identified peaks from FIG. 55 are displayed in Table 39 below.

TABLE 38

Compound 3 Form M XRPD Peaks

| 2 Theta (°) | d-spacing (Å) | Intensity (%) |
|---|---|---|
| 5.16 ± 0.20 | 17.119 ± 0.663 | 62 |
| 7.19 ± 0.20 | 12.280 ± 0.341 | 68 |
| 7.45 ± 0.20 | 11.850 ± 0.318 | 85 |
| 8.28 ± 0.20 | 10.671 ± 0.257 | 62 |
| 10.36 ± 0.20 | 8.530 ± 0.164 | 9 |
| 13.15 ± 0.20 | 6.727 ± 0.102 | 15 |
| 14.44 ± 0.20 | 6.131 ± 0.084 | 25 |
| 14.95 ± 0.20 | 5.923 ± 0.079 | 100 |
| 15.39 ± 0.20 | 5.752 ± 0.074 | 21 |
| 16.27 ± 0.20 | 5.443 ± 0.066 | 9 |
| 18.34 ± 0.20 | 4.834 ± 0.052 | 20 |
| 18.50 ± 0.20 | 4.793 ± 0.051 | 32 |
| 19.14 ± 0.20 | 4.634 ± 0.048 | 67 |
| 19.80 ± 0.20 | 4.480 ± 0.045 | 31 |
| 20.21 ± 0.20 | 4.390 ± 0.043 | 31 |
| 20.86 ± 0.20 | 4.255 ± 0.040 | 20 |
| 21.19 ± 0.20 | 4.189 ± 0.039 | 26 |
| 21.74 ± 0.20 | 4.085 ± 0.037 | 49 |
| 21.91 ± 0.20 | 4.053 ± 0.037 | 37 |
| 22.81 ± 0.20 | 3.896 ± 0.034 | 52 |
| 23.79 ± 0.20 | 3.738 ± 0.031 | 72 |
| 24.12 ± 0.20 | 3.687 ± 0.030 | 17 |
| 24.92 ± 0.20 | 3.571 ± 0.028 | 37 |
| 26.22 ± 0.20 | 3.396 ± 0.025 | 57 |
| 26.64 ± 0.20 | 3.344 ± 0.025 | 19 |
| 27.01 ± 0.20 | 3.299 ± 0.024 | 8 |
| 27.39 ± 0.20 | 3.254 ± 0.023 | 10 |
| 27.95 ± 0.20 | 3.190 ± 0.022 | 12 |
| 28.62 ± 0.20 | 3.116 ± 0.021 | 21 |

TABLE 38-continued

Compound 3 Form M XRPD Peaks

| 2 Theta (°) | d-spacing (Å) | Intensity (%) |
|---|---|---|
| 28.97 ± 0.20 | 3.079 ± 0.021 | 11 |
| 29.64 ± 0.20 | 3.012 ± 0.020 | 14 |

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. An isolated crystalline form of Compound 3:

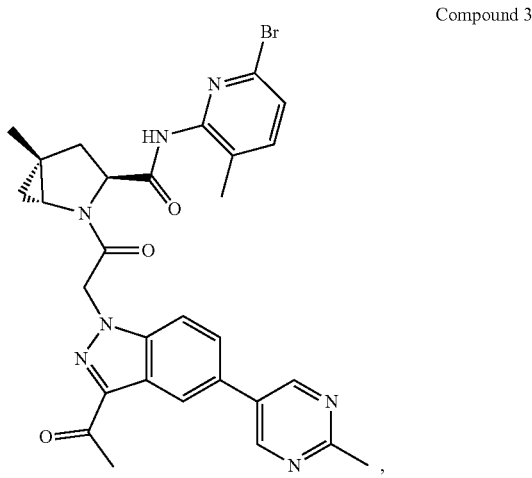

Compound 3 wherein the isolated crystalline form is:
Form B, characterized by a powder X-ray diffraction (PXRD) pattern comprising at least three 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°; or
Form A, characterized by a powder X-ray diffraction (PXRD) pattern comprising at least one 2theta values selected from 2.6±0.4°, 3.6±0.4°, and 3.8±0.4°; or
Form M, characterized by a powder X-ray diffraction (PXRD) pattern comprising at least three 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°.

2. The isolated crystalline form of claim 1, wherein the isolated crystalline form is Form B of Compound 3, and the PXRD pattern comprises at least four 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°.

3. The isolated crystalline form of claim 1, wherein the isolated crystalline form is Form B of Compound 3, and the PXRD pattern comprises at least five 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°.

4. The isolated crystalline form of claim 1, wherein the isolated crystalline form is Form B of Compound 3, and the PXRD pattern comprises at least six 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°.

5. The isolated crystalline form of claim 1, wherein the isolated crystalline form is Form B of Compound 3, and the PXRD pattern comprises at least seven 2theta values selected from 16.2±0.4°, 15.7±0.4°, 4.5±0.4°, 22.6±0.4°, 17.4±0.4°, 22.0±0.4°, 8.3±0.4°, 16.1±0.4°, 21.1±0.4°, 18.7±0.4°, 18.3±0.4°, 23.9±0.4°, and 27.5±0.4°.

6. The isolated crystalline form of claim 1, wherein the isolated crystalline form is Form B of Compound 3, and the PXRD pattern comprises at least the 2theta value of 16.2±0.4° and/or the 2theta value of 15.7±0.4°.

7. The isolated crystalline form of claim 1, wherein the isolated crystalline form is Form A of Compound 3, and the PXRD pattern comprises at least two 2theta values selected from 2.6±0.4°, 3.6±0.4°, and 3.8±0.4°.

8. The isolated crystalline form of claim 1, wherein the isolated crystalline form is Form A of Compound 3, and the PXRD pattern comprises the 2theta values selected from 2.6±0.4°, 3.6±0.4°, and 3.8±0.4°.

9. The isolated crystalline form of claim 1, wherein the isolated crystalline form is Form A of Compound 3, and the PXRD pattern comprises at least six 2theta values selected 9.3±0.4°, 11.7±0.4°, 9.5±0.4°, 7.6±0.4°, 6.7±0.4°, 6.0±0.4°, 5.7±0.4°, 5.6±0.4°, 5.4±0.4°, and 4.2±0.4°.

10. The isolated crystalline form of claim 1, wherein the isolated crystalline form is Form A of Compound 3, and the PXRD pattern comprises at least seven 2theta values selected from 9.3±0.4°, 11.7±0.4°, 9.5±0.4°, 7.6±0.4°, 6.7±0.4°, 6.0±0.4°, 5.7±0.4°, 5.6±0.4°, 5.4±0.4°, and 4.2±0.4°.

11. The isolated crystalline form of claim 1, wherein the isolate crystalline form is Form A of Compound 3, and the PXRD pattern comprises at least the 2theta value of 2.6±0.4° and/or the 2theta value of 3.6±0.4°.

12. The isolated crystalline form of claim 1, wherein the isolated crystalline form is Form M of Compound 3, and the PXRD pattern comprises at least four 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°.

13. The isolated crystalline form of claim 1, wherein the isolated crystalline form is Form M of Compound 3, and the PXRD pattern comprises at least five 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°.

14. The isolated crystalline form of claim 1, wherein the isolated crystalline form is Form M of Compound 3, and the PXRD pattern comprises at least six 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°.

15. The isolated crystalline form of claim 1, wherein the isolated crystalline form is Form M of Compound 3, and the PXRD pattern comprises at least seven 2theta values selected from 15.0±0.4°, 7.5±0.4°, 23.8±0.4°, 7.2±0.4°, 19.1±0.4°, 5.2±0.4°, 8.3±0.4°, 26.2±0.4°, 22.8±0.4°, 21.7±0.4°, and 24.9±0.4°.

16. The isolated crystalline form of claim 1, wherein the isolated crystalline form is Form M of Compound 3, and the PXRD pattern comprises at least the 2theta value of 15.0±0.4° and/or the 2theta value of 7.5±0.4°.

17. The isolated crystalline form of claim 1, wherein the peaks are within ±0.3° 2theta.

18. A pharmaceutical composition comprising the isolated crystalline form of claim 1 in a pharmaceutically acceptable excipient for solid dosage delivery.

19. A method for the treatment of a Complement Factor D mediated disorder comprising administering to a subject in need thereof a therapeutically effective amount of the isolated crystalline form or pharmaceutical composition thereof according to claim 1, optionally in a pharmaceutically acceptable excipient for solid dosage delivery.

20. The method of claim 19, wherein the subject is a human.

* * * * *